United States Patent
Ruane et al.

(10) Patent No.: US 12,303,619 B2
(45) Date of Patent: *May 20, 2025

(54) POLYMER IMPLANTS

(71) Applicant: Foundry Therapeutics, Inc., Menlo Park, CA (US)

(72) Inventors: Patrick H. Ruane, El Dorado Hills, CA (US); Jackie Joe Hancock, Berkeley, CA (US); Koon Kiat Teu, Singapore (SG); Daniel Boon Lim Seet, Singapore (SG); Wei Li Lee, Singapore (SG); Honglei Wang, Singapore (SG)

(73) Assignee: Foundry Therapeutics, Inc., Menlo Park, CA (US)

( * ) Notice: Subject to any disclaimer, the term of this patent is extended or adjusted under 35 U.S.C. 154(b) by 1100 days.

This patent is subject to a terminal disclaimer.

(21) Appl. No.: 17/250,747

(22) PCT Filed: Aug. 27, 2019

(86) PCT No.: PCT/US2019/048437
§ 371 (c)(1),
(2) Date: Feb. 26, 2021

(87) PCT Pub. No.: WO2020/047013
PCT Pub. Date: Mar. 5, 2020

(65) Prior Publication Data
US 2021/0308338 A1    Oct. 7, 2021

Related U.S. Application Data

(60) Provisional application No. 62/723,478, filed on Aug. 28, 2018, provisional application No. 62/742,357, filed on Oct. 6, 2018, provisional application No. 62/832,429, filed on Apr. 11, 2019.

(30) Foreign Application Priority Data

Oct. 6, 2018    (WO) ................. PCT/US2018/054777

(51) Int. Cl.
*A61L 27/58*    (2006.01)
*A61L 27/18*    (2006.01)
*A61L 27/54*    (2006.01)

(52) U.S. Cl.
CPC ............... *A61L 27/58* (2013.01); *A61L 27/18* (2013.01); *A61L 27/54* (2013.01); *A61L 2300/402* (2013.01); *A61L 2300/604* (2013.01); *A61L 2430/02* (2013.01)

(58) Field of Classification Search
CPC .......... A61L 27/58; A61L 27/18; A61L 27/54; A61L 2300/402; A61L 2300/604; A61L 2430/02; A61L 2300/602; A61K 47/26; A61K 47/34; A61K 9/0024; A61K 9/7007; A61K 31/445; A61P 23/02; A61P 25/04; A61P 29/00
See application file for complete search history.

(56) References Cited

U.S. PATENT DOCUMENTS

| | | |
|---|---|---|
| 4,601,893 A | 7/1986 | Cardinal |
| 4,666,704 A | 5/1987 | Shalati et al. |
| 4,919,939 A | 4/1990 | Baker |
| 5,227,165 A | 7/1993 | Domb et al. |
| 5,451,408 A | 9/1995 | Mezei et al. |
| 5,458,582 A | 10/1995 | Nakao |
| 5,540,912 A | 7/1996 | Roorda et al. |
| 5,618,563 A | 4/1997 | Berde et al. |
| 5,700,485 A | 12/1997 | Berde et al. |
| 5,747,060 A | 5/1998 | Sackler et al. |
| 5,807,306 A | 9/1998 | Shapland et al. |
| 5,919,473 A | 7/1999 | Elkhoury |
| 5,931,809 A | 8/1999 | Gruber et al. |
| 5,942,241 A | 8/1999 | Chasin et al. |
| 6,046,187 A | 4/2000 | Berde et al. |
| 6,149,937 A | 11/2000 | Camu et al. |
| 6,214,387 B1 | 4/2001 | Berde et al. |
| 6,248,345 B1 | 6/2001 | Goldenheim et al. |
| 6,326,020 B1 | 12/2001 | Kohane et al. |
| 6,451,335 B1 | 9/2002 | Goldenheim et al. |
| 6,699,908 B2 | 3/2004 | Sackler et al. |
| 6,913,760 B2 | 7/2005 | Carr et al. |
| 7,074,426 B2 | 7/2006 | Kochinke |
| 7,220,433 B2 | 5/2007 | Cui et al. |
| 7,723,291 B2 | 5/2010 | Beals et al. |
| 7,727,954 B2 | 6/2010 | McKay |
| 7,741,273 B2 | 6/2010 | McKay |
| 7,824,703 B2 | 11/2010 | Scifert et al. |
| 7,947,301 B2 | 5/2011 | Bischoff et al. |
| 7,993,390 B2 | 8/2011 | Miller et al. |
| 8,067,026 B2 | 11/2011 | Ranade et al. |
| 8,080,059 B2 | 12/2011 | Fell |
| 8,153,149 B2 | 4/2012 | Verity |
| 8,202,531 B2 | 6/2012 | McKay |
| 8,221,358 B2 | 7/2012 | McKay |

(Continued)

FOREIGN PATENT DOCUMENTS

| | | |
|---|---|---|
| AU | 2012201226 B2 | 8/2014 |
| AU | 2013200515 B2 | 1/2016 |

(Continued)

OTHER PUBLICATIONS

International Search Report and Written Opinion dated Feb. 17, 2022, International Application No. PCT/US2021/071861, 10 pages.

(Continued)

*Primary Examiner* — Lezah Roberts
*Assistant Examiner* — Abdulrahman Abbas
(74) *Attorney, Agent, or Firm* — Fortem IP LLP

(57) ABSTRACT

The present technology relates to polymer implants. In some embodiments, the polymer implant may have a volume having minimum cross-sectional dimension of 400 μm. The polymer implant may be configured to be implanted within a mammalian body for at least 3 days without undergoing core acidification.

20 Claims, 54 Drawing Sheets

(56) References Cited

U.S. PATENT DOCUMENTS

| | | |
|---|---|---|
| 8,231,891 B2 | 7/2012 | King |
| 8,246,571 B2 | 8/2012 | Simonton et al. |
| 8,257,393 B2 | 9/2012 | Cichocki |
| 8,357,388 B2 | 1/2013 | McKay |
| 8,420,600 B2 | 4/2013 | Burch et al. |
| 8,430,852 B2 | 4/2013 | Bischoff et al. |
| 8,470,360 B2 | 6/2013 | McKay |
| 8,523,569 B2 | 9/2013 | Neshat |
| 8,524,267 B2 | 9/2013 | Zanella et al. |
| 8,575,092 B2 | 11/2013 | Domb |
| 8,591,531 B2 | 11/2013 | Buevich et al. |
| 8,603,528 B2 | 12/2013 | Kronenthal |
| 8,623,396 B2 | 1/2014 | Gray et al. |
| 8,629,172 B2 | 1/2014 | McKay et al. |
| 8,632,839 B2 | 1/2014 | Stopek et al. |
| 8,652,504 B2 | 2/2014 | Li et al. |
| 8,652,525 B2 | 2/2014 | Moses et al. |
| 8,663,192 B2 | 3/2014 | Hester et al. |
| 8,697,117 B2 | 4/2014 | Zilberman |
| 8,703,119 B2 | 4/2014 | Yankelson et al. |
| 8,708,966 B2 | 4/2014 | Allen et al. |
| 8,715,223 B2 | 5/2014 | McKay |
| 8,728,493 B2 | 5/2014 | Burton et al. |
| 8,728,509 B2 | 5/2014 | McKay |
| 8,750,983 B2 | 6/2014 | Bonutti |
| 8,758,798 B2 | 6/2014 | Stopek et al. |
| 8,795,713 B2 | 8/2014 | Makower et al. |
| 8,809,530 B1 | 8/2014 | Wu et al. |
| 8,822,492 B2 | 9/2014 | Schachter |
| 8,846,068 B2 | 9/2014 | Wohabrebbi et al. |
| 8,865,205 B2 | 10/2014 | Shalaby |
| 8,877,226 B2 | 11/2014 | Zanella et al. |
| 8,889,173 B2 | 11/2014 | Zanella et al. |
| 8,900,620 B2 | 12/2014 | Fulmer et al. |
| 8,911,765 B2 | 12/2014 | Moses et al. |
| 8,920,867 B2 | 12/2014 | Stopek et al. |
| 8,951,552 B2 | 2/2015 | Shalaby et al. |
| 8,956,642 B2 | 2/2015 | Hobot et al. |
| 8,968,767 B2 | 3/2015 | McKay |
| 8,969,397 B2 | 3/2015 | Burright et al. |
| 8,980,317 B2 | 3/2015 | King |
| 8,999,368 B2 | 4/2015 | McDonald et al. |
| 9,005,634 B2 | 4/2015 | McDonald et al. |
| 9,011,965 B2 | 4/2015 | Gan et al. |
| 9,023,114 B2 | 5/2015 | Buevich et al. |
| 9,125,814 B2 | 9/2015 | He et al. |
| 9,125,917 B2 | 9/2015 | McKay et al. |
| 9,132,087 B2 | 9/2015 | Lichter et al. |
| 9,132,194 B2 | 9/2015 | McKay |
| 9,155,707 B2 | 10/2015 | Ying et al. |
| 9,161,903 B2 | 10/2015 | Drapeau et al. |
| 9,173,732 B2 | 11/2015 | Langer et al. |
| 9,198,758 B2 | 12/2015 | McKay |
| 9,205,052 B2 | 12/2015 | Kim et al. |
| 9,211,285 B2 | 12/2015 | McKay et al. |
| 9,265,733 B2 | 2/2016 | McKay |
| 9,283,283 B2 | 3/2016 | Giammona et al. |
| 9,289,409 B2 | 3/2016 | Zanella et al. |
| 9,295,462 B2 | 3/2016 | Choy et al. |
| 9,302,903 B2 | 4/2016 | Park et al. |
| 9,320,708 B2 | 4/2016 | Scifert et al. |
| 9,351,924 B2 | 5/2016 | Cho et al. |
| 9,352,137 B2 | 5/2016 | Simonton et al. |
| 9,358,223 B2 | 6/2016 | King |
| 9,375,420 B2 | 6/2016 | King |
| 9,402,918 B2 | 8/2016 | Koyakutty et al. |
| 9,402,973 B2 | 8/2016 | Phillips et al. |
| 9,457,176 B2 | 10/2016 | Lee et al. |
| 9,504,749 B2 | 11/2016 | McKay |
| 9,522,113 B2 | 12/2016 | Spada et al. |
| 9,549,920 B2 | 1/2017 | Wohabrebbi et al. |
| 9,566,241 B2 | 2/2017 | Ravis et al. |
| 9,597,132 B2 | 3/2017 | Houff |
| 9,610,194 B2 | 4/2017 | De Juan et al. |
| 9,610,243 B2 | 4/2017 | Clay et al. |
| 9,623,222 B2 | 4/2017 | McKay |
| 9,629,818 B2 | 4/2017 | Nadkarni et al. |
| 9,655,994 B2 | 5/2017 | McKay |
| 9,668,974 B2 | 6/2017 | Amselem et al. |
| 9,669,117 B2 | 6/2017 | Campbell et al. |
| 9,694,079 B2 | 7/2017 | Ottoboni et al. |
| 9,700,567 B2 | 7/2017 | Zanella et al. |
| 9,724,300 B2 | 8/2017 | Yamashita et al. |
| 9,764,066 B2 | 9/2017 | Sim et al. |
| 9,821,091 B2 | 11/2017 | Hossainy et al. |
| 9,833,548 B2 | 12/2017 | McKay et al. |
| 9,861,590 B2 | 1/2018 | Stopek et al. |
| 9,987,233 B2 | 6/2018 | Helliwell et al. |
| 11,202,754 B2 | 12/2021 | Naga et al. |
| 11,224,570 B2 | 1/2022 | Naga et al. |
| 11,964,076 B2 | 4/2024 | Wang et al. |
| 11,969,500 B2 | 4/2024 | Naga et al. |
| 2001/0044651 A1 | 11/2001 | Steinke et al. |
| 2001/0055607 A1 | 12/2001 | Levin |
| 2002/0106410 A1 | 8/2002 | Masters |
| 2003/0022876 A1 | 1/2003 | Ashton et al. |
| 2003/0036803 A1 | 2/2003 | McGhan |
| 2003/0118649 A1 | 6/2003 | Gao et al. |
| 2003/0152637 A1 | 8/2003 | Chasin et al. |
| 2003/0157162 A1 | 8/2003 | Krugner-Higby et al. |
| 2003/0190341 A1 | 10/2003 | Shalaby et al. |
| 2003/0215496 A1 | 11/2003 | Patel et al. |
| 2004/0109893 A1 | 6/2004 | Chen et al. |
| 2004/0249441 A1 | 12/2004 | Miller et al. |
| 2005/0019404 A1 | 1/2005 | Sung et al. |
| 2005/0043786 A1 | 2/2005 | Chu et al. |
| 2005/0048115 A1 | 3/2005 | Mangena et al. |
| 2005/0152957 A1 | 7/2005 | Cleary et al. |
| 2005/0158382 A1 | 7/2005 | Cruz et al. |
| 2005/0206048 A1 | 9/2005 | Ryu et al. |
| 2005/0266077 A1 | 12/2005 | Royer |
| 2006/0034887 A1 | 2/2006 | Pelissier |
| 2006/0052823 A1* | 3/2006 | Mirizzi ............ A61B 17/12195 606/214 |
| 2006/0079558 A1 | 4/2006 | Aberg et al. |
| 2006/0079559 A1 | 4/2006 | Aberg et al. |
| 2006/0269475 A1 | 11/2006 | Ryu et al. |
| 2007/0071790 A1 | 3/2007 | Ameer et al. |
| 2007/0134292 A1 | 6/2007 | Suokas et al. |
| 2007/0173787 A1 | 7/2007 | Huang et al. |
| 2007/0178138 A1 | 8/2007 | Pal et al. |
| 2007/0258939 A1 | 11/2007 | Lewis et al. |
| 2008/0089923 A1 | 4/2008 | Burkstrand et al. |
| 2008/0095849 A1 | 4/2008 | Wu et al. |
| 2008/0132922 A1 | 6/2008 | Buevich et al. |
| 2008/0154241 A1 | 6/2008 | Burkstrand et al. |
| 2008/0228193 A1 | 9/2008 | Matityahu |
| 2008/0241212 A1 | 10/2008 | Moses et al. |
| 2008/0311191 A1 | 12/2008 | Nangia et al. |
| 2009/0076595 A1 | 3/2009 | Lindquist et al. |
| 2009/0087380 A1 | 4/2009 | Fasching et al. |
| 2009/0123508 A1 | 5/2009 | Cheng et al. |
| 2009/0142400 A1 | 6/2009 | Hiles et al. |
| 2009/0155326 A1 | 6/2009 | Mack et al. |
| 2009/0177229 A1 | 7/2009 | Gulotta et al. |
| 2009/0182425 A1 | 7/2009 | Duda et al. |
| 2009/0198197 A1 | 8/2009 | Bischoff et al. |
| 2009/0263321 A1 | 10/2009 | McDonald et al. |
| 2009/0263441 A1 | 10/2009 | McKay |
| 2009/0263443 A1 | 10/2009 | King |
| 2009/0263451 A1 | 10/2009 | King |
| 2009/0264472 A1 | 10/2009 | Wohabrebbi et al. |
| 2009/0264477 A1 | 10/2009 | Zanella et al. |
| 2009/0264489 A1 | 10/2009 | Hildebrand et al. |
| 2009/0325879 A1 | 12/2009 | Norton et al. |
| 2010/0023126 A1 | 1/2010 | Grotz |
| 2010/0055437 A1 | 3/2010 | Fink et al. |
| 2010/0158970 A1 | 6/2010 | Tipton et al. |
| 2010/0168808 A1 | 7/2010 | Citron |
| 2010/0198278 A1 | 8/2010 | Cobian et al. |
| 2010/0203100 A1 | 8/2010 | Cobian et al. |
| 2010/0203102 A1 | 8/2010 | Wohabrebbi |
| 2010/0222873 A1* | 9/2010 | Atanasoska ............ A61L 31/16 606/301 |

(56) References Cited

U.S. PATENT DOCUMENTS

| | | |
|---|---|---|
| 2010/0249783 A1 | 9/2010 | Trieu |
| 2011/0027331 A1 | 2/2011 | Hobot |
| 2011/0060309 A1 | 3/2011 | Lee et al. |
| 2011/0081422 A1 | 4/2011 | Masinde et al. |
| 2011/0082545 A1 | 4/2011 | Freund |
| 2011/0129801 A1 | 6/2011 | Barman |
| 2011/0137243 A1 | 6/2011 | Hossainy et al. |
| 2011/0152839 A1 | 6/2011 | Cima et al. |
| 2011/0184037 A1 | 7/2011 | Haddock et al. |
| 2011/0206752 A1 | 8/2011 | Carreno et al. |
| 2011/0224245 A1 | 9/2011 | Schachter |
| 2011/0281882 A1 | 11/2011 | Zhang et al. |
| 2012/0009240 A1 | 1/2012 | Stopek et al. |
| 2012/0097194 A1 | 4/2012 | McDaniel et al. |
| 2012/0100192 A1 | 4/2012 | Penhasi et al. |
| 2012/0114740 A1 | 5/2012 | Garcia et al. |
| 2012/0165795 A1 | 6/2012 | Seiler et al. |
| 2012/0239001 A1 | 9/2012 | Barry et al. |
| 2012/0263761 A1 | 10/2012 | McDonald et al. |
| 2012/0316199 A1 | 12/2012 | Ward et al. |
| 2013/0018321 A1 | 1/2013 | McKay |
| 2013/0071463 A1 | 3/2013 | Palasis et al. |
| 2013/0136811 A1 | 5/2013 | Schachter |
| 2013/0158652 A1 | 6/2013 | Palasis et al. |
| 2013/0164347 A1 | 6/2013 | Gensini et al. |
| 2013/0261594 A1 | 10/2013 | Stopek et al. |
| 2013/0280272 A1 | 10/2013 | Trogden et al. |
| 2014/0052183 A1 | 2/2014 | Freese |
| 2014/0065202 A1 | 3/2014 | Ito |
| 2014/0072608 A1 | 3/2014 | Logothetidis et al. |
| 2014/0086971 A1 | 3/2014 | Hall et al. |
| 2014/0088347 A1 | 3/2014 | Frigstad et al. |
| 2014/0105956 A1 | 4/2014 | Banerjee et al. |
| 2014/0107159 A1 | 4/2014 | Ebersole et al. |
| 2014/0170204 A1 | 6/2014 | Desai et al. |
| 2014/0193466 A1 | 7/2014 | Lawrence et al. |
| 2014/0193504 A1 | 7/2014 | Wooley et al. |
| 2014/0214175 A1 | 7/2014 | Barron et al. |
| 2014/0255464 A1 | 9/2014 | Hakimimehr et al. |
| 2014/0271770 A1 | 9/2014 | Clay et al. |
| 2014/0287053 A1 | 9/2014 | Helliwell et al. |
| 2015/0018969 A1 | 1/2015 | Fulmer et al. |
| 2015/0024031 A1 | 1/2015 | Rabinow et al. |
| 2015/0024116 A1 | 1/2015 | Matson et al. |
| 2015/0038415 A1 | 2/2015 | Zupancich |
| 2015/0039097 A1 | 2/2015 | Biris |
| 2015/0150988 A1 | 6/2015 | Shalaby et al. |
| 2015/0246001 A1 | 9/2015 | Zupancich et al. |
| 2015/0272877 A1 | 10/2015 | Shi et al. |
| 2015/0290170 A1 | 10/2015 | Liu et al. |
| 2015/0342964 A1 | 12/2015 | Gray et al. |
| 2016/0038632 A1 | 2/2016 | Shah et al. |
| 2016/0089335 A1 | 3/2016 | Ohri et al. |
| 2016/0136094 A1 | 5/2016 | Criscione et al. |
| 2016/0144040 A1 | 5/2016 | Cheng |
| 2016/0144067 A1 | 5/2016 | Armbruster et al. |
| 2016/0151257 A1* | 6/2016 | Klingman ............ A61K 8/0208 424/401 |
| 2016/0184340 A1 | 6/2016 | Kritikou |
| 2016/0287367 A1 | 10/2016 | Rontal |
| 2016/0331853 A1 | 11/2016 | Taub |
| 2016/0339152 A1 | 11/2016 | Bonutti et al. |
| 2016/0354309 A1 | 12/2016 | Heitzmann et al. |
| 2017/0014337 A1 | 1/2017 | Walsh |
| 2017/0079929 A1 | 3/2017 | Davey |
| 2017/0112935 A1 | 4/2017 | Holzer et al. |
| 2017/0128632 A1 | 5/2017 | McJames |
| 2017/0182168 A1 | 6/2017 | Ottoboni et al. |
| 2017/0196499 A1 | 7/2017 | Hunter |
| 2017/0196508 A1 | 7/2017 | Hunter |
| 2017/0216597 A1 | 8/2017 | Hou et al. |
| 2017/0239183 A1 | 8/2017 | Reynolds et al. |
| 2017/0246117 A1 | 8/2017 | Helliwell et al. |
| 2017/0281778 A1 | 10/2017 | Ottoboni et al. |
| 2018/0092855 A1 | 4/2018 | Kim et al. |
| 2019/0351108 A1 | 11/2019 | Wang et al. |
| 2020/0009293 A1 | 1/2020 | Teu et al. |
| 2020/0246255 A1 | 8/2020 | Naga et al. |
| 2020/0368398 A1 | 11/2020 | Naga et al. |
| 2021/0186868 A1 | 6/2021 | Naga et al. |
| 2021/0361827 A1 | 11/2021 | Teu et al. |
| 2022/0072207 A1 | 3/2022 | Wang et al. |
| 2022/0117885 A1 | 4/2022 | Naga et al. |
| 2022/0183963 A1 | 6/2022 | Kim et al. |
| 2022/0183964 A1 | 6/2022 | Naga et al. |
| 2023/0136789 A1 | 5/2023 | Ruane et al. |
| 2024/0016774 A1 | 1/2024 | Kim et al. |

FOREIGN PATENT DOCUMENTS

| | | |
|---|---|---|
| CN | 1344156 A | 4/2002 |
| CN | 1655738 A | 8/2005 |
| CN | 1762331 A | 4/2006 |
| CN | 102000366 A | 4/2011 |
| CN | 102341133 A | 2/2012 |
| CN | 103405748 A | 11/2013 |
| CN | 103703079 A | 4/2014 |
| CN | 104474595 A | 4/2015 |
| CN | 104474595 B | 1/2017 |
| CN | 106344521 A | 1/2017 |
| EP | 0311065 B1 | 2/1994 |
| EP | 1868662 B1 | 5/2010 |
| EP | 2197419 A2 | 6/2010 |
| EP | 2209469 A2 | 7/2010 |
| EP | 2229171 A2 | 9/2010 |
| EP | 2262481 A2 | 12/2010 |
| EP | 2285363 A2 | 2/2011 |
| EP | 2288352 A2 | 3/2011 |
| EP | 2288353 A2 | 3/2011 |
| EP | 2368522 A1 | 9/2011 |
| EP | 2444074 A2 | 4/2012 |
| EP | 2444075 A2 | 4/2012 |
| EP | 2696851 A1 | 2/2014 |
| EP | 2719717 A1 | 4/2014 |
| EP | 3000463 A1 | 3/2016 |
| EP | 3085359 A1 | 10/2016 |
| EP | 2195073 B1 | 3/2017 |
| EP | 2911647 B1 | 3/2018 |
| EP | 2444075 B1 | 9/2018 |
| EP | 3518999 A1 | 8/2019 |
| EP | 3691618 A1 | 8/2020 |
| EP | 3737433 A1 | 11/2020 |
| EP | 3793536 A1 | 3/2021 |
| EP | 3843710 A1 | 7/2021 |
| GB | 201505527 | 5/2015 |
| JP | H02119866 A | 5/1990 |
| JP | 2006512312 A | 4/2006 |
| JP | 2009511196 A | 3/2009 |
| JP | 2012017329 A | 1/2012 |
| JP | 2015522649 A | 8/2015 |
| JP | 2016528949 A | 9/2016 |
| JP | 2018511410 A | 4/2018 |
| WO | 9509613 A1 | 4/1995 |
| WO | 9858653 A1 | 12/1998 |
| WO | 9936071 A1 | 7/1999 |
| WO | 2004089291 A2 | 10/2004 |
| WO | 2006099409 A3 | 3/2007 |
| WO | 2007047420 A2 | 4/2007 |
| WO | 2008061355 A1 | 5/2008 |
| WO | 2008127411 A1 | 10/2008 |
| WO | 2008131089 A2 | 10/2008 |
| WO | 2008136856 A2 | 11/2008 |
| WO | 2009069151 A2 | 6/2009 |
| WO | 2009113972 A2 | 9/2009 |
| WO | 2009129432 A2 | 10/2009 |
| WO | 2009129433 A2 | 10/2009 |
| WO | 2009129439 A2 | 10/2009 |
| WO | 2009129453 A2 | 10/2009 |
| WO | 2009129456 A2 | 10/2009 |
| WO | 2009129460 A2 | 10/2009 |
| WO | 2009129464 A2 | 10/2009 |
| WO | 2009129491 A2 | 10/2009 |
| WO | 2009129494 A2 | 10/2009 |
| WO | 2009129509 A2 | 10/2009 |

(56) References Cited

FOREIGN PATENT DOCUMENTS

| | | | |
|---|---|---|---|
| WO | 2009129519 | A2 | 10/2009 |
| WO | 2009129527 | A2 | 10/2009 |
| WO | 2009129531 | A2 | 10/2009 |
| WO | 2010016832 | A1 | 2/2010 |
| WO | 2010075298 | A2 | 7/2010 |
| WO | 2010088697 | A2 | 8/2010 |
| WO | 2011098578 | A2 | 8/2011 |
| WO | 2011139594 | A2 | 11/2011 |
| WO | 2012064963 | A1 | 5/2012 |
| WO | 2012142318 | A1 | 10/2012 |
| WO | 2013013123 | A1 | 1/2013 |
| WO | 2013040325 | A1 | 3/2013 |
| WO | 2014016428 | A1 | 1/2014 |
| WO | 2014059558 | A1 | 4/2014 |
| WO | 2014064140 | A1 | 5/2014 |
| WO | 2014066653 | A1 | 5/2014 |
| WO | 2014137454 | A1 | 9/2014 |
| WO | 2014172572 | A1 | 10/2014 |
| WO | 2014204708 | A1 | 12/2014 |
| WO | 2015015278 | A1 | 2/2015 |
| WO | 2015135907 | A1 | 9/2015 |
| WO | 2016123352 | A1 | 8/2016 |
| WO | 2016159885 | A1 | 10/2016 |
| WO | 2017019829 | A1 | 2/2017 |
| WO | 2017034363 | A1 | 3/2017 |
| WO | 2017075232 | A1 | 5/2017 |
| WO | 2017146819 | A1 | 8/2017 |
| WO | 2018009637 | A1 | 1/2018 |
| WO | 2018063096 | A1 | 4/2018 |
| WO | 2018067882 | A1 | 4/2018 |
| WO | 2018172494 | A1 | 9/2018 |
| WO | 2018227293 | A1 | 12/2018 |
| WO | 2019071243 | A1 | 4/2019 |
| WO | 2019136490 | | 7/2019 |
| WO | 2019221853 | A1 | 11/2019 |
| WO | 2019221853 | A8 | 11/2019 |
| WO | 2019071243 | A8 | 3/2020 |
| WO | 2020046973 | A1 | 3/2020 |
| WO | 2020047013 | A1 | 3/2020 |
| WO | 2020210764 | A1 | 10/2020 |
| WO | 2020210770 | A2 | 10/2020 |
| WO | 2021178930 | A1 | 9/2021 |
| WO | 2022082196 | A1 | 4/2022 |
| WO | 2023056422 | A1 | 4/2023 |

OTHER PUBLICATIONS

De Clercq et al., "Preclinical evaluation of local prolonged release of paclitaxel from gelatin microspheres for the prevention of recurrence of peritoneal carcinomatosis in advanced ovarian cancer", Science Reports, vol. 9, No. 14881, Oct. 16, 2019, 19 pages.
Ball et al., Electrospun Solid Dispersions of Maraviroc for Rapid Intravaginal Preexposure Prophylaxis of HIV, Antimicrobial Agents and Chemotherapy, Aug. 2014, vol. 58, No. 8, p. 4855-4865.
Bassi et al., Polymeric films as a promising carrier for bioadhesive drug delivery: Development, characterization and optimization, Saudi Pharmaceutical Journal, (2017) 25, 32-43.
Curley et al., Prolonged Regional Nerve Blockade Injectable Biodegradable Bupivacaine/Polyester Microspheres, Anesthesiology, 1996, 84, 1401-10.
Drager, Christiane et al., Prolonged Intercostal Nerve Blockade in Sheep Using Controlled-release of Bupivacaine and Dexamethasome from Polymer Microspheres, Anesthesiology, vol. 89, No. 4, Oct. 1998, pp. 969-979.
Epstein-Barash et al., Prolonged duration local anesthesia with minimal toxicity, PNAS, Apr. 28, 2009, vol. 106, No. 17, 7125-7130.
European Search Report dated Apr. 30, 2020; European Patent Application No. 17856916.6; 10 pages.
Farid et al., Promote Recurrent Aphthous Ulcer Healing with Low Dose Predisolone Bilayer Mucoadhesive Buccal Film, Current Drug Delivery, vol. 14, No. 1, Jan. 9, 2017, pp. 123-125.
Fites et al., Controlled Drug Release through Polymeric Films, Journal of Pharmaceutical Sciences, vol. 59, No. 5, May 1970, 610-613.
Friess, Wolfgang, Review Article: Collagen—biomaterial for drug delivery, European Journal of Pharmaceutics and Biopharmaceutics, 45 (1998) 113-136.
International Search Report and Written Opinion mailed Feb. 19, 2019; International Application No. PCT/US2018/054777; 15 pages.
International Search Report and Written Opinion mailed Feb. 21, 2019; International Application No. PCT/US2018/054779; 17 pages.
International Search Report and Written Opinion mailed Jul. 24, 2019; International Application No. PCT/US2019/027104; 14 pages.
International Search Report and Written Opinion mailed Jul. 3, 2020; International Application No. PCT/US2020/027852; 14 pages.
International Search Report and Written Opinion mailed Jun. 17, 2020; International Application No. PCT/US2020/027861; 11 pages.
International Search Report and Written Opinion mailed May 10, 2019; International Application No. PCT/US2018/054780; 13 pages.
International Search Report and Written Opinion mailed May 23, 2019; International Application No. PCT/US2019/012795; 15 pages.
International Search Report and Written Opinion mailed Nov. 14, 2019; International Application No. PCT/US2019/048437; 15 pages.
International Search Report and Written Opinion mailed Nov. 20, 2019; International Application No. PCT/US2019/048386; 13 pages.
Irfan et al., Orally disintegrating films: A modern expansion in drug delivery system, Saudi Pharmaceutical Journal, (2016) 24, 537-546.
Ito et al., Three-Layered Microcapsules as a Long-Term Sustained Release Injection Preparation, International Journal of Pharmaceuticals, vol. 384, No. 1-2, Jan. 1, 2010, pp. 53-59.
Jain, Anjali et al., Injectable formulations of ply(lactic acid) and its copolymers in clinical use, Advaned Drug Delivery Reviews, vol. 107, Jul. 14, 2016, pp. 213-227.
Kanagale et al., Formulation and Optimization of Porous Osmotic Pump-based Controlled Release System and Oxybutynin, AAPA PharmSciTech 2007, 8 (3), Article 53, 7 pages.
Karki et al., Thin films as an emerging platform for drug delivery, Asian Journal of Pharmaceutical Sciences, II, (2016), 559-574.
Kau et al., Sustained Release of Lidocaine from Solvent-Free Biodegradable Poly [(d,I)-Lactide-co-Glycolide] (PLGA): In Vitro and In Vivo Study, Materials, 2014, 17 pages.
Knecht et al.; Mechanical testing of fixation techniques for scaffold-based tissue-engineered grafts; Journal of Biomedical Materials Research Part B: Applied Biomaterials; vol. 83, No. 1; Feb. 22, 2007; pp. 50-57.
Lee et al., "Results of a model analysis of the cost-effectiveness of liraglutide versus exenatide added to metformin, glimepiride, or both for the treatment of type 2 diabetes in the United States", Clinical Therapeutics, vol. 32, No. 10, 2010, 12 pages.
Liu et al.; Less harmful acidic degradation of poly(lactic-co-glycolic acid) bone tissue engineering scaffolds through titania nanoparticle addition; International Journal of Nanomedicine; vol. 1, No. 4; Jan. 1, 2006; pp. 541-545.
Liu et al: "Paclitaxel or 5-fluorouracil/esophageal stent combinations as a novel approach for the treatment of esophageal cancer", Biomaterials, vol. 53, Jun. 1, 2015 (Jun. 1, 2015), pp. 592-599.
McAlvin et al., Local Toxicity from Local Anesthetic Polymeric Microparticles, Anesth Analg., Apr. 2013, 116(4): 794-803.
Ohri et al., Inhibition by Local Bupivacaine-Releasing Microspheres of Acute Postoperative Pain from Hairy Skin Incision, www.anesthesia-analgesia.org, Sep. 2013, vol. 117, No. 3, 14 pages.
Padera et al., Local myotoxicity from sustained release of bupivacaine from microparticles, Anesthesiology, May 2008, 108(5): 921-928.
PCT International Search Report for PCT/SG/2016/050158 mailed Jun. 15, 2016.
Roy et al., Effects of plasticizers and surfactants on the film forming properties of hydroxypropyl methylcellulose for the coating of diclofenac sodium tablets, Saudi Pharmaceutical Journal (2009) 17, 233-241.
Santamaria et al., Drug delivery systems for prolonged duration local anesthesia, Materials Today, vol. 20, No. 1, Jan./Feb. 2017, 22 pages.

(56) References Cited

OTHER PUBLICATIONS

Seo et al., Polyurethane membrane with porous surface for controlled drug release in drug eluting stent, Biomaterials Research, 2014, 18:15, 5 pages.
Shaikh et al., "Engineering Stent Based Delivery System for Esophageal Cancer Using Docetaxel", Molecular Pharmaceutics, vol. 12, No. 7, Jul. 6, 2015 (Jul. 6, 2015), pp. 2305-2317.
Shipton, Edward A., New Formulations of Local Anaesthetics—Part I, Anesthesiology Research and Practice, 2012, 12 pages.
Shona Pek, Sustained Release of Bupivacaine for Post-Surgical Pain Relief Using Core-Shell Microspheres, Journal of Materials Chemistry B, 2014, 9 pages.
Sokolsky-Papkov et al., Long-Acting Poly (DL: Lactic Acid-Castor Oil) 3:7-Bupivacaine Formulation: Effect of Hydrophobic Additives, Pharmaceutical Research, Jun. 2011, 10 pages.
Tanabe et al., Controlled Indomethacin Release from Mucoadhesive Film: In Vitro and Clinical Evaluations, Yakugaku Zasshi Journal of the Pharmaceutical Society of Japan, vol. 128, No. 11, Nov. 1, 2008, pp. 1673-1679.
Weiniger, et al., Extended release formulations for local anaesthetic agents, Anaesthesia 2012, 67, 906-916.
Yamamura et al., Pain Relief of Oral Ulcer by Dibucaine-film, Elsevier Science Publishers, Amsterdam, NL, vol. 83, 1999, pp. 625-626.
Yan et al., Towards nanoporous polymer thin film-based drug delivery systems, Thin Solid Films, 517 (2009), 1794-1798.
Zorzetto et al., From micro-to nanostructured implantable device for local anesthetic delivery, International Journal of Nanomedicine, Jun. 8, 2016, 2695-2709.
International Search Report and Written Opinion dated Oct. 30, 2017; International Application No. PCT/SG2017/050481; 10 pages.
Hong, Y., et al., "Generating Elastic, Biodegradable Polyurethane/ Poly(lactide-co-glycolide) Fibrous Sheets with Controlled Antibiotic Release via Two-Stream Electrospinning", Biomacromolecules, 2008, 1200-1207.
Jethara et al., Sustained Release Drug Delivery Systems: a Patent Overview, Aperito Journal of Drug Designing and Pharmacology, 2014: 1:1, 15 pages.
Jin, et al., "A PTX/nitinol stent combination with temperature-responsive phase-change 1-hexadecanol for magnetocaloric drug delivery: Magnetocaloric drug release and esophagus tissue penetration", Biomaterials, 153 (2018) 49-58.
Kolek, Matthew J., et al., "Use of an Antibacterial Envelope is Associated with Reduced Cardiac Implantable Electronic Device Infections in High-Risk Patients", Pacing and Clinical Electrophysiology, vol. 36, Mar. 2013, 354-361.
Lei, L, et al., "5-Fluorouracil-loaded multilayered films for drug controlled releasing stent application: Drug release, microstructure, and ex vivo permeation behaviors, Journal of Controlled Release,, vol. 146, No. 1, Aug. 17, 2010, pp. 45-53."
Rong et al., PLC films incorporated with paclitaxel/5-flourouracil: Effects of formulation and spacial architecture on drug release, International Journal of Pharmaceutics 427 (2012) 242-251.
Lee, et al., "Gemcitabine-releasing polymeric films for covered self-expandable metallic stent in treatment of gastrointestinal cancer", International Journal of Pharmaceutics, vol. 427, 2012, pp. 276-283.
Liu et al., "Evaluation of two polymeric blends (EVA/PLA and EVA/PEG) as coating film materials for paclitaxel-eluting stent application", J Mater Sci: Mater Med (2011) 22: 327-337.
NIHR HSC, et al., "AIGISRx Antibacterial Envelope for Preventing Infection in Implanted Cardiac Devices", Birmingham NIHR Horizon Scanning Centre NIHR HSC Horizon Scanning Review 2012 XP055320647 Retrieved from the Internet URLhttpwwwhsr icnihracuktopicsaigisrxantibacterialenvelopeforpreventinginfection inimplantedcardiacdevices.
Tarakji et al., "Cardiac implantable electronic device infections: Presentation, management, and patient outcomes", Heart Rhythm, vol. 7, No. 8, Aug. 2010, 6 pages.
Voigt et al., "Continued rise in rates of cardiovascular implantable electronic device infections in the United States; temporal trends and causative insights", Pace, vol. 33, Apr. 2010, 6 pages.
Chun, et al., "Gastrointestinal and Biliary Stents", Journal of Gastroenterology and Hepatology Foundation and Blackwell Publishing Asia Pty Ltd, vol. 25, 2010, pp. 234-243.
Goindi, et al., "Development of Novel Ionic Liquid-Based Microemulsion Formulation for Dermal Delivery of 5-Fluorouracil", AAPS PharmSciTech 2014 15(4):810-821 (Year: 2014).
Guo, et al., "A type of esophageal stent coating composed of one 5-fluorouracil-containing EVA layer and one drug-free protective layer: In vitro release, permeation and mechanical properties", Journal of Controlled Release 2007 118:318-324 (Year: 2007).
Tallury, et al., "Effects of solubilizing surfactants and loading of antiviral, antimicrobial, and antifungal drugs on their release rates from ethylene vinyl acetate copolymer", Dental Materials 2007 23:977-982 (Year: 2007).
Yuan, et al., "Fabrication of a Delaying Biodegradable Magnesium Alloy-Based Esophageal Stent via Coating Elastic Polymer", Materials 2016 9(384):1-11 (Year: 2016).

* cited by examiner

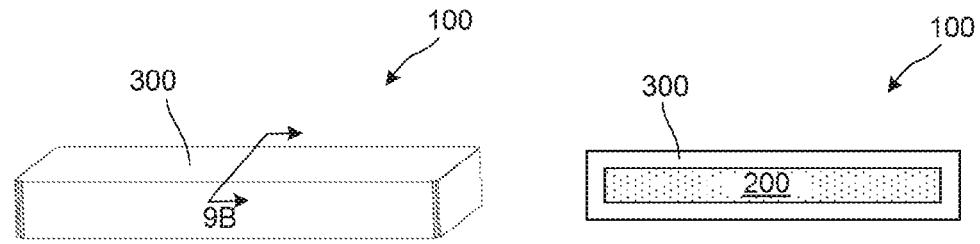
*FIG. 9A*            *FIG. 9B*
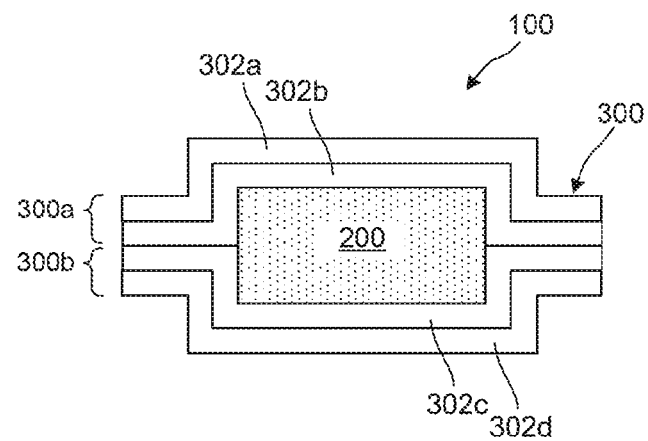
*FIG. 10*
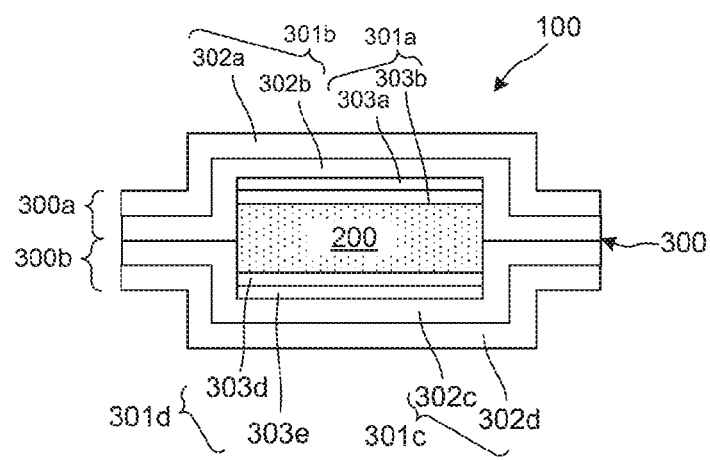
*FIG. 11*

Fig. 2 Scanning electron microscope picture of a ra-PLGA (50:50) tablet after 30 days of incubation in phosphate buffer, pH 7.4 at 37°C. (From Ref.[13].)

*taken from Avgoustakis, K., *Synthesis and Evaluation of Some Poly(Lactide-co-Glycolides) for Use in Sustained Release Tablets*, Ph.D. thesis, University of London, 1992.

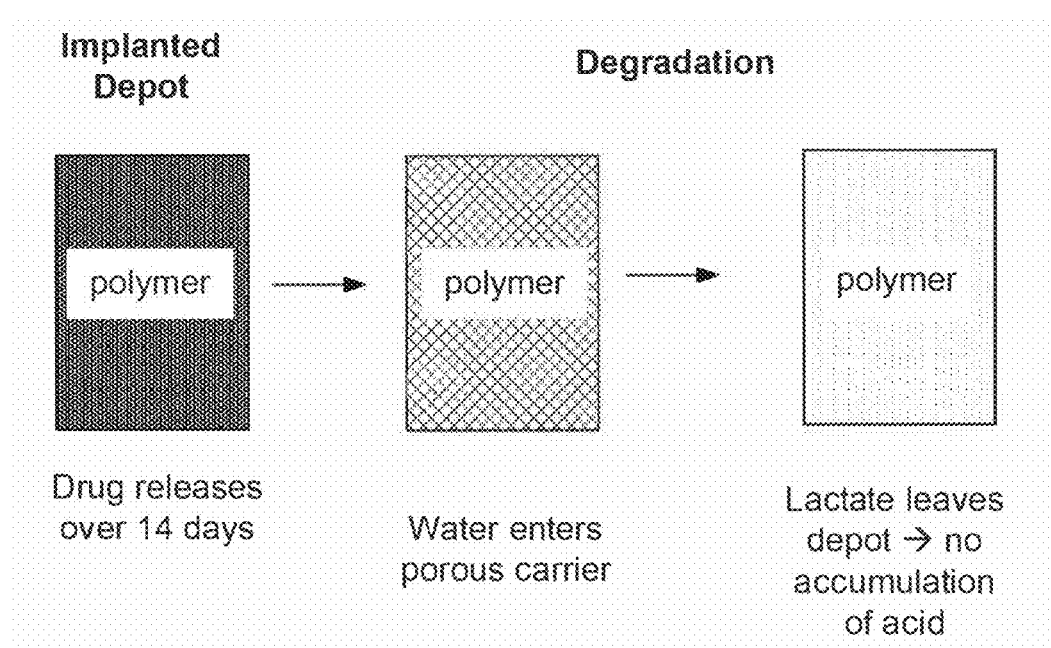
*FIG. 19A*
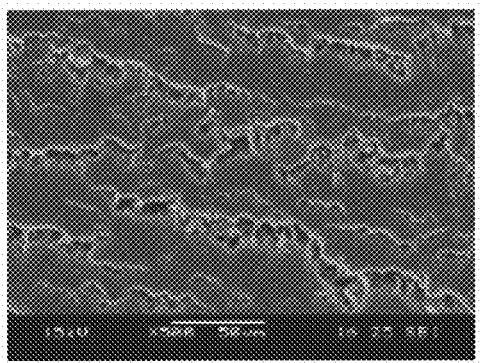
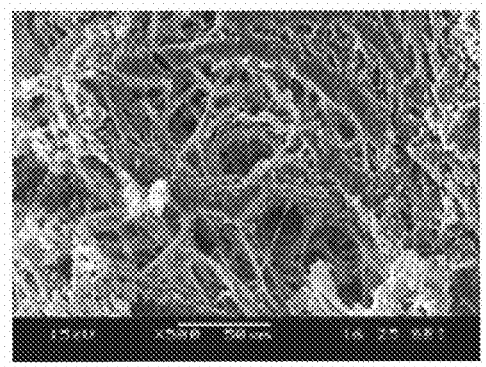
*FIG. 19B*  *FIG. 19C*

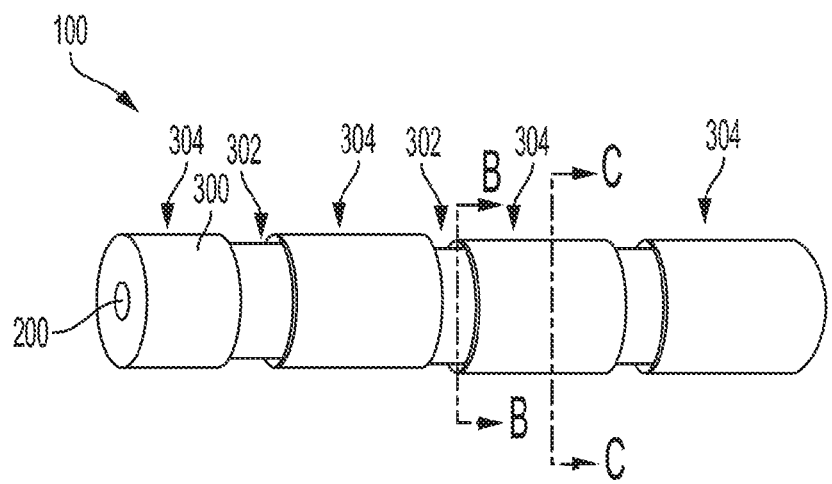
FIG. 24A
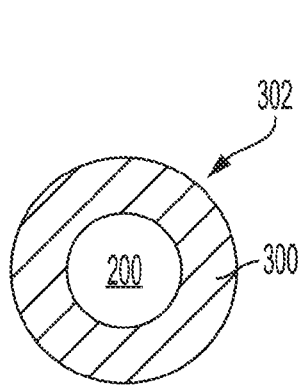 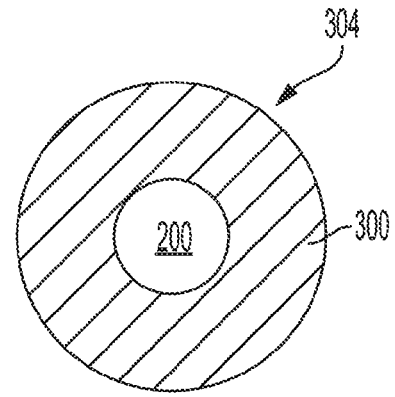
FIG. 24B  FIG. 24C

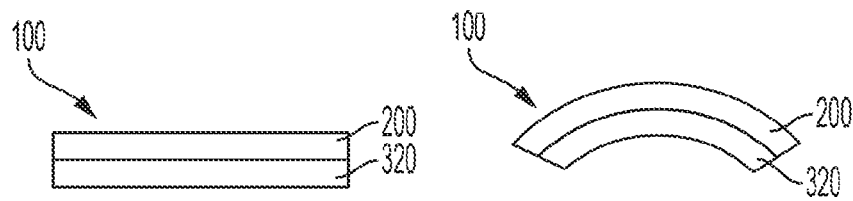
*FIG. 41A*  *FIG. 41B*
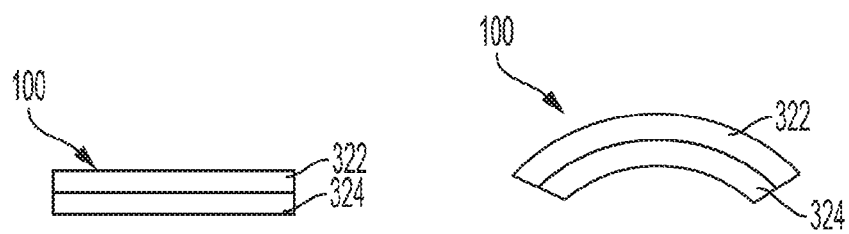
*FIG. 42A*  *FIG. 42B*
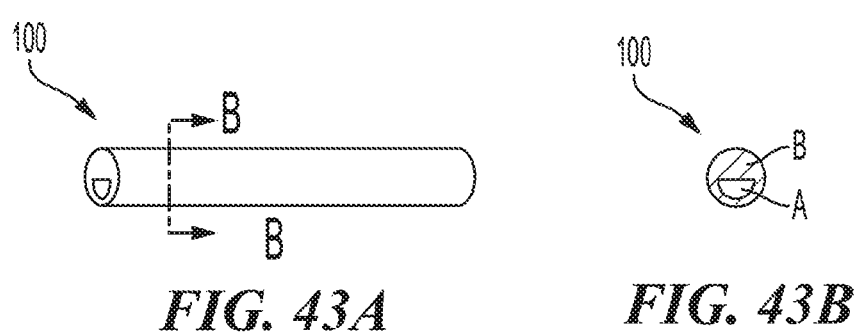
*FIG. 43A*  *FIG. 43B*
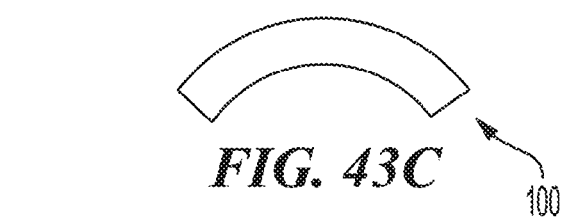
*FIG. 43C*
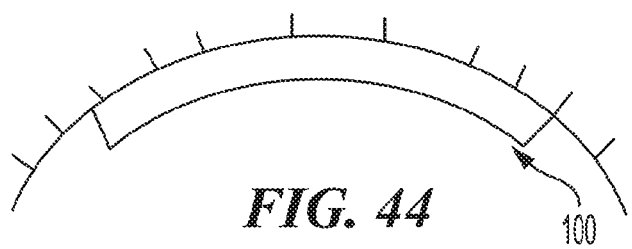
*FIG. 44*
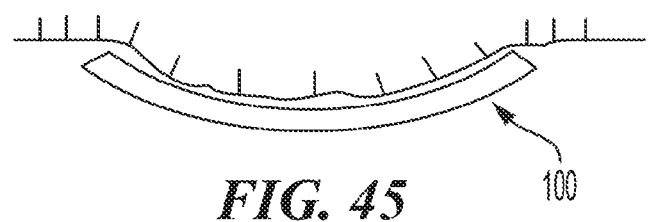
*FIG. 45*

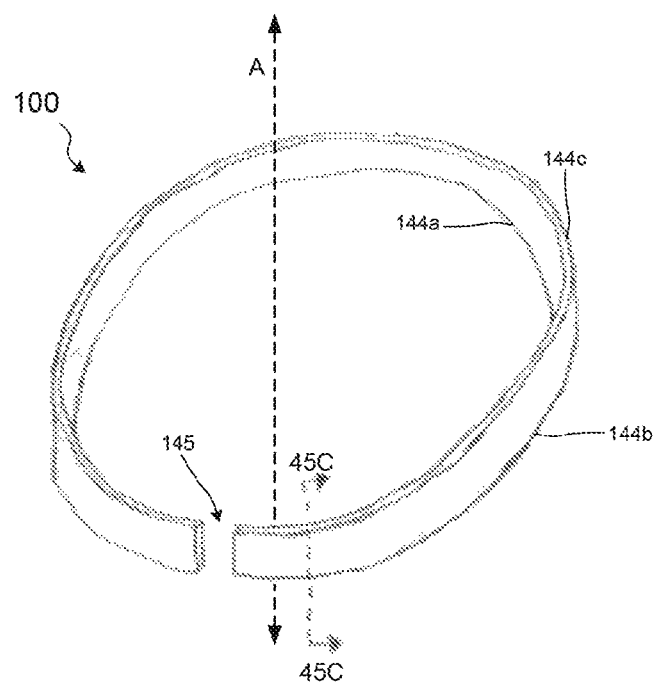
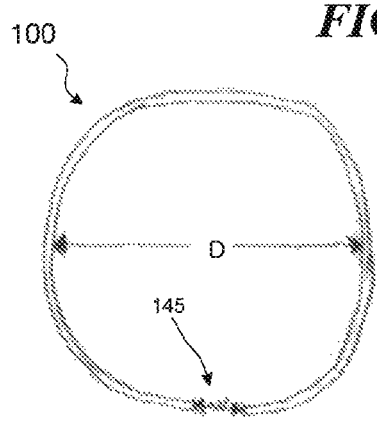 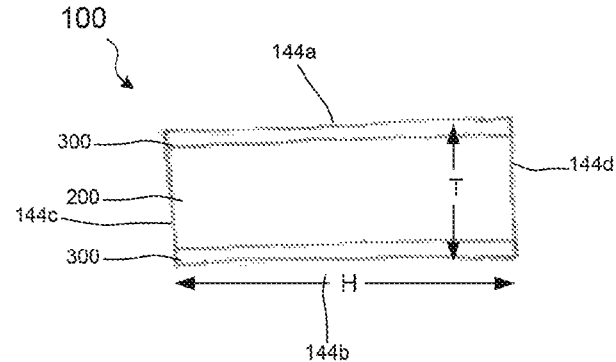
FIG. 49A
FIG. 49B          FIG. 49C

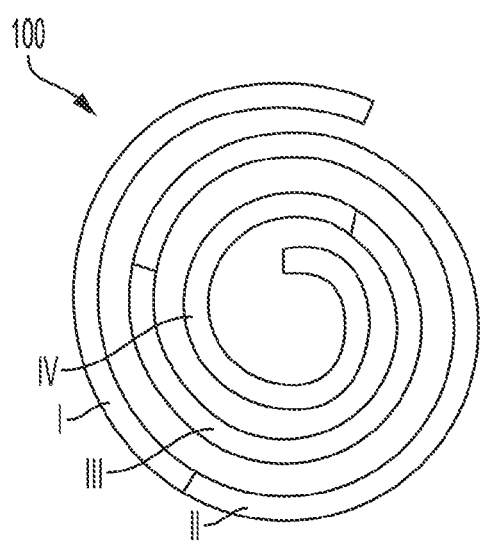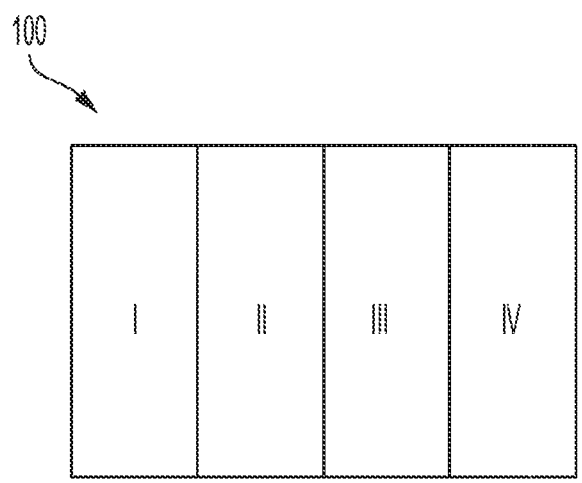
*FIG. 50A*  *FIG. 50B*

| | Surgical Procedure | Nerve target(s) | Anatomical Access/ Placement |
|---|---|---|---|
| ORTHOPEDIC | Fibula Fracture Repair | Sciatic nerve | |
| | | Parasacral nerve | |
| | | Popliteal sciatic nerve | |
| | Anterior cruciate ligament reconstruction | Femoral nerve | |
| | | Sciatic nerve | |
| | Posterior cruciate ligament reconstruction | Parasacral nerve | |
| | Total knee arthroplasty | femoral nerve | femoral triangle |
| | | saphenous nerve | adductor canal |
| | | genicular nerves (superior lateral, superior medial, inferior medial) | |
| | | Intra-capsular nerves | Periosteum |
| | | | Supratellar pouch/region |
| | | | Medial and lateral gutters |
| | | | Posterior capsule |
| | | Extra-capsular nerves | Quadraceps tendon |
| | | | Arthrotomy line |
| | | | Skin incision line |
| | Ankle fusion and Total ankle arthroplasty | Subgluteal sciatic nerve | |
| | | Parasacral nerve | |
| | | Popliteal sciatic nerve | |
| | Total hip arthroplasty | Lumbar plexus | Psoas compartment |
| | | Sacral plexus | |
| | | Femoral nerve | |
| | | Sciatic nerve | |
| | | Obturator nerve | |
| | Hip fracture | Sciatic nerve | fascia iliaca compartment |
| | | Femoral nerve | |
| | | Obturator nerve | |
| | | Superior gluteal nerve | |
| | Shoulder arthroplasty | Brachial Plexus | Cervical paravertebral |
| | Rotator cuff repair | | Interscalene |
| | Arm fractures (scapula, humerous, radius, ulna) | | Supraclavicular |
| | Elbow arthroplasty | Brachial Plexus | Cervical paravertebral |
| | Wrist arthroplasty | | Infraclavicular |
| | Upper limb trauma | | Axilliary |
| | Wrist and hand | Ulnar, median, radial and cutaneous forearm | antecubital fossa |
| | Spinal fusion | | |
| | Joint fusion | | |
| | Open reduction | | |

*FIG. 61A*

| | Surgical Procedure | Nerve target(s) | Anatomical Access/ Placement |
|---|---|---|---|
| CHEST | Open reconstruction | Intercostal | Thoracic paravertebral |
| | Thoracotomy | | |
| | Esophageus | | |
| | Cardiac | | |
| | Lung resection | | |
| | Thoracic | | |
| BREAST | | Intercostal nerve | Infraclavicular |
| | Augmentation | Pectoral (lateral and median) | Between serratus anterior muscle and latissimus dorsi muscle |
| | Reduction | | |
| | Reconstruction | | |
| Gynecology & Obstetrics | Myomectomy (uterine fibroid removal) | | |
| | Caesarean section | | |
| | Hysterectomy | | |
| | Oophorectomy (ovary removal) | | |
| | Pelvic floor reconstruction | | |
| General, Abdominal & Urology | Proctocolectomy (rectum and | | |
| | Pancreatectomy | | |
| | Appendectomy | | |
| | Hemorrhoidectomy | | |
| | Cholecystectomy (gall bladder removal) | | |
| | Kidney transplant | | |
| | Nephrectomy | | |
| | Radical prostatectomy | | |
| | Nephrectomy | | |
| | Gastrectomy | | |
| | Small bowel resection | | |
| | Splenectomy | | |
| | Incisional hernia repair | Transverse abdominus plane (TAP) | |
| | Inguinal hernai repair | | |
| | Sigmoidectomy | | |
| | Liver resection | | |
| | Enterostomy | | |
| | Rectum resection | | |
| | Kidney stone removal | | |
| | Cystectomy (urinary bladder removal) | | |
| Throat | Tonsillectomy | | |
| | Submucosal resection/reconstruction of nasal septum | | |

*FIG. 61B*

| | Surgical Procedure | Nerve target(s) | Anatomical Access/ Placement |
|---|---|---|---|
| Ear, Nose & | Rhinoplasty | | |
| | Sinus (sinusitus) | | |
| | Inner ear surgery | | |
| | Parotidectomy | | |
| | Submandibular gland surgery | | |
| Oral & Maxillofacial | Dentoalveolar | | |
| | Dental implant | | |
| | Orthognathic jaw | | |
| | Temporomandibular joint (TMJ) | | |
| | Reconstruction | | |
| Oncology | Tumor resection | | |
| Cosmetic | Liposuction | | |

*FIG. 61C*

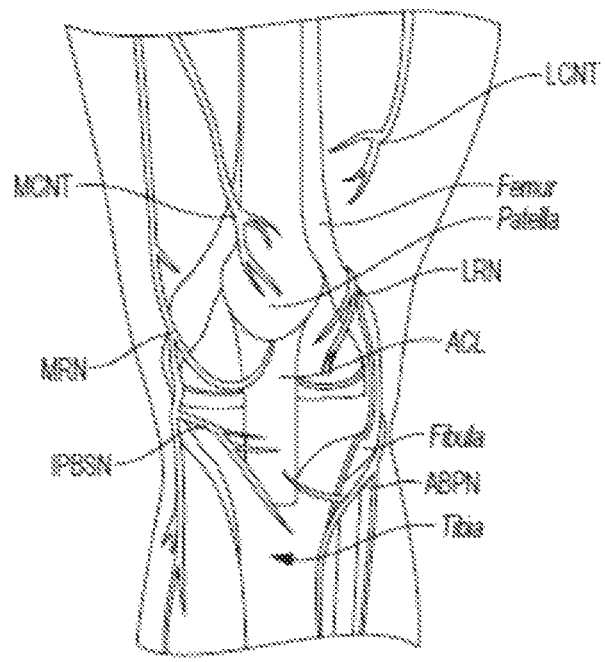
FIG. 62A
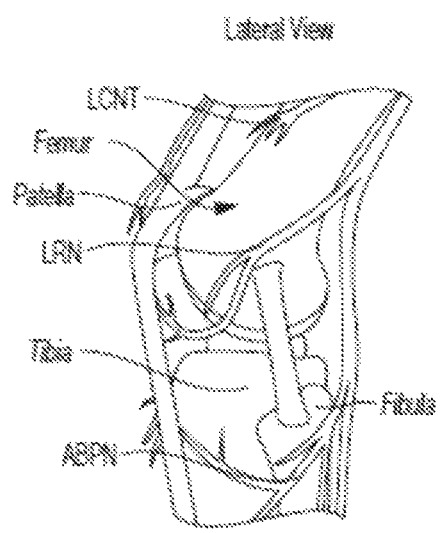 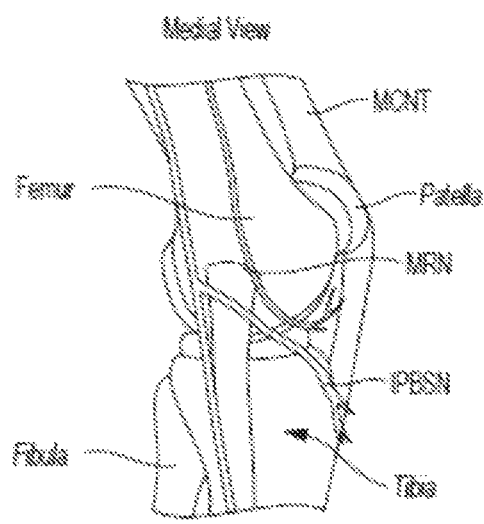
FIG. 62B  FIG. 62C

POLYMER IMPLANTS

CROSS-REFERENCE TO RELATED APPLICATIONS

The present application is a 371 U.S. national phase application of International Application No. PCT/US2019/048437, filed Aug. 27, 2019, which claims the benefit of priority to PCT Application No. PCT/US18/54777, filed Oct. 6, 2018, U.S. Patent Application No. 62/742,357, filed Oct. 6, 2018, and U.S. Patent Application No. 62/723,478, filed Aug. 28, 2018, each of which is incorporated by reference herein in its entirety.

TECHNICAL FIELD

The present technology relates to degradable polymer implants that do not undergo core acidification in vivo.

BACKGROUND OF THE INVENTION

Implantable systems for the controlled release of therapeutic agents offer advantages over other drug delivery methods, such as oral or parenteral methods. Devices comprised of biocompatible and/or biodegradable polymers and therapeutic agents can be implanted in clinically desirable anatomic locations, thereby providing localized delivery of select agents. This localized delivery enables a substantial proportion of the agent to reach the intended target and undesirable systemic side effects can be avoided. However, these systems often suffer from a lack of a true controlled release mechanism in that they typically provide a burst release of drug upon contact with surrounding physiologic fluids followed by a residual release of drug.

In order to improve drug release in certain polymer carriers, hydrophilic polymers, such as polysorbate, have been added to these carriers as wetting agents to accelerate or to enhance drug release from biocompatible polymers such polyethylene glycol (PEG) in oral formulations (Akbari, J., et al., ADV. PHARM. BULL., 2015, 5 (3): 435-441). However, these formulations are intended to provide an immediate release of a hydrophobic drug into a hydrophilic environment (the in vivo physiologic fluid), where a substantial portion of the entire drug payload is immediately or aggressively released, not a variable or sustained controlled release.

While these drug release kinetics may be desirable in some clinical applications, a controlled, sustained release of a therapeutic agent can be of clinical benefit in certain circumstances. In particular, it may be desirable to implant a biodegradable carrier holding a large dose of a therapeutic agent for a controlled, sustained release over time. This may have particular value when the carrier loaded with therapeutic agent is implanted in conjunction with an interventional or surgical procedure and, optionally, alongside or as part of an implantable medical device.

Thus, a need exists for biocompatible implantable systems capable of providing a highly controlled release of drug.

SUMMARY

The present technology relates to polymer implants. In some embodiments, the implants are depots for controlled release of a therapeutic agent to treat a medical condition and associated systems and methods. For example, some embodiments of the technology relate to depots for local, sustained release of a therapeutic agent at a surgical or interventional site and associated systems and methods. In some embodiments, the polymer implants may not include any therapeutic agent and/or be configured for drug delivery. For example, in some aspects of the technology, the polymer implant is a biodegradable orthopedic implant.

The subject technology is illustrated, for example, according to various aspects described below, including with reference to FIGS. 1-70. Various examples of aspects of the subject technology are described as numbered clauses (1, 2, 3, etc.) for convenience. These are provided as examples and do not limit the subject technology.

1. A depot for the treatment of postoperative pain via sustained, controlled release of an analgesic, comprising:
   a therapeutic region comprising the analgesic;
   a control region comprising a bioresorbable polymer and a releasing agent mixed with the polymer, wherein the releasing agent is configured to dissolve when the depot is placed in vivo to form diffusion openings in the control region; and
   wherein the depot is configured to be implanted at a treatment site in vivo and, while implanted, release the analgesic at the treatment site for no less than 7 days.

2. The depot of clause 1, wherein the analgesic in the therapeutic region comprises at least 50% of the total weight of the depot.

3. The depot of clause 1 or clause 2, wherein the depot is configured to release the analgesic at the treatment site for no less than 14 days.

4. The depot of clause 3, wherein about 20% to about 50% of the analgesic is released in the first about 3 to about 5 days of the 14 days, and wherein at least 80% of the remaining analgesic is released in the last 11 days of the 14 days.

5. The depot of clause 3, wherein about 20% to about 40% of the analgesic is released in the first 3 days of the 14 days, and wherein at least 80% of the remaining analgesic is released in the last 11 days of the 14 days.

6. The depot of any one of clauses 3 to 5, wherein at least 90% of the remaining analgesic is released in the last 11 days of the 14 days.

7. The depot of any one of clauses 3 to 6, wherein no more than 15% of the amount of analgesic is released in the first 2 days of the 14 days.

8. The depot of any one of clauses 3 to 7, wherein no more than 20% of the amount of analgesic is released in the first 2 days of the 14 days.

9. The depot of any one of clauses 3 to 8, wherein no more than 25% of the amount of analgesic is released in the first 3 days of the 14 days.

10. The depot of any one of clauses 3 to 9, wherein no more than 30% of the amount of analgesic is released in the first 3 days of the 14 days.

11. The depot of any one of the preceding clauses, wherein the depot is configured to release the analgesic at a first rate for a first period of time and at a second rate for a second period of time.

12. The depot of clause 11, wherein the first rate is greater than the second rate.

13. The depot of clause 11, wherein the first period of time is greater than the second period of time.

14. The depot of clause 11, wherein the first period of time is less than the second period of time.

15. The depot of any one of the preceding clauses, wherein the depot is configured to release at least 90% of the analgesic in the therapeutic region within 14 days.

16. The depot of any one of the preceding clauses, wherein the depot is configured to release about 100 mg to about 500 mg of analgesic to the treatment site per day.

17. The depot of any one of the preceding clauses, wherein the depot is configured to release about 20 mg to about 600 mg of analgesic to the treatment site per day.

18. The depot of any one of the preceding clauses, wherein the depot is configured to release about 30 mg to about 500 mg of analgesic to the treatment site per day.

19. The depot of any one of the preceding clauses, wherein the depot is configured to release about 40 mg to about 500 mg of analgesic to the treatment site per day.

20 The depot of any one of the preceding clauses, wherein the depot is configured to release about 50 mg to about 500 mg of analgesic to the treatment site per day.

21 The depot of any one of the preceding clauses, wherein the depot is configured to release about 100 mg to about 600 mg of analgesic to the treatment site per day.

22. The depot of any one of the preceding clauses, wherein the depot is configured to release about 450 mg to about 550 mg of analgesic to the treatment site per day.

23. The depot of any one of the preceding clauses, wherein the depot is configured to release about 100 mg to about 400 mg of analgesic to the treatment site per day.

24. The depot of any one of the preceding clauses, wherein the depot is configured to release about 100 mg to about 300 mg of analgesic to the treatment site per day.

25. The depot of any one of the preceding clauses, wherein the depot comprises a plurality of depots. The depot of any one of the preceding clauses, wherein the depot comprises two, three, four, five, six, seven, eight, nine, or 10 depots.

26 The depot of any one of the preceding clauses, wherein the depot is configured to release no more than 300 mg of analgesic per day within the first 3 days, and no more than 200 mg per day in the remaining days.

27. The depot of any one of the preceding clauses, wherein the depot is configured to release no more than 150 mg of analgesic per day within the first 3 days, and no more than 100 mg per day in the remaining days.

28. The depot of any one of the preceding clauses, wherein no more than 400 mg of analgesic is released within any day of the 14 days.

29. The depot of any one of the preceding clauses, wherein no more than 300 mg of analgesic is released within any day of the 14 days.

30. The depot of any one of the preceding clauses, wherein no more than 250 mg of analgesic is released within any day of the 14 days.

31. The depot of any one of the preceding clauses, wherein no more than 200 mg of analgesic is released within any day of the 14 days.

32. The depot of any one of the preceding clauses, wherein no more than 150 mg of analgesic is released within any day of the 14 days.

33. The depot of any one of the preceding clauses, wherein no more than 100 mg of analgesic is released within any day of the 14 days.

34. The depot of any one of the preceding clauses, wherein the depot is configured to release the analgesic agent at the treatment site in vivo for no less than 1 day, no less than 2 days, no less than 3 days, no less than 4 days, no less than 5 days, no less than 6 days, no less than 7 days, no less than 8 days, no less than 9 days, no less than 10 days, no less than 11 days, no less than 12 days, no less than 13 days, no less than 14 days, no less than 15 days, no less than 16 days, no less than 17 days, no less than 18 days, no less than 19 days, no less than 20 days, no less than 21 days, no less than 22 days, no less than 23 days, no less than 24 days, no less than 25 days, no less than 26 days, no less than 27 days, no less than 28 days, no less than 29 days, no less than 30 days, no less than 40 days, no less than 50 days, no less than 60 days, no less than 70 days, no less than 90 days, no less than 100 days, no less than 200 days, no less than 300 days, or no less than 365 days.

35. The depot of any one of the preceding clauses, wherein the concentration of the analgesic in the blood plasma of a mammalian patient on day 10 is no less than 70% of the concentration of the analgesic in the blood plasma of the patient on day 5.

36. The depot of any one of the preceding clauses, wherein the therapeutic region comprises a covered portion and an exposed portion, wherein the covered portion is covered by the control region such that, when the depot is initially positioned at the treatment site in vivo, the control region is between the covered portion of the therapeutic region and physiologic fluids at the treatment site and the exposed portion of the therapeutic region is exposed to the physiologic fluids.

37. The depot of any one of the preceding clauses, wherein,
 the depot has a total surface area comprising the exposed surface area of the control region plus the exposed surface area of the therapeutic region, and
 when the depot is initially positioned at the treatment site in vivo, a ratio of the exposed surface area of the therapeutic region to the exposed surface area of the control region is from about 5% to about 20%, or from about 5% to about 15%, or from about 5% to about 10%.

38. The depot of clause 37, wherein the exposed surface area of the control region is less than the exposed surface area of the therapeutic region.

39. The depot of clause 37, wherein the exposed surface area of the control region is greater than the exposed surface area of the therapeutic region.

40. The depot of any one of the preceding clauses, wherein the control region is a first control region, and wherein the depot comprises a second control region.

41. The depot of clause 40, wherein the first control region is disposed at a first side of the therapeutic region and the second control region is disposed at a second side of the therapeutic region opposite the first side.

42. The depot of any one of the preceding clauses, wherein the depot comprises a plurality of control regions and a plurality of therapeutic regions, and wherein each of the therapeutic regions is separated from an adjacent one of the therapeutic regions by one or more control regions.

43. The depot of clause 42, wherein each of the therapeutic regions and each of the control regions is a micro-thin layer.

44. The depot of clause 42 or clause 43, wherein the depot comprises from about 2 to about 100 therapeutic regions.

45. The depot of clause 42 or clause 43, wherein the depot comprises from about 2 to about 50 therapeutic regions.

46. The depot of clause 42 or clause 43, wherein the depot comprises from about 2 to about 10 therapeutic regions.

47. The depot of any one of clauses 1 to 41, wherein the therapeutic region is enclosed by the control region such that, when the depot is positioned at the treatment site in vivo, the control region is between the therapeutic region and physiologic fluids at the treatment site.

48. The depot of any one of the preceding clauses, wherein the control region comprises a first control layer and a second control layer.

49. The depot of clause 48, wherein the second control layer is adjacent to the therapeutic region and the first control layer encapsulates/encloses the therapeutic region and the second control layer.

50. The depot of clause 48 or clause 49, wherein the first control layer and the second control layer together enclose the therapeutic region.

51. The depot of any one of clauses 48 to 50, wherein the first control layer is disposed at a first side of the therapeutic region and the second control layer is disposed at a second side of the therapeutic region opposite the first side.

52. The depot of any one of clauses 48 to 51, wherein the first control layer comprises a first plurality of sub-layers and the second control layer comprises a second plurality of sub-layers.

53. The depot of any one of clauses 48 to 52, wherein the first control layer includes a first amount of the releasing agent and the second control layer includes a second amount of the releasing agent different than the first amount.

54. The depot of any one of clauses 48 to 53, wherein the second control layer is positioned between the first control layer and the therapeutic region, and wherein the first control layer includes a first concentration of the releasing agent and the second control layer includes a second concentration of the releasing agent greater than the first concentration.

55. The depot of any one of clauses 48 to 53, wherein the second control layer is positioned between the first control layer and the therapeutic region, and wherein the first control layer includes a first concentration of the releasing agent and the second control layer includes a second concentration of the releasing agent less than the first concentration.

56. The depot of any one of clauses 48 to 55, wherein the second control layer is positioned between the first control layer and the therapeutic region, and wherein
the first control layer includes up to 5% by weight of the releasing agent, up to 10% by weight of the releasing agent, up to 15% by weight of the releasing agent, up to 20% by weight of the releasing agent, up to 25% by weight of the releasing agent, up to 30% by weight of the releasing agent, up to 35% by weight of the releasing agent, up to 40% by weight of the releasing agent, up to 45% by weight of the releasing agent, or 50% by weight of the releasing agent, and
the second control layer includes up to 5% by weight of the releasing agent, up to 10% by weight of the releasing agent, up to 15% by weight of the releasing agent, up to 20% by weight of the releasing agent, up to 25% by weight of the releasing agent, up to 30% by weight of the releasing agent, up to 35% by weight of the releasing agent, up to 40% by weight of the releasing agent, up to 45% by weight of the releasing agent, or up to 50% by weight of the releasing agent.

57. The depot of any one of clauses 48 to 56, wherein the second control layer is positioned between the first control layer and the therapeutic region, and wherein the first control layer includes a first amount of the releasing agent and the second control layer includes a second amount of the releasing agent, the second amount being at least 2×, at least 3×, at least 4×, or at least 5× the first amount.

58. The depot of any one of the preceding clauses, wherein a thickness of the control region is less than or equal to 1/10 of a thickness of the therapeutic region.

59. The depot of any one of the preceding clauses, wherein a thickness of the control region is less than or equal to 1/12.5 of a thickness of the therapeutic region.

60. The depot of any one of the preceding clauses, wherein a thickness of the control region is less than or equal to 1/15 of a thickness of the therapeutic region.

61. The depot of any one of the preceding clauses, wherein a thickness of the control region is less than or equal to 1/17.5 of a thickness of the therapeutic region.

62. The depot of any one of the preceding clauses, wherein a thickness of the control region is less than or equal to 1/20 of a thickness of the therapeutic region.

63. The depot of any one of the preceding clauses, wherein a thickness of the control region is less than or equal to 1/22.5 of a thickness of the therapeutic region.

64. The depot of any one of the preceding clauses, wherein a thickness of the control region is less than or equal to 1/25 of a thickness of the therapeutic region.

65. The depot of any one of the preceding clauses, wherein a thickness of the control region is less than or equal to 1/30 of a thickness of the therapeutic region.

66. The depot of any one of the preceding clauses, wherein a thickness of the control region is less than or equal to 1/40 of a thickness of the therapeutic region.

67. The depot of any one of the preceding clauses, wherein a thickness of the control region is less than or equal to 1/50 of a thickness of the therapeutic region.

68. The depot of any one of the preceding clauses, wherein a thickness of the control region is less than or equal to 1/75 of a thickness of the therapeutic region.

69. The depot of any one of the preceding clauses, wherein a thickness of the control region is less than or equal to 1/100 of a thickness of the therapeutic region.

70. The depot of any one of the preceding clauses, wherein a thickness of the control region is less than or equal to 1/125 of a thickness of the therapeutic region.

71. The depot of any one of the preceding clauses, wherein a thickness of the control region is less than or equal to 1/150 of a thickness of the therapeutic region.

72. The depot of any one of the preceding clauses, wherein a thickness of the control region is less than or equal to 1/175 of a thickness of the therapeutic region.

73. The depot of any one of the preceding clauses, wherein a thickness of the control region is less than or equal to 1/200 of a thickness of the therapeutic region.

74. The depot of any one of the preceding clauses, wherein the depot is a flexible solid that is structurally capable of being handled by a clinician during the normal course of a surgery without breaking into multiple pieces and/or losing its general shape.

75. The depot of any one of the preceding clauses, wherein the depot is configured to be placed in the knee of a patient and release the analgesic in vivo for up to 7 days without breaking into multiple pieces.

76. The depot of any one of the preceding clauses, wherein the depot has a width and a thickness, and wherein a ratio of the width to the thickness is 15 or greater.

77. The depot of any one of the preceding clauses, wherein the depot has a width and a thickness, and wherein a ratio of the width to the thickness is 16 or greater.

78. The depot of any one of the preceding clauses, wherein the depot has a width and a thickness, and wherein a ratio of the width to the thickness is 17 or greater.

79. The depot of any one of the preceding clauses, wherein the depot has a width and a thickness, and wherein a ratio of the width to the thickness is 18 or greater.

80. The depot of any one of the preceding clauses, wherein the depot has a width and a thickness, and wherein a ratio of the width to the thickness is 19 or greater.

81. The depot of any one of the preceding clauses, wherein the depot has a width and a thickness, and wherein a ratio of the width to the thickness is 20 or greater.

82. The depot of any one of the preceding clauses, wherein the depot has a width and a thickness, and wherein a ratio of the width to the thickness is 21 or greater.

83. The depot of clause 76, wherein the ratio is 30 or greater.

84. The depot of clause 76, wherein the ratio is 40 or greater.

85. The depot of any one of the preceding clauses, wherein the depot has a surface area and a volume, and wherein a ratio of the surface area to volume is at least 1.

86. The depot of any one of the preceding clauses, wherein the diffusion openings include at least one or more pores and/or one or more channels.

87. The depot of any one of the preceding clauses, wherein the two or more micro-thin layers of the bioresorbable polymer are bonded via heat compression to form the therapeutic region.

88. The depot of any one of the preceding clauses, wherein the control region and the therapeutic region are bonded via heat compression.

89. The depot of any one of the preceding clauses, wherein the control region and the therapeutic region are thermally bonded.

90. The depot of any one of the preceding clauses, wherein dissolution of the releasing agent following in vivo placement in the treatment site causes the control region and the therapeutic region to transition from a state of lesser porosity to a state of greater porosity to facilitate the release of the analgesic from the depot.

91. The depot of any one of the preceding clauses, wherein the control region does not include the analgesic at least prior to implantation of the depot at the treatment site.

92. The depot of any one of clauses 1 to 90, wherein the control region comprises an analgesic different from the analgesic in the therapeutic region.

93. The depot of any one of the preceding clauses, wherein the therapeutic region does not include any releasing agent prior to implantation of the depot at the treatment site.

94. The depot of any one of the preceding clauses, wherein the releasing agent is a first releasing agent and the therapeutic region includes a second releasing agent mixed with the analgesic.

95. The depot of any one of clauses 1 to 94, wherein the releasing agent is a first releasing agent and the polymer is a first polymer, and the therapeutic region includes a second releasing agent and a second polymer mixed with the analgesic.

96. The depot of any one of clauses 1 to 94, wherein the first releasing agent is the same as the second releasing agent.

97. The depot of any one of clauses 1 to 94, wherein the first releasing agent is the different than the second releasing agent.

98. The depot of any one of clauses 1 to 96, wherein a concentration of the first releasing agent within the control region is the greater than a concentration of the second releasing agent within the therapeutic region.

99. The depot of any one of clauses 1 to 98, wherein a concentration of the first releasing agent within the control region is the less than a concentration of the second releasing agent within the therapeutic region.

100. The depot of any one of clauses 1 to 98, wherein a concentration of the first releasing agent within the control region is the same as a concentration of the second releasing agent within the therapeutic region.

101. The depot of any one of clauses 1 to 98, wherein a concentration of the first releasing agent within the control region is different than a concentration of the second releasing agent within the therapeutic region.

102. The depot of any one of the preceding clauses, wherein the therapeutic region includes a plurality of microlayers.

103. The depot of any one of the preceding clauses, wherein the mass of the analgesic comprises at least 50% of the mass of the depot.

104. The depot of any one of the preceding clauses, wherein the ratio of the mass of the analgesic in the depot to the depot polymer mass is at least 3:1.

105. The depot of any one of the preceding clauses, wherein the ratio of the mass of the analgesic in the depot to the depot polymer mass is at least 4:1.

106. The depot of any one of the preceding clauses, wherein the ratio of the mass of the analgesic in the depot to the depot polymer mass is at least 5:1.

107. The depot of any one of the preceding clauses, wherein a ratio of the mass of the analgesic in the depot to the depot polymer mass is at least 6:1.

108. The depot of any one of the preceding clauses, wherein a ratio of the mass of the analgesic in the depot to the depot polymer mass is at least 7:1.

109. The depot of any one of the preceding clauses, wherein a ratio of the mass of the analgesic in the depot to the depot polymer mass is at least 8:1.

110. The depot of any one of the preceding clauses, wherein a ratio of the mass of the analgesic in the depot to the depot polymer mass is at least 10:1.

111. The depot of any one of the preceding clauses, wherein a ratio of the mass of the analgesic in the depot to the depot polymer mass is at least 16:1.

112. The depot of any one of the preceding clauses, wherein the therapeutic region includes at least 60% by weight of the analgesic, 60% by weight of the analgesic, at least 70% by weight of the analgesic, at least 80% by weight of the analgesic, at least 90% by weight of the analgesic, or 100% by weight of the analgesic.

113. The depot of any one of the preceding clauses, wherein the depot includes at least 15% by weight of the analgesic, at least 20% by weight of the analgesic, at least 30% by weight of the analgesic, at least 40% by weight of the analgesic, at least 50% by weight of the analgesic, at least 60% by weight of the analgesic, at least 70% by weight of the analgesic, at least 80% by weight of the analgesic, at least 90% by weight of the analgesic, or 100% by weight of the analgesic.

114. The depot of any one of the preceding clauses, wherein the analgesic comprises at least one of: simple analgesics, local anesthetics, NSAIDs and opioids.

115. The depot of any one of the preceding clauses, wherein the analgesic comprises a local anesthetic selected from at least one of bupivacaine, ropivacaine, mepivacaine, and lidocaine.

116. The depot of any one of the preceding clauses, wherein the analgesic comprises a local anesthetic free base.

117. The depot of any one of the preceding clauses, wherein the analgesic comprises a local anesthetic free base and a salt.

118. The depot of any one of the preceding clauses, wherein the analgesic comprises a local anesthetic free base, a salt, and a hydrate.

119. The depot of any one of the preceding clauses, further comprising an antibiotic, an antifungal, and/or an antimicrobial, wherein the antibiotic, the antifungal, and/or the antimicrobial is selected from at least one of amoxicillin, amoxicillin/clavulanate, cephalexin, ciprofloxacin, clindamycin, metronidazole, azithromycin, levofloxacin, sulfamethoxazole/trimethoprim, tetracycline(s), minocycline, tigecycline, doxycycline, rifampin, triclosan, chlorhexidine, penicillin(s), aminoglycides, quinolones, fluoroquinolones, vancomycin, gentamycin, cephalosporin(s), carbapenems, imipenem, ertapenem, antimicrobial peptides, cecropin-mellitin, magainin, dermaseptin, cathelicidin, α-defensins, and α-protegrins, ketoconazole, clortrimazole, miconazole, econazole, intraconazole, fluconazole, bifoconazole, terconazole, butaconazole, tioconazole, oxiconazole, sulconazole, saperconazole, voriconazole, terbinafine, amorolfine, naftifine, griseofulvin, haloprogin, butenafine, tolnaftate, nystatin, cyclohexamide, ciclopirox, flucytosine, terbinafine, and amphotericin B.

120. The depot of any one of the preceding clauses, further comprising an anti-inflammatory agent selected from at least one of steroids, prednisone, betamethasone, cortisone, dexamethasone, hydrocortisone and methylprednisolone, non-steroidal anti-inflammatory drugs (NSAIDs), aspirin, Ibuprofen, naproxen sodium, diclofenac, diclofenac-misoprostol, celecoxib, piroxicam, indomethacin, meloxicam, ketoprofen, sulindac, diflunisal, nabumetone, oxaprozin, tolmetin, salsalate, etodolac, fenoprofen, flurbiprofen, ketorolac, meclofenamate, mefenamic acid, and COX-2 inhibitors.

121. The depot of any one of the preceding clauses, further comprising at least one of: epinephrine, clonidine, transexamic acid.

122. The depot of any one of the preceding clauses, wherein the releasing agent is a non-ionic surfactant.

123. The depot of any one of the preceding clauses, wherein the releasing agent has hydrophilic properties.

124. The depot of any one of the preceding clauses, wherein the releasing agent is a polysorbate.

125. The depot of any one of the preceding clauses, wherein the releasing agent is Tween 20.

126. The depot of any one of clauses 1 to 124, wherein the releasing agent is Tween 80.

127. The depot of any one of the preceding clauses, wherein the releasing agent is non-polymeric.

128. The depot of any one of the preceding clauses, wherein the releasing agent is not a plasticizer.

129. The depot of any one of the preceding clauses, wherein the polymer is configured to degrade only after substantially all of the analgesic has been released from the depot.

130. The depot of any one of the preceding clauses, wherein the polymer is a copolymer.

131. The depot of any one of clauses 1 to 129, wherein the polymer is a terpolymer.

132. The depot of any one of the preceding clauses, wherein the polymer includes at least one of polyglycolide (PGA), polycaprolactone (PCL), poly(DL-lactic acid) (PLA), poly(alpha-hydroxy acids), poly(lactide-co-glycolide) (PLGA or DLG), poly(DL-lactide-co-caprolactone) (DL-PLCL), poly(trimethylene carbonate) (PTMC), polydioxanone (PDO), poly(4-hydroxy butyrate) (PHB), polyhydroxyalkanoates (PHA), poly(phosphazene), polyphosphate ester), poly(amino acid), polydepsipeptides, poly(butylene succinate) (PBS), polyethylene oxide, polypropylene fumarate, polyiminocarbonates, poly(lactide-co-caprolactone) (PLCL), poly(glycolide-co-caprolactone) (PGCL) copolymer, poly(D,L-lactic acid), polyglycolic acid, poly(L-lactide-co-D,L-lactide), poly(L-lactide-co-glycolide), poly (D,L-lactide-co-glycolide), poly(gycolide-trimethylene carbonate), poly(ethyl glutamate-co-glutamic acid), poly(tert-butyloxy-carbonylmethyl glutamate), poly(glycerol sebacate), tyrosine-derived polycarbonate, poly 1,3-bis-(p-carboxyphenoxy) hexane-co-sebacic acid, polyphosphazene, ethyl glycinate polyphosphazene, polycaprolactone co-butylacrylate, a copolymer of polyhydroxybutyrate, a copolymer of maleic anhydride, a copolymer of poly(trimethylene carbonate), polyethylene glycol (PEG), hydroxypropylmethylcellulose and cellulose derivatives, polysaccharides (such as hyaluronic acid, chitosan and starch), proteins (such as gelatin and collagen) or PEG derivatives, polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D-lactide, D,L-lactide, L-lactide, D,L-lactide-caprolactone (DL-CL), D,L-lactide-glycolide-caprolactone (DL-G-CL), dextrans, vinylpyrrolidone, polyvinyl alcohol (PVA), PVA-g-PLGA, PEGT-PBT copolymer (polyactive), methacrylates, poly(N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate) hydroxypropyl cellulose, hydroxypropyl methylcellulose, hydroxyethyl methylcellulose, carboxymethylcellulose or salts thereof, Carbopol®, poly(hydroxyethylmethacrylate), poly (methoxyethylmethacrylate), poly(methoxyethoxy-ethylmethacrylate), polymethylmethacrylate (PMMA), methylmethacrylate (MMA), gelatin, polyvinyl alcohols, propylene glycol, and poly(DL-lactide-co-glycolide-co-caprolactone).

133. The depot of any one of the preceding clauses, wherein the polymer is one of poly(DL-lactide-co-glycolide-co-caprolactone) and poly(DL-lactide-co-glycolide) (PLGA).

134. The depot of any one of clauses 1 to 129, wherein the polymer is poly(DL-lactide-co-glycolide-co-caprolactone) in a molar ratio of 60:30:10.

135. The depot of any one of clauses 1 to 129, wherein the polymer is poly(DL-lactide-co-glycolide) (PLGA) in a molar ratio of 50:50.

136. The depot of any one of the preceding clauses, wherein the polymer is ester-terminated.

137. The depot of any one of the preceding clauses, wherein the polymer is a terpolymer that includes three polymers selected from the following: polyglycolide (PGA), polycaprolactone (PCL), poly(L-lactic acid) (PLA), poly (DL-lactic acid) (PLA), poly(trimethylene carbonate) (PTMC), polydioxanone (PDO), poly(4-hydroxy butyrate) (PHB), polyhydroxyalkanoates (PHA), poly(phosphazene), and polyethylene glycol.

138. The depot of any one of the preceding clauses, wherein the polymer is a first polymer, and the therapeutic region includes a second polymer mixed with the analgesic.

139. The depot of clause 138, wherein the first polymer and the second polymer are the same.

140. The depot of clause 138, wherein the first polymer and the second polymer are different.

141. The depot of any one of clauses 138 to 140, wherein the first polymer and/or the second polymer include at least one of polyglycolide (PGA), polycaprolactone (PCL), poly (DL-lactic acid) (PLA), poly(alpha-hydroxy acids), poly (lactide-co-glycolide) (PLGA or DLG), poly(DL-lactide-co-caprolactone) (DL-PLCL), poly(trimethylene carbonate) (PTMC), polydioxanone (PDO), poly(4-hydroxy butyrate) (PHB), polyhydroxyalkanoates (PHA), poly(phosphazene), polyphosphate ester), poly(amino acid), polydepsipeptides, poly(butylene succinate) (PBS), polyethylene oxide, polypropylene fumarate, polyiminocarbonates, poly(lactide-co-caprolactone) (PLCL), poly(glycolide-co-caprolactone) (PGCL) copolymer, poly(D,L-lactic acid), polyglycolic acid, poly(L-lactide-co-D,L-lactide), poly(L-lactide-co-glycolide), poly(D,L-lactide-co-glycolide), poly(gycolide-trimethylene carbonate), poly(ethyl glutamate-co-glutamic acid), poly(tert-butyloxy-carbonylmethyl glutamate), poly(glycerol sebacate), tyrosine-derived polycarbonate, poly 1,3-bis-(p-carboxyphenoxy) hexane-co-sebacic acid, polyphosphazene, ethyl glycinate polyphosphazene, polycaprolactone co-butylacrylate, a copolymer of polyhydroxybutyrate, a copolymer of maleic anhydride, a copolymer of poly(trimethylene carbonate), polyethylene glycol (PEG), hydroxypropylmethylcellulose and cellulose derivatives, polysaccharides (such as hyaluronic acid, chitosan and starch), proteins (such as gelatin and collagen) or PEG derivatives, polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D-lactide, D,L-lactide, L-lactide, D,L-lactide-caprolactone (DL-CL), D,L-lactide-glycolide-caprolactone (DL-G-CL), dextrans, vinylpyrrolidone, polyvinyl alcohol (PVA), PVA-g-PLGA, PEGT-PBT copolymer (polyactive), methacrylates, poly(N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate) hydroxypropyl cellulose, hydroxypropyl methylcellulose, hydroxyethyl methylcellulose, carboxymethylcellulose or salts thereof, Carbopol®, poly(hydroxyethylmethacrylate), poly(methoxyethylmethacrylate), poly(methoxyethoxy-ethylmethacrylate), polymethylmethacrylate (PMMA), methylmethacrylate (MMA), gelatin, polyvinyl alcohols, propylene glycol, poly(DL-lactide-co-glycolide-co-caprolactone).

142. The depot of any one of clauses 138 to 140, wherein the first polymer and/or the second polymer is selected from the following: poly(DL-lactide-co-glycolide-co-caprolactone) and poly(DL-lactide-co-glycolide) (PLGA).

143. The depot of any one of clauses 138 to 140, wherein the first polymer and/or the second polymer is poly(DL-lactide-co-glycolide-co-caprolactone) and has a molar ratio of 60:30:10.

144. The depot of any one of clauses 138 to 140, wherein the first polymer and/or the second polymer is poly(DL-lactide-co-glycolide) and has a molar ratio of 50:50.

145. The depot of any one of clauses 138 to 144, wherein the first polymer and/or the second polymer is ester-terminated.

146. The depot of any one of clauses 138 to 140, wherein the first polymer and/or the second polymer is a terpolymer that includes three polymers selected from the following: polyglycolide (PGA), polycaprolactone (PCL), poly(L-lactic acid) (PLA), poly(trimethylene carbonate) (PTMC), polydioxanone (PDO), poly(4-hydroxy butyrate) (PHB), polyhydroxyalkanoates (PHA), poly(phosphazene), and polyethylene glycol.

147. The depot of any one of clauses 1 to 146, wherein the ratio of the releasing agent to the polymer in the control region is no more than 1:2.

148. The depot of any one of clauses 1 to 146, wherein the ratio of the releasing agent to the polymer in the control region is no more than 1:3.

149. The depot of any one of clauses 1 to 146, wherein the ratio of the releasing agent to the polymer in the control region is no more than 1:4.

150. The depot of any one of clauses 1 to 146, wherein the ratio of the releasing agent to the polymer in the control region is no more than 1:5.

151. The depot of any one of clauses 1 to 146, wherein the ratio of the releasing agent to the polymer in the control region is no more than 1:6.

152. The depot of any one of clauses 1 to 146, wherein the ratio of the releasing agent to the polymer in the control region is no more than 1:7.

153. The depot of any one of clauses 1 to 146, wherein the ratio of the releasing agent to the polymer in the control region is no more than 1:8.

154. The depot of any one of clauses 1 to 146, wherein the ratio of the releasing agent to the polymer in the control region is no more than 1:9.

155. The depot of any one of clauses 1 to 146, wherein the ratio of the releasing agent to the polymer in the control region is no more than 1:10.

156. The depot of any one of clauses 1 to 146, wherein the ratio of the releasing agent to the polymer in the control region is no more than 1:11.

157. The depot of any one of clauses 1 to 146, wherein the ratio of the releasing agent to the polymer in the control region is at least 1:1.

158. The depot of any one of clauses 1 to 146, wherein the ratio of the releasing agent to the polymer in the control region is at least 2:1.

159. The depot of any one of clauses 1 to 146, wherein the ratio of the releasing agent to the polymer in the control region is at least 3:1.

160. The depot of any one of clauses 1 to 146, wherein the ratio of the releasing agent to the polymer in the control region is at least 4:1.

161. The depot of any one of clauses 1 to 146, wherein the ratio of the releasing agent to the polymer in the control region is at least 5:1.

162. The depot of any one of clauses 1 to 146, wherein the ratio of the releasing agent to the polymer in the control region is at least 6:1.

163. The depot of any one of clauses 1 to 146, wherein the ratio of the releasing agent to the polymer in the control region is at least 7:1.

164. The depot of any one of clauses 1 to 146, wherein the ratio of the releasing agent to the polymer in the control region is at least 8:1.

165. The depot of any one of clauses 1 to 146, wherein the ratio of the releasing agent to the polymer in the control region is at least 9:1.

166. The depot of any one of clauses 1 to 146, wherein the ratio of the releasing agent to the polymer in the control region is at least 10:1.

167. The depot of any one of clauses 1 to 146, wherein the ratio of the releasing agent to the polymer in the control region is at least 15:1.

168. The depot of any one of the preceding clauses, wherein:
the polymer is a first polymer and the therapeutic region further includes a second polymer,
the depot has a depot polymer mass equivalent to a mass of the first polymer plus a mass of the second polymer, and a ratio of a mass of the analgesic in the depot to the depot polymer mass is approximately 1:1

169. The depot of clause 168, wherein the first polymer is the same as the second polymer.

170. The depot of clause 168, wherein the first polymer is different than the second polymer.

171. The depot of any one of clauses 168 to 170, wherein the ratio of the mass of the analgesic in the depot to the depot polymer mass is at least 2:1.

172. The depot of any one of clauses 168 to 170, wherein the ratio of the mass of the analgesic in the depot to the depot polymer mass is at least 3:1.

173. The depot of any one of clauses 168 to 170, wherein the ratio of the mass of the analgesic in the depot to the depot polymer mass is at least 4:1.

174. The depot of any one of clauses 168 to 170, wherein the ratio of the mass of the analgesic in the depot to the depot polymer mass is approximately 5:1.

175. The depot of any one of clauses 168 to 170, wherein a ratio of the mass of the analgesic in the depot to the depot polymer mass is at least 6:1.

176. The depot of any one of clauses 168 to 170, wherein a ratio of the mass of the analgesic in the depot to the depot polymer mass is at least 7:1.

177. The depot of any one of clauses 168 to 170, wherein a ratio of the mass of the analgesic in the depot to the depot polymer mass is at least 8:1.

178. The depot of any one of clauses 168 to 170, wherein a ratio of the mass of the analgesic in the depot to the depot polymer mass is at least 10:1.

179. The depot of any one of clauses 168 to 170, wherein a ratio of the mass of the analgesic in the depot to the depot polymer mass is at least 16:1.

180. The depot of any one of the preceding clauses, wherein the analgesic is a local anesthetic, and wherein the release of the analgesic to the treatment site over the five days inhibits the growth of bacteria and fungi.

181. The depot of clause 180, wherein depot is configured to inhibit the growth of bacteria and fungi such that a number of bacteria on the depot is 10×, 20×, 30×, 40×, or 50× less than a number of bacteria present on a comparable depot containing no analgesic.

182. The depot of any one of the preceding clauses, wherein the release of analgesic is at a level sufficiently high to create a sensory block, thereby treating postoperative pain, but sufficiently low to avoid a motor block.

183. The depot of any one of the preceding clauses, wherein the release of the analgesic provides motor sparing relief from postoperative pain.

184. A depot for sustained, controlled release of a therapeutic agent, comprising:
   a therapeutic region comprising the therapeutic agent;
   a control region comprising a bioresorbable polymer and a releasing agent mixed with the polymer, wherein the releasing agent is configured to dissolve when the depot is placed in contact with a fluid to form diffusion openings in the control region; and
   wherein, when the depot is placed in contact with a fluid, the depot is configured to release the therapeutic agent into the surrounding fluid for no less than 14 days, and wherein about 20% to about 50% of the therapeutic agent is released in the first about 3 to about 5 days of the 14 days, and wherein at least 80% of the remaining therapeutic agent is released in the last 11 days of the 14 days.

185. The depot of clause 184, wherein at least 85% of the remaining therapeutic agent is released in the last 11 days of the 14 days.

186. The depot of clause 184, wherein at least 90% of the remaining therapeutic agent is released in the last 11 days of the 14 days.

187. The depot of clause 184, wherein at least 95% of the remaining therapeutic agent is released in the last 11 days of the 14 days.

188. The depot of any one of clauses 184 to 187, wherein no more than 15% of the amount of therapeutic agent is released in the first 2 days of the 14 days.

189. The depot of any one of clauses 184 to 187, wherein no more than 20% of the amount of therapeutic agent is released in the first 2 days of the 14 days.

190. The depot of any one of clauses 184 to 187, wherein no more than 25% of the amount of therapeutic agent is released in the first 3 days of the 14 days.

191. The depot of any one of clauses 184 to 187, wherein no more than 30% of the amount of therapeutic agent is released in the first 3 days of the 14 days.

192. The depot of any one of clauses 184 to 187, wherein the releasing agent is configured to dissolve when the depot is placed in contact with phosphate buffered saline to form diffusion openings.

193. A method for treating postoperative pain, comprising:
   positioning a depot at a treatment site in vivo having physiologic fluids, the depot comprising (a) a control region including a bioresorbable polymer and a releasing agent mixed with the polymer, and (b) a therapeutic region including at least 50% by weight of an analgesic; and
   releasing analgesic from the depot to the treatment site for no less than seven days.

194. The method of clause 193, further comprising dissolving the releasing agent at a first rate and degrading the polymer at a second rate, wherein the first rate is greater than the second rate.

195. The method of clause 193 or clause 194, further comprising dissolving the releasing agent in response to contact between the control region and the physiologic fluids at the treatment site.

196. The method of any one of clauses 193 to 195, further comprising creating diffusion openings in the control region via the dissolution of the releasing agent in response to physiologic fluids at the treatment site.

197. The method of any one of clauses 193 to 196, wherein the releasing agent is a first releasing agent and the therapeutic region includes a second releasing agent, and wherein the method further comprises creating microchannels in the therapeutic region and the control region via dissolution of the first and/or second releasing agents.

198. The method of any one of clauses 193 to 197, wherein at least some of the microchannels penetrate both the therapeutic region and the control region.

199. The method of any one of clauses 193 to 198, wherein the therapeutic region comprises a plurality of microlayers, and wherein at least some of the microchannels extend through consecutive microlayers.

200. The method of any one of clauses 193 to 159, wherein the control region comprises a first plurality of microlayers and the therapeutic region comprises a second plurality of microlayers, and wherein at least some of the microchannels extend through the first and second plurality of microlayers.

201. The method of any one of clauses 193 to 200, further including increasing a porosity of the depot via dissolution of the releasing agent.

202. The method of any one of clauses 193 to 201, wherein the analgesic is released one or more times in substantially discrete doses after implantation.

203. The method of any one of clauses 193 to 202, wherein the analgesic is released continuously for at least seven days after implantation.

204. The method of any one of clauses 193 to 203, wherein the analgesic is released for no less than 10 days.

205. The method of any one of clauses 193 to 203, wherein the analgesic is released for no less than 14 days.

206. The method of any one of clauses 193 to 205, wherein no more than 20% of the amount of analgesic is released in the first day of the seven days.

207. The method of any one of clauses 193 to 206, further comprising securing the depot to the treatment site via an attachment means.

208. The method of any one of clauses 193 to 207, wherein the attachment means is coupled to the depot prior to implantation.

209. The method of any one of clauses 193 to 208, wherein the depot is a first depot and the method further comprises positioning a second depot at the treatment site.

210. The method of clause 209, wherein the first and second depots together release at least 1400 mg of the analgesic to the treatment site over a period of no less than seven days.

211. A method for treating postoperative pain associated with orthopedic surgery with any of the depots of clauses 1 to 192, 240 to 242, and 288 to 444 and/or systems of clauses 226 to 239.

212. A method for treating postoperative pain in a patient following orthopedic surgery, the method comprising:
 implanting a plurality of depots at a site of the surgery, each of the depots comprising (a) a control region including a bioresorbable polymer and a releasing agent mixed with the polymer, and (b) a therapeutic region including at least 50% by weight of an analgesic; and
 releasing analgesic from the depot to the site for no less than seven days.

213. A method for treating postoperative pain in a patient following orthopedic surgery, the method comprising:
 implanting a depot at a site of the surgery, the depot comprising (a) a control region including a bioresorbable polymer and a releasing agent mixed with the polymer, and (b) a therapeutic region including at least 50% by weight of an analgesic; and
 releasing analgesic from the depot to the site for no less than seven days.

214. A method for treating postoperative pain in a patient following total knee arthroplasty, comprising:
 positioning a depot in a knee of the patient, the depot comprising (a) a control region including a bioresorbable polymer and a releasing agent mixed with the polymer, and (b) a therapeutic region including at least 50% by weight of an analgesic; and
 releasing analgesic from the depot to the patient's knee for no less than seven days.

215. The method of clause 214, wherein the depot is any of the depots of clauses 1 to 192, 240 to 242, and 288 to 444.

216. The method of clause 214 or clause 215, wherein positioning the depot comprises placing at least one depot in at least one of: suprapatellar pouch, lateral gutter, medial gutter, posterior capsule, quadricep tendon, skin incision, arthrotomy, adductor canal, saphenous nerve, genicular nerve.

217. The method of any one of clauses 214 to 216, wherein positioning the depot comprises positioning at least one depot adjacent at least one of a saphenous nerve, an adductor canal, and a femoral nerve.

218. The method of any one of clauses 214 to 217, wherein positioning the depot comprises intracapsular placement of at least one depot.

219. The method of any one of clauses 214 to 218, wherein positioning the depot comprises extracapsular placement of at least one depot.

220. The method of any one of clauses 214 to 219, wherein positioning the depot comprises intracapsular placement without interfering with articulation of the knee.

221. The method of clause 220, wherein placing at least one depot at at least one of: suprapatellar pouch, lateral gutter, medial gutter, posterior capsule, quadricep tendon, skin incision, arthrotomy, adductor canal.

222. A system for treating postoperative pain associated with orthopedic surgery, the system comprising:
 a plurality of depots, each of which is any of the depots described in the previous clauses, wherein the plurality of depots are configured to be implanted at a treatment site of a patient and release the analgesic to the treatment site.

223. The system of clause 222, wherein the depots are configured to release analgesic to the treatment site for at least 7 days, at least 8 days, at least 9 days, at least 10 days, at least 11 days, at least 12 days, at least 13 days, or at least 14 days.

224. The system of clause 223, wherein the depots are configured to collectively release no more than 250 mg of analgesic per day within the first 3 days, and no more than 150 mg per day in the remaining days.

225. A system for treating postoperative pain, comprising:
 a delivery system; and
 a depot configured to be implanted at a treatment site in vivo with the delivery system, wherein the depot comprises any of the depots of clauses 1 to 192, 240 to 242, and 288 to 444.

226. A system for treating postoperative pain, comprising:
 an attachment means; and
 a depot configured to be implanted at a treatment site in vivo and secured at the treatment site via the attachment means, wherein the depot comprises any of the depots of clauses 1 to 192, 240 to 242, and 288 to 444.

227. The system of clause 187, wherein the attachment means is coupled to the depot prior to implantation.

228. The system of clause 187 or clause 227, wherein the attachment means is at least one of a suture, a tine, a barb, a hook, and a screw.

229. The system of any one of clauses 226 to 228, wherein the pain is associated with orthopedic surgery.

230. The system of any one of clauses 226 to 229, wherein the pain is associated with joint replacement surgery.

231. The system of any one of clauses 226 to 230, wherein the pain is associated with a knee replacement surgery.

232. The system of any one of clauses 226 to 230, wherein the pain is associated with a partial knee replacement surgery.

233. The system of any one of clauses 226 to 230, wherein the pain is associated with a total knee replacement surgery.

234. The system of any one of clauses 226 to 230, wherein the pain is associated with a revision surgery of a knee replacement surgery.

235. The system of any one of clauses 226 to 234, wherein the depot is configured to be positioned adjacent at least one of a saphenous nerve, an adductor canal, and a femoral nerve.

236. The system of any one of clauses 226 to 235, wherein the depot is configured to be positioned adjacent at least one of a posterior capsule of the knee, a superior region of the patella, or an incision into the knee capsule.

237. The system of any one of clauses 226 to 191, wherein the depot is configured to be positioned within the knee capsule within the medial and/or lateral gutters.

238. A system for treating postoperative pain, comprising a delivery system and any of the depots of clauses 1 to 192, 240 to 242, and 288 to 444.

239. A system for treating postoperative pain, comprising a plurality of depots, any of which comprising any of the depots of clauses 1 to 192, 240 to 242, and 288 to 444.

240. A depot for the release of a therapeutic agent to treat or manage a particular condition or disease, comprising:
- a therapeutic region comprising the therapeutic agent and a bioresorbable polymer carrier;
- a control region comprising a bioresorbable polymer layer and a releasing agent mixed with the polymer, wherein the releasing agent is configured to dissolve over a first period of time following in vivo placement to form diffusion openings in the control region; and
- wherein the depot is configured to be implanted at a treatment site in vivo and, while implanted, release the therapeutic agent at the treatment site for a second period of time;
- wherein the second period of time is greater than the first period of time;
- wherein following the second period of time the polymer carrier of the therapeutic region and the polymer layer of the control region comprise a highly porous polymer structure configured to degrade in vivo without core acidification.

241. The depot of clause 240, wherein the highly porous polymer structure at the end of the second period of time has a mass that is no greater than 50% of the mass of the depot prior to in vivo placement.

242. The depot of clause 240 or clause 241, wherein the highly porous polymer structure is configured to degrade in vivo via surface erosion.

243. A method for treating postoperative pain following a non-orthopedic surgical procedure, comprising:
- positioning a depot at a treatment site in vivo having physiologic fluids, the depot comprising (a) a control region including a bioresorbable polymer and a releasing agent mixed with the polymer, and (b) a therapeutic region including at least 50% by weight of an analgesic;
- dissolving the releasing agent in response to contact between the releasing agent and the physiologic fluids, thereby forming diffusion openings in the control region; and
- releasing analgesic through the diffusion openings from the therapeutic region to the treatment site for no less than five days.

244. The method of clause 243, wherein the surgical procedure comprises at least one of: a thoracotomy, an esophageal surgery, a cardiac surgery, a lung resection, or a thoracic surgery.

245. The method of clause 244, wherein the treatment site comprises a thoracic paravertebral space.

246. The method of clause 244 or clause 245, wherein the analgesic released from the depot at least partially blocks an intercostal nerve.

247. The method of clause 243, wherein the surgical procedure comprises at least one of: a mastectomy, a breast augmentation, a breast reduction, or a breast reconstruction.

248. The method of clause 247, wherein the treatment site comprises an infraclavicular space.

249. The method of clause 247 or clause 248, wherein the analgesic released from the depot at least partially blocks at least one of: an intercostal nerve, a medial pectoral nerve, or a lateral pectoral nerve.

250. The method of clause 243, wherein the surgical procedure comprises at least one of: a myomectomy, a Caesarean section, a hysterectomy, an oophorectomy, or a pelvic floor reconstruction.

251. The method of clause 243, wherein the surgical procedure comprises at least one of: a proctocolectomy, a pancreatectomy, an appendectomy, a hemorrhoidectomy, a cholecystectomy, a kidney transplant, a nephrectomy, a radical prostatectomy, a gastrectomy, a small bowel resection, a splenectomy, an incisional hernia repair, an inguinal hernia repair, a sigmoidectomy, a liver resection, an enterostomy, a rectum resection, a kidney stone removal, or a cystectomy.

252. The method of clause 251, wherein the analgesic released from the depot at least partially blocks a nerve at or adjacent to a transverse abdominis plane.

253. The method of clause 243, wherein the surgical procedure comprises at least one of: a tonsillectomy, a submucosal resection, a rhinoplasty, a sinus surgery, an inner ear surgery, a parotidectomy, or a submandibular gland surgery.

254. The method of clause 243, wherein the surgical procedure comprises at least one of: a dentoalveolar surgery, a dental implant, an orthognathic surgery, a temporomandibular joint (TMJ) surgery, or an oral reconstruction surgery.

255. The method of clause 243, wherein the surgical procedure comprises a tumor resection.

256. The method of clause 243, wherein the surgical procedure comprises liposuction.

257. The method of any one of clauses 243 to 256, further comprising dissolving the releasing agent at a first rate and degrading the polymer at a second rate, wherein the first rate is greater than the second rate.

258. The method of any one of clauses 243 to 257, wherein the analgesic is released for no less than 10 days.

259. The method of any one of clauses 243 to 258, wherein the analgesic is released for no less than 14 days.

260. The method of any one of clauses 243 to 259, wherein no more than 20% of the amount of analgesic is released in the first day of the five days.

261. The method of any one of clauses 243 to 260, further comprising securing the depot to the treatment site via an attachment means.

262. The method of clause 261, wherein the attachment means is coupled to the depot prior to implantation.

263. The method of any one of clauses 243 to 262, wherein the depot is a first depot and the method further comprises positioning a second depot at the treatment site.

264. The method of clause 263, wherein the first and second depots together release at least 1400 mg of the analgesic to the treatment site over a period of no less than seven days.

265. The method of any one of clauses 243 to 264, wherein no more than 400 mg of the therapeutic agent is released within any day of the five days.

266. A method for treating postoperative pain following a non-orthopedic surgical procedure, comprising:
positioning a depot at a treatment site in vivo having physiologic fluids, the depot comprising (a) a control region including a bioresorbable polymer and a releasing agent mixed with the polymer, and (b) a therapeutic region including at least 50% by weight of an analgesic; and
releasing analgesic from the depot to the treatment site for no less than five days.

267. The method of clause 266, wherein the surgical procedure comprises at least one of: a thoracotomy, an esophageal surgery, a cardiac surgery, a lung resection, or a thoracic surgery.

268. The method of clause 267, wherein the treatment site comprises a thoracic paravertebral space.

269. The method of clause 267 or 268, wherein the analgesic released from the depot at least partially blocks an intercostal nerve.

270. The method of clause 266, wherein the surgical procedure comprises at least one of: a mastectomy, a breast augmentation, a breast reduction, or a breast reconstruction.

271. The method of clause 270, wherein the treatment site comprises an infraclavicular space.

272. The method of clause 270 or 271, wherein the analgesic released from the depot at least partially blocks at least one of: an intercostal nerve, a medial pectoral nerve, or a lateral pectoral nerve.

273. The method of clause 266, wherein the surgical procedure comprises at least one of: a myomectomy, a caesarean section, a hysterectomy, an oophorectomy, or a pelvic floor reconstruction.

274. The method of clause 266, wherein the surgical procedure comprises at least one of: a proctocolectomy, a pancreatectomy, an appendectomy, a hemorrhoidectomy, a cholecystectomy, a kidney transplant, a nephrectomy, a radical prostatectomy, a gastrectomy, a small bowel resection, a splenectomy, an incisional hernia repair, an inguinal hernia repair, a sigmoidectomy, a liver resection, an enterostomy, a rectum resection, a kidney stone removal, or a cystectomy.

275. The method of clause 274, wherein the analgesic released from the depot at least partially blocks a nerve at or adjacent to a transverse abdominis plane.

276. The method of clause 266, wherein the surgical procedure comprises at least one of: a tonsillectomy, a submucosal resection, a rhinoplasty, a sinus surgery, an inner ear surgery, a parotidectomy, or a submandibular gland surgery.

277. The method of clause 266, wherein the surgical procedure comprises at least one of: a dentoalveolar surgery, a dental implant, an orthognathic surgery, a temporomandibular joint (TMJ) surgery, or an oral reconstruction surgery.

278. The method of clause 266, wherein the surgical procedure comprises a tumor resection.

279. The method of clause 266, wherein the surgical procedure comprises liposuction.

280. A method for treating postoperative pain following a surgical procedure involving a patient's chest, the method comprising:
positioning a depot proximate to an intercostal nerve at a treatment site having physiologic fluids, the depot comprising (a) a control region including a bioresorbable polymer and a releasing agent mixed with the polymer, and (b) a therapeutic region including at least 50% by weight of an analgesic; and
releasing analgesic from the depot to the intercostal nerve for no less than five days.

281. The method of clause 280, wherein the surgical procedure comprises at least one of: a thoracotomy, an esophageal surgery, a cardiac surgery, a lung resection, or a thoracic surgery.

282. The method of clause 280 or 281, wherein the treatment site comprises a thoracic paravertebral space.

283. A method for treating postoperative pain following a surgical procedure involving a patient's breast, the method comprising:
positioning a depot proximate to an intercostal and/or pectoral nerve at a treatment site having physiologic fluids, the depot comprising (a) a control region including a bioresorbable polymer and a releasing agent mixed with the polymer, and (b) a therapeutic region including at least 50% by weight of an analgesic; and
releasing analgesic from the depot to the intercostal and/or pectoral nerve for no less than five days.

284. The method of clause 283, wherein the surgical procedure comprises at least one of: a mastectomy, a breast augmentation, a breast reduction, or a breast reconstruction.

285. The method of clause 283 or 284, wherein the treatment site comprises an intraclavicular space.

286. A method for treating postoperative pain following a general, abdominal, or urological surgical procedure, the method comprising:
positioning a depot proximate to a transverse abdominis plane at a treatment site having physiologic fluids, the depot comprising (a) a control region including a bioresorbable polymer and a releasing agent mixed with the polymer, and (b) a therapeutic region including at least 50% by weight of an analgesic; and
releasing analgesic from the depot to the intercostal and/or pectoral nerve for no less than five days.

287. The method of clause 286, wherein the surgical procedure comprises at least one of: a proctocolectomy, a pancreatectomy, an appendectomy, a hemorrhoidectomy, a cholecystectomy, a kidney transplant, a nephrectomy, a radical prostatectomy, a gastrectomy, a small bowel resection, a splenectomy, an incisional hernia repair, an inguinal hernia repair, a sigmoidectomy, a liver resection, an enterostomy, a rectum resection, a kidney stone removal, or a cystectomy.

288. A depot for sustained, controlled release of a therapeutic agent, the depot comprising:
a therapeutic region comprising the therapeutic agent; and
a control region comprising a bioresorbable polymer and a releasing agent mixed with the polymer, wherein the releasing agent is configured to dissolve when the depot is placed in vivo to form diffusion openings in the control region;
wherein the depot is configured such that, following submersion of the depot in buffer solution for seven days, the flexural strength of the depot decreases by no more than 75%.

289. The depot of clause 288, wherein the depot is configured such that, following submersion of the depot in buffer solution for seven days, the flexural strength of the depot decreases by no more than 70%.

290. The depot of clause 288, wherein the depot is configured such that, following submersion of the depot in buffer solution for seven days, the flexural strength of the depot decreases by no more than 65%.

291. The depot of clause 288, wherein the depot is configured such that, following submersion of the depot in buffer solution for seven days, the flexural strength of the depot decreases by no more than 60%.

292. The depot of clause 288, wherein the depot is configured such that, following submersion of the depot in buffer solution for seven days, the flexural strength of the depot decreases by no more than 55%.

293. The depot of clause 288, wherein the depot is configured such that, following submersion of the depot in buffer solution for seven days, the flexural strength of the depot decreases by no more than 50%.

294. The depot of clause 288, wherein the depot is configured such that, following submersion of the depot in buffer solution for seven days, the flexural strength of the depot decreases by no more than 45%.

295. A depot for sustained, controlled release of a therapeutic agent, the depot comprising:
    a therapeutic region comprising the therapeutic agent; and
    a control region comprising a bioresorbable polymer and a releasing agent mixed with the polymer, wherein the releasing agent is configured to dissolve when the depot is placed in vivo to form diffusion openings in the control region;
    wherein the depot is configured such that, following submersion of the depot in buffer solution until approximately 75% of the therapeutic agent by weight has been released, the flexural strength of the depot decreases by no more than 75%.

296. The depot of clause 295, wherein the depot is configured such that, following submersion of the depot in buffer solution until approximately 75% of the therapeutic agent by weight has been released, the flexural strength of the depot decreases by no more than 70%.

297. The depot of clause 295, wherein the depot is configured such that, following submersion of the depot in buffer solution until approximately 75% of the therapeutic agent by weight has been released, the flexural strength of the depot decreases by no more than 65%.

298. The depot of clause 295, wherein the depot is configured such that, following submersion of the depot in buffer solution until approximately 75% of the therapeutic agent by weight has been released, the flexural strength of the depot decreases by no more than 60%.

299. The depot of clause 295, wherein the depot is configured such that, following submersion of the depot in buffer solution until approximately 75% of the therapeutic agent by weight has been released, the flexural strength of the depot decreases by no more than 55%.

300. The depot of clause 295, wherein the depot is configured such that, following submersion of the depot in buffer solution until approximately 75% of the therapeutic agent by weight has been released, the flexural strength of the depot decreases by no more than 50%.

301. The depot of clause 295, wherein the depot is configured such that, following submersion of the depot in buffer solution until approximately 75% of the therapeutic agent by weight has been released, the flexural strength of the depot decreases by no more than 45%.

302. A depot for the treatment of postoperative pain via sustained, controlled release of an analgesic, comprising:
    a therapeutic region comprising the analgesic;
    a control region comprising a bioresorbable polymer and a releasing agent mixed with the polymer, wherein the releasing agent is configured to dissolve when the depot is placed in vivo to form diffusion openings in the control region;
    wherein the depot is configured to be implanted at a treatment site in vivo and, while implanted, release the analgesic at the treatment site for no less than 14 days, and
    wherein about 20% to about 40% of the analgesic is released in the first 3 days of the 14 days, and wherein at least 80% of the remaining analgesic is released in the last 11 days of the 14 days.

303. A depot for the treatment of postoperative pain via sustained, controlled release of an analgesic, comprising:
    a therapeutic region comprising the analgesic;
    a control region comprising a bioresorbable polymer and a releasing agent mixed with the polymer, wherein the releasing agent is configured to dissolve when the depot is placed in vivo to form diffusion openings in the control region;
    wherein the depot is configured to be implanted at a treatment site in vivo and, while implanted, release the analgesic at the treatment site for no less than 3 days, and
    wherein the control region does not include the analgesic at least prior to implantation of the depot at the treatment site.

304. A depot for the treatment of postoperative pain via sustained, controlled release of an analgesic, comprising:
    a therapeutic region comprising the analgesic;
    a control region comprising a bioresorbable polymer and a releasing agent mixed with the polymer, wherein the releasing agent is configured to dissolve when the depot is placed in vivo to form diffusion openings in the control region; and
    wherein the depot is configured to be implanted at a treatment site in vivo and, while implanted, release the analgesic at the treatment site for no less than 3 days, wherein the control region comprises an analgesic different from the analgesic in the therapeutic region.

305. A depot for the treatment of postoperative pain via sustained, controlled release of an analgesic, comprising:
    a therapeutic region comprising the analgesic;
    a control region comprising a bioresorbable polymer and a releasing agent mixed with the polymer, wherein the releasing agent is configured to dissolve when the depot is placed in vivo to form diffusion openings in the control region;
    wherein the depot is configured to be implanted at a treatment site in vivo and, while implanted, release the analgesic at the treatment site for no less than 3 days, and
    wherein the releasing agent is a first releasing agent and the therapeutic region includes a second releasing agent mixed with the analgesic.

306. A depot for the treatment of postoperative pain via sustained, controlled release of an analgesic, comprising:
    a therapeutic region comprising the analgesic;
    a control region comprising a bioresorbable polymer and a releasing agent mixed with the polymer, wherein the releasing agent is configured to dissolve when the depot is placed in vivo to form diffusion openings in the control region;
    wherein the depot is configured to be implanted at a treatment site in vivo and, while implanted, release the analgesic at the treatment site for no less than 3 days, and
    wherein the releasing agent is a first releasing agent and the polymer is a first polymer, and the therapeutic region includes a second releasing agent and a second polymer mixed with the analgesic.

307. A depot for the treatment of postoperative pain via sustained, controlled release of an analgesic, comprising:
a therapeutic region comprising the analgesic;
a control region comprising a bioresorbable polymer and a releasing agent mixed with the polymer, wherein the releasing agent is configured to dissolve when the depot is placed in vivo to form diffusion openings in the control region;
wherein the depot is configured to be implanted at a treatment site in vivo and, while implanted, release the analgesic at the treatment site for no less than 3 days, and
wherein a thickness of the control region is less than or equal to 1/10, 1/12.5, 1/15, 1/17.5, 1/20, 1/22.5, 1/25, 1/30, 1/40, 1/50, 1/60, 1/70, 1/80, 1/90, or 1/100 of a thickness of the therapeutic region.

308. A depot for the treatment of postoperative pain via sustained, controlled release of an analgesic, comprising:
a therapeutic region comprising the analgesic;
a control region comprising a bioresorbable polymer and a releasing agent mixed with the polymer, wherein the releasing agent is configured to dissolve when the depot is placed in vivo to form diffusion openings in the control region;
wherein the depot is configured to be implanted at a treatment site in vivo and, while implanted, release the analgesic at the treatment site for no less than 3 days, and
wherein a thickness of the control region is less than or equal to 1/75 of a thickness of the therapeutic region.

309. A depot for the treatment of postoperative pain via sustained, controlled release of an analgesic, comprising:
a therapeutic region comprising the analgesic;
a control region comprising a bioresorbable polymer and a releasing agent mixed with the polymer, wherein the releasing agent is configured to dissolve when the depot is placed in vivo to form diffusion openings in the control region;
wherein the depot is configured to be implanted at a treatment site in vivo and, while implanted, release the analgesic at the treatment site for no less than 3 days, and
wherein a thickness of the control region is less than or equal to 1/100 of a thickness of the therapeutic region.

310. A depot for the treatment of postoperative pain via sustained, controlled release of an analgesic, comprising:
a therapeutic region comprising the analgesic; and
a control region comprising a bioresorbable polymer and a releasing agent mixed with the polymer, wherein the releasing agent is configured to dissolve when the depot is placed in vivo to form diffusion openings in the control region,
wherein the depot is configured to be implanted at a treatment site in vivo and, while implanted, release the analgesic at the treatment site for no less than 3 days, and
wherein the first control layer includes a first amount of the releasing agent and the second control layer includes a second amount of the releasing agent different than the first amount.

311. A depot for the treatment of postoperative pain via sustained, controlled release of an analgesic, comprising:
a therapeutic region comprising the analgesic;
a control region comprising a bioresorbable polymer and a releasing agent mixed with the polymer, wherein the releasing agent is configured to dissolve when the depot is placed in vivo to form diffusion openings in the control region;
wherein the depot is configured to be implanted at a treatment site in vivo and, while implanted, release the analgesic at the treatment site for no less than 3 days,
wherein the depot has a total surface area comprising the exposed surface area of the cover region plus the exposed surface area of the therapeutic region, and
wherein, when the depot is initially positioned at the treatment site in vivo, a ratio of the exposed surface area of the therapeutic region to the exposed surface area of the cover region is from about 5% to about 20%, or from about 5% to about 15%, or from about 5% to about 10%.

312. A depot for the controlled, sustained release of a therapeutic agent, comprising:
a therapeutic region comprising the therapeutic agent, the therapeutic region elongated along a first axis; and
a control region at least partially surrounding the therapeutic region and elongated along the first axis, the control region comprising a bioresorbable polymer and a releasing agent mixed with the polymer, wherein the releasing agent is configured to dissolve when the depot is placed in vivo to form diffusion openings in the control region;
wherein the depot is configured to be implanted at a treatment site in vivo and, while implanted, release the therapeutic agent at the treatment site for a period of time not less than 3 days.

313. The depot of any one of the preceding clauses, wherein the depot is at least 5 times longer along the first axis than a maximum transverse dimension along a second axis orthogonal to the first.

314. The depot of any one of the preceding clauses, wherein the depot is at least 10 times longer along the first axis than a maximum transverse dimension along a second axis orthogonal to the first.

315. The depot of any one of the preceding clauses, wherein the depot is substantially columnar.

316. The depot of any one of the preceding clauses, wherein the depot is substantially cylindrical.

317. The depot of any one of the preceding clauses, wherein the therapeutic region is substantially cylindrical.

318. The depot of any one of the preceding clauses, further comprising at least one opening extending through the therapeutic region.

319. The depot of any one of the preceding clauses, wherein the opening forms a cylindrical lumen extending parallel to the first axis.

320. The depot of any of the preceding clauses, wherein the opening comprises a lumen extending along a second axis substantially perpendicular to the first axis.

321. The depot of any of the preceding clauses, further comprising a plurality of elongated openings extending parallel to the second axis.

322. The depot of any one of the preceding clauses, wherein the therapeutic region comprises a plurality of separate elongated sub-regions extending substantially parallel to the first axis.

323. The depot of any one of the preceding clauses, wherein each of the elongated sub-regions is substantially cylindrical.

324. The depot of any one of the preceding clauses, wherein each of the elongated sub-regions are radially separated from one another by the control region.

325. The depot of any one of the preceding clauses, wherein a radially outermost dimension of the depot varies along the first axis.

326. The depot of any one of the preceding clauses, wherein a radially outermost dimension of the therapeutic region varies along the first axis.

327. The depot of any one of the preceding clauses, wherein the therapeutic region is a series of separate regions, covered by and connected by a continuous control region.

328. The depot of the preceding clauses, wherein the control region is narrower in the regions without an internal therapeutic region.

329. The depot of the preceding clauses, wherein the control region is designed to bend or break during or after delivery.

330. The depot of any one of the preceding clauses, wherein the control region has a variable thickness along a length of the depot along the first axis.

331. The depot of any one of the preceding clauses, wherein the control region has a thickness that varies radially around the first axis.

332. The depot of any one of the preceding clauses, wherein the variable thickness of the control region causes the depot to curve or bend when deployed in vivo.

333. The depot of any one of the preceding clauses, wherein the depot is configured to curve or bend preferentially when placed in contact with physiological fluids in vivo.

334. The depot of any one of the preceding clauses, wherein the depot comprises an elongated polymer strip having a length between its longitudinal ends and a width between lateral edges, the length greater than the width, and wherein the depot has a preset shape in an expanded configuration in which the strip is curled about an axis with the width of the strip facing the axis, thereby forming a ring-like shape.

335. The depot of any one of the preceding clauses, wherein the depot forms an annular or semi-annular shape.

336. The depot of any one of the preceding clauses, wherein the depot has a first region and a second region, each extending longitudinally and coextensive with one another over all or a portion of their respective lengths, the first region having a first elasticity and the second region having a second elasticity less than the first elasticity.

337. The depot of the preceding clause, wherein the depot has been stretched beyond the elastic hysteresis point of the second region such that, when released from a delivery device, the depot transitions from a straightened state to a curved state in which the second region pulls the depot into the curved shape.

338. The depot of any one of the preceding clauses, wherein the depot has a first region and a second region, each extending longitudinally and coextensive with one another over all or a portion of their respective lengths, the first region being more hydrophilic than the second region.

339. The depot of the preceding clause, wherein, when released from a delivery device, the depot transitions from a straightened state to a curved state in which the second region pulls the depot into the curved shape.

340. The depot of any one of the preceding clauses, wherein the control region has first and second portions having a first thickness, the first and second portions separated along the first axis by a third portion having a second thickness different from the first.

341. The depot of any one of the preceding clauses, wherein the depot extends along the first axis from a first end to a second end, and wherein the control region has a thickness that increases from the first end to the second end.

342. The depot of any one of the preceding clauses, wherein the depot extends along the first axis from a first end to a second end, and wherein the control region does not cover the therapeutic region at the first end of the depot.

343. The depot of any one of the preceding clauses, wherein the depot extends along the first axis from a first end to a second end, and wherein the control region does not cover the therapeutic region at the first end or the second end.

344. The depot of any one of the preceding clauses, wherein the control region has a plurality of discrete openings formed therein.

345. The depot of any one of the preceding clauses, wherein the control region has an opening elongated along the first axis.

346. The depot of any one of the preceding clauses, wherein the elongated opening in the control region extends along the entire length of the depot.

347. The depot of any one of the preceding clauses, wherein the control region comprises a plurality of circular apertures formed therein.

348. The depot of any one of the preceding clauses, wherein the therapeutic region is a first therapeutic region, the depot further comprising a second therapeutic region, each of the first and second therapeutic regions being elongated along the first axis, wherein the first and second therapeutic regions are configured to release the therapeutic agent at different rates.

349. The depot of any one of the preceding clauses, wherein the therapeutic region is a first therapeutic region, the depot further comprising a second therapeutic region, each of the first and second therapeutic regions being elongated along the first axis, wherein the first and second therapeutic regions comprise different therapeutic agents.

350. The depot of any one of the preceding clauses, wherein the first and second therapeutic regions are coaxially aligned.

351. The depot of any one of the preceding clauses, wherein the first and second therapeutic regions extend parallel to one another along a length of the depot.

352. The depot of any one of the preceding clauses, further comprising a barrier region configured to dissolve in vivo more slowly than the control region or the therapeutic region.

353. The depot of any one of the preceding clauses, further comprising a barrier region configured to slow the passage of physiological fluids in vivo therethrough to the control region or the therapeutic region.

354. The depot of any one of the preceding clauses, wherein the barrier region is disposed coaxially with the therapeutic region, such that the control region at least partially surrounds both the therapeutic region and the barrier region.

355. The depot of any one of the preceding clauses, wherein the barrier region is a first barrier region, the depot further comprising a second barrier region, the first and second barrier regions separated axially from one another by the therapeutic region.

356. The depot of any one of the preceding clauses, wherein the first and second barrier regions have different dimensions.

357. The depot of any one of the preceding clauses, wherein the barrier region is disposed coaxially with the control region, such that the control region and barrier region together at least partially surround the therapeutic region.

358. The depot of any one of the preceding clauses, wherein the first and second barrier regions are separated axially from one another by the control region.

359. The depot of any one of the preceding clauses, wherein the depot extends along the first axis from a first end to a second end, and wherein the barrier region is disposed over the first end of the depot.

360. The depot of any one of the preceding clauses, wherein the depot extends along the first axis from a first end to a second end, and wherein the barrier region comprises a first end cap disposed over the first end of the depot and a second end cap disposed over the second end of the depot.

361. The depot of any one of the preceding clauses, wherein the therapeutic region comprises a covered portion and an exposed portion, wherein the covered portion is covered by the control region such that, when the depot is initially positioned at the treatment site in vivo, the control region is between the covered portion of the therapeutic region and physiologic fluids at the treatment site and the exposed portion of the therapeutic region is exposed to the physiologic fluids.

362. The depot of any one of the preceding clauses, wherein the therapeutic agent in the therapeutic region comprises at least 50% of the total weight of the depot.

363. The depot of any one of the preceding clauses, wherein the period of time is not less not less than 7 days, than 15 days, not less than 30 days, not less than 45 days, not less than 60 days, or not less than 90 days.

364. The depot of any one of the preceding clauses, wherein about 40% to about 60% of the therapeutic agent in the therapeutic region is released in the first half of the period of time.

365. The depot of any one of the preceding clauses, wherein at least 90% of the therapeutic agent in the therapeutic region is released within the period of time.

366. The depot of any one of the preceding clauses, wherein the depot is configured to release about 2 µg to about 5 mg of the therapeutic agent to the treatment site per day.

367. The depot of any one of the preceding clauses, wherein the depot is configured to release the therapeutic agent at the treatment site in vivo for no less than 8 days, no less than 9 days, no less than 10 days, no less than 11 days, no less than 12 days, no less than 13 days, no less than 14 days, no less than 15 days, no less than 16 days, no less than 17 days, no less than 18 days, no less than 19 days, no less than 20 days, no less than 21 days, no less than 22 days, no less than 23 days, no less than 24 days, no less than 25 days, no less than 26 days, no less than 27 days, no less than 28 days, no less than 29 days, no less than 30 days, no less than 40 days, no less than 50 days, no less than 60 days, no less than 70 days, no less than 90 days, no less than 100 days, no less than 200 days, no less than 300 days, or no less than 365 days.

368. The depot of any one of the preceding clauses, wherein the therapeutic agent is released at a substantially steady state rate throughout the period of time.

369. The depot of any one of the preceding clauses, wherein,
the depot has a total surface area comprising the exposed surface area of the control region plus the exposed surface area of the therapeutic region, and
when the depot is initially positioned at the treatment site in vivo, a ratio of the exposed surface area of the therapeutic region to the exposed surface area of the control region is from about 5% to about 20%, or from about 5% to about 15%, or from about 5% to about 10%.

370. The depot of any one of the preceding clauses, wherein the exposed surface area of the control region is less than the exposed surface area of the therapeutic region.

371. The depot of any one of the preceding clauses, wherein the exposed surface area of the control region is greater than the exposed surface area of the therapeutic region.

372. The depot of any one of the preceding clauses, wherein the control region is a first control region, and wherein the depot comprises a second control region.

373. The depot of any one of the preceding clauses, wherein the first control region is disposed at a first side of the therapeutic region and the second control region is disposed at a second side of the therapeutic region opposite the first side.

374. The depot of any one of the preceding clauses, wherein the depot comprises a plurality of control regions and a plurality of therapeutic regions, and wherein each of the therapeutic regions is separated from an adjacent one of the therapeutic regions by one or more control regions.

375. The depot of any one of the preceding clauses, wherein the depot comprises from about 2 to about 10 therapeutic regions.

376. The depot of any one of the preceding clauses, wherein the control region comprises a first control layer and a second control layer.

377. The depot of any one of the preceding clauses, wherein the second control layer is adjacent to the therapeutic region and the first control layer encapsulates/encloses the therapeutic region and the second control layer.

378. The depot of any one of the preceding clauses, wherein the first control layer and the second control layer together enclose the therapeutic region.

379. The depot of any one of the preceding clauses, wherein the first control layer comprises a first plurality of sub-layers and the second control layer comprises a second plurality of sub-layers.

380. The depot of any one of the preceding clauses, wherein the first control layer includes a first amount of the releasing agent and the second control layer includes a second amount of the releasing agent different than the first amount.

381. The depot of any one of the preceding clauses, wherein the second control layer is positioned between the first control layer and the therapeutic region, and wherein the first control layer includes a first concentration of the releasing agent and the second control layer includes a second concentration of the releasing agent greater than the first concentration.

382. The depot of any one of the preceding clauses, wherein the second control layer is positioned between the first control layer and the therapeutic region, and wherein the first control layer includes a first concentration of the releasing agent and the second control layer includes a second concentration of the releasing agent less than the first concentration.

383. The depot of any one of the preceding clauses, wherein the second control layer is positioned between the first control layer and the therapeutic region, and wherein the first control layer includes up to 5% by weight of the releasing agent, up to 10% by weight of the releasing agent, up to 15% by weight of the releasing agent, up to 20% by weight of the releasing agent, up to 25% by weight of the releasing agent, up to 30% by weight of the releasing agent, up to 35% by weight of the releasing agent, up to 40% by weight of the releasing agent, up to 45% by weight of the releasing agent, or 50% by weight of the releasing agent; and the second control layer includes up to 5% by weight of the releasing agent, up to 10% by weight of the releasing agent, up to 15% by weight of the releasing agent, up to 20% by weight of the releasing agent, up to 25% by weight of the releasing agent, up to 30% by weight of the releasing agent, up to 35% by weight of the releasing agent, up to 40% by weight of the releasing agent, up to 45% by weight of the releasing agent, or up to 50% by weight of the releasing agent.

384. The depot of any one of the preceding clauses, wherein the second control layer is positioned between the first control layer and the therapeutic region, and wherein the first control layer includes a first amount of the releasing agent and the second control layer includes a second amount of the releasing agent, the second amount being at least 2×, at least 3×, at least 4×, or at least 5× the first amount.

385. The depot of any one of the preceding clauses, wherein a thickness of the control region is less than or equal to 1/10, 1/12.5, 1/15, 1/17.5, 1/20, 1/22.5, 1/25, 1/27.5, 1/30, 1/32.5, 1/35, 1/37.5, 1/40, 1/42.5, 1/45, 1/47.5, 1/50, 1/55, 1/60, 1/65, 1/70, 1/75, 1/80, 1/85, 1/90, 1/95, or 1/100 of a thickness of the therapeutic region.

386. The depot of any one of the preceding clauses, wherein the depot comprises an elongate columnar structure configured to be implanted in a patient.

387. The depot of any one of the preceding clauses, wherein the depot comprises one of a plurality of beads or microspheres.

388. The depot of any one of the preceding clauses, wherein the beads or microspheres have varying release profiles.

389. The depot of any one of the preceding clauses, wherein the beads or microspheres comprise varying amounts of therapeutic agent.

390. The depot of any one of the preceding clauses, wherein the beads or microspheres comprise varying thicknesses of their respective control regions.

391. The depot of any one of the preceding clauses, wherein the beads of microspheres have varying dimensions.

392. The depot of any one of the preceding clauses, wherein the depot comprises one of a plurality of pellets.

393. The depot of any one of the preceding clauses, wherein the pellets have varying release profiles.

394. The depot of any one of the preceding clauses, wherein the pellets comprise varying amounts of therapeutic agent.

395. The depot of any one of the preceding clauses, wherein the pellets comprise varying thicknesses of their respective control regions.

396. The depot of any one of the preceding clauses, wherein the pellets have varying dimensions.

397. The depot of any one of the preceding clauses, wherein the pellets are substantially cylindrical.

398. The depot of any one of the preceding clauses, wherein the depot comprises a plurality of substantially cylindrical beads, each comprising a therapeutic region and control region and wherein the plurality of beads are substantially aligned along a common longitudinal axis.

399. The depot of any one of the preceding clauses, wherein the depot is biodegradable and/or bioerodible.

400. The depot of any one of the preceding clauses, wherein the depot is a flexible solid that is structurally capable of being handled by a clinician during the normal course of a surgery without breaking into multiple pieces and/or losing its general shape.

401. The depot of any one of the preceding clauses, wherein the depot is configured to be subcutaneously placed within a patient and release the therapeutic agent in vivo for up to 7 days without breaking into multiple pieces.

402. The depot of any one of the preceding clauses, wherein the depot has a surface area and a volume, and wherein a ratio of the surface area to volume is at least 1.

403. The depot of any one of the preceding clauses, wherein the diffusion openings include at least one or more pores and/or one or more channels.

404. The depot of any one of the preceding clauses, wherein dissolution of the releasing agent following in vivo placement in the treatment site causes the control region and the therapeutic region to transition from a state of lesser porosity to a state of greater porosity to facilitate the release of the therapeutic agent from the depot.

405. The depot of any one of the preceding clauses, wherein the releasing agent is a first releasing agent and the therapeutic region includes a second releasing agent mixed with the therapeutic agent.

406. The depot of any one of the preceding clauses, wherein the releasing agent is a first releasing agent and the polymer is a first polymer, and the therapeutic region includes a second releasing agent and a second polymer mixed with the therapeutic agent.

407. The depot of any one of the preceding clauses, wherein the first releasing agent is the same as the second releasing agent.

408. The depot of any one of the preceding clauses, wherein the first releasing agent is the different than the second releasing agent.

409. The depot of any one of the preceding clauses, wherein a concentration of the first releasing agent within the control region is the greater than a concentration of the second releasing agent within the therapeutic region.

410. The depot of any one of the preceding clauses, wherein a concentration of the first releasing agent within the control region is the less than a concentration of the second releasing agent within the therapeutic region.

411. The depot of any one of the preceding clauses, wherein a concentration of the first releasing agent within the control region is the same as a concentration of the second releasing agent within the therapeutic region.

412. The depot of any one of the preceding clauses, wherein a concentration of the first releasing agent within the control region is different than a concentration of the second releasing agent within the therapeutic region.

413. The depot of any one of the preceding clauses, wherein the therapeutic region includes a plurality of microlayers.

414. The depot of any one of the preceding clauses, wherein the mass of the therapeutic agent comprises at least 50% of the mass of the depot.

415. The depot of any one of the preceding clauses, wherein the ratio of the mass of the therapeutic agent in the depot to the depot polymer mass is at least at least 1:1, at least 2:1, 3:1, at least 4:1, at least 5:1, at least 6:1, at least 7:1, at least 8:1, at least 9:1, at least 10:1, or at least 16:1.

416. The depot of any one of the preceding clauses, wherein the therapeutic region comprises a bioresorbable polymer and the therapeutic agent.

417. The depot of any one of the preceding clauses, wherein the therapeutic region includes at least 40% by weight of the therapeutic agent, at least 50% by weight of the therapeutic agent, at least 60% by weight of the therapeutic agent, 60% by weight of therapeutic agent, at least 70% by weight of the therapeutic agent, at least 80% by weight of the therapeutic agent, at least 90% by weight of the therapeutic agent, or 100% by weight of the therapeutic agent.

418. The depot of any one of the preceding clauses, wherein the depot includes at least 15% by weight of the therapeutic agent, at least 20% by weight of the therapeutic agent, at least 30% by weight of the therapeutic agent, at least 40% by weight of the therapeutic agent, at least 50% by weight of the therapeutic agent, at least 60% by weight of the therapeutic agent, at least 70% by weight of the therapeutic agent, at least 80% by weight of the therapeutic agent, at least 90% by weight of the therapeutic agent, 99% by weight of the therapeutic agent, or 99.99% by weight of the therapeutic agent.

419. The depot of any one of the preceding clauses, wherein the releasing agent is a non-ionic surfactant.

420. The depot of any one of the preceding clauses, wherein the releasing agent has hydrophilic properties.

421. The depot of any one of the preceding clauses, wherein the releasing agent is a polysorbate.

422. The depot of any one of the preceding clauses, wherein the releasing agent is Tween 20.

423. The depot of any one of the preceding clauses, wherein the releasing agent is Tween 80.

424. The depot of any one of the preceding clauses, wherein the releasing agent is non-polymeric.

425. The depot of any one of the preceding clauses, wherein the releasing agent is not a plasticizer.

426. The depot of any one of the preceding clauses, wherein the polymer is configured to degrade only after substantially all of the therapeutic agent has been released from the depot.

427. The depot of any one of the preceding clauses, wherein the polymer is a copolymer.

428. The depot of any one of the preceding clauses, wherein the polymer is a terpolymer.

429. The depot of any one of the preceding clauses, wherein the polymer includes at least one of polyglycolide (PGA), polycaprolactone (PCL), poly(DL-lactic acid) (PLA), poly(alpha-hydroxy acids), poly(lactide-co-glycolide) (PLGA or DLG), poly(DL-lactide-co-caprolactone) (DL-PLCL), poly(trimethylene carbonate) (PTMC), polydioxanone (PDO), poly(4-hydroxy butyrate) (PHB), polyhydroxyalkanoates (PHA), poly(phosphazene), polyphosphate ester), poly(amino acid), polydepsipeptides, poly(butylene succinate) (PBS), polyethylene oxide, polypropylene fumarate, polyiminocarbonates, poly(lactide-co-caprolactone) (PLCL), poly(glycolide-co-caprolactone) (PGCL) copolymer, poly(D,L-lactic acid), polyglycolic acid, poly(L-lactide-co-D,L-lactide), poly(L-lactide-co-glycolide), poly (D,L-lactide-co-glycolide), poly(gycolide-trimethylene carbonate), poly(ethyl glutamate-co-glutamic acid), poly(tert-butyloxy-carbonylmethyl glutamate), poly(glycerol sebacate), tyrosine-derived polycarbonate, poly 1,3-bis-(p-carboxyphenoxy) hexane-co-sebacic acid, polyphosphazene, ethyl glycinate polyphosphazene, polycaprolactone co-butylacrylate, a copolymer of polyhydroxybutyrate, a copolymer of maleic anhydride, a copolymer of poly(trimethylene carbonate), polyethylene glycol (PEG), hydroxypropylmethylcellulose and cellulose derivatives, polysaccharides (such as hyaluronic acid, chitosan and starch), proteins (such as gelatin and collagen) or PEG derivatives, polyaspirins, polyphosphagenes, pre-gelatinized starch, hyaluronic acid, chitosans, gelatin, alginates, albumin, fibrin, vitamin E analogs, such as alpha tocopheryl acetate, d-alpha tocopheryl succinate, D-lactide, D,L-lactide, L-lactide, D,L-lactide-caprolactone (DL-CL), D,L-lactide-glycolide-caprolactone (DL-G-CL), dextrans, vinylpyrrolidone, polyvinyl alcohol (PVA), PVA-g-PLGA, PEGT-PBT copolymer (polyactive), methacrylates, poly(N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate) hydroxypropyl cellulose, hydroxypropyl methylcellulose, hydroxyethyl methylcellulose, carboxymethylcellulose or salts thereof, Carbopol®, poly(hydroxyethylmethacrylate), poly(methoxyethylmethacrylate), poly(methoxyethoxy-ethylmethacrylate), polymethylmethacrylate (PMMA), polyvinyl alcohols, propylene glycol, and poly(DL-lactide-co-glycolide-co-caprolactone).

430. The depot of any one of the preceding clauses, wherein the polymer is one of poly(DL-lactide-co-glycolide-co-caprolactone) and poly(DL-lactide-co-glycolide) (PLGA).

431. The depot of any one of the preceding clauses, wherein the polymer is poly(DL-lactide-co-glycolide-co-caprolactone) in a molar ratio of about 60:30:10.

432. The depot of any one of the preceding clauses, wherein the polymer is poly(DL-lactide-co-glycolide) (PLGA) in a molar ratio of between about 10:90 and about 90:10.

433. The depot of any one of the preceding clauses, wherein the polymer is poly(DL-lactide-co-glycolide) (PLGA) in a molar ratio of about 50:50.

434. The depot of any one of the preceding clauses, wherein the polymer is ester-terminated.

435. The depot of any one of the preceding clauses, wherein the polymer is a terpolymer that includes three polymers selected from the following: polyglycolide (PGA), polycaprolactone (PCL), poly(L-lactic acid) (PLA), poly (DL-lactic acid) (PLA), poly(trimethylene carbonate) (PTMC), polydioxanone (PDO), poly(4-hydroxy butyrate) (PHB), polyhydroxyalkanoates (PHA), poly(phosphazene), and polyethylene glycol.

436. The depot of any one of the preceding clauses, wherein the polymer is a first polymer, and the therapeutic region includes a second polymer mixed with the therapeutic agent.

437. The depot of any one of the preceding clauses, wherein the first polymer and/or the second polymer include at least one of polyglycolide (PGA), polycaprolactone (PCL), poly(DL-lactic acid) (PLA), poly(alpha-hydroxy acids), poly(lactide-co-glycolide) (PLGA or DLG), poly (DL-lactide-co-caprolactone) (DL-PLCL), poly(trimethylene carbonate) (PTMC), polydioxanone (PDO), poly(4-hydroxy butyrate) (PHB), polyhydroxyalkanoates (PHA), poly(phosphazene), polyphosphate ester), poly(amino acid), polydepsipeptides, poly(butylene succinate) (PBS), polyethylene oxide, polypropylene fumarate, polyiminocarbonates, poly(lactide-co-caprolactone) (PLCL), poly(glycolide-co-caprolactone) (PGCL) copolymer, poly(D,L-lactic acid), polyglycolic acid, poly(L-lactide-co-D,L-lactide), poly(L-lactide-co-glycolide), poly(D,L-lactide-co-glycolide), poly (gycolide-trimethylene carbonate), poly(ethyl glutamate-co-glutamic acid), poly(tert-butyloxy-carbonylmethyl glutamate), poly(glycerol sebacate), tyrosine-derived polycarbonate, poly 1,3-bis-(p-carboxyphenoxy) hexane-co-sebacic acid, polyphosphazene, ethyl glycinate polyphosphazene, polycaprolactone co-butylacrylate, a copolymer of polyhydroxybutyrate, a copolymer of maleic anhydride, a copolymer of poly(trimethylene carbonate), polyethylene glycol (PEG), hydroxypropylmethylcellulose and cellulose derivatives, polysaccharides (such as hyaluronic acid, chitosan and starch), proteins (such as gelatin and collagen) or PEG derivatives, polyaspirins, polyphosphagenes, pre-gelatinized starch, hyaluronic acid, chitosans, gelatin, alginates, albumin, fibrin, vitamin E analogs, such as alpha tocopheryl acetate, d-alpha tocopheryl succinate, D-lactide, D,L-lactide, L-lactide, D,L-lactide-caprolactone (DL-CL), D,L-lactide-glycolide-caprolactone (DL-G-CL), dextrans, vinylpyrrolidone, polyvinyl alcohol (PVA), PVA-g-PLGA, PEGT-PBT copolymer (polyactive), methacrylates, poly(N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate) hydroxypropyl cellulose, hydroxypropyl methylcellulose, hydroxyethyl methylcellulose, carboxymethylcellulose or salts thereof, Carbopol®, poly(hydroxyethylmethacrylate), poly(methoxyethylmethacrylate), poly(methoxyethoxy-ethylmethacrylate), polymethylmethacrylate (PMMA), polyvinyl alcohols, propylene glycol, poly(DL-lactide-co-glycolide-co-caprolactone).

438. The depot of any one of the preceding clauses, wherein the first polymer and/or the second polymer selected from the following: poly(DL-lactide-co-glycolide-co-caprolactone) and poly(DL-lactide-co-glycolide) (PLGA).

439. The depot of any one of the preceding clauses, wherein the first polymer and/or the second polymer is poly(DL-lactide-co-glycolide-co-caprolactone) and has a molar ratio of about 60:30:10.

440. The depot of any one of the preceding clauses, wherein the first polymer and/or the second polymer is poly(DL-lactide-co-glycolide) and has a molar ratio of about 50:50.

441. The depot of any one of the preceding clauses, wherein the first polymer and/or the second polymer is ester-terminated.

442. The depot of any one of the preceding clauses, wherein the first polymer and/or the second polymer is a terpolymer that includes three polymers selected from the following: polyglycolide (PGA), polycaprolactone (PCL), poly(L-lactic acid) (PLA), poly(trimethylene carbonate) (PTMC), polydioxanone (PDO), poly(4-hydroxy butyrate) (PHB), polyhydroxyalkanoates (PHA), poly(phosphazene), and polyethylene glycol.

443. The depot of any one of the preceding clauses, wherein the ratio of the polymer to the releasing agent in the control region is at least 1:1, at least 2:1, at least 3:1, at least 4:1, at least 5:1, at least 6:1, at least 7:1, at least 8:1, at least 9:1, at least 10:1, or at least 15:1

444. The depot of any one of the preceding clauses, wherein the releasing agent is configured to dissolve when the depot is placed in contact with phosphate buffered saline to form diffusion openings.

445. A system for delivering a therapeutic agent to a treatment site, the system comprising:
  a shaft having a lumen;
  a pusher operatively coupled to the lumen; and
  a depot disposed within the lumen and configured to be displaced from the shaft via activation of the pusher, the depot comprising:
    a therapeutic region comprising the therapeutic agent, the therapeutic region elongated along a first axis;
    a control region at least partially surrounding the therapeutic region and elongated along the first axis, the control region comprising a bioresorbable polymer and a releasing agent mixed with the polymer, wherein the releasing agent is configured to dissolve when the depot is placed in vivo to form diffusion openings in the control region; and
    wherein the depot is configured to be implanted at a treatment site in vivo and, while implanted, release the therapeutic agent at the treatment site for a period of time not less than 3 days.

446. The system of clause 445, wherein the depot comprises the depot of any one of the preceding clauses.

447. The system of clause 445, wherein the shaft comprises a needle, and wherein the pusher comprises a plunger.

448. A system for delivering a therapeutic agent to a treatment site, the system comprising:
  an expandable member configured to be expanded from a reduced-volume configuration for delivery to an expanded-volume configuration for deployment at the treatment site; and
  a depot carried by the expandable member, the depot comprising:
    a therapeutic region comprising the therapeutic agent, the therapeutic region elongated along a first axis;
    a control region at least partially surrounding the therapeutic region and elongated along the first axis, the control region comprising a bioresorbable polymer and a releasing agent mixed with the polymer, wherein the releasing agent is configured to dissolve when the depot is placed in vivo to form diffusion openings in the control region; and wherein the depot is configured to be implanted at a treatment site in vivo and, while implanted, release the therapeutic agent at the treatment site for a period of time not less than 3 days.

449. The system of clause 448, wherein the depot comprises the depot of any one of the preceding clauses.

450. The system of any one of the preceding clauses, wherein the expandable member comprises a stent.

451. The system of any one of the preceding clauses, wherein the expandable member comprises a spherical, semi-spherical, ellipsoid, or semi-ellipsoid structure.

452. The system of any one of the preceding clauses, wherein the expandable member comprises a curved outer surface, and wherein the depot is disposed over the curved outer surface.

453. The system of any one of the preceding clauses, wherein the depot substantially covers at least one surface of the expandable member.

454. The system of any one of the preceding clauses, wherein the expandable member comprises a shape-memory material.

455. The system of any one of the preceding clauses, wherein the depot is disposed in a lubricious coating and wherein the lubricious coating comprises a hydrogel.

456. A method for delivering a therapeutic agent to a treatment site within a body:
  positioning a depot at a treatment site in vivo having physiologic fluids, the depot comprising:
    a therapeutic region comprising the therapeutic agent, the therapeutic region elongated along a first axis;
    a control region at least partially surrounding the therapeutic region and elongated along the first axis, the control region comprising a bioresorbable polymer and a releasing agent mixed with the polymer; and allowing the releasing agent to dissolve at the treatment site to form diffusion openings in the control region, thereby releasing the therapeutic agent from the depot to the treatment site for a period of time not less than 3 days.

457. The method of clause 456, wherein the depot comprises the depot of any one of the preceding clauses.

458. The method of any one of the preceding clauses, wherein positioning the depot comprises inserting the depot subcutaneously at the treatment site via a needle.

459. The method of any one of the preceding clauses, wherein positioning the depot comprises positioning the depot proximate to a nerve bundle at the treatment site.

460. The method of any one of the preceding clauses, further comprising dissolving the releasing agent at a first rate and degrading the polymer at a second rate, wherein the first rate is greater than the second rate.

461. The method of any one of the preceding clauses, further comprising dissolving the releasing agent in response to contact between the control region and the physiologic fluids at the treatment site.

462. The method of any one of the preceding clauses, further comprising creating diffusion openings in the control region via the dissolution of the releasing agent in response to physiologic fluids at the treatment site.

463. The method of any one of the preceding clauses, wherein the releasing agent is a first releasing agent and the therapeutic region includes a second releasing agent, and wherein the method further comprises creating microchannels in the therapeutic region and the control region via dissolution of the first and/or second releasing agents.

464. The method of any one of the preceding clauses, wherein at least some of the microchannels penetrate both the therapeutic region and the control region.

465. The method of any one of the preceding clauses, further including increasing a porosity of the depot via dissolution of the releasing agent.

466. The method of any one of the preceding clauses, wherein the therapeutic agent is released one or more times in substantially discrete doses after implantation.

467. The method of any one of the preceding clauses, wherein the therapeutic agent is released at a substantially steady state rate for the period of time.

468. The method of any one of the preceding clauses, wherein the period of time is not less than 8 days, no less than 9 days, no less than 10 days, no less than 11 days, no less than 12 days, no less than 13 days, no less than 14 days, no less than 15 days, no less than 16 days, no less than 17 days, no less than 18 days, no less than 19 days, no less than 20 days, no less than 21 days, no less than 22 days, no less than 23 days, no less than 24 days, no less than 25 days, no less than 26 days, no less than 27 days, no less than 28 days, no less than 29 days, no less than 30 days, no less than 40 days, no less than 50 days, no less than 60 days, no less than 70 days, no less than 90 days, no less than 100 days, no less than 200 days, no less than 300 days, or no less than 365 days.

469. The method of any one of the preceding clauses, wherein the depot is a first depot and the method further comprises positioning a second depot at the treatment site.

470. A method, comprising:
positioning a depot within an intracapsular space of a knee joint, the depot comprising:
a polymer matrix including a polymer having an acid as a degradation byproduct, wherein at least a portion of the polymer matrix has a volume with a minimum cross-sectional dimension of at least 400 µm before degradation of the polymer begins;
wherein, when the depot is (a) submerged in aqueous media for a duration sufficient for a molecular weight of the polymer and/or a mass of the polymer matrix to decrease by about 25% to about 75%, and (b) subsequently submerged in a buffer solution and broken up such that an interior region of the depot is in fluid communication with the surrounding buffer solution, a pH of the surrounding buffer solution is within about 0.5 units of the pH of the buffer solution before the depot is placed in the buffer solution.

471. The method of clause 470, wherein positioning the depot at the knee joint includes positioning the depot at a suprapatellar region of the intracapsular space.

472. The method of any one of the preceding clauses, wherein positioning the depot at the knee joint includes positioning the depot at a lateral gutter of the intracapsular space.

473. The method of any one of the preceding clauses, wherein positioning the depot at the knee joint includes positioning the depot at a medial gutter of the intracapsular space.

474. The method of any one of the preceding clauses, wherein positioning the depot at the knee joint includes positioning the depot at a lateral gutter of the intracapsular space.

475. The method of any one of the preceding clauses, wherein the polymer is a polyhydoxyalkanoate (PHA).

476. The method of any one of the preceding clauses, wherein the polymer is synthetic.

477. The method of any one of the preceding clauses, wherein the polymer is naturally occurring.

478. The method of any one of the preceding clauses, wherein the polymer is a polyester.

479. The method of any one of the preceding clauses, wherein the polymer includes one or more of poly(lactic acid), polylactide, and poly(glycolic acid).

480. The method of any one of the preceding clauses, wherein the acid is a carboxylic acid.

481. The method of any one of the preceding clauses, wherein the acid is one or both of lactic acid and glycolic acid.

482. The method of any one of the preceding clauses, wherein submersion in the aqueous solution is continuous over the duration.

483. The method of any one of the preceding clauses, further comprising a releasing agent mixed with the polymer.

484. The method of any one of the preceding clauses, further comprising a therapeutic agent mixed with the polymer.

485. The method of any one of the preceding clauses, wherein the duration is sufficient for a molecular weight of the polymer matrix to be reduced by about 25% to about 75%, and the duration is sufficient for a mass of the polymer matrix to be reduced by about 25% to about 75%.

486. The method of any one of the preceding clauses, wherein the depot is submerged in the aqueous solution for a duration sufficient for the molecular weight or the mass of the polymer matrix to decrease by about 30% to about 70%.

487. The method of any one of the preceding clauses, wherein the depot is submerged in the aqueous solution for a duration sufficient for the molecular weight or the mass of the polymer matrix to decrease by about 35% to about 65%.

488. The method of any one of the preceding clauses, wherein the depot is submerged in the aqueous solution for a duration sufficient for the molecular weight or the mass of the polymer matrix to decrease by about 40% to about 60%.

489. The method of any one of the preceding clauses, wherein the depot is submerged in the aqueous solution for a duration sufficient for the molecular weight or the mass of the polymer matrix to decrease by about 45% to about 55%.

490. The method of any one of the preceding clauses, wherein the polymer comprises at least 10% w/w of the polymer matrix.

491. The method of any one of the preceding clauses, wherein the polymer comprises at least 15% w/w of the polymer matrix.

492. The method of any one of the preceding clauses, wherein the polymer comprises at least 20% w/w of the polymer matrix.

493. The method of any one of the preceding clauses, wherein the polymer comprises at least 25% w/w of the polymer matrix.

494. The method of any one of the preceding clauses, wherein the polymer comprises at least 30% w/w of the polymer matrix.

495. The method of any one of the preceding clauses, wherein the polymer comprises at least 35% w/w of the polymer matrix.

496. The method of any one of the preceding clauses, wherein the polymer comprises at least 40% w/w of the polymer matrix.

497. The method of any one of the preceding clauses, wherein the polymer comprises at least 45% w/w of the polymer matrix.

498. The method of any one of the preceding clauses, wherein the polymer comprises at least 50% w/w of the polymer matrix.

499. The method of any one of the preceding clauses, wherein the cross-sectional dimension is at least 500 µm.

500. The method of any one of the preceding clauses, wherein the cross-sectional dimension is at least 600 µm.

501. The method of any one of the preceding clauses, wherein the cross-sectional dimension is at least 700 µm.

502. The method of any one of the preceding clauses, wherein the cross-sectional dimension is at least 800 µm.

503. The method of any one of the preceding clauses, wherein the cross-sectional dimension is at least 900 µm.

504. The method of any one of the preceding clauses, wherein the cross-sectional dimension is at least 1 mm.

505. The method of any one of the preceding clauses, wherein the cross-sectional dimension is at least 1.5 mm.

506. The method of any one of the preceding clauses, wherein the cross-sectional dimension is at least 2.0 mm.

507. The method of any one of the preceding clauses, wherein the cross-sectional dimension is at least 2.5 mm.

508. The method of any one of the preceding clauses, wherein the cross-sectional dimension is at least 3.0 mm.

509. The method of any one of the preceding clauses, wherein the cross-sectional dimension is at least 3.5 mm.

510. The method of any one of the preceding clauses, wherein the cross-sectional dimension is at least 4.0 mm.

511. The method of any one of the preceding clauses, wherein the cross-sectional dimension is at least 4.5 mm.

512. The method of any one of the preceding clauses, wherein the cross-sectional dimension is at least 5.0 mm.

513. The method of any one of the preceding clauses, wherein the cross-sectional dimension is at least 5.5 mm.

514. The method of any one of the preceding clauses, wherein the cross-sectional dimension is at least 6.0 mm.

515. The method of any one of the preceding clauses, wherein the polymer is a copolymer.

516. The method of any one of the preceding clauses, wherein the polymer is a terpolymer.

517. The method of any one of the preceding clauses, wherein a pH of the surrounding buffer solution is within about 0.4 units of the pH of the buffer solution before the depot is placed in the buffer solution.

518. The method of any one of the preceding clauses, wherein a pH of the surrounding buffer solution is within about 0.3 units of the pH of the buffer solution before the depot is placed in the buffer solution.

519. The method of any one of the preceding clauses, wherein a pH of the surrounding buffer solution is within about 0.2 units of the pH of the buffer solution before the depot is placed in the buffer solution.

520. The method of any one of the preceding clauses, wherein a pH of the surrounding buffer solution is within about 0.1 units of the pH of the buffer solution before the depot is placed in the buffer solution.

521. The method of any one of the preceding clauses, wherein the polyester is poly(lactic-co-glycolic acid).

522. The method of any one of the preceding clauses, wherein the polymer is one of poly(DL-lactide-co-glycolideco-caprolactone) and poly(DL-lactide-co-glycolide) (PLGA).

523. The method of any one of the preceding clauses, wherein the polyester is poly(DL-lactide-co-glycolide-co-caprolactone) in a molar ratio of 60:30:10.

524. The method of any one of the preceding clauses, wherein the polyester is poly(DL-lactide-coglycolide) (PLGA) in a molar ratio of 50:50.

525. The method of any one of the preceding clauses, wherein the depot is submerged in the buffer solution immediately after being removed from the aqueous solution.

526. The method of any one of the preceding clauses, wherein the aqueous media is water.

527. The method of any one of the preceding clauses, wherein the aqueous media has a substantially neutral pH.

528. The method of any one of the preceding clauses, wherein the cross-sectional dimension is a thickness.

529. The method of any one of the preceding clauses, wherein the depot is configured to be implanted within a mammalian body for at least 7 days without undergoing core acidification.

530. The method of any one of the preceding clauses, wherein the depot is configured to be implanted within a mammalian body at a treatment site for at least 7 days without substantially altering a local pH level at the treatment site.

531. A depot comprising:
   a polymer matrix including a polymer having an acid as a degradation byproduct, wherein at least a portion of the polymer matrix has a volume with a minimum cross-sectional dimension of at least 400 µm before degradation of the polymer begins;
   wherein, when the depot is (a) submerged in aqueous media for a duration sufficient for a molecular weight of the polymer and/or a mass of the polymer matrix to decrease by about 25% to about 75%, and (b) subsequently submerged in a buffer solution and broken up such that an interior region of the depot is in fluid communication with the surrounding buffer solution, a pH of the surrounding buffer solution is within about 0.5 units of the pH of the buffer solution before the depot is placed in the buffer solution.

532. The depot of clause 531, wherein the polymer is a polyhydroxyalkanoate (PHA).

533. The depot of clause 531 or clause 532, wherein the polymer is synthetic.

534. The depot of clause 531 or clause 532, wherein the polymer is naturally occurring.

535. The depot of any one of the preceding clauses, wherein the polymer is a polyalphahydroxy acid (AHA).

536. The depot of any one of the preceding clauses, wherein the buffer solution is buffered to a physiologic pH.

537. The depot of any one of the preceding clauses, wherein the buffer solution is buffered to a pH of about 7.4.

538. The depot of any one of the preceding clauses, wherein the polymer is a polyester.

539. The depot of any one of the preceding clauses, wherein the polymer includes one or more of poly(lactic acid), polylactide, and poly(glycolic acid).

540. The depot of any one of the preceding clauses, wherein the acid is a carboxylic acid.

541. The depot of clause 540, wherein the carboxylic acid has a pKa less than or equal to 7.0.

542. The depot of clause 540, wherein the carboxylic acid has a pKa less than or equal to 7.1.

543. The depot of clause 540, wherein the carboxylic acid has a pKa less than or equal to 7.2.

544. The depot of clause 540, wherein the carboxylic acid has a pKa less than or equal to 7.3.

545. The depot of clause 540, wherein the carboxylic acid has a pKa less than or equal to 7.4.

546. The depot of any one of the preceding clauses, wherein the acid is one or both of lactic acid and glycolic acid.

547. The depot of any one of the preceding clauses, wherein submersion in the aqueous solution is continuous over the duration.

548. The depot of any one of the preceding clauses, further comprising a releasing agent mixed with the polymer.

549. The depot of any one of the preceding clauses, further comprising a therapeutic agent mixed with the polymer.

550. The depot of any one of the preceding clauses, wherein the duration is sufficient for a molecular weight of the polymer matrix to be reduced by about 25% to about 75%, and the duration is sufficient for a mass of the polymer matrix to be reduced by about 25% to about 75%.

551. The depot of any one of the preceding clauses, wherein the depot is submerged in the aqueous solution for a duration sufficient for the molecular weight or the mass of the polymer matrix to decrease by about 30% to about 70%.

552. The depot of any one of the preceding clauses, wherein the depot is submerged in the aqueous solution for a duration sufficient for the molecular weight or the mass of the polymer matrix to decrease by about 35% to about 65%.

553. The depot of any one of the preceding clauses, wherein the depot is submerged in the aqueous solution for a duration sufficient for the molecular weight or the mass of the polymer matrix to decrease by about 40% to about 60%.

554. The depot of any one of the preceding clauses, wherein the depot is submerged in the aqueous solution for a duration sufficient for the molecular weight or the mass of the polymer matrix to decrease by about 45% to about 55%.

555. The depot of any one of the preceding clauses, wherein the polymer comprises at least 10% w/w of the polymer matrix.

556. The depot of any one of the preceding clauses, wherein the polymer comprises at least 15% w/w of the polymer matrix.

557. The depot of any one of the preceding clauses, wherein the polymer comprises at least 20% w/w of the polymer matrix.

558. The depot of any one of the preceding clauses, wherein the polymer comprises at least 25% w/w of the polymer matrix.

559. The depot of any one of the preceding clauses, wherein the polymer comprises at least 30% w/w of the polymer matrix.

560. The depot of any one of the preceding clauses, wherein the polymer comprises at least 35% w/w of the polymer matrix.

561. The depot of any one of the preceding clauses, wherein the polymer comprises at least 40% w/w of the polymer matrix.

562. The depot of any one of the preceding clauses, wherein the polymer comprises at least 45% w/w of the polymer matrix.

563. The depot of any one of the preceding clauses, wherein the polymer comprises at least 50% w/w of the polymer matrix.

564. The depot of any one of the preceding clauses, wherein the cross-sectional dimension is at least 500 µm.

565. The depot of any one of the preceding clauses, wherein the cross-sectional dimension is at least 600 µm.

566. The depot of any one of the preceding clauses, wherein the cross-sectional dimension is at least 700 µm.

567. The depot of any one of the preceding clauses, wherein the cross-sectional dimension is at least 800 µm.

568. The depot of any one of the preceding clauses, wherein the cross-sectional dimension is at least 900 µm.

569. The depot of any one of the preceding clauses, wherein the cross-sectional dimension is at least 1 mm.

570. The depot of any one of the preceding clauses, wherein the cross-sectional dimension is at least 1.5 mm.

571. The depot of any one of the preceding clauses, wherein the cross-sectional dimension is at least 2.0 mm.

572. The depot of any one of the preceding clauses, wherein the cross-sectional dimension is at least 2.5 mm.

573. The depot of any one of the preceding clauses, wherein the cross-sectional dimension is at least 3.0 mm.

574. The depot of any one of the preceding clauses, wherein the cross-sectional dimension is at least 3.5 mm.

575. The depot of any one of the preceding clauses, wherein the cross-sectional dimension is at least 4.0 mm.

576. The depot of any one of the preceding clauses, wherein the cross-sectional dimension is at least 4.5 mm.

577. The depot of any one of the preceding clauses, wherein the cross-sectional dimension is at least 5.0 mm.

578. The depot of any one of the preceding clauses, wherein the cross-sectional dimension is at least 5.5 mm.

579. The depot of any one of the preceding clauses, wherein the cross-sectional dimension is at least 6.0 mm.

580. The depot of any one of the preceding clauses, wherein the polymer is a copolymer.

581. The depot of any one of the preceding clauses, wherein the polymer is a terpolymer.

582. The depot of any one of the preceding clauses, wherein a pH of the surrounding buffer solution is within about 0.4 units of the pH of the buffer solution before the depot is placed in the buffer solution.

583. The depot of any one of the preceding clauses, wherein a pH of the surrounding buffer solution is within about 0.3 units of the pH of the buffer solution before the depot is placed in the buffer solution.

584. The depot of any one of the preceding clauses, wherein a pH of the surrounding buffer solution is within about 0.2 units of the pH of the buffer solution before the depot is placed in the buffer solution.

585. The depot of any one of the preceding clauses, wherein a pH of the surrounding buffer solution is within about 0.1 units of the pH of the buffer solution before the depot is placed in the buffer solution.

586. The depot of any one of the preceding clauses, wherein the polyester is poly(lactic-co-glycolic acid).

587. The depot of any one of the preceding clauses, wherein the polymer is one of poly(DL-lactide-co-glycolideco-caprolactone) and poly(DL-lactide-co-glycolide) (PLGA).

588. The depot of any one of the preceding clauses, wherein the polyester is poly(DL-lactide-co-glycolide-co-caprolactone) in a molar ratio of 60:30:10.

589. The depot of any one of the preceding clauses, wherein the polyester is poly(DL-lactide-coglycolide) (PLGA) in a molar ratio of 50:50.

590. The depot of any one of the preceding clauses, wherein the depot is submerged in the buffer solution immediately after being removed from the aqueous solution.

591. The depot of any one of the preceding clauses, wherein the aqueous media is water.

592. The depot of any one of the preceding clauses, wherein the aqueous media has a substantially neutral pH.

593. The depot of any one of the preceding clauses, wherein the cross-sectional dimension is a thickness.

594. The depot of any one of the preceding clauses, wherein the depot is configured to be implanted within a mammalian body for at least 7 days without undergoing core acidification.

595. The depot of any one of the preceding clauses, wherein the depot is configured to be implanted within a mammalian body at a treatment site for at least 7 days without substantially altering a local pH level at the treatment site.

596. A method, comprising:
implanting a treatment member in a mammalian body, the treatment member comprising:
a polymer matrix including a polymer having an acid as a degradation byproduct, wherein at least a portion of the polymer matrix has a volume with a minimum cross-sectional dimension of at least 400 μm before degradation of the polymer begins,
wherein, when the treatment member is (a) submerged in aqueous media for a duration sufficient for a molecular weight of the polymer and/or a mass of the polymer matrix to decrease by about 25% to about 75%, and (b) subsequently submerged in a buffer solution and broken up such that an interior region of the treatment member is in fluid communication with the surrounding buffer solution, a pH of the surrounding buffer solution is within about 0.5 units of the pH of the buffer solution before the depot is placed in the buffer solution.

597. The method of any one of the preceding clauses, wherein the polymer is a polyhydoxyalkanoate (PHA).

598. The method of any one of the preceding clauses, wherein the polymer is synthetic.

599. The method of any one of the preceding clauses, wherein the polymer is naturally occurring.

600. The method of any one of the preceding clauses, wherein the polymer is a polyester.

601. The method of any one of the preceding clauses, wherein the polymer includes one or more of poly(lactic acid), polylactide, and poly(glycolic acid).

602. The method of any one of the preceding clauses, wherein the acid is a carboxylic acid.

603. The method of any one of the preceding clauses, wherein the acid is one or both of lactic acid and glycolic acid.

604. The method of any one of the preceding clauses, wherein submersion in the aqueous solution is continuous over the duration.

605. The method of any one of the preceding clauses, further comprising a releasing agent mixed with the polymer.

606. The method of any one of the preceding clauses, further comprising a therapeutic agent mixed with the polymer.

607. The method of any one of the preceding clauses, wherein the duration is sufficient for a molecular weight of the polymer matrix to be reduced by about 25% to about 75%, and the duration is sufficient for a mass of the polymer matrix to be reduced by about 25% to about 75%.

608. The method of any one of the preceding clauses, wherein the treatment member is submerged in the aqueous solution for a duration sufficient for the molecular weight or the mass of the polymer matrix to decrease by about 30% to about 70%.

609. The method of any one of the preceding clauses, wherein the treatment member is submerged in the aqueous solution for a duration sufficient for the molecular weight or the mass of the polymer matrix to decrease by about 35% to about 65%.

610. The method of any one of the preceding clauses, wherein the treatment member is submerged in the aqueous solution for a duration sufficient for the molecular weight or the mass of the polymer matrix to decrease by about 40% to about 60%.

611. The method of any one of the preceding clauses, wherein the treatment member is submerged in the aqueous solution for a duration sufficient for the molecular weight or the mass of the polymer matrix to decrease by about 45% to about 55%.

612. The method of any one of the preceding clauses, wherein the polymer comprises at least 10% of the polymer matrix.

613. The method of any one of the preceding clauses, wherein the polymer comprises at least 15% of the polymer matrix.

614. The method of any one of the preceding clauses, wherein the polymer comprises at least 20% of the polymer matrix.

615. The method of any one of the preceding clauses, wherein the polymer comprises at least 25% of the polymer matrix.

616. The method of any one of the preceding clauses, wherein the polymer comprises at least 30% of the polymer matrix.

617. The method of any one of the preceding clauses, wherein the polymer comprises at least 35% of the polymer matrix.

618. The method of any one of the preceding clauses, wherein the polymer comprises at least 40% of the polymer matrix.

619. The method of any one of the preceding clauses, wherein the polymer comprises at least 45% of the polymer matrix.

620. The method of any one of the preceding clauses, wherein the polymer comprises at least 50% of the polymer matrix.

621. The method of any one of the preceding clauses, wherein the cross-sectional dimension is at least 500 µm.

622. The method of any one of the preceding clauses, wherein the cross-sectional dimension is at least 600 µm.

623. The method of any one of the preceding clauses, wherein the cross-sectional dimension is at least 700 µm.

624. The method of any one of the preceding clauses, wherein the cross-sectional dimension is at least 800 µm.

625. The method of any one of the preceding clauses, wherein the cross-sectional dimension is at least 900 µm.

626. The method of any one of the preceding clauses, wherein the cross-sectional dimension is at least 1 mm.

627. The method of any one of the preceding clauses, wherein the cross-sectional dimension is at least 1.5 mm.

628. The method of any one of the preceding clauses, wherein the cross-sectional dimension is at least 2.0 mm.

629. The method of any one of the preceding clauses, wherein the cross-sectional dimension is at least 2.5 mm.

630. The method of any one of the preceding clauses, wherein the cross-sectional dimension is at least 3.0 mm.

631. The method of any one of the preceding clauses, wherein the cross-sectional dimension is at least 3.5 mm.

632. The method of any one of the preceding clauses, wherein the cross-sectional dimension is at least 4.0 mm.

633. The method of any one of the preceding clauses, wherein the cross-sectional dimension is at least 4.5 mm.

634. The method of any one of the preceding clauses, wherein the cross-sectional dimension is at least 5.0 mm.

635. The method of any one of the preceding clauses, wherein the cross-sectional dimension is at least 5.5 mm.

636. The method of any one of the preceding clauses, wherein the cross-sectional dimension is at least 6.0 mm.

637. The method of any one of the preceding clauses, wherein the polymer is a copolymer.

638. The method of any one of the preceding clauses, wherein the polymer is a terpolymer.

639. The method of any one of the preceding clauses, wherein a pH of the surrounding buffer solution is within about 0.4 units of the pH of the buffer solution before the treatment member is placed in the buffer solution.

640. The method of any one of the preceding clauses, wherein a pH of the surrounding buffer solution is within about 0.3 units of the pH of the buffer solution before the treatment member is placed in the buffer solution.

641. The method of any one of the preceding clauses, wherein a pH of the surrounding buffer solution is within about 0.2 units of the pH of the buffer solution before the treatment member is placed in the buffer solution.

642. The method of any one of the preceding clauses, wherein a pH of the surrounding buffer solution is within about 0.1 units of the pH of the buffer solution before the treatment member is placed in the buffer solution.

643. The method of any one of the preceding clauses, wherein the polyester is poly(lactic-co-glycolic acid).

644. The method of any one of the preceding clauses, wherein the polymer is one of poly(DL-lactide-co-glycolideco-caprolactone) and poly(DL-lactide-co-glycolide) (PLGA).

645. The method of any one of the preceding clauses, wherein the polyester is poly(DL-lactide-co-glycolide-co-caprolactone) in a molar ratio of 60:30:10.

646. The method of any one of the preceding clauses, wherein the polyester is poly(DL-lactide-coglycolide) (PLGA) in a molar ratio of 50:50.

647. The method of any one of the preceding clauses, wherein the treatment member is submerged in the buffer solution immediately after being removed from the aqueous solution.

648. The method of any one of the preceding clauses, wherein the aqueous media is water.

649. The method of any one of the preceding clauses, wherein the aqueous media has a substantially neutral pH.

650. The method of any one of the preceding clauses, wherein the cross-sectional dimension is a thickness.

651. The method of any one of the preceding clauses, wherein the treatment member is configured to be implanted within a mammalian body for at least 7 days without undergoing core acidification.

652. The method of any one of the preceding clauses, wherein the treatment member is configured to be implanted within a mammalian body at a treatment site for at least 7 days without substantially altering a local pH level at the treatment site.

653. The method of any one of the preceding clauses, wherein the treatment member does not include a therapeutic agent.

654. A treatment member configured to be implanted within a mammalian body, the treatment member comprising:
 a polymer matrix including a polymer having an acid as a degradation byproduct, wherein at least a portion of the polymer matrix has a volume with a minimum cross-sectional dimension of at least 400 µm before degradation of the polymer begins;
 wherein, when the treatment member is (a) submerged in aqueous media for a duration sufficient for a molecular weight of the polymer and/or a mass of the polymer matrix to decrease by about 25% to about 75%, and (b) subsequently submerged in a buffer solution and broken up such that an interior region of the depot is in fluid communication with the surrounding buffer solution, a pH of the surrounding buffer solution is within about 0.5 units of the pH of the buffer solution before the depot is placed in the buffer solution.

655. The treatment member of clause 653, wherein the polymer is a polyhydoxyalkanoate (PHA).

656. The treatment member of clause 653 or clause 654, wherein the polymer is synthetic.

657. The treatment member of clause 653 or clause 654, wherein the polymer is naturally occurring.

658. The treatment member of any one of the preceding clauses, wherein the polymer is a polyester.

659. The treatment member of any one of the preceding clauses, wherein the polymer includes one or more of poly(lactic acid), polylactide, and poly(glycolic acid).

660. The treatment member of any one of the preceding clauses, wherein the acid is a carboxylic acid.

661. The treatment member of any one of the preceding clauses, wherein the acid is one or both of lactic acid and glycolic acid.

662. The treatment member of any one of the preceding clauses, wherein submersion in the aqueous solution is continuous over the duration.

663. The treatment member of any one of the preceding clauses, further comprising a releasing agent mixed with the polymer.

664. The treatment member of any one of the preceding clauses, further comprising a therapeutic agent mixed with the polymer.

665. The treatment member of any one of the preceding clauses, wherein the duration is sufficient for a molecular weight of the polymer matrix to be reduced by about 25% to about 75%, and the duration is sufficient for a mass of the polymer matrix to be reduced by about 25% to about 75%.

666. The treatment member of any one of the preceding clauses, wherein the treatment member is submerged in the aqueous solution for a duration sufficient for the molecular weight or the mass of the polymer matrix to decrease by about 30% to about 70%.

667. The treatment member of any one of the preceding clauses, wherein the treatment member is submerged in the aqueous solution for a duration sufficient for the molecular weight or the mass of the polymer matrix to decrease by about 35% to about 65%.

668. The treatment member of any one of the preceding clauses, wherein the treatment member is submerged in the aqueous solution for a duration sufficient for the molecular weight or the mass of the polymer matrix to decrease by about 40% to about 60%.

669. The treatment member of any one of the preceding clauses, wherein the treatment member is submerged in the aqueous solution for a duration sufficient for the molecular weight or the mass of the polymer matrix to decrease by about 45% to about 55%.

670. The treatment member of any one of the preceding clauses, wherein the polymer comprises at least 10% w/w of the polymer matrix.

671. The treatment member of any one of the preceding clauses, wherein the polymer comprises at least 15% w/w of the polymer matrix.

672. The treatment member of any one of the preceding clauses, wherein the polymer comprises at least 20% w/w of the polymer matrix.

673. The treatment member of any one of the preceding clauses, wherein the polymer comprises at least 25% w/w of the polymer matrix.

674. The treatment member of any one of the preceding clauses, wherein the polymer comprises at least 30% w/w of the polymer matrix.

675. The treatment member of any one of the preceding clauses, wherein the polymer comprises at least 35% w/w of the polymer matrix.

676. The treatment member of any one of the preceding clauses, wherein the polymer comprises at least 40% w/w of the polymer matrix.

677. The treatment member of any one of the preceding clauses, wherein the polymer comprises at least 45% w/w of the polymer matrix.

678. The treatment member of any one of the preceding clauses, wherein the polymer comprises at least 50% w/w of the polymer matrix.

679. The treatment member of any one of the preceding clauses, wherein the cross-sectional dimension is at least 500 μm.

680. The treatment member of any one of the preceding clauses, wherein the cross-sectional dimension is at least 600 μm.

681. The treatment member of any one of the preceding clauses, wherein the cross-sectional dimension is at least 700 μm.

682. The treatment member of any one of the preceding clauses, wherein the cross-sectional dimension is at least 800 μm.

683. The treatment member of any one of the preceding clauses, wherein the cross-sectional dimension is at least 900 μm.

684. The treatment member of any one of the preceding clauses, wherein the cross-sectional dimension is at least 1 mm.

685. The treatment member of any one of the preceding clauses, wherein the cross-sectional dimension is at least 1.5 mm.

686. The treatment member of any one of the preceding clauses, wherein the cross-sectional dimension is at least 2.0 mm.

687. The treatment member of any one of the preceding clauses, wherein the cross-sectional dimension is at least 2.5 mm.

688. The treatment member of any one of the preceding clauses, wherein the cross-sectional dimension is at least 3.0 mm.

689. The treatment member of any one of the preceding clauses, wherein the cross-sectional dimension is at least 3.5 mm.

690. The treatment member of any one of the preceding clauses, wherein the cross-sectional dimension is at least 4.0 mm.

691. The treatment member of any one of the preceding clauses, wherein the cross-sectional dimension is at least 4.5 mm.

692. The treatment member of any one of the preceding clauses, wherein the cross-sectional dimension is at least 5.0 mm.

693. The treatment member of any one of the preceding clauses, wherein the cross-sectional dimension is at least 5.5 mm.

694. The treatment member of any one of the preceding clauses, wherein the cross-sectional dimension is at least 6.0 mm.

695. The treatment member of any one of the preceding clauses, wherein the polymer is a copolymer.

696. The treatment member of any one of the preceding clauses, wherein the polymer is a terpolymer.

697. The treatment member of any one of the preceding clauses, wherein a pH of the surrounding buffer solution is within about 0.4 units of the pH of the buffer solution before the treatment member is placed in the buffer solution.

698. The treatment member of any one of the preceding clauses, wherein a pH of the surrounding buffer solution is within about 0.3 units of the pH of the buffer solution before the treatment member is placed in the buffer solution.

699. The treatment member of any one of the preceding clauses, wherein a pH of the surrounding buffer solution is within about 0.2 units of the pH of the buffer solution before the treatment member is placed in the buffer solution.

700. The treatment member of any one of the preceding clauses, wherein a pH of the surrounding buffer solution is within about 0.1 units of the pH of the buffer solution before the treatment member is placed in the buffer solution.

701. The treatment member of any one of the preceding clauses, wherein the polyester is poly(lactic-co-glycolic acid).

702. The treatment member of any one of the preceding clauses, wherein the polymer is one of poly(DL-lactide-co-glycolideco-caprolactone) and poly(DL-lactide-co-glycolide) (PLGA).

703. The treatment member of any one of the preceding clauses, wherein the polyester is poly(DL-lactide-co-glycolide-cocaprolactone) in a molar ratio of 60:30:10.

704. The treatment member of any one of the preceding clauses, wherein the polyester is poly(DL-lactide-coglycolide) (PLGA) in a molar ratio of 50:50.

705. The treatment member of any one of the preceding clauses, wherein the treatment member is submerged in the buffer solution immediately after being removed from the aqueous solution.

706. The treatment member of any one of the preceding clauses, wherein the aqueous media is water.

707. The treatment member of any one of the preceding clauses, wherein the aqueous media has a substantially neutral pH.

708. The treatment member of any one of the preceding clauses, wherein the cross-sectional dimension is a thickness.

709. The treatment member of any one of the preceding clauses, wherein the treatment member is configured to be implanted within a mammalian body for at least 7 days without undergoing core acidification.

710. The treatment member of any one of the preceding clauses, wherein the treatment member is configured to be implanted within a mammalian body at a treatment site for at least 7 days without substantially altering a local pH level at the treatment site.

711. The treatment member of any one of the preceding clauses, wherein the treatment member is a biodegradable orthopedic implant.

712. The treatment member of any one of the preceding clauses, wherein the treatment member is a biodegradable implant selected from the group consisting of pin, screw, plate, rod, tack, suture anchor, spine cage, scaffold and bone graft.

713. The treatment member of any one of the preceding clauses, wherein the treatment member does not include a therapeutic agent.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

FIG. 9A is an isometric view of a depot in accordance with some embodiments of the present technology.

FIG. 9B is a cross-sectional view of the depot shown in FIG. 9A.

FIG. 10 is a cross-sectional view of a depot in accordance with some embodiments of the present technology.

FIG. 11 is a cross-sectional view of a depot in accordance with some embodiments of the present technology.

FIG. 19A is a schematic representation of the degradation of the depots of the present technology.

FIGS. 19B and 19C are scanning electron microscope ("SEM") images of cross-sections of depots of the present technology at different timepoints during degradation.

FIG. 24A is a perspective view of a depot in accordance with some embodiments of the present technology.

FIG. 24B is cross-sectional view of the depot shown in FIG. 24A taken along line B-B.

FIG. 24C is cross-sectional view of the depot shown in FIG. 24A taken along line C-C.

FIG. 41A is a side view of a depot in a straightened state in accordance with some embodiments of the present technology.

FIG. 41B is a side view of the depot shown in FIG. 41A in a curved state.

FIG. 42A is a side view of a depot in a straightened state in accordance with some embodiments of the present technology.

FIG. 42B is a side view of the depot shown in FIG. 42A in a curved state.

FIG. 43A is a perspective view of a depot in a straightened state in accordance with some embodiments of the present technology.

FIG. 43B is cross-sectional view of the depot shown in FIG. 43A taken along line B-B.

FIG. 43C is a side view of the depot shown in FIG. 43A in a curved state.

FIG. 44 is a side view of a depot deployed at a target site in a body in accordance with some embodiments of the present technology.

FIG. 45 is a side view of a depot deployed at a target site in a body in accordance with some embodiments of the present technology.

FIGS. 49A-49C are perspective, top, and side views, respectively, of a depot in accordance with some embodiments of the present technology.

FIG. 50A is an end view of a depot in a curled state in accordance with some embodiments of the present technology.

FIG. 50B is a side view of the depot shown in FIG. 50A in an uncurled state.

FIG. 61 is a table showing common surgical procedures for which the depots of the present technology may be utilized for treating postoperative pain. FIG. 61 also shows nerve targets and anatomical access/placement associated with the different surgeries.

FIGS. 62A-62C are anterior, lateral, and medial views of a human knee, showing the location of the nerves innervating the knee.

DETAILED DESCRIPTION

The present technology relates to implantable depots for the sustained, controlled release of therapeutic agents, and associated devices, systems, and methods of use. Examples of the depots of the present technology and associated release kinetics are described below with reference to FIGS. 2-52C and Section I. Selected examples of the depots of the present technology and associated release profiles are described below with reference to FIGS. 53-59C and Section II.

Selected devices, systems, and methods for using the depots of the present technology for treating postoperative pain associated with orthopedic surgery are described below with reference to FIGS. 60A-65 and Section III. Selected devices, systems, and methods for using the depots of the present technology for treating postoperative pain associated with other surgeries are described below at Section IV. Selected treatment members of the present technology are described below at Section V.

I. Examples of Depots of the Present Technology

Figure 1:
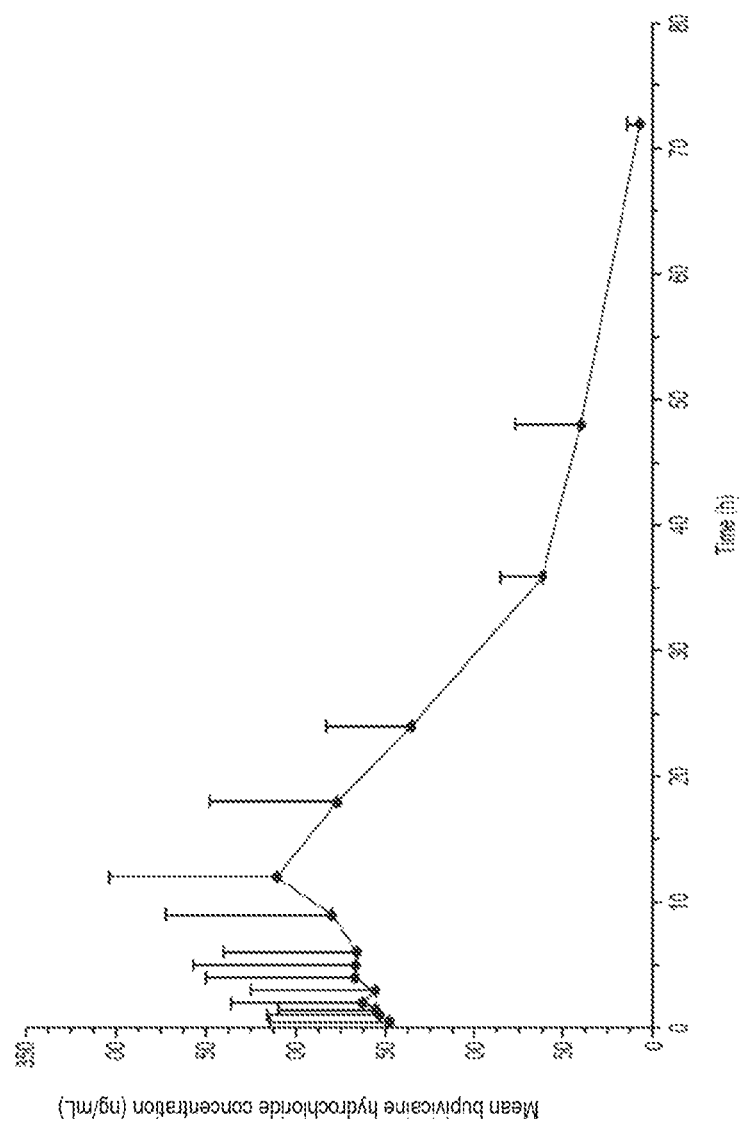
FIG. 1 depicts the release of a therapeutic agent over time from a prior art drug delivery system.

As noted previously, prior art drug delivery systems often suffer from a lack of a true controlled release mechanism in that they typically provide a burst of drug upon contact with surrounding physiologic fluids followed by a residual release of drug. For example, FIG. 1 shows an example prior art biodegradable polymer-based delivery system, in which the drug concentration in plasma peaked within 15 hours of implantation, thereby illustrating a duration of effect that is inadequate.

Disclosed herein are implantable depots and associated devices, systems, and methods for treating (i.e., preventing, reducing, and/or eliminating) postoperative pain via sustained, controlled release of a therapeutic agent while the depot is implanted at a treatment site in vivo. Many embodiments of the present technology comprise one or more depots configured to be implanted at or near a surgical site of a patient to treat pain following a surgery. While implanted in vivo, the depot(s) are configured to release a therapeutic agent (such as an analgesic) to the surgical site in a controlled, prescribed manner for at least 3 days following implantation.

As used herein, a "depot" comprises a composition configured to administer at least one therapeutic agent to a treatment site in the body of a patient in a controlled, sustained manner. The depot also comprises the therapeutic agent itself. A depot may comprise a physical structure or carrier to configured to perform or enhance one or more functions related to treatment, such as facilitating implantation and/or retention in a treatment site (e.g., tissue at the intracapsular and/or extracapsular space of a knee joint), modulating the release profile of the therapeutic agent (e.g., creating a two-phase release profile), increasing release towards a treatment site, reducing release away from a treatment site, or combinations thereof. In some embodiments, a "depot" includes but is not limited to films, sheets, strips, ribbons, capsules, coatings, matrices, wafers, pills, pellets, or other pharmaceutical delivery apparatus or a combination thereof. Moreover, as used herein, "depot" may refer to a single depot, or may refer to multiple depots. As an example, the statement "The depot may be configured to release 2 g of therapeutic agent to a treatment site" describes (a) a single depot that is configured to release 2 g of therapeutic agent to a treatment site, and (b) a plurality of depots that collectively are configured to release 2 g of therapeutic agent to a treatment site.

Figure 2:
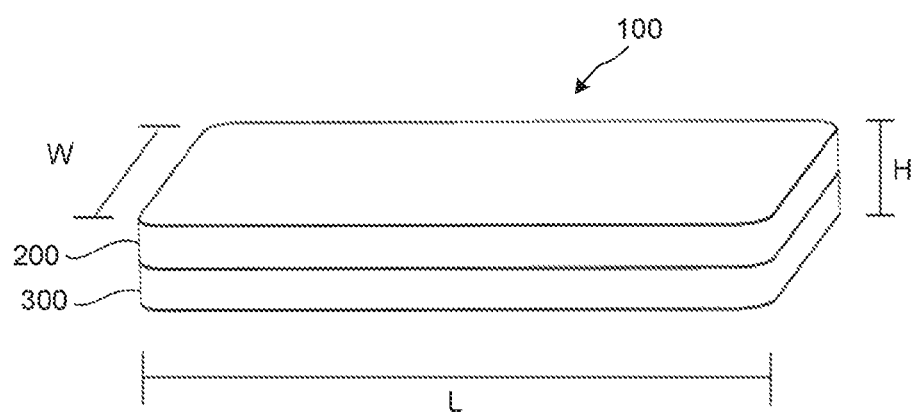
FIG. 2 is an isometric view of a depot configured in accordance with the present technology.

FIG. 2 is an isometric view of an implantable depot 100 in accordance with several embodiments of the present technology. The depot 100 may be a thin, multi-layered polymer film configured to be implanted at a treatment site comprising a therapeutic region 200 containing a therapeutic agent (such as an analgesic), and a control region 300 configured to regulate the release of the therapeutic agent from the depot 100 in a controlled and sustained manner. The depot 100 may include a high therapeutic payload of the therapeutic agent, especially as compared to other known films of equal thickness or polymer weight percentage, while exhibiting mechanical properties (e.g., flexural strength) sufficient to withstand storage, handling, implantation, and/or retention in the treatment site. For example, in some embodiments, the depot 100 comprises at least 50% by weight of the therapeutic agent.

The control region 300 may comprise at least one bioresorbable polymer and at least one releasing agent mixed with the polymer, and the therapeutic region 200 may comprise at least one bioresorbable polymer and at least one releasing agent mixed with the polymer and the therapeutic agent. The control region 300 may optionally include a therapeutic agent, or the control region 300 may include no therapeutic agent at all. The therapeutic region 200 may optionally include no releasing agent at all. The releasing agent in the control region 300 may be the same or may be different from the releasing agent in the therapeutic region 200. The bioresorbable polymer in the control region 300 may be the same or may be different from the bioresorbable polymer in the therapeutic region 200. As detailed below, in some embodiments the therapeutic region 200 and/or the control region 300 may have different constituents and/or formulations.

When exposed to a fluid (e.g., physiologic fluid), the releasing agent can have a dissolution rate that is faster than the degradation rate of the bioresorbable polymer. Accordingly, when a fluid contacts the depot 100 (e.g., after implantation of the depot 100 in a treatment site), the releasing agent dissolves within the surrounding polymer of the control region 300 and/or therapeutic region 200 faster than the polymer degrades. As the releasing agent dissolves, the space vacated by the dissolved releasing agent forms diffusion openings (e.g., channels, voids, pores, etc.) in the surrounding polymer region. The formation of diffusion openings may enhance the release of therapeutic agent from the polymer region and into the surrounding physiologic fluid. In some embodiments, the release rate of the therapeutic agent is higher when there are diffusion openings in the polymer region, compared to when there are no diffusion openings in the polymer region.

The concentration and type of releasing agent, among other parameters, can be selected to regulate the release of the therapeutic agent from the therapeutic region 200 and/or through the control region 300 into the surrounding fluid at a controlled dosage rate over a desired period of time. For example, a higher concentration of releasing agent may increase the release rate of the therapeutic agent, while a lower concentration of releasing agent may decrease the release rate of the therapeutic agent. The therapeutic region 200 may comprise a different concentration and/or type of releasing agent than the control region 300, or may comprise the same concentration and/or type of releasing agent.

The position and/or geometry of the control region 300 can be configured to modulate the release profile of the therapeutic agent from the therapeutic region 200. As shown in FIG. 2, at least a portion of the control region 300 may be disposed on or adjacent the therapeutic region 200 such that, when the depot 100 is initially positioned in vivo, the control region 300 is between at least a portion of the therapeutic region 200 and physiologic fluids at the treatment site. For example, the control region 300 can cover all or a portion of one or more surfaces of the therapeutic region 200. When the depot 100 is exposed to physiologic fluids, the therapeutic agent elutes from the exposed surfaces of the therapeutic region 200 and through the control region 300 by way of the diffusion openings created by dissolution of the releasing agent. In general, the therapeutic agent elutes from the exposed surfaces of the therapeutic region 200 at a faster (e.g., greater) rate than through the control region 300. As a result, the control region 300 prolongs the release of the therapeutic agent from the therapeutic region 200 to provide for longer release times and regulates the dosage rate, e.g., to provide the desired degree of pain relief and avoid complications related to overdosing.

The depot of the present technology is configured to release a therapeutic agent in a highly controlled, predetermined manner that is specifically tailored to the medical condition being treated and the therapeutic agent used. As described in greater detail below in Section II, the release kinetics of the depots may be customized for a particular application by varying one or more aspects of the depot's composition and/or structure, such as the shape and/or size of the depot, therapeutic region 200, and/or control region 300; the exposed surface area of the therapeutic region 200; the type of polymer (in the therapeutic region 200 and/or in the control region 300); the weight percentage of the therapeutic agent, the polymer, and/or the releasing agent (within a particular region or generally throughout the depot 100); and the composition of the therapeutic region 200 and the control region 300.

Figure 3:
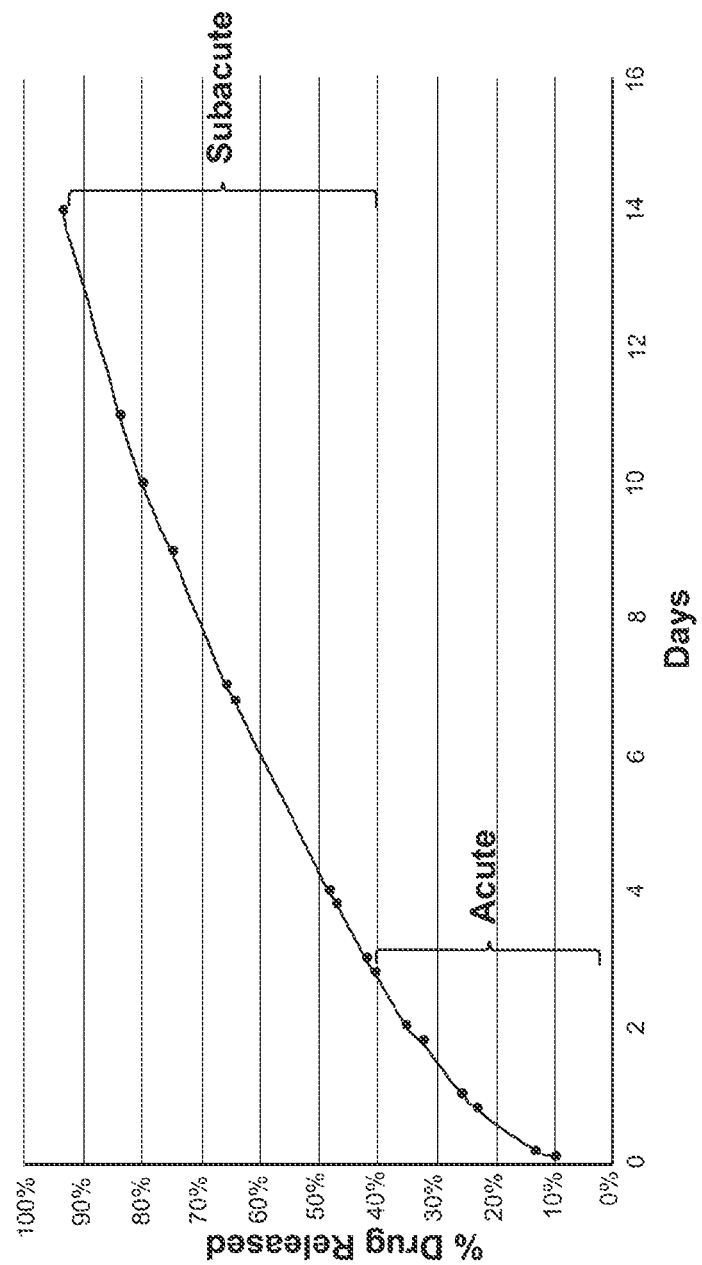
FIG. 3 depicts the release profile over time of one or more depots of the present technology.

As shown in FIG. 3, in many embodiments the depot 100 (or a system of depots 100) is configured to release a disproportionately larger volume of a therapeutic agent per day for a first period of time than for a longer second period of time. In some embodiments, the depot 100 (or a system of depots 100) is configured to release the therapeutic agent for at least 14 days post-implantation (or post-immersion in a fluid), where a controlled burst of about 20% to about 50% of the therapeutic agent payload is released in the first 3-5 days, and at least 80% of the remaining therapeutic agent payload is released at a slower rate over the last 10-11 days. In some embodiments, at least 90% of the therapeutic agent payload is released by the end of 14 days.

A two-stage, second-order release profile-such as that shown in FIG. 3—may be especially beneficial in the context of treating pain resulting from a total knee arthroplasty ("TKA"). TKA patients typically experience the greatest pain within the first 1-3 days following surgery (clinically referred to as "acute pain") with increasingly less pain over the next 7-10 days (clinically referred to as "subacute pain"). The acute period often overlaps or coincides with the patient's inpatient care (usually 1-3 days), and the subacute period generally begins when the patient is discharged and returns home. The two-stage, second-order release profile shown in FIG. 3 is also beneficial for other surgical applications, such as other orthopedic applications (e.g., ligament repair/replacement and other damage to the knee, shoulder, ankle, etc.) or non-orthopedic surgical applications. Excessive pain following any surgery may extend inpatient care, cause psychological distress, increase opioid consumption, and/or impair patient participation in physical therapy, any of which may prolong the patient's recovery and/or mitigate the extent of recovery. Pain relief during the subacute period may be particularly complicated to manage, as patient compliance with the prescribed pain management regimen drops off when patients transition from an inpatient to home environment.

To address the foregoing challenges in post-surgical pain management, the depot 100 (or depot system comprising multiple depots 100) of the present technology may have a release profile tailored to meet the pain management needs specific to the acute and subacute periods. For example, to address the greater acute pain that occurs immediately following surgery, the depot 100 may be configured to release the therapeutic agent at a faster rate for the first 3-5 days after implantation (as shown in FIG. 3) compared to a subsequent period of 9-11 days. In some embodiments, the depot 100 may deliver a local anesthetic at a rate of from about 150 mg/day to about 400 mg/day during this first, acute period. To address the diminishing pain during the subacute period, the depot 100 may be configured to release the therapeutic agent at a slower rate for the remaining 9-11 days. In some embodiments, the depot 100 may deliver a local anesthetic at a rate of from about 50 mg/day to about 250 mg/day during this second, subacute period. In some embodiments, the rate of release continuously decreases throughout the first period and/or the second period.

The release profile of the depot 100 may be tuned to release a therapeutic agent for other durations and/or at other release rates by adjusting the structure, composition, and the process by which the depot is manufactured. For example, in some embodiments the depot 100 may be configured to release the therapeutic agent at a constant rate throughout the entire duration of release. In particular embodiments, the depot 100 may be configured to release the therapeutic agent at a constant rate for a first period of time and at a non-constant rate for a second period of time (which may occur before or after the first period of time).

In some embodiments, the depot 100 is configured to release no more than 20%, no more than 25%, no more than 30%, no more than 35%, no more than 40%, no more than 45%, no more than 50%, no more than 55%, no more than 60%, no more than 65%, or no more than 70% of the therapeutic agent in the first day, 2 days, 3 days, 4 days, 5 days, 6 days, 8 days, 9 days, 10 days, 11 days, 12 days, or 13 days of the duration of release, and wherein at least 75%, at least 80%, at least 85%, at least 90%, at least 95%, or 100% of the remaining therapeutic agent is released in the remaining days of the duration of release. The intended duration of release may be at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days, at least 22 days, at least 23 days, at least 24 days, at least 25 days, at least 26 days, at least 27 days, at least 28 days, at least 29 days, or at least 30 days.

In some embodiments, the depot 100 is configured to release at least 70%, at least 75%, at least 80%, at least 85%, at least 90%, at least 95%, at least 96%, at least 97%, at least 98%, at least 99%, or 100% of the therapeutic agent in the depot 100 within the intended duration of treatment. The intended duration of treatment may be at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days, at least 22 days, at least 23 days, at least 24 days, at least 25 days, at least 26 days, at least 27 days, at least 28 days, at least 29 days, at least 30 days, at least 40 days, at least 50 days, at least 60 days, at least 70 days, at least 90 days, at least 100 days, at least 200 days, at least 300 days, or at least 365 days.

In some embodiments, the depot 100 is configured to release from about 50 mg/day to about 600 mg/day, 100 mg/day to about 500 mg/day, or from about 100 mg/day to about 400 mg/day, or from about 100 mg/day to about 300 mg/day of the therapeutic agent to the treatment site. In general, the release rate can be selected to deliver the desired dosage to provide the extent of pain relief needed at a given time after the surgical procedure, control toxicity, and deliver the therapeutic agent for a sufficient period of time for pain relief.

In some embodiments, the depot 100 is configured to release from about 50 mg/day to about 600 mg/day, from about 100 mg/day to about 500 mg/day, or from about 100 mg/day to about 400 mg/day, or from about 100 mg/day to about 300 mg/day of the therapeutic agent to the treatment site within a first period of release. The depot 100 can further be configured to release from about 500 mg/day to about 600 mg/day, about 100 mg/day to about 500 mg/day, or from about 100 mg/day to about 400 mg/day, or from about 100 mg/day to about 300 mg/day of the therapeutic agent to the treatment site within a second period of release. The release rate during the first period may be the same as, different than, less than, or greater than the release rate during the second period. Moreover, the first period may be longer or shorter than the second period. The first period may occur before or after the second period.

In some embodiments, the depot 100 is configured to release no more than 50 mg, no more than 100 mg, no more than 150 mg, no more than 200 mg, no more than 250 mg, no more than 300 mg, no more than 350 mg, no more than 400 mg, no more than 450 mg, no more than 500 mg, no more than 600 mg, no more than 700 mg, no more than 800 mg, no more than 900 mg, no more than 1000 mg, at least 10 mg, at least 20 mg, at least 30 mg, at least 40 mg, at least 50 mg, at least 60 mg, at least 70 mg, at least 80 mg, at least 90 mg, at least 100 mg, at least 110 mg, at least 120 mg, at least 130 mg, at least 140 mg, at least 150 mg, at least 160 mg, at least 170 mg, at least 180 mg, at least 190 mg, at least 200 mg, at least 210 mg, at least 220 mg, at least 230 mg, at least 240 mg, at least 250 mg, at least 260 mg, at least 270 mg, at least 280 mg, at least 290 mg, or at least 300 mg of the therapeutic agent within any day of a first period of release. This may be useful for providing different degrees of pain relief at different times after the surgical procedure, and it may also be useful to control toxicity. In such embodiments, the depot 100 may be configured to release no more than 50 mg, no more than 100 mg, no more than 150 mg, no more than 200 mg, no more than 250 mg, no more than 300 mg, no more than 350 mg, no more than 400 mg, no more than 450 mg, no more than 500 mg, no more than 600 mg, no more than 700 mg, no more than 800 mg, no more than 900 mg, no more than 1000 mg, at least 10 mg, at least 20 mg, at least 30 mg, at least 40 mg, at least 50 mg, at least 60 mg, at least 70 mg, at least 80 mg, at least 90 mg, at least 100 mg, at least 110 mg, at least 120 mg, at least 130 mg, at least 140 mg, at least 150 mg, at least 160 mg, at least 170 mg, at least 180 mg, at least 190 mg, at least 200 mg, at least 210 mg, at least 220 mg, at least 230 mg, at least 240 mg, at least 250 mg, at least 260 mg, at least 270 mg, at least 280 mg, at least 290 mg, or at least 300 mg of the therapeutic agent within any day of a second period of release. The first period of release and/or the second period of release may be 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, or 30 days. The depot 100 may be configured to release the therapeutic agent at a first rate during the first period and at a second rate during the second period. The first rate may be the same as, different than, less than, or greater than the second rate. In some embodiments, the first rate is at least 2-fold, 3-fold, 4-old, 5-fold, 6-fold, 7-fold, 8-fold, 9-fold, or 10-fold greater than the second rate, or vice versa. Moreover, the first period may be longer or shorter than the second period. The first period may come before or after the second period.

In some embodiments, the depot 100 is configured to release no more than 50 mg, no more than 100 mg, no more than 150 mg, no more than 200 mg, no more than 250 mg, no more than 300 mg, no more than 350 mg, no more than 400 mg, no more than 450 mg, no more than 500 mg, no more than 600 mg, no more than 700 mg, no more than 800 mg, no more than 900 mg, or no more than 1000 mg of therapeutic agent within any day of the duration of release.

In some embodiments, the depot 100 is configured to release the therapeutic agent at a treatment site in vivo and/or in the presence of one or more fluids for no less than 1 day, no less than 2 days, no less than 3 days, no less than 4 days, no less than 5 days, no less than 6 days, no less than 7 days, no less than 8 days, no less than 9 days, no less than 10 days, no less than 11 days, no less than 12 days, no less than 13 days, no less than 14 days, no less than 15 days, no less than 16 days, no less than 17 days, no less than 18 days, no less than 19 days, no less than 20 days, no less than 21 days, no less than 22 days, no less than 23 days, no less than 24 days, no less than 25 days, no less than 26 days, no less than 27 days, no less than 28 days, no less than 29 days, no less than 30 days, no less than 40 days, no less than 50 days, no less than 60 days, no less than 70 days, no less than 90 days, no less than 100 days, no less than 200 days, no less than 300 days, or no less than 365 days.

The release kinetics of the depots of the present technology may be tuned for a particular application by varying one or more aspects of the depot's structure and/or composition, such as the exposed surface area of the therapeutic region 200, the porosity of the control region 300 during and after dissolution of the releasing agent, the concentration of the therapeutic agent in the therapeutic region, the post-manufacturing properties of the polymer, the structural integrity of the depots to avoid a sudden release of the therapeutic agent, the relative thicknesses of the therapeutic region 200 compared to the control region 300, and other properties of the depots. Several embodiments of depots of the present technology combine one or more of these properties in a manner that produces exceptional two-phase release profiles in animal studies that significantly outperform existing injectable or implantable systems, while also overcoming the shortcomings of disclosed prophetic devices. For example, several embodiments have exhibited two-phase release profiles that deliver an adequate mass of therapeutic agent to treat pain associated with joint replacement surgery or other applications over a 14-day period while maintaining sufficient structural integrity to withstand the forces of a joint to avoid a sudden release of too much therapeutic agent. This surprising result enables depots of the present technology to at least reduce, if not replace, opioids and/or enhance other existing pain relief systems for orthopedic surgical applications, non-orthopedic surgical applications, and for other applications (e.g., oncological).

For example, the release profile can be tuned by, at least in part, controlling the amount of exposed surface area of the therapeutic region 200 because depots having a therapeutic region 200 covered only partially by a control region 300 (see, for example, FIGS. 2, 4-8, and 13) will generally release a higher proportion of the total payload over a shorter period of time as compared to embodiments where the therapeutic region 200 is completely encapsulated by the control region 300 (see, for example, FIGS. 9A-12). More specifically, depot designs having a therapeutic region 200 with exposed surfaces will typically release the therapeutic agent at a high, substantially linear rate for a first period of time and then at a lower, substantially linear rate for a second period of time. Alternatively, depot designs having a therapeutic region 200 with surfaces that are substantially covered by one or more control regions 300 may achieve a zero-order release such that the release of the payload of therapeutic agent is at substantially the same rate.

Figure 4:
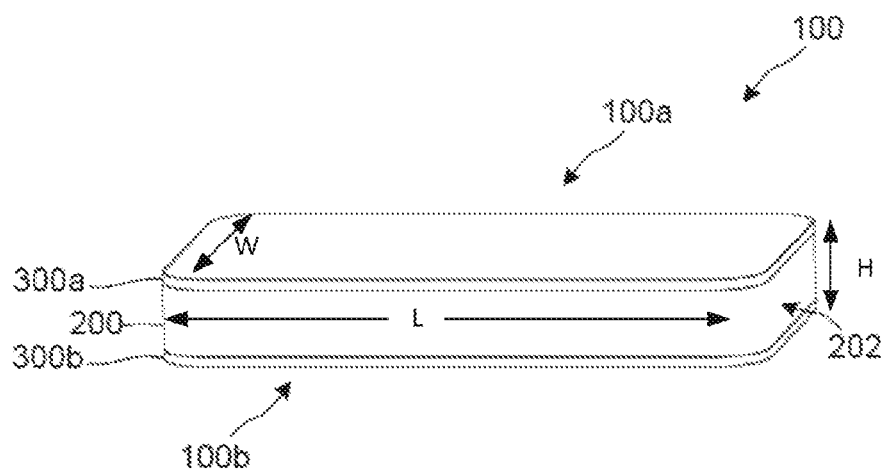
FIG. 4 is an isometric view of a depot in accordance with some embodiments of the present technology.

As shown in FIG. 4, in some embodiments the depot 100 may comprise a multi-layer polymer film having a therapeutic region 200 and first and second control regions 300*a*, 300*b* positioned at opposite surfaces 100*a*, 100*b* of the therapeutic region 200. The depot 100 may be in the form of a flexible, rectangular strip having a length L, a width W, and a height H (or thickness). In some embodiments, the depot 100 has (a) a length L of from about 5-40 mm, about 10-30 mm, about 15-20 mm, about 20-35 mm, about 20-30 mm, about 20-25 mm, about 26-30 mm, about 5 mm, about 10 mm, about 11 mm, about 12 mm, about 13 mm, about 14 mm, about 15 mm, about 16 mm, about 17 mm, about 18 mm, about 19 mm about 20 mm, about 21 mm, about 22 mm, about 23 mm, about 24 mm, about 25 mm, about 26 mm, about 27 mm, about 28 mm, about 29 mm, about 30 mm, about 10-15 mm, about 12-16 mm, about 15-20 mm, about 21-23 mm, about 22-24 mm, about 23-25 mm, about 24-26 mm, about 25-27 mm, about 26-28 mm, about 27-29 mm, or about 28-30 mm, (b) a width W of from about 5-40 mm, about 10-30 mm, about 15-20 mm, about 20-35 mm, about 20-30 mm, about 20-25 mm, about 26-30 mm, about 5 mm, about 10 mm, about 11 mm, about 12 mm, about 13 mm, about 14 mm, about 15 mm, about 16 mm, about 17 mm, about 18 mm, about 19 mm about 20 mm, about 21 mm, about 22 mm, about 23 mm, about 24 mm, about 25 mm, about 26 mm, about 27 mm, about 28 mm, about 29 mm, about 30 mm, about 10-15 mm, about 12-16 mm, about 15-20 mm, about 21-23 mm, about 22-24 mm, about 23-25 mm, about 24-26 mm, about 25-27 mm, about 26-28 mm, about 27-29 mm, or about 28-30 mm (c) a height H of from about 0.4 mm to about 4 mm, about 1 mm to about 3 mm, about 1 mm to about 2 mm, at least 0.4 mm, at least 0.5 mm, at least 0.6 mm, at least 0.7 mm, at least 0.8 mm, at least 0.9 mm, at least 1 mm, at least 1.2 mm, at least 1.4 mm, at least 1.5 mm, at least 1.6 mm, at least 1.7 mm, at least 1.8 mm, at least 2 mm, at least about 3 mm, no more than 0.5 mm, no more than 0.6 mm, no more than 0.7 mm, no more than 0.8 mm, no more than 0.9 mm, etc.). In some embodiments, the depot 100 may have a L×W×H of about 26 mm×about 16 mm×about 1 mm, and in some embodiments, about 27 mm×about 17 mm×about 1 mm. In some embodiments, the depot 100 may have other shapes and/or dimensions, such as those detailed below Additionally, some embodiments of the depot shown in FIG. 4 are configured such that a thickness of the control regions 300*a* and 300*b*, either individually or collectively, is less than or equal to 1/10 of a thickness of the therapeutic region 200. The thickness of the control regions 300*a* and 300*b*, either individually or collectively, can further be no more than 1/12.5, 1/15, 1/17.5, 1/20, 1/22.5, 1/25, 1/30, 1/40, 1/50, 1/75, or 1/100 of the thickness of the therapeutic region 200. In those embodiments with multiple sub-control regions, one or more of the sub-control regions may individually be less than or equal to 1/10, 1/12.5, 1/15, 1/17.5, 1/20, 1/22.5, 1/25, 1/27.5, 1/30, 1/32.5, 1/35, 1/37.5, 1/40, 1/42.5, 1/45, 1/47.5, 1/50, 1/55, 1/60, 1/65, 1/70, 1/75, 1/80, 1/85, 1/90, 1/95, or 1/100 of a thickness of the therapeutic region. In those embodiments where the control region comprises a single control region, the control region may have a thickness that is less than or equal to 1/10, 1/12.5, 1/15, 1/17.5, 1/20, 1/22.5, 1/25, 1/27.5, 1/30, 1/32.5, 1/35, 1/37.5, 1/40, 1/42.5, 1/45, 1/47.5, 1/50, 1/55, 1/60, 1/65, 1/70, 1/75, 1/80, 1/85, 1/90, 1/95, or 1/100 of a thickness of the therapeutic region. In those embodiments with multiple sub-control regions, one or more of the sub-control regions may individually be less than or equal to 1/10, 1/12.5, 1/15, 1/17.5, 1/20, 1/22.5, 1/25, 1/27.5, 1/30, 1/32.5, 1/35, 1/37.5, 1/40, 1/42.5, 1/45, 1/47.5, 1/50, 1/55, 1/60, 1/65, 1/70, 1/75, 1/80, 1/85, 1/90, 1/95, or 1/100 of a thickness of the depot. In those embodiments where the control region comprises a single control region, the control region may have a thickness that is less than or equal to 1/10, 1/12.5, 1/15, 1/17.5, 1/20, 1/22.5, 1/25, 1/27.5, 1/30, 1/32.5, 1/35, 1/37.5, 1/40, 1/42.5, 1/45, 1/47.5, 1/50, 1/55, 1/60, 1/65, 1/70, 1/75, 1/80, 1/85, 1/90, 1/95, or 1/100 of a thickness of the depot.

The control regions 300*a*, 300*b* may only cover a portion of the therapeutic region 200 such that a portion of each of the lateral surfaces (e.g., sidewall) of the therapeutic region 200 is exposed to physiologic fluids immediately upon implantation of the depot 100 in vivo. For example, at least prior to implantation, the exposed surfaces of the therapeutic region 200 may account for about 2% to about 15%, about 3% to about 12%, about 5% to about 10%, about 6% to about 8%, about 2%, about 3%, about 4%, about 5%, about 6%, about 7%, about 8%, about 9%, about 10% of the surface area of the depot 100. In some embodiments, at least prior to implantation, the ratio of the exposed surfaces of the therapeutic region 200 to the exposed surfaces of the control region 300 may be about 2% to about 15%, about 3% to about 12%, about 5% to about 10%, about 6% to about 8%, about 2%, about 3%, about 4%, about 5%, about 6%, about 7%, about 8%, about 9%, about 10% of the surface area of the depot 100.

When the depot 100 is exposed to physiologic fluids (or any similar fluid in an in vitro setting), the therapeutic agent will elute from the exposed surfaces 202 (in addition to through the control regions 300*a*, 300*b*), such that the therapeutic agent is released faster than if the therapeutic region 200 had no exposed regions. As such, the surface area of the exposed surfaces 202 may be tailored to provide an initial, controlled burst, followed by a tapering release (for example, similar to that shown at FIG. 3). The initial, more aggressive release of the therapeutic agent is slowed in part by the control regions 300a, 300b that initially reduce the surface area of the therapeutic region 200 exposed to the fluids. Unlike the depots 100 of the present technology, many conventional drug-eluting technologies provide an initial, uncontrolled burst release of drug when exposed to physiologic fluids. Several embodiments of depots of the present technology not only enable enough therapeutic agent to be implanted for several days' or weeks' worth of dosage to achieve a sustained, durable, in vivo pharmacological treatment, but they also release the therapeutic agent as prescribed and thereby prevent a substantial portion of the entire payload being released in an uncontrolled manner that could potentially result in complications to the patient and/or reduce the remaining payload such that there is not enough therapeutic agent remaining in the depot to deliver a therapeutic amount for the remaining duration of release.

In some embodiments, the depot 100 shown in FIG. 4 is configured such that about 20% to about 50% of the analgesic is released in the first about 3 days to about 5 days of the 14 days, and wherein at least 80% of the remaining analgesic is released in the last about 9 days to about 11 days of the 14 days. This release profile provides higher dosages of the therapeutic agent during the acute period after surgery compared to the subacute period. In some embodiments, the depot 100 shown in FIG. 4 is configured to release about 100 mg to about 500 mg of analgesic to the treatment site per day, and in some cases no more than 400 mg or no more than 300 mg of analgesic per day within the first 3 days of implantation and no more than 200 mg per day in the remaining days.

Several embodiments of the depot 100 shown in FIG. 4 are also configured to maintain their structural integrity even after a substantial portion of the releasing agent has eluted from the depot 100. As the releasing agent(s) dissolves and therapeutic agent(s) elutes, the functional mechanical aspects of the depot 100 may change over time. Such mechanical aspects include structural integrity, flexural strength, tensile strength, or other mechanical characteristics of the depot. If a depot 100 experiences too much degradation too fast, it may fail mechanically and release an undesirable burst of therapeutic agent into the body. Several embodiments of depots 100 shown in FIG. 4 are loaded with enough therapeutic agent to deliver 100 mg to 500 mg of the therapeutic agent per day while still being able to maintain its structural integrity such that depot remains largely intact up to at least 14 days after implantation. A depot can be sufficiently intact, for example, if it does not fracture into multiple component pieces with two or more of the resulting pieces being at least 5% of the previous size of the depot. Alternatively, or additionally, a depot can be considered to be sufficiently intact if the release rate of the therapeutic agent does not increase by more than a factor of three as compared to the release rate of therapeutic agent in a control depot submerged in a buffered solution.

The therapeutic agent can be at least 50%-95% by weight of the total weight of the depot 100 before implantation, or 55%-85% by weight of the total weight of the depot 100 before implantation, or 60%-75% by weight of the total weight of the depot 100 before implantation. Likewise, the polymer may be no more than 5%-50% by weight of the total weight of the depot 100 before implantation, or 10%-50% by weight of the total weight of the depot 100 before implantation, or 15%-45% by weight of the total weight of the depot 100 before implantation, or 20%-40% by weight of the total weight of the depot 100 before implantation, or no more than 25%, no more than 30%, no more than 35%, or no more than 40%. The ratio of the mass of the therapeutic agent in the depot 100 to the mass of the polymer in the depot 100 can be at least 16:1, 15:1, 14:1, 13:1, 12:1, 11:1, 10:1, 9:1, 8:1, 7:1, 6:1, 5:1, 4:1, 3:1, or 2:1.

Several embodiments of the depot 100 shown in FIG. 4 having one or more combinations of the parameters described in the preceding paragraphs have provided exceptional results in animal studies as described herein. For example, a depot 100 was configured such that (a) the thickness of the control regions 300a-b were each or collectively less than or equal to 1/50 of the thickness of the therapeutic region 200, (b) the mass of therapeutic agent payload was sufficient to release about 100 mg to about 500 mg of analgesic to the treatment site per day, and (c) the structural integrity was such that the depot remained largely intact for at least 14 days after implantation. These embodiments were able to release about 20% to about 50% of the analgesic payload in the first about 3 days to about 5 days of the 14 days, and then release at least 80% of the remaining analgesic payload in the last about 9 days to about 11 days of the 14 days. This was unexpected because, at least in part, (a) providing such a large payload of therapeutic agent in the therapeutic region was expected to cause the depot 100 fail mechanically on or before 14 days post-implant, and (b) no disclosed devices had achieved a release profile wherein about 20% to about 50% of the analgesic was released in the first about 3 days to about 5 days of the 14 days, and then at least 80% of the remaining analgesic was released in the last about 9 days to about 11 days of the 14 days.

Figure 5:
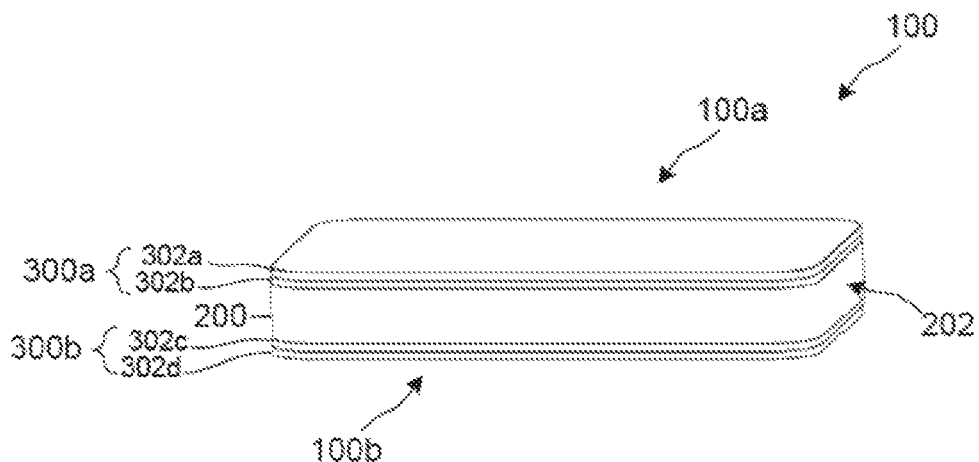
FIG. 5 is an isometric view of a depot in accordance with some embodiments of the present technology.

In some embodiments, one or more control regions 300 of the depot 100 may comprise two or more sub-control regions. For example, as shown in FIG. 5, the depot 100 may have a first control region 300a and a second control region 300b, each of which comprises first and second sub-control regions 302a, 302b and 302c, 302d, respectively. The first and second control regions 300a, 300b and/or one, some or all of the sub-control regions 302a-302d may have the same or different amounts of releasing agent, the same or different concentrations of releasing agent, the same or different releasing agents, the same or different amounts of polymer, the same or different polymers, the same or different polymer to releasing agent ratios, and/or the same or different thicknesses. In some embodiments, the concentration of the releasing agent in the individual outer control sub-regions 302a, 302d is less than the concentration of the releasing agent in the individual inner control sub-regions 302b, 302c such that the outer portion of the collective control region will elute the therapeutic agent more slowly than the inner portion of the collective control region. In some embodiments, the concentration of the releasing agent in the individual outer control sub-regions 302a, 302d is greater than the concentration of the releasing agent in the individual inner control sub-regions 302b, 302c. In those embodiments where the control region includes more than two sub-regions, the concentration of releasing agent per sub-region or layer may increase, decrease, or remain constant as the sub-control regions are farther away from the therapeutic region 200.

In certain embodiments, the outer control sub-regions include at least 5% by weight of the releasing agent, at least 10% by weight of the releasing agent, at least 15% by weight of the releasing agent, at least 20% by weight of the releasing agent, at least 25% by weight of the releasing agent, at least 30% by weight of the releasing agent, at least 35% by weight of the releasing agent, at least 40% by weight of the releasing agent, at least 45% by weight of the releasing agent, or at least 50% by weight of the releasing agent. In some embodiments, the inner control sub-regions include at least 5% by weight of the releasing agent, at least 10% by weight of the releasing agent, at least 15% by weight of the releasing agent, at least 20% by weight of the releasing agent, at least 25% by weight of the releasing agent, at least 30% by weight of the releasing agent, at least 35% by weight of the releasing agent, at least 40% by weight of the releasing agent, at least 45% by weight of the releasing agent, or at least 50% by weight of the releasing agent. In some embodiments, the outer control sub-regions may include a first amount of the releasing agent and the inner control sub-regions may include a second amount of the releasing agent, where the second amount is at least 200%, at least 300%, at least 400%, or at least 500% greater than the first amount.

Figure 6:
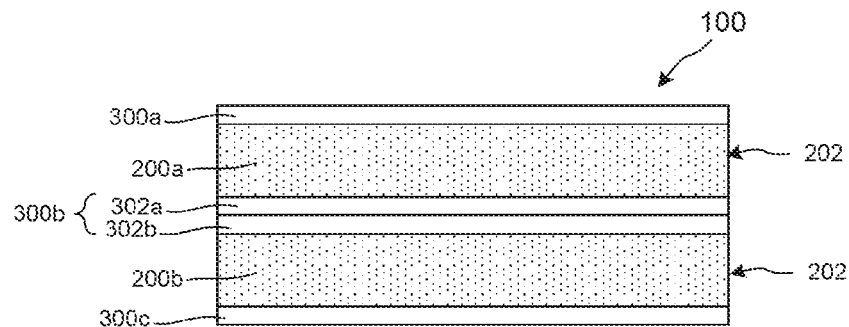
FIG. 6 is a cross-sectional view of a depot in accordance with some embodiments of the present technology.
Figure 7:
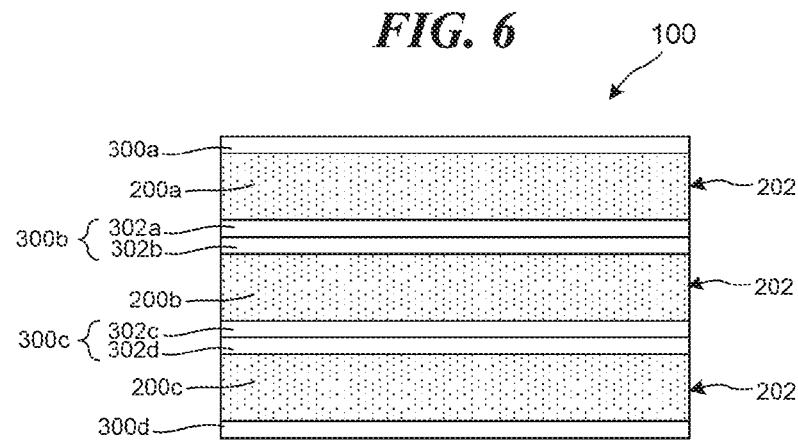
FIG. 7 is a cross-sectional view of a depot in accordance with some embodiments of the present technology.
Figure 8:
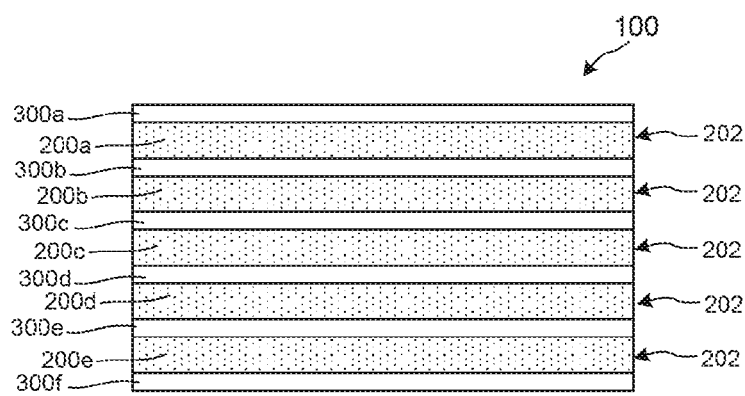
FIG. 8 is a cross-sectional view of a depot in accordance with some embodiments of the present technology.

FIGS. 6-8 show depot embodiments having a plurality of alternating therapeutic regions 200 and control regions 300 in accordance with the present technology. The depot 100 may have two or more control regions 300 and/or sub-regions 302 (e.g., 2, 3, 4, 5, 6, 7, 8, 9, 10, 20, etc.), and the depot 100 may have one or more therapeutic regions 200 and/or sub-regions 202 (e.g., 1, 2, 3, 4, 5, 6, 7, 10, 15, 20, etc.) surrounded by at least one control region 300 and/or sub-region 302. In some embodiments, each of the therapeutic regions 200 may comprise a single layer and/or each of the control regions 300 may comprise a single layer. In some embodiments, one, some, or all of the therapeutic regions 200 may comprise multiple layers and/or one, some, or all of the control regions 300 may comprise multiple layers. In some embodiments, for example as shown in FIGS. 6 and 7, two or more sub-regions 302a-b (FIG. 6) and 302a-b and 302c-d (FIG. 7) may be adjacent to each other between sub-regions 202 of the therapeutic region 200. Moreover, one or more of the individual control regions 300 and/or one or more of the therapeutic regions 200 may have the same or different amounts and/or types of releasing agent, and one or more of the therapeutic regions may have the same or different amounts and/or types of therapeutic agent.

The embodiments shown in FIGS. 6-8 may be beneficial where the therapeutic region comprises a large payload of the therapeutic agent (e.g., equivalent to many days, weeks or months of dosage). These embodiments may be beneficial because, with such a large payload, should the therapeutic region 200 be exposed to the body abruptly, the entire payload may be released prematurely, subjecting the patient to an abnormally and undesirably high dose of the therapeutic agent. For example, if the integrity of the control region 300 were compromised, the patient may be exposed in vivo to the therapeutic agent at a higher rate than intended, potentially resulting in a clinical complication. Particularly with respect to the administration of local anesthetics (e.g., bupivacaine, ropivacaine, etc.), manufacturing guidelines recommend no more than 400 mg should be administered within a 24-hour period. However, multiple studies have demonstrated that doses higher than 400 mg from extended release products are safe due to their slower release over an extended period of time. Regardless, in the event that a control region 300 is compromised, it is desirable for the patient to be subjected only to a fraction of the total payload, whereby the fraction to which the patient is exposed if prematurely released would be within safety margins for the particular therapeutic agent. The structural integrity of the control regions 300, as well as that of the therapeutic region(s) 200, is an important property for depots with large masses of therapeutic agents that are to be delivered over a long period of time.

To address this concern, in some embodiments of the present technology, the depot 100 may comprise multiple therapeutic regions 200 separated by one or more control regions 300 (for example, as shown in FIGS. 6-8). Such a configuration allows the therapeutic agent in each therapeutic region 200 (which carries a fraction of the total payload), to be individually sequestered. In the event a particular control region is compromised, only the fractional payload corresponding to the therapeutic region associated with the compromised control region would prematurely release. For example, in some of the foregoing embodiments, the total payload of the depot 100 may be at least 100 mg, at least 150 mg, at least 200 mg, at least 300 mg, at least 400 mg, at least 500 mg, at least 600 mg, at least 700 mg, at least 800 mg, at least 900 mg, or at least 1000 mg of therapeutic agent, such as an analgesic (e.g., bupivacaine, ropivacaine, etc.). Likewise, in some embodiments the fractional payload of each therapeutic region or sub-region may be up to 1%, up to 5%, up to 10%, up to 15%, up to 20%, up to 25%, up to 30%, up to 40%, up to 50%, up to 60%, up to 70%, up to 80%, up to 90%, or up to 100% of the total payload contained within the depot 100. As a result, if any single sub-region 202 of the therapeutic region 200 is compromised, it can release only a proportionate fraction of the total payload of the depot.

In some embodiments, each of the therapeutic regions and each of the control regions is a micro-thin layer, i.e., having a layer thickness that is less than 1 mm. In some embodiments, the depot comprises from about 2 to about 100 therapeutic regions, or from about 2 to about 50 therapeutic regions, or from about 2 to about 10 therapeutic regions.

FIGS. 9A-11 show some aspects of the present technology in which the depots 100 may have one or more therapeutic regions 200 completely enclosed or surrounded by one or more control regions 300. In contrast to the previously described embodiments, at least one therapeutic region of such fully-enclosed embodiments does not have any exposed surface area. For example, as shown in FIGS. 9A and 9B, in some embodiments the depot 100 may comprise a therapeutic region 200 surrounded or fully-enclosed by a control region 300 such that no portion of the therapeutic region 200 is exposed through the control region 300. As a result, the control region 300 substantially prevents contact between the therapeutic agent and physiologic fluids, thereby preventing an uncontrolled, burst release of the therapeutic agent when implanted. Over time, the releasing agent imbedded in the polymer of the control region 300 contacts physiologic fluids and dissolves, thereby forming diffusion openings in the control region. The combination of the restriction imposed by the control region and the diffusion openings formed by dissolution of the releasing agent enables a controlled release of the therapeutic agent from the depot over the course of several days, weeks, or months. Although the depot 100 is shown as a rectangular, thin film in FIGS. 9A and 9B, in other embodiments the depot 100 may have other shapes, sizes, or forms.

FIG. 10 illustrates a depot 100 having a therapeutic region 200 fully-enclosed by a control region 300 having a first control region 300a and a second control region 300b. As depicted in FIG. 10, in some embodiments the therapeutic region 200 may be sandwiched between the first control region 300a and the second control region 300b, and the first and second control regions 300a-b may be bonded via heat compression around the therapeutic region 200 to enclose the therapeutic region 200 therebetween. In certain embodiments, a bioresorbable polymer may be wrapped around the entire depot and sealed on the top or bottom surface creating a control region structure similar to that depicted in FIG. 9A. The outer portion of the first and second control regions 300a-b may be incorporated as the final wrapped layer to seal the edges. Additionally, the first and second control regions 300a-b can be integrally formed with each other using dip coating and/or spray coating techniques, such as dipping the therapeutic region 200 in a solution of the control region material or spraying a solution of control region material onto the surfaces of the therapeutic region 200.

In FIG. 10, the first control region 300a can have first and second sub-regions 302a-b, and the second control region 300b can have first and second sub-regions 302c-d. The first control region 300a can define a top control region member, and the first and second sub-regions 302a-b can comprise a first top control layer and a second top control layer, respectively. The second control region 300b can define a bottom control region member, and the first and second sub-regions 302c-d can comprise a first bottom control layer and a second bottom control layer, respectively. The first and second top/bottom control layers can be any variation of the first and second control sub-regions discussed above with reference to FIG. 5. In addition, the first top control layer of the top control region member may have the same or different properties (e.g., thickness, polymer, releasing agent, concentration of releasing agent, total amount of releasing agent, polymer to releasing agent ratio, etc.) as the first bottom control layer of the bottom control region member. Similarly, the second top control layer of the top control region member may have the same or different properties as the second bottom control layer of the bottom control region member. Variations in the loading and construction of the layers may be designed into the depot 100 to achieve a release profile or kinetics that suits the objectives of the intended therapy. In other embodiments, the first control region 300a and/or the second control region 300b has a single layer.

FIG. 11 shows some embodiments in which the depot 100 may have a therapeutic region 200 fully-enclosed by a control region 300 having different sub-region configurations. The depot 100 of FIG. 11 includes a first control region 300a and a second control region 300b that together fully enclose the therapeutic region 200. In contrast to the depot 100 shown in FIG. 10, the first control region 300a has an outer top control region 301a with first and second top sub-control regions 302a and 302b, respectively, and an inner top control region 301b with first and second top layers 303a and 303b. The first and second top layers 303a-b are over only the top surface of the therapeutic region 200, while the first and second top sub-control regions 302a-b cover a portion of the lateral surfaces of the therapeutic region 200 and the inner top control region 301b. The second control region 300b has an outer bottom control region 301c with first and second bottom sub-control regions 302c and 302d, respectively, and an inner bottom control region 301d with first and second bottom layers 303d and 303e, respectively. As such, when the depot 100 is positioned at the treatment site in vivo, the outer top and bottom control regions 301a and 301c are between: (a) the therapeutic region 200 and the inner top and bottom control regions 301b and 301d, respectively, and (b) physiologic fluids at the treatment site. In certain embodiments, such as that shown in FIG. 11, one or more of the outer top/bottom control regions 301a/301c may comprise one or more control sub-regions, and one or more inner top/bottom control regions 301b/301d may include one or more control sub-regions.

Figure 12:
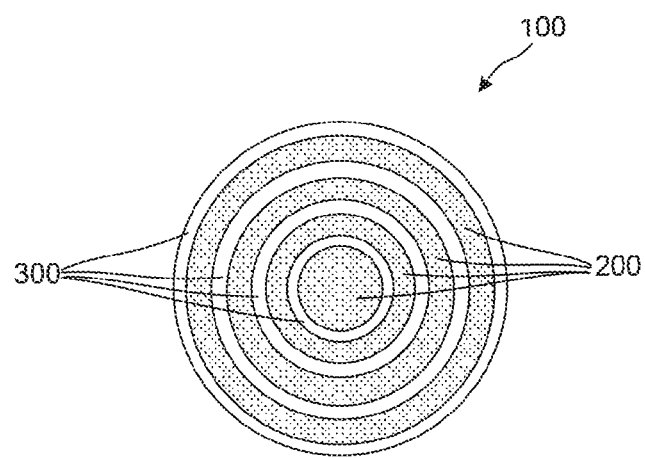
FIG. 12 is a cross-sectional view of a depot in accordance with some embodiments of the present technology.

FIG. 12 shows a cross-section of a spherical depot 100 in accordance with several embodiments of the present technology having a plurality of alternating therapeutic regions 200 and control regions 300 in accordance with the present technology. The depot 100 may have two or more control regions 300 (e.g., 2, 3, 4, 5, 6, 7, 8, 9, 10, 20, etc.), and the depot may have one or more therapeutic regions 200 (e.g., 1, 2, 3, 4, 5, 6, 7, 10, 15, 20, etc.) surrounded by at least one control region 300. In some embodiments, each of the therapeutic regions 200 may comprise a single layer and/or each of the control regions 300 may comprise a single layer. In some embodiments, one, some, or all of the therapeutic regions 200 may comprise multiple layers and/or one, some, or all of the control regions 300 may comprise multiple layers. Moreover, one or more of the individual control regions 200 and/or one or more of the therapeutic regions 300 may have the same or different amounts and/or types of releasing agent, and one or more of the therapeutic regions 200 may have the same or different amounts and/or types of therapeutic agent.

Figure 13:
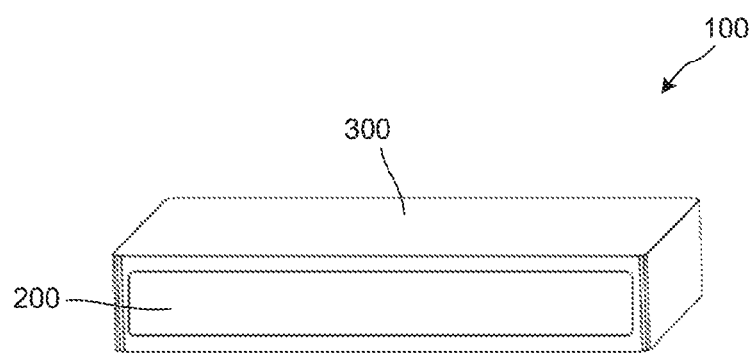
FIG. 13 is an isometric view of a depot in accordance with some embodiments of the present technology.

FIG. 13 shows a depot 100 in accordance with several embodiments of the present technology having a therapeutic region 200 enclosed on the top and bottom surfaces as well as two of the four lateral surfaces by a control region 300. This configuration is expected to release the therapeutic agent more slowly, at least initially, compared to a depot with the same dimensions and fully exposed lateral surfaces (see, e.g., the depot 100 shown in FIG. 4).

The release kinetics of the depots of the present technology may also be tuned for a particular application by varying the shape and size of the depot 100. Depending on the therapeutic dosage needs, anatomical targets, etc., the depot 100 can be different sizes, shapes, and forms for implantation and/or injection in the body by a clinical practitioner. The shape, size, and form of the depot 100 should be selected to allow for ease in positioning the depot at the target tissue site, and to reduce the likelihood of, or altogether prevent, the depot from moving after implantation or injection. This may be especially true for depots being positioned within a joint (such as a knee joint), wherein the depot is a flexible solid that is structurally capable of being handled by a clinician during the normal course of a surgery without breaking into multiple pieces and/or losing its general shape. Additionally, the depot may be configured to be placed in the knee of a patient and release the analgesic in vivo for up to 7 days without breaking into multiple pieces.

Some of the form factors producible from the depot 100 or to be used adjunctive to the depot for implantation and fixation into the body include: strips, ribbons, hooks, rods, tubes, patches, corkscrew-formed ribbons, partial or full rings, nails, screws, tacks, rivets, threads, tapes, woven forms, t-shaped anchors, staples, discs, pillows, balloons, braids, tapered forms, wedge forms, chisel forms, castellated forms, stent structures, suture buttresses, coil springs, sponges, capsules, coatings, matrices, wafers, sheets, strips, ribbons, pills, and pellets.

The depot 100 may also be processed into a component of the form factors mentioned in the previous paragraph. For example, the depot could be rolled and incorporated into tubes, screws, tacks, or the like. In the case of woven embodiments, the depot may be incorporated into a multilayer woven film/braid/mesh wherein some of the filaments used are not the inventive device. In one example, the depot is interwoven with Dacron, polyethylene or the like. For the sake of clarity, any form factor corresponding to the depot of the present technology, including those where only a portion or fragment of the form factor incorporates the depot, may be referred to herein as a "depot."

Figure 14A:
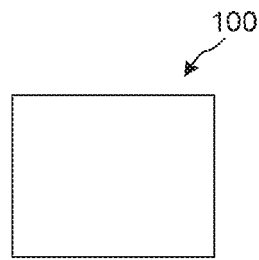
FIGS. 14A-14H are depots having different cross-sectional areas and shapes in accordance with the present technology.
Figure 14B:
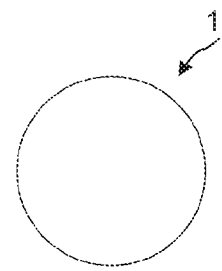
Figure 14C:
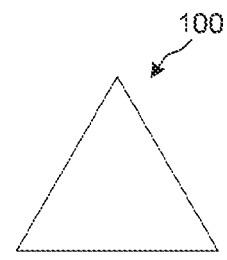
Figure 14D:
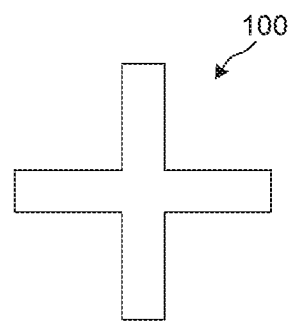
Figure 14E:
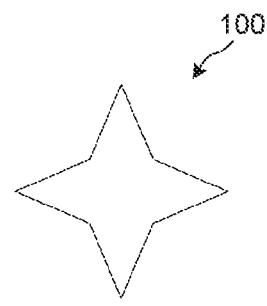
Figure 14F:
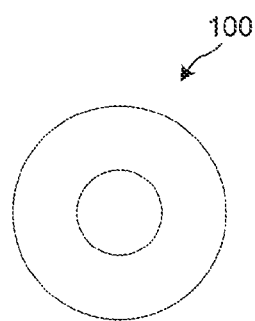
Figure 14G:
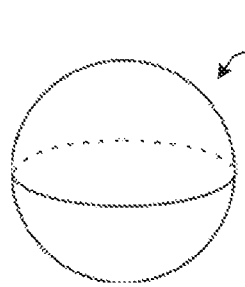
Figure 14H:
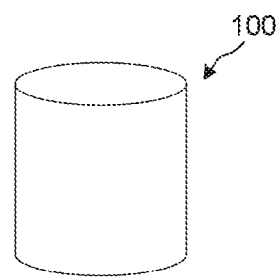

As shown in the cross-sectional views of FIGS. 14A-14H, in various embodiments, the depot 100 can be shaped like a sphere, a cylinder such as a rod or fiber, a flat surface such as a disc, film, ribbon, strip or sheet, a paste, a slab, microparticles, nanoparticles, pellets, mesh or the like. FIG. 14A shows a rectilinear depot 100. FIG. 14B shows a circular depot 100. FIG. shows a triangular depot 100. FIG. 14D show cross-like depot 100, FIG. 14E shows a star-like depot 100, and FIG. 14F shows a toroidal depot 100. FIG. 14G shows a spheroid depot 100, and FIG. 14H shows a cylindrical depot 100. The shape of the depot 100 can be selected according to the anatomy to fit within a given space and provide the desired fixation and flexibility properties. This is because the fit, fixation and flexibility of the depot may enhance the ease of implanting the depot, ensure delivery of the therapeutic agent to the target site, and prolong the durability of the implant in dynamic implant sites.

In various embodiments, the depot can be different sizes, for example, the depot may be a length of from about 0.4 mm to 100 mm and have a diameter or thickness of from about 0.01 to about 5 mm. In various embodiments, the depot may have a layer thickness of from about 0.005 to 5.0 mm, such as, for example, from 0.05 to 2.0 mm. In some embodiments, the shape may be a rectangular or square sheet having a ratio of width to thickness in the range of 20 or greater, 25 or greater, 30 or greater, 35 or greater, 40 or greater, 45 or greater, or 50 or greater.

In some embodiments, a thickness of the control region (a single sub-control region or all sub-control regions combined) is less than or equal to 1/10, 1/12.5, 1/15, 1/17.5, 1/20, 1/22.5, 1/25, 1/27.5, 1/30, 1/32.5, 1/35, 1/37.5, 1/40, 1/42.5, 1/45, 1/47.5, 1/50, 1/55, 1/60, 1/65, 1/70, 1/75, 1/80, 1/85, 1/90, 1/95, or 1/100 of a thickness of the therapeutic region. In those embodiments with multiple sub-control regions, one or more of the sub-control regions may individually be less than or equal to 1/10, 1/12.5, 1/15, 1/17.5, 1/20, 1/22.5, 1/25, 1/27.5, 1/30, 1/32.5, 1/35, 1/37.5, 1/40, 1/42.5, 1/45, 1/47.5, 1/50, 1/55, 1/60, 1/65, 1/70, 1/75, 1/80, 1/85, 1/90, 1/95, or 1/100 of a thickness of the therapeutic region. In those embodiments where the control region comprises a single control region, the control region may have a thickness that is less than or equal to 1/10, 1/12.5, 1/15, 1/17.5, 1/20, 1/22.5, 1/25, 1/27.5, 1/30, 1/32.5, 1/35, 1/37.5, 1/40, 1/42.5, 1/45, 1/47.5, 1/50, 1/55, 1/60, 1/65, 1/70, 1/75, 1/80, 1/85, 1/90, 1/95, or 1/100 of a thickness of the therapeutic region. In those embodiments with multiple sub-control regions, one or more of the sub-control regions may individually be less than or equal to 1/10, 1/12.5, 1/15, 1/17.5, 1/20, 1/22.5, 1/25, 1/27.5, 1/30, 1/32.5, 1/35, 1/37.5, 1/40, 1/42.5, 1/45, 1/47.5, 1/50, 1/55, 1/60, 1/65, 1/70, 1/75, 1/80, 1/85, 1/90, 1/95, or 1/100 of a thickness of the depot. In those embodiments where the control region comprises a single control region, the control region may have a thickness that is less than or equal to 1/10, 1/12.5, 1/15, 1/17.5, 1/20, 1/22.5, 1/25, 1/27.5, 1/30, 1/32.5, 1/35, 1/37.5, 1/40, 1/42.5, 1/45, 1/47.5, 1/50, 1/55, 1/60, 1/65, 1/70, 1/75, 1/80, 1/85, 1/90, 1/95, or 1/100 of a thickness of the depot.

In some embodiments, the depot 100 has a width and a thickness, and a ratio of the width to the thickness is 21 or greater. In some embodiments, the ratio is 22 or greater, 23 or greater, 24 or greater, 25 or greater, 26 or greater, 27 or greater, 28 or greater, 29 or greater, 30 or greater, 35 or greater, 40 or greater, 45 or greater, or 50 or greater.

In some embodiments, the depot 100 has a surface area and a volume, and a ratio of the surface area to volume is at least 1, at least 1.5, at least 2, at least 2.5, or at least 3.

In any of the foregoing embodiments shown and described above with respect to FIGS. 2-14H, dissolution of the releasing agent(s) and elution of the therapeutic agent(s) can change functional mechanical aspects of the depot 100 over time. Such mechanical aspects include structural integrity, flexural strength, tensile strength, or other mechanical characteristics of the depot 100. In some instances, undesirable degradation of the depot 100, such as premature degradation, can cause mechanical failure of the depot 100 and a corresponding undesirable burst release of therapeutic agent into the body. Accordingly, it can be beneficial for the depot 100 to maintain sufficient flexural strength and/or mechanical integrity in vivo for at least a predetermined period of time or until a predetermined proportion of therapeutic agent has been released from the depot 100. The depot 100 can be considered to maintain its structural integrity if the depot 100 remains largely intact with only partial or gradual reduction due to elution of therapeutic agent or dissolution of the control layers or releasing agent. The depot 100 can be considered to lose its structural integrity if it separates (e.g., fractures) into multiple component pieces, for example, with two or more of the resulting pieces being at least 5% of the previous size of the depot 100. Alternatively, or additionally, the depot 100 can be considered to lose its structural integrity if the release rate of the therapeutic agent increases by more than a factor of three as compared to the release rate of therapeutic agent in a control depot submerged in a buffered solution.

In some embodiments, the depot 100 is configured to maintain its structural integrity in vivo for at least a predetermined length of time. For example, the depot 100 can be configured to maintain its structural integrity in vivo for at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days, at least 22 days, at least 23 days, at least 24 days, at least 25 days, at least 26 days, at least 27 days, at least 28 days, at least 29 days, or at least 30 days, at least 40 days, at least 50 days, at least 60 days, at least 70 days, at least 90 days, at least 100 days, at least 200 days, at least 300 days, or at least 365 days.

In some embodiments, the depot 100 is configured to maintain its structural integrity in vivo until at least a predetermined proportion of therapeutic agent payload has been released from the depot. For example, the depot 100 can be configured to maintain its structural integrity in vivo until at least 5% by weight of the original payload has been released, at least 10% by weight of the original payload has been released, at least 15% by weight of the original payload has been released, at least 20% by weight of the original payload has been released, at least 25% by weight of the original payload has been released, at least 30% by weight of the original payload has been released, at least 35% by weight of the original payload has been released, at least 40% by weight of the original payload has been released, at least 45% by weight of the original payload has been released, at least 50% by weight of the original payload has been released, at least 55% by weight of the original payload has been released, at least 60% by weight of the original payload has been released, at least 65% by weight of the original payload has been released, at least 70% by weight of the original payload has been released, at least 75% by weight of the original payload has been released, at least 80% by weight of the original payload has been released, at least 85% by weight of the original payload has been released, at least 90% by weight of the original payload has been released, or until at least 95% by weight of the original payload has been released.

One aspect of the structural integrity of the depot 100 when it is in vivo can be quantified using a bend test, such as a three-point bend test that measures flexural properties including the flexural strength and/or maximum flexural stress sustained by a specimen before breaking. Such a bend test may represent (e.g., simulate) the forces that the depot 100 will encounter in vivo in an anatomical joint (e.g., a knee joint). In one example, a depot can be subjected to a three-point bend test based on ASTM-D790-17, "Standard Test Methods for Flexural Properties of Unreinforced and Reinforced Plastics and Electrical Insulating Materials." The text of this standard is hereby incorporated by reference in its entirety. The depot 100 may be suspended in a medium configured to simulate in vivo conditions, for example a phosphate buffered saline (PBS) at approximately 37° C. The bend test may be performed after different time periods of submersion in the medium to evaluate changes in the flexural strength of the depot 100 over time in simulated in vivo conditions.

Figure 15:
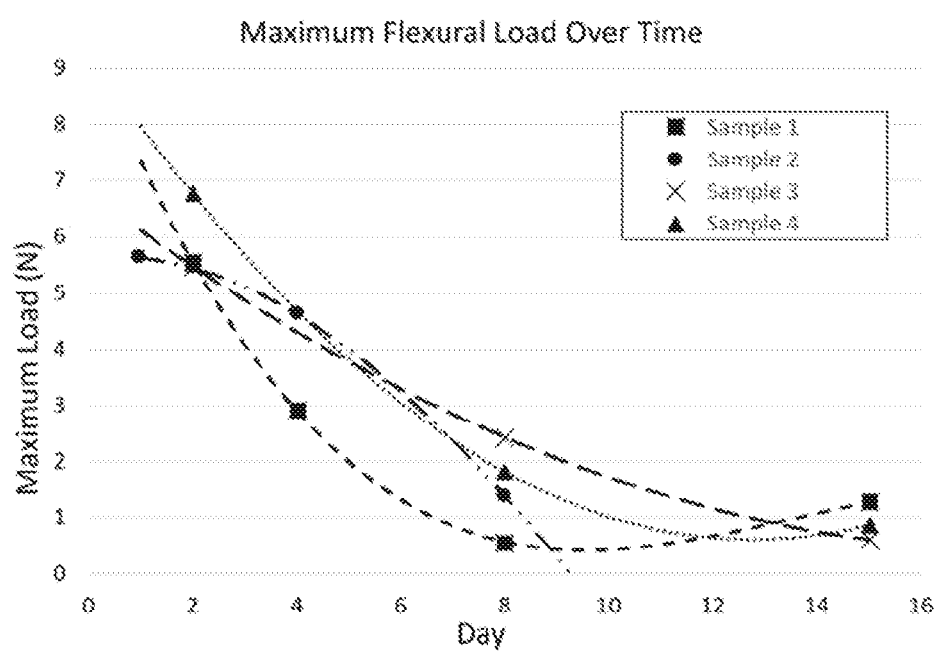
FIG. 15 depicts the maximum flexural load of an implant over time from testing performed on implant samples submerged in buffered solution.

Table 1 shows the maximum flexural load sustained by four different samples of the depot 100 at different time periods following submersion in the medium as measured using a three-point bend test with maximum deflection set at 2.13 mm. The values in Table 1 reflect measurements made from two instances of each of the listed samples. FIG. 15 is a graph illustrating these values plotted graphically and fitted with trendlines. In each of these four samples, the depot 100 includes a therapeutic region 200 surrounded by upper and lower control regions 300a-b as shown and described above with reference to FIG. 4 or 5. The therapeutic region 200 has exposed lateral surfaces 202 between the first and second control regions 300a-b. The depots 100 each have lateral dimensions of approximately 2.5 cm by 1.5 cm, with a thickness of approximately 1 mm.

Sample 1 is a depot having a therapeutic region with a ratio by weight of releasing agent to polymer to therapeutic agent of 0.5:10:20. The polymer in this sample is P (DL) GACL with a PDLLA:PGA:PCL ratio of 6:3:1, the releasing agent is Tween 20, and the therapeutic agent is bupivacaine hydrochloride. In this sample, the depot includes a first control region 300a comprising a single control layer over the upper surface of the therapeutic region 200 and a second control region 300b comprising single control layer over the lower surface of the therapeutic region 200, as shown and described above with reference to FIG. 4. Each control region 300a-b individually has a ratio of releasing agent to polymer of 5:10.

Sample 2 is a depot having a therapeutic region 200 with a ratio by weight of releasing agent to polymer to therapeutic agent of 1:10:20. The polymer in this sample is PLGA with a PLA:PGA ratio of 1:1, the releasing agent is Tween 20, and the therapeutic agent is bupivacaine hydrochloride. Similar to Sample 1, the depot of Sample 2 includes a control region 300 comprising a first control region 300a with a single control layer over the upper surface of the therapeutic region 200 and a second control region 300b comprising a single control layer over the lower surface of the therapeutic region 200, as shown and described above with reference to FIG. 4. Each control region 300a-b individually has a ratio of releasing agent to polymer of 5:10.

Sample 3 is a depot having therapeutic region 200 with a ratio by weight of releasing agent to polymer to therapeutic agent of 5:10:20. The polymer in this sample is P (DL) GACL with a PDLLA:PGA:PCL ratio of 6:3:1, the releasing agent is Tween 20, and the therapeutic agent is bupivacaine hydrochloride. In this sample, the depot includes a control region 300 comprising a first control region 300a with two sub-control regions 302a-b over the upper surface of the therapeutic region 200, and a second control region 300b with two sub-control regions 302c-d, as shown and described above with reference to FIG. 5. Each of the inner sub-control regions 302b and 302c contacts the surface of the therapeutic region 200 and has a ratio of releasing agent to polymer of 5:10, and each of the outer sub-control regions 302a and 302d has a ratio of releasing agent to polymer of 1:10. The depot of Sample 3, therefore, includes a total of four sub-control regions.

Sample 4 is a depot having a therapeutic region 200 with a ratio by weight of releasing agent to polymer to therapeutic agent of 5:10:20. The polymer in this sample is PLGA with a PLA:PGA ratio of 1:1, the releasing agent is Tween 20, and the therapeutic agent is bupivacaine hydrochloride. As with Sample 3, the depot of Sample 4 includes a control region 300 having first and second control region 300a-b that each have two sub-control regions 302a-b and 302c-d, respectively, as shown and described with respect to FIG. 5. The depot of Sample 4 according also has a total of four sub-control regions 302a-d, two over the upper surface of the therapeutic region 200 and two over the lower surface of the therapeutic region 200. The inner of the sub-control regions 302b and 302c has a ratio of releasing agent to polymer of 5:10, and the outer of the sub-control regions 302a and 302d has a ratio of releasing agent to polymer of 1:10.

TABLE 1

| Depot Sample | Day 0 | Day 1 | Day 3 | Day 7 | Day 14 | Day 28 |
| --- | --- | --- | --- | --- | --- | --- |
| Sample 1: P(DL)GACL 6:3:1 2 control layers | No break | 5.553 N 1.25 lbf | 2.903 N 0.0653 lbf | 0.569 N 0.134 lbf | 1.263 N 0.284 lbf | Not tested |
| Sample 2: PLGA 1:1 2 control layers | 5.623 N 1.264 lbf | 5.447 N 1.22 lbf | 4.623 N 1.04 lbf | 1.386 N 0.312 lbf | Not tested | Not tested |
| Sample 3: P(DL)GACL 6:3:1 4 control layers | No break | 5.474 N 1.23 lbf | Not tested | 2.430 N 0.546 lbf | 0.605 N 0.136 lbf | Sample degraded |

TABLE 1-continued

| Depot Sample | Day 0 | Day 1 | Day 3 | Day 7 | Day 14 | Day 28 |
|---|---|---|---|---|---|---|
| Sample 4: PLGA 1:1 4 control layers | No break | 6.763 N 1.52 lbf | Not tested | 1.816 N 0.408 lbf | 0.869 N 0.195 lbf | Sample degraded |

As shown in Table 1, all samples were intact and maintained sufficient structural integrity after 14 days of being suspended in the medium to withstand a bending force before fracturing. Although the maximum load tolerated by each sample decreased over time, the flexural strength of these samples at 14 days was sufficient to maintain the structural integrity desired for implantation in an active joint, such as the knee or shoulder. As shown above, for two of the samples tested at 28 days, the samples had degraded such that the test could not be performed because the sample was no longer structurally intact. In such instances, it may be desirable to configure the depots such that all or substantially all the therapeutic agent payload has been released from the depot prior to its degradation and loss of structural integrity.

In this series of experiments summarized in Table 1, the sample depots are generally flexible at Day 0 before submersion in PBS. Following submersion, the flexural strength of the depots decreased such that the depots became more brittle with time. Yet, at 7-14 days, the depots were still sufficiently functionally intact. Without being bound by theory, it is believed that after the therapeutic agent has eluted, the depots gradually become an empty polymer matrix. For example, after 14-28 days in the solution, the depots may weigh only approximately 30% of their starting weight before submersion in the PBS. At this lower weight and in the porous state, the depots may be more brittle, with lower flexural strength and less resistance to bending loads.

As noted above, it can be advantageous for the depots 100 to maintain their structural integrity and flexural strength even while they gradually degrade as the therapeutic agent payload releases into the body. In some embodiments, the depot 100 can be configured such that, in in vitro testing utilizing a three-point bend test, the flexural strength of the depot 100 decreases by no more than 95%, no more than 90%, no more than 85%, no more than 80%, no more than 75%, no more than 70%, no more than 65%, no more than 60%, no more than 55%, no more than 50%, no more than 45%, no more than 40%, no more than 35%, no more than 30%, no more than 25%, no more than 20%, no more than 15%, no more than 10%, or no more than 5% after being submerged in PBS for a predetermined period of time. In various embodiments, the predetermined period of time that the depot 100 is submerged in PBS before being subjected to the three-point bend test is 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, after 21 days, after 22 days, 23 days, 24 days, 25 days, 26 days, 27 days, 28 days, or more. In at least some embodiments, the change in flexural strength of the depot 100 can be measured between day 0 (e.g., before submersion in the PBS) and a subsequent time after some period of submersion in PBS. In other embodiments, the change in flexural strength of the depot 100 can be measured between day 1 (e.g., after 24 hours of submersion in PBS) and a subsequent time following longer submersion in PBS.

In some embodiments, the depot 100 can be configured such that, in in vitro testing utilizing a three-point bend test, the flexural strength of the depot 100 decreases by no more than 95%, no more than 90%, no more than 85%, no more than 80%, no more than 75%, no more than 70%, no more than 65%, no more than 60%, no more than 55%, no more than 50%, no more than 45%, no more than 40%, no more than 35%, no more than 30%, no more than 25%, no more than 20%, no more than 15%, no more than 10%, or no more than 5% over the time period in which a predetermined percentage of the initial therapeutic agent payload is released while the depot 100 is submerged in PBS. In various embodiments, the predetermined percentage of payload released when the depot 100 is submerged in PBS before being subjected to the three-point bend test is about 5%, about 10%, about 15%, about 20%, about 25%, about 30%, about 35%, about 40%, about 45%, about 50%, about 55%, about 60%, about 65%, about 70%, about 75%, about 80%, about t 85%, about 90%, or about 95%. As noted above, in at least some embodiments, the change in flexural strength of the depot 100 can be measured between day 0 (prior to submersion in PBS) or day 1 (after 24 hours of submersion in PBS) and a subsequent following longer submersion in PBS.

In some embodiments, the depot 100 has (a) lateral dimensions of about 1.0-3.0 cm, (b) a thickness of about 0.5-2.5 mm, and (c) a payload of therapeutic agent sufficient to release about 100 mg to about 500 mg of therapeutic agent per day for up to 7, 8, 9, 10, 11, 12, 13, 14, 15, 16, 17, 18, 19, or 20 days, and the depot 100 is configured to remain sufficiently mechanically intact to provide sustained, controlled release of therapeutic agent for at least 7 days. Such embodiments of the depot 100 can comprise the therapeutic region 200 with a therapeutic agent and the control region 300. The control region 300 can have first and second control regions 300a-b, such as those shown and described above with reference to FIGS. 4-13, and the control region 300 comprises a bioresorbable polymer and a releasing agent mixed with the bioresorbable polymer. The releasing agent is configured to dissolve when the depot 100 is placed in vivo to form diffusion openings in the control region 300. The depot 100 is further configured such that, following submersion of the depot 100 in a buffer solution for seven days, the flexural strength of the depot 100 decreases by no more than 75%, or by no more than 70%, or by no more than 65%, or by no more than 60%, or by no more than 55%, or by no more than 50%, or by no more than 45%

In some embodiments, the depot 100 has (a) lateral dimensions of about 1.0-3.0 cm, (b) a thickness of about 0.5-2.5 mm, and (c) a payload of therapeutic agent sufficient to release about 100 mg to about 500 mg of therapeutic agent per day for up to 7, 8, 9, 10, 11, 12, 13, 14, 15, 16, 17, 18, 19, or 20 days, and the depot 100 is configured to remain sufficiently mechanically intact to provide sustained, controlled release of therapeutic agent for at least 7 days. Such embodiments of the depot 100 can comprise the therapeutic region 200 with a therapeutic agent and the control region 300. The control region 300 can have first and second control regions 300a-b, such as those shown and described above with reference to FIGS. 4-13, and the control region 300 comprises a bioresorbable polymer and a releasing agent mixed with the bioresorbable polymer. The releasing agent is configured to dissolve when the depot 100 is placed in vivo to form diffusion openings in the control region 300. The depot is further configured such that, following submersion of the depot in buffer solution until approximately 75% of the therapeutic agent by weight has been released, the flexural strength of the depot decreases by no more than 75%, or by no more than 70%, or by no more than 65%, or by no more than 60%, or by no more than 55%, or by no more than 50%, or by no more than 45%.

A. Therapeutic Region

The total payload and release kinetics of the depots 100 of the present technology may be tuned for a particular application by varying the composition of the therapeutic region 200. In many embodiments, the therapeutic region 200 may include a high therapeutic payload of a therapeutic agent, especially as compared to other known polymer devices of equal thickness or polymer weight percentage. For example, the depots 100 of the present technology may comprise at least 15% by weight of the therapeutic agent, at least 20% by weight of the therapeutic agent, at least at least 25% by weight of the therapeutic agent, at least 30% by weight of the therapeutic agent, at least 35% by weight of the therapeutic agent, at least 40% by weight of the therapeutic agent, at least 45% by weight of the therapeutic agent, at least 50% by weight of the therapeutic agent, at least 55% by weight of the therapeutic agent, at least 60% by weight of the therapeutic agent, at least 65% by weight of the therapeutic agent, at least 70% by weight of the therapeutic agent, at least 75% by weight of the therapeutic agent, at least 80% by weight of the therapeutic agent, at least 85% by weight of the therapeutic agent, at least 90% by weight of the therapeutic agent, at least 95% by weight of the therapeutic agent, or 100% by weight of the therapeutic agent.

The therapeutic agent may be any of the therapeutic agents disclosed herein, for example in Section C ("Therapeutic Agents") below.

In various embodiments of the depots 100 disclosed herein, the therapeutic region 200 may take several different forms. In some embodiments (for example, FIG. 4), the therapeutic region 200 may comprise a single layer comprised of a therapeutic agent, a therapeutic agent mixed with a bioresorbable polymer, or a therapeutic agent mixed with a bioresorbable polymer and a releasing agent. In some embodiments, the therapeutic region 200 itself may comprise a structure having multiple layers or sub-regions of therapeutic agent (and/or bioresorbable polymer and/or releasing agent). Some or all layers or sub-regions of such a multiple layer therapeutic region 200 may be directly adjacent (i.e., in contact with) one another (laterally or axially), and/or some or all layers or sub-regions may be spaced apart with one or more other regions therebetween (such as control region(s) 300 and/or barrier region(s))). In some embodiments, 2, 3, 4, 5, 6, 7, 8, 9, 10 or more therapeutic sub-regions or layers may be grouped together and spaced apart from another therapeutic region or group of therapeutic sub-regions or layers (having the same or different numbers of layers as the other group) with one or more other regions therebetween (such as control region(s) 300 and/or barrier region(s))) (see, for example, FIG. 5, FIG. 6, etc.).

In any of the depot embodiments disclosed herein, the ratio of the mass of the therapeutic agent in the depot to the mass of polymer in the depot is at least 3:1, 3.5:1, 4:1, 4.5:1, 5:1, 5.5:1, 6:1, 6.5:1, 7:1, 8:1, 9:1, 10:1, 11:1, 12:1, 13:1, 14:1, 15:1, or 16:1.

In any of the depot embodiments disclosed herein, the ratio of the mass of the polymer in the therapeutic region 200 to the mass of therapeutic agent in the therapeutic region 200 is at least 1:1, 1:1.5, 1:2, 1:2.5, 1:3, 1:3.5, 1:4, 1:4.5, 1:5, 1:5.5, 1:6, 1:6.5, 1:7, 1:7.5, 1:8, 1:8.5, 1:9, 1:9.5, or 1:10.

In any of the embodiments disclosed herein, the weight ratio of releasing agent to polymer in the therapeutic region 200 may be 1:1, 1:1.5, 1:2, 1:3, 1:4, 1:5, 1:6, 1:7, 1:8, 1:9, 1:10, 1:11, 1:12, 1:13, 1:14, 1:15, or 1:16.

In some embodiments, the ratio of releasing agent to polymer to therapeutic agent in the therapeutic region 200 is of from about 0.1:10:20 to about 2:10:20, about 0.1:10:20 to about 1:10:20, about 0.1:10:20 to about 0.5:10:20, about 0.5:10:20 to about 0.1:10:20, or about 0.5:10:20 to about 1:10:20.

In any of the embodiments disclosed herein having a single therapeutic region 200, the therapeutic region 200 may have a thickness of from about 5 µm to 100 µm, 5 µm to 50 µm, 5 µm to 25 µm, 5 µm to 10 µm, 5 µm to 7 µm, 7 µm to 9 µm, 10 µm to 80 µm, 10 µm to 70 µm, 10 µm to 60 µm, 20 µm to 60 µm, 15 µm to 50 µm, about 15 µm, about 20 µm, about 25 µm, about 30 µm, about 35 µm, about 40 µm, about 45 µm, about 50 µm, about 55 µm, about 60 µm, about 65 µm, about 70 µm, about 75 µm, about 80 µm, about 85 µm, about 90 µm, about 95 µm, about 100 µm, 100 µm to 2 mm, 100 µm to 1.5 mm, 100 µm to 1 mm, 100 µm to 200 µm, 200 µm to 300 µm, 300 µm to 400 µm, 400 µm to 500 µm, 500 µm to 600 µm, 600 µm to 700 µm, 700 µm to 800 µm, 800 µm to 900 µm, 900 µm to 1 mm, 1 mm to 1.5 mm, 200 µm to 600 µm, 400 µm to 1 mm, 500 µm to 1.1 mm, 800 µm to 1.1 mm, about 200 µm, about 300 µm, about 400 µm, about 500 µm, about 600 µm, about 700 µm, about 800 µm, about 900 µm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, or about 2 mm.

In those embodiments having multiple therapeutic regions and/or sub-regions, the individual sub-regions or combinations of some or all sub-regions may have a thickness of from about 5 µm to 100 µm, 5 µm to 50 µm, 5 µm to 25 µm, 5 µm to 10 µm, 5 µm to 7 µm, 7 µm to 9 µm, 10 µm to 80 µm, 10 µm to 70 µm, 10 µm to 60 µm, 20 µm to 60 µm, 15 µm to 50 µm, about 15 µm, about 20 µm, about 25 µm, about 30 µm, about 35 µm, about 40 µm, about 45 µm, about 50 µm, about 55 µm, about 60 µm, about 65 µm, about 70 µm, about 75 µm, about 80 µm, about 85 µm, about 90 µm, about 95 µm, about 100 µm, 100 µm to 2 mm, 100 µm to 1.5 mm, 100 µm to 1 mm, 100 µm to 200 µm, 200 µm to 300 µm, 300 µm to 400 µm, 400 µm to 500 µm, 500 µm to 600 µm, 600 µm to 700 µm, 700 µm to 800 µm, 800 µm to 900 µm, 900 µm to 1 mm, 1 mm to 1.5 mm, 200 µm to 600 µm, 400 µm to 1 mm, 500 µm to 1.1 mm, 800 µm to 1.1 mm, about 200 µm, about 300 µm, about 400 µm, about 500 µm, about 600 µm, about 700 µm, about 800 µm, about 900 µm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, or about 2 mm.

The therapeutic regions 200 of the present technology may comprise at least 15% by weight of the therapeutic agent, at least 20% by weight of the therapeutic agent, at least at least 25% by weight of the therapeutic agent, at least 30% by weight of the therapeutic agent, at least 35% by weight of the therapeutic agent, at least 40% by weight of the therapeutic agent, at least 45% by weight of the therapeutic agent, at least 50% by weight of the therapeutic agent, at least 55% by weight of the therapeutic agent, at least 60% by weight of the therapeutic agent, at least 65% by weight of the therapeutic agent, at least 70% by weight of the therapeutic agent, at least 75% by weight of the therapeutic agent, at least 80% by weight of the therapeutic agent, at least 85% by weight of the therapeutic agent, at least 90% by weight of the therapeutic agent, at least 95% by weight of the therapeutic agent, or 100% by weight of the therapeutic agent.

In any of the embodiments disclosed herein, the therapeutic region 200 may include of from about 0.1%-10% by weight of the releasing agent, about 0.1%-6% by weight of the releasing agent, 0.2%-10% by weight of the releasing agent, about 0.3%-6% by weight of the releasing agent, about 0.1%-1% by weight of the releasing agent, about 0.1%-0.5% by weight of the releasing agent, 1%-2% by weight of the releasing agent, about 1%-3% by weight of the releasing agent, or about 2%-6% by weight of the releasing agent. In those embodiments having multiple therapeutic regions or sub-regions, one or more of the therapeutic regions or sub-therapeutic regions may individually include of from about 0.1%-10% by weight of the releasing agent, about 0.1%-6% by weight of the releasing agent, 0.2%-10% by weight of the releasing agent, about 0.3%-6% by weight of the releasing agent, about 0.1%-1% by weight of the releasing agent, about 0.1%-0.5% by weight of the releasing agent, 1%-2% by weight of the releasing agent, about 1%-3% by weight of the releasing agent, or about 2%-6% by weight of the releasing agent. The therapeutic region 200 may not include any releasing agent. In those embodiments having multiple therapeutic regions and/or sub-regions, one, some, or all of the individual therapeutic regions and/or sub-regions may not include any releasing agent.

In any of the embodiments disclosed herein, the therapeutic region 200 may include no more than 5% by weight of the polymer, no more than 10% by weight of the polymer, no more than 15% by weight of the polymer, no more than 20% by weight of the polymer, no more than 25% by weight of the polymer, no more than 30% by weight of the polymer, no more than 35% by weight of the polymer, no more than 40% by weight of the polymer, no more than 45% by weight of the polymer, or no more than 50% by weight of the polymer. In those embodiments having multiple therapeutic regions or sub-regions, one or more of the therapeutic regions or sub-therapeutic regions may individually include no more than 5% by weight of the polymer, no more than 10% by weight of the polymer, no more than 15% by weight of the polymer, no more than 20% by weight of the polymer, no more than 25% by weight of the polymer, no more than 30% by weight of the polymer, no more than 35% by weight of the polymer, no more than 40% by weight of the polymer, no more than 45% by weight of the polymer, or no more than 50% by weight of the polymer. In some embodiments, the therapeutic region 200 may not include any polymer.

In those embodiments disclosed herein where the therapeutic region 200 includes multiple therapeutic regions or sub-regions, some or all of the therapeutic regions or sub-therapeutic regions may have the same or different amounts of releasing agent, the same or different concentrations of releasing agent, the same or different releasing agents, the same or different amounts of polymer, the same or different polymers, the same or different polymer to releasing agent ratios, the same or different amounts of therapeutic agents, the same or different types of therapeutic agents, and/or the same or different thicknesses. Moreover, a single therapeutic region or sub-region may comprise a single type of polymer or multiple types of polymers, a single type of releasing agent or multiple types of releasing agents, and/or a single type of therapeutic agent or multiple types of therapeutic agents. In those embodiments having multiple therapeutic regions and/or sub-regions, one, some, or all of the individual therapeutic regions and/or sub-regions may not include any polymer.

In some embodiments the therapeutic region 200 (or one or more therapeutic sub-regions) comprises the therapeutic agent as an essentially pure compound or formulated with a pharmaceutically acceptable carrier such as diluents, adjuvants, excipients or vehicles known to one skilled in the art

B. Control Region

The composition of the control region 300 may also be varied. For example, in many embodiments, the control region 300 does not include any therapeutic agent at least prior to implantation of the depot at the treatment site. In some embodiments, the control region 300 may include a therapeutic agent which may be the same as or different than the therapeutic agent in the therapeutic region 200.

Within the control region 300, the amount of releasing agent may be varied to achieve a faster or slower release of the therapeutic agent. In those embodiments where both the therapeutic region 200 and control region 300 include a releasing agent, the type of releasing agent within the therapeutic region 200 may be the same or different as the releasing agent in the control region 300. In some embodiments, a concentration of a first releasing agent within the control region is the greater than a concentration of a second releasing agent (the same or different as the first releasing agent) within the therapeutic region. In some embodiments, a concentration of the releasing agent within the control region is less than a concentration of the releasing agent within the therapeutic region. In some embodiments, a concentration of the releasing agent within the control region 300 is the same as a concentration of the releasing agent within the therapeutic region 200.

In various embodiments of the depots disclosed herein, the control region 300 may take several different forms. In some embodiments (for example, FIG. 4), the control region 300 may comprise a single layer on either side of the therapeutic region 200 comprised of a bioresorbable polymer mixed with a releasing agent. In some embodiments, the control region 300 itself may comprise a structure having multiple layers or sub-regions of bioresorbable polymer and releasing agent. Some or all layers or sub-regions of such a multiple layer control region 300 may be directly adjacent (i.e., in contact with) one another (laterally or axially), and/or some or all layers or sub-regions may be spaced apart with one or more other regions therebetween (such as therapeutic region(s) 200 and/or barrier region(s))). In some embodiments, 2, 3, 4, 5, 6, 7, 8, 9, 10 or more control sub-regions or layers may be grouped together and spaced apart from another control region or group of control sub-regions or layers (having the same or different numbers of layers as the other group) with one or more other regions therebetween (such as therapeutic region(s) 200 and/or barrier region(s))) (see, for example, FIG. 5, FIG. 6, etc.).

Without being bound by theory, it is believed that such a multilayer configuration improves the control region's ability to control the release of the therapeutic agent as compared to a single layer control region, even if the multilayer configuration has the same or lower thickness as the single layer control region. The channels left by dissolution of the releasing agent in both microlayers and/or sub-regions of the control region create a path for a released therapeutic agent to travel that is longer and, potentially, more cumbersome to traverse as compared to the more direct path created by the channels in the single layer control region. The control region(s) and/or sub-regions thereby regulate the therapeutic agent release rate by allowing a releasing agent to form independent non-contiguous channels through one or more control regions and/or sub-regions. In those embodiments having multiple control layers or sub-regions, some or all of the control layers or sub-regions may be heat compressed together. The one or more control regions, heat-compressed first or not, may be heat compressed together with the therapeutic region 200. Having a control region 300 with multiple layers may provide a more linear, controlled release of the therapeutic agent over time (beyond the first day of implantation). In addition, layering of the control region 300 may also contribute to a more flexible, structurally competent depot (as compared to a depot having a therapeutic region comprised of pure therapeutic agent). Such durability is beneficial for the clinician when handling/manipulating the depot 100 before and while positioning the depot 100 at a treatment site.

In any of the embodiments disclosed herein having a single control region 300, the thickness of the control region 300 may be of from about 5 μm to 100 μm, 5 μm to 50 μm, 5 μm to 25 μm, 5 μm to 10 μm, 5 μm to 7 μm, 7 μm to 9 μm, 10 μm to 80 μm, 10 μm to 70 μm, 10 μm to 60 μm, 20 μm to 60 μm, 15 μm to 50 μm, about 15 μm, about 20 μm, about 25 μm, about 30 μm, about 35 μm, about 40 μm, about 45 μm, about 50 μm, about 55 μm, about 60 μm, about 65 μm, about 70 μm, about 75 μm, about 80 μm, about 85 μm, about 90 μm, about 95 μm, or about 100 μm. In those embodiments having multiple control regions and/or sub-regions, the individual sub-regions or combinations of some or all sub-regions may have a thickness of from about 5 μm to 100 μm, 5 μm to 50 μm, 5 μm to 25 μm, 5 μm to 10 μm, 5 μm to 7 μm, 7 μm to 9 μm, 10 μm to 80 μm, 10 μm to 70 μm, 10 μm to 60 μm, 20 μm to 60 μm, 15 μm to 50 μm, about 15 μm, about 20 μm, about 25 μm, about 30 μm, about 35 μm, about 40 μm, about 45 μm, about 50 μm, about 55 μm, about 60 μm, about 65 μm, about 70 μm, about 75 μm, about 80 μm, about 85 μm, about 90 μm, about 95 μm, or about 100 μm.

In any of the embodiments disclosed herein, the weight ratio of releasing agent to polymer in the control region 300 may be 2:1, 1.5:1, 1:1, 1:1.5, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, or 1:25.

In any of the embodiments disclosed herein, the control region 300 may include at least 5% by weight of the releasing agent, at least 10% by weight of the releasing agent, at least 15% by weight of the releasing agent, at least 20% by weight of the releasing agent, at least 25% by weight of the releasing agent, at least 30% by weight of the releasing agent, at least 35% by weight of the releasing agent, at least 40% by weight of the releasing agent, at least 45% by weight of the releasing agent, or at least 50% by weight of the releasing agent. In those embodiments having multiple control regions or sub-regions, one or more of the control regions or sub-control regions may individually include at least 5% by weight of the releasing agent, at least 10% by weight of the releasing agent, at least 15% by weight of the releasing agent, at least 20% by weight of the releasing agent, at least 25% by weight of the releasing agent, at least 30% by weight of the releasing agent, at least 35% by weight of the releasing agent, at least 40% by weight of the releasing agent, at least 45% by weight of the releasing agent, or at least 50% by weight of the releasing agent.

In any of the embodiments disclosed herein, the control region 300 may include at least 5% by weight of the polymer, at least 10% by weight of the polymer, at least 15% by weight of the polymer, at least 20% by weight of the polymer, at least 25% by weight of the polymer, at least 30% by weight of the polymer, at least 35% by weight of the polymer, at least 40% by weight of the polymer, at least 45% by weight of the polymer, at least 50% by weight of the polymer, at least 55% by weight of the polymer, at least 60% by weight of the polymer, at least 65% by weight of the polymer, at least 70% by weight of the polymer, at least 75% by weight of the polymer, at least 80% by weight of the polymer, at least 85% by weight of the polymer, at least 90% by weight of the polymer, at least 95% by weight of the polymer, or 100% by weight of the polymer. In those embodiments having multiple control regions or sub-regions, one or more of the control regions or sub-control regions may individually include at least 5% by weight of the polymer, at least 10% by weight of the polymer, at least 15% by weight of the polymer, at least 20% by weight of the polymer, at least 25% by weight of the polymer, at least 30% by weight of the polymer, at least 35% by weight of the polymer, at least 40% by weight of the polymer, at least 45% by weight of the polymer, at least 50% by weight of the polymer, at least 55% by weight of the polymer, at least 60% by weight of the polymer, at least 65% by weight of the polymer, at least 70% by weight of the polymer, at least 75% by weight of the polymer, at least 80% by weight of the polymer, at least 85% by weight of the polymer, at least 90% by weight of the polymer, at least 95% by weight of the polymer, or 100% by weight of the polymer.

In those embodiments disclosed herein where the control region 300 includes multiple control regions or sub-regions, some or all of the control regions or sub-control regions may have the same or different amounts of releasing agent, the same or different concentrations of releasing agent, the same or different releasing agents, the same or different amounts of polymer, the same or different polymers, the same or different polymer to releasing agent ratios, and/or the same or different thicknesses. A single control region or sub-region may comprise a single type of polymer or multiple types of polymers and/or a single type of releasing agent or multiple types of releasing agents.

C. Therapeutic Agents

The therapeutic agent carried by the depots 100 of the present technology may be any biologically active substance (or combination of substances) that provides a therapeutic effect in a patient in need thereof. As used herein, "therapeutic agent" or "drug" may refer to a single therapeutic agent, or may refer to a combination of therapeutic agents. In some embodiments, the therapeutic agent may include only a single therapeutic agent, and in some embodiments, the therapeutic agent may include two or more therapeutic agents for simultaneous or sequential release.

In several embodiments, the therapeutic agent includes an analgesic agent. The term "analgesic agent" or "analgesic" includes one or more local or systemic anesthetic agents that are administered to reduce, prevent, alleviate or remove pain entirely. The analgesic agent may comprise a systemic and/or local anesthetic, narcotics, and/or anti-inflammatory agents. The analgesic agent may comprise the pharmacologically active drug or a pharmaceutically acceptable salt thereof. Suitable local anesthetics include, but are not limited to, bupivacaine, ropivacaine, mepivacaine, etidocaine, levobupivacaine, trimecaine, carticaine, articaine, lidocaine, prilocaine, benzocaine, procaine, tetracaine, chloroprocaine, and combinations thereof. Preferred local anesthetics include bupivacaine, lidocaine, and ropivacaine. Typically, local anesthetics produce anesthesia by inhibiting excitation of nerve endings or by blocking conduction in peripheral nerves. Such inhibition is achieved by anesthetics reversibly binding to and inactivating sodium channels. Sodium influx through these channels is necessary for the depolarization of nerve cell membranes and subsequent propagation of impulses along the course of the nerve. When a nerve loses depolarization and capacity to propagate an impulse, the individual loses sensation in the area supplied by the nerve. Any chemical compound possessing such anesthetic properties is suitable for use in the present technology.

In some embodiments, the therapeutic agent includes narcotics, for example, cocaine, and anti-inflammatory agents. Examples of appropriate anti-inflammatory agents include steroids, such as prednisone, betamethasone, cortisone, dexamethasone, hydrocortisone, and methylprednisolone. Other appropriate anti-inflammatory agents include non-steroidal anti-inflammatory drugs (NSAIDs), such as aspirin, Ibuprofen, naproxen sodium, diclofenac, diclofenac-misoprostol, celecoxib, piroxicam, indomethacin, meloxicam, ketoprofen, sulindac, diflunisal, nabumetone, oxaprozin, tolmetin, salsalate, etodolac, fenoprofen, flurbiprofen, ketorolac, meclofenamate, mefenamic acid, and other COX-2 inhibitors, and combinations thereof.

In some embodiments, the therapeutic agent comprises an antibiotic, an antimicrobial or antifungal agent or combinations thereof. For example, suitable antibiotics and antimicrobials include, but are not limited to, amoxicillin, amoxicillin/clavulanate, cephalexin, ciprofloxacin, clindamycin, metronidazole, azithromycin, levofloxacin, sulfamethoxazole/trimethoprim, tetracycline(s), minocycline, tigecycline, doxycycline, rifampin, triclosan, chlorhexidine, penicillin(s), aminoglycides, quinolones, fluoroquinolones, vancomycin, gentamycin, cephalosporin(s), carbapenems, imipenem, ertapenem, antimicrobial peptides, cecropin-mellitin, magainin, dermaseptin, cathelicidin, α-defensins, and α-protegrins. Antifungal agents include, but are not limited to, ketoconazole, clortrimazole, miconazole, econazole, intraconazole, fluconazole, bifoconazole, terconazole, butaconazole, tioconazole, oxiconazole, sulconazole, saperconazole, voriconazole, terbinafine, amorolfine, naftifine, griseofulvin, haloprogin, butenafine, tolnaftate, nystatin, cyclohexamide, ciclopirox, flucytosine, terbinafine, and amphotericin B.

The depot of any one of the preceding clauses, wherein the analgesic is a local anesthetic, and wherein the release of the analgesic to the treatment site over the five days inhibits the growth of bacteria and fungi.

In some embodiments, the therapeutic agent is a local anesthetic and release of the anesthetic to the treatment site over the duration of delivery inhibits the growth of bacteria and fungi. In some embodiments, the depot is configured to inhibit the growth of bacteria and fungi such that a number of bacteria on the depot is 10×, 20×, 30×, 40×, or 50X less than a number of bacteria present on a comparable depot containing no analgesic.

In several embodiments, the therapeutic agent may be an adrenocorticostatic, a β-adrenolytic, an androgen or antiandrogen, an antianemic, a antiparasitic, an anabolic, an anesthetic or analgesic, an analeptic, an antiallergic, an antiarrhythmic, an anti-arteriosclerotic, an antibiotic, an antidiabetic, an antifibrinolytic, an anticonvulsive, an angiogenesis inhibitor, an anticholinergic, an enzyme, a coenzyme or a corresponding inhibitor, an antihistaminic, an antihypertensive, an antihypotensive, an anticoagulant, an antimycotic, an antiseptic, an anti-infective, an antihemorrhagic, a β-receptor antagonist, a calcium channel antagonist, an antimyasthenic, an antiphlogistic, an antipyretic, an antirheumatic, a cardiotonic, a chemotherapeutic, a coronary dilator, a cytostatic, a glucocorticoid, a hemostatic, an immunoglobulin or its fragment, a chemokine, a cytokine, a mitogen, a cell differentiation factor, a cytotoxic agent, a hormone, an immunosuppressant, an immunostimulant, a morphine antagonist, an muscle relaxant, a narcotic, a vector, a peptide, a (para) sympathicomimetic, a (para) sympatholytic, a protein, a cell, a selective estrogen receptor modulator (SERM), a sedating agent, an antispasmodic, a substance that inhibits the resorption of bone, a vasoconstrictor or vasodilator, a virustatic or a wound-healing agent.

In various embodiments, the therapeutic agent comprises a drug used in the treatment of cancer or a pharmaceutically acceptable salt thereof. Such chemotherapeutic agents include antibodies, alkylating agents, angiogenesis inhibitors, antimetabolites, DNA cleavers, DNA crosslinkers, DNA intercalators, DNA minor groove binders, enediynes, heat shock protein 90 inhibitors, histone deacetylase inhibitors, immunomodulators, microtubule stabilizers, nucleoside (purine or pyrimidine) analogs, nuclear export inhibitors, proteasome inhibitors, topoisomerase (I or II) inhibitors, tyrosine kinase inhibitors, and serine/threonine kinase inhibitors. Specific therapeutic agents include, but are not limited to, adalimumab, ansamitocin P3, auristatin, bendamustine, bevacizumab, bicalutamide, bleomycin, bortezomib, busulfan, callistatin A, camptothecin, capecitabine, carboplatin, carmustine, cetuximab, cisplatin, cladribin, cytarabin, cryptophycins, dacarbazine, dasatinib, daunorubicin, docetaxel, doxorubicin, duocarmycin, dynemycin A, epothilones, etoposide, floxuridine, fludarabine, 5-fluorouracil, gefitinib, gemcitabine, ipilimumab, hydroxyurea, imatinib, infliximab, interferons, interleukins, beta-lapachone, lenalidomide, irinotecan, maytansine, mechlorethamine, melphalan, 6-mercaptopurine, methotrexate, mitomycin C, nilotinib, oxaliplatin, paclitaxel, procarbazine, suberoylanilide hydroxamic acid (SAHA), 6-thioguanidine, thiotepa, teniposide, topotecan, trastuzumab, trichostatin A, vinblastine, vincristine, vindesine, and tamoxifen. Any aforementioned therapeutic agent, or combination thereof, can be incorporated into the depot/implant embodiments described herein to administer a controlled, sustained, localized release of anti-cancer agent(s) for the treatment of cancer. The potential oncology indications include: esophageal cancer, stomach cancer, lung cancer, liver cancer, pancreatic cancer, prostate cancer, bile duct cancer, ovarian cancer, uterine cancer, head and neck cancer, soft tissue sarcoma, adrenal cancer, anal cancer, appendix cancer, bladder cancer, bone cancer, brain cancer, breast cancer, cervical cancer, colorectal cancer, sinus cancer, oral cancer, kidney cancer, thyroid cancer, uterine cancer, leukemia, intestinal cancer, testicular cancer, skin cancer, Hodgkin lymphoma, non-Hodgkin lymphoma, vaginal cancer, multiple myeloma, and neuroendocrine tumors.

In some embodiments, the therapeutic agent comprises a botulinum toxin (or neurotoxin) drug used in the treatment of various neuromuscular and/or neuroglandular disorders and neuropathies associated with pain. The botulinum toxin (or neurotoxin) may comprise the pharmacologically active drug or a pharmaceutically acceptable salt thereof. The botulinum toxin (or neurotoxin) as described and used herein may be selected from a variety of strains of *Clostridium botulinum* and may comprise the pharmacologically active drug or a pharmaceutically acceptable salt thereof. In one embodiment, the botulinum toxin is selected from the group consisting of botulinum toxin types A, B, C, D, E, F and G. In a preferred embodiment, the botulinum toxin is botulinum toxin type A. Commercially available botulinum toxin, BOTOX® (Allergan, Inc., Irvine, CA), consists of a freeze-dried, purified botulinum toxin type A complex, albumin and sodium chloride packaged in sterile, vacuum-dried form.

The paralytic effect of botulinum toxin is the most common benefit of commercial therapeutics, where muscles are relaxed in order to treat muscle dystonias, wrinkles and the like. However, it has been shown that in addition to its anti-cholinergic effects on muscle and smooth muscle, the neurotoxin can have therapeutic effects on other non-muscular cell types, and on inflammation itself. For example, it has been shown that cholinergic goblet cells, which produce mucus throughout the airway system, react to and can be shut down by introduction of botulinum toxin. Research also shows that botulinum toxin has direct anti-inflammatory capabilities. All of these therapeutic effects, muscle, smooth muscle, goblet cell and anti-inflammatory affects, may be derived from delivery of the toxin from the inventive devices.

A pharmaceutically acceptable salt refers to those salts that retain the biological effectiveness and properties of neutral therapeutic agents and that are not otherwise unacceptable for pharmaceutical use. Pharmaceutically acceptable salts include salts of acidic or basic groups, which groups may be present in the therapeutic agents. The therapeutic agents used in the present technology that are basic in nature are capable of forming a wide variety of salts with various inorganic and organic acids. Pharmaceutically acceptable acid addition salts of basic therapeutic agents used in the present technology are those that form non-toxic acid addition salts, i.e., salts comprising pharmacologically acceptable anions, such as the hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts. The therapeutic agents of the present technology that include an amino moiety may form pharmaceutically acceptable salts with various amino acids, in addition to the acids mentioned above. Suitable base salts are formed from bases which form non-toxic salts and examples are the aluminum, calcium, lithium, magnesium, potassium, sodium, zinc and diethanolamine salts.

A pharmaceutically acceptable salt may involve the inclusion of another molecule such as water or another biologically compatible solvent (a solvate), an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterions.

The therapeutic agent or pharmaceutically acceptable salt thereof may be an essentially pure compound or be formulated with a pharmaceutically acceptable carrier such as diluents, adjuvants, excipients or vehicles known to one skilled in the art. The carrier(s) must be "acceptable" in the sense of being compatible with the other ingredients of the formulations and not deleterious to the recipient thereof. For example, diluents include lactose, dextrose, sucrose, mannitol, sorbitol, cellulose, glycine and the like. For examples of other pharmaceutically acceptable carriers, see Remington: THE SCIENCE AND PRACTICE OF PHARMACY (21st Edition, University of the Sciences in Philadelphia, 2005).

The therapeutic agent or pharmaceutically acceptable salt form may be jet milled or otherwise passed through a sieve to form consistent particle sizes further enabling the regulated and controlled release of the therapeutic agent. This process may be particularly helpful for highly insoluble therapeutic agents.

An important criterion for determining the amount of therapeutic agent needed for the treatment of a particular medical condition is the release rate of the drug from the depot of the present technology. The release rate is controlled by a variety of factors, including, but not limited to, the rate that the releasing agent dissolves in vivo into the surrounding fluid, the in vivo degradation rate of the bioresorbable polymer or copolymer utilized. For example, the rate of release may be controlled by the use of multiple control regions between the therapeutic region and the physiological fluid. See, for example, FIGS. 6-8.

Suitable dosage ranges utilizing the depot of the present technology are dependent on the potency of the particular therapeutic agent, but are generally about 0.001 mg to about 500 mg of drug per kilogram body weight, for example, from about 0.1 mg to about 200 mg of drug per kilogram body weight, and about 1 to about 100 mg/kg-body wt. per day. Dosage ranges may be readily determined by methods known to one skilled in the art. Dosage unit forms will generally contain between about 1 mg to about 500 mg of active ingredient. For example, commercially available bupivacaine hydrochloride, marketed under the brand name Marcaine™ (Pfizer; New York, NY), is generally administered as a peripheral nerve block using a dosage range of 37.5-75 mg in a 0.25% concentration and 25 mg up to the daily maximum level (up to 400 mg) in a 0.5% concentration (Marcaine®™ package insert; FDA Reference ID: 3079122). In addition, commercially available ropivacaine hydrochloride, marketed under the brand name Naropin® (Fresenius Kabi USA, LLC; Lake Zurich, IL), is administered in doses of 5-300 mg for minor and major nerve blocks (Naropin® package insert; Reference ID: 451112G). Suitable dosage ranges for the depot of the present technology are equivalent to the commercially available agents customarily administered by injection.

In some aspects of the technology, the therapeutic region 200 may include multiple layers. In such embodiments, the multiple layers may improve efficient loading of therapeutic agents. For example, multilayering may be a direct and effective way of loading substantial amounts of therapeutic agent. It can often be challenging to load a large amount of therapeutic agent in a single film layer, even by increasing the drug to polymer ratio or increasing the thickness of the layer. Even when the thickness of the therapeutic region can be theoretically increased to load more drug, consistent fabrication of a thick therapeutic region via casting could prove to be a challenge. In contrast, the stacking and bonding of thin films or sheets, each with a predetermined load of therapeutic agent, may present as a more reliable casting alternative. Data from an example of loading an analgesic (i.e., ropivacaine) is provided in Table 2.

TABLE 2

|  | Drug load (ug) | Thickness (mm) |
|---|---|---|
| Single layer | 212.66 | 0.019 |
| Five layers | 1120.83 | 0.046 |
| Multiple | 5.27 | 2.42 |

As but one example, a single layer loaded with ropivacaine and having a thickness of 0.019 mm was produced. A 5-layer film sample, where each layer was loaded with ropivacaine, having a thickness of 0.046 mm was also produced. Even though the thickness of the 5-layer film sample was only 2.42 times the thickness of the single layer, the load of therapeutic agent in the 5-layer sample was 5.27 times that of the single layer sample. Accordingly, the multilayering approach enabled a substantially higher density of therapeutic agent.

As described above, heat compression bonding of multiple layers enables an effective reduction in film thickness and an increased density of therapeutic agent loading. In the example illustrated in Table 2, the multilayer structure enabled a 124% increase in the density of the therapeutic agent. In other embodiments, the increase in density of the therapeutic agent enabled by a multilayer structure of the therapeutic region may be approximately 50%, 75%, 100%, 125%, 150% or 200%.

mers used as base components of the depots of the present technology may break down or degrade after the therapeutic agent is fully released. The bioresorbable polymers are also "bioerodible," in that they will erode or degrade over time due, at least in part, to contact with substances found in the surrounding tissue, fluids or by cellular action.

Criteria for the selection of the bioresorbable polymer suitable for use in the present technology include: 1) in vivo safety and biocompatibility; 2) therapeutic agent loading capacity; 3) therapeutic agent releasing capability; 4) degradation profile; 5) potential for inflammatory response; and 6) mechanical properties, which may relate to form factor and manufacturability. As such, selection of the bioresorbable polymer may depend on the clinical objectives of a particular therapy and may involve trading off between competing objectives. For example, PGA (polyglycolide) is known to have a relatively fast degradation rate, but it is also fairly brittle. Conversely, polycaprolactone (PCL) has a relatively slow degradation rate and is quite elastic. Copolymerization provides some versatility if it is clinically desirable to have a mix of properties from multiple polymers. For biomedical applications, particularly as a bioresorbable depot for drug release, a polymer or copolymer using at least one of poly(L-lactic acid) (PLA), PCL, and PGA are generally preferred. The physical properties for some of these polymers are provided in Table 3 below.

TABLE 3

| Materials | Tg (° C.) | Tm (° C.) | Elastic Modulus (GPa) | Tensile Strength (MPa) | Tensile Elongation (%) | Degradation Time (months) |
|---|---|---|---|---|---|---|
| PLA | 45-60 | 150-162 | 0.35-3.5 | 21-60 | 2.5-6 | 12-16 |
| PLLA | 55-65 | 170-200 | 2.7-4.14 | 15.5-150 | 3-10 | >24 |
| PDLA | 50-60 | — | 1.0-3.45 | 27.6-50 | 2-10 | 6-12 |
| PLA/PGA (50:50) | 40-50 | — | 1.0-4.34 | 41.4-55.2 | 2-10 | 3 |
| PGA | 35-45 | 220-233 | 6.0-7.0 | 60-99.7 | 1.5-20 | 6-12 |
| PCL | −60--65 | 58-65 | 0.21-0.44 | 20.7-42 | 300-1000 | >24 |

D. Polymers

The depots 100 of the present technology are comprised of bioresorbable polymers. In some embodiments, both the therapeutic region 200 and the control region 300 comprise a polymer (or mix of polymers), which can be the same or different polymer (or mix of polymers) in the same or different amount, concentration, and/or weight percentage. In some embodiments, the control region 300 comprises a polymer and the therapeutic region 200 does not include a polymer. In some embodiments, the therapeutic region 200 comprises a polymer and the control region 300 does not include a polymer. At least as used in this section, "the polymer" applies to a polymer that may be used in the therapeutic region 200 and/or in the control region 300.

The bioresorbable polymers used in the present technology preferably have a predetermined degradation rate. The terms "bioresorbable," or "bioabsorbable," mean that a polymer will be absorbed within the patient's body, for example, by a cell or tissue. These polymers are "biodegradable" in that all or parts the polymeric film will degrade over time by the action of enzymes, by hydrolytic action and/or by other similar mechanisms in the patient's body. In various embodiments, the bioresorbable polymer film can break down or degrade within the body to non-toxic components while a therapeutic agent is being released. Poly- In many embodiments, the polymer may include polyglycolide (PGA). PGA is one of the simplest linear aliphatic polyesters. It is prepared by ring opening polymerization of a cyclic lactone, glycolide. It is highly crystalline, with a crystallinity of 45-55%, and thus is not soluble in most organic solvents. It has a high melting point (220-225° C.), and a glass transition temperature of 35-40° C. (Vroman, L., et al., Materials, 2009, 2:307-44). Rapid in vivo degradation of PGA leads to loss of mechanical strength and a substantial local production of glycolic acid, which in substantial amounts may provoke an inflammatory response.

In many embodiments, the polymer may include polylactide (PLA). PLA is a hydrophobic polymer because of the presence of methyl(—CH3) side groups off the polymer backbone. It is more resistant to hydrolysis than PGA because of the steric shielding effect of the methyl side groups. The typical glass transition temperature for representative commercial PLA is 63.8° C., the elongation at break is 30.7%, and the tensile strength is 32.22 MPa (Vroman, 2009). Regulation of the physical properties and biodegradability of PLA can be achieved by employing a hydroxy acids co-monomer component or by racemization of D- and L-isomers (Vroman, 2009). PLA exists in four forms: poly(L-lactic acid) (PLLA), poly(D-lactic acid) (PDLA), meso-poly(lactic acid) and poly(D,L-lactic acid)

(PDLLA), which is a racemic mixture of PLLA and PDLA. PLLA and PDLLA have been the most studied for biomedical applications.

Copolymerization of PLA (both L- and D,L-lactide forms) and PGA yields poly(lactide-co-glycolide) (PLGA), which is one of the most commonly used degradable polymers for biomedical applications. In many embodiments, the polymer may include PLGA. Since PLA and PGA have significantly different properties, careful choice of PLGA composition can enable optimization of performance in intended clinical applications. Physical property modulation is even more significant for PLGA copolymers. When a composition is comprised of 25-75% lactide, PLGA forms amorphous polymers which are very hydrolytically unstable compared to the more stable homopolymers. This is demonstrated in the degradation times of 50:50 PLGA, 75:25 PLGA, and 85:15 PLGA, which are 1-2 months, 4-5 months and 5-6 months, respectively. In some embodiments, the polymer may be an ester-terminated poly(DL-lactide-co-glycolide) in a molar ratio of 50:50 (DURECT Corporation).

In some embodiments, the polymer may include polycaprolactone (PCL). PCL is a semi-crystalline polyester with high organic solvent solubility, a melting temperature of 55-60° C., and glass transition temperature of −54° C. (Vroman, 2009). PCL has a low in vivo degradation rate and high drug permeability, thereby making it more suitable as a depot for longer term drug delivery. For example, Capronor® is a commercial contraceptive PCL product that is able to deliver levonorgestrel in vivo for over a year. PCL is often blended or copolymerized with other polymers like PLLA, PDLLA, or PLGA. Blending or copolymerization with polyethers expedites overall polymer erosion. Additionally, PCL has a relatively low tensile strength (~23 MPa), but very high elongation at breakage (4700%), making it a very good elastic biomaterial. PCL also is highly processable, which enables many potential form factors and production efficiencies.

Suitable bioresorbable polymers and copolymers for use in the present technology include, but are not limited to, poly(alpha-hydroxy acids), poly(lactide-co-glycolide) (PLGA or DLG), poly(DL-lactide-co-caprolactone) (DL-PLCL), polycaprolactone (PCL), poly(L-lactic acid) (PLA), poly(trimethylene carbonate) (PTMC), polydioxanone (PDO), poly(4-hydroxy butyrate) (PHB), polyhydroxyalkanoates (PHA), poly(phosphazene), polyphosphate ester), poly(amino acid), polydepsipeptides, poly(butylene succinate) (PBS), polyethylene oxide, polypropylene fumarate, polyiminocarbonates, poly(lactide-co-caprolactone) (PLCL), poly(glycolide-co-caprolactone) (PGCL) copolymer, poly(D,L-lactic acid), polyglycolic acid, poly(L-lactide-co-D,L-lactide), poly(L-lactide-co-glycolide), poly(D,L-lactide-co-glycolide), poly(gycolide-trimethylene carbonate), poly(glycolide-co-carolactone) (PGCL), poly(ethyl glutamate-co-glutamic acid), poly(tert-butyloxy-carbonylmethyl glutamate), poly(glycerol sebacate), tyrosine-derived polycarbonate, poly 1,3-bis-(p-carboxyphenoxy) hexane-co-sebacic acid, polyphosphazene, ethyl glycinate polyphosphazene, polycaprolactone co-butylacrylate, a copolymer of polyhydroxybutyrate, a copolymer of maleic anhydride, a copolymer of poly(trimethylene carbonate), polyethylene glycol (PEG), hydroxypropylmethylcellulose and cellulose derivatives, polysaccharides (such as hyaluronic acid, chitosan and starch), proteins (such as gelatin and collagen) or PEG derivatives and copolymers thereof. Other suitable polymers or copolymers include polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D-lactide, D,L-lactide, L-lactide, D,L-lactide-caprolactone (DL-CL), D,L-lactide-glycolide-caprolactone (DL-G-CL), dextrans, vinylpyrrolidone, polyvinyl alcohol (PVA), PVA-g-PLGA, PEGT-PBT copolymer (polyactive), methacrylates, poly(N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate) hydroxypropyl cellulose, hydroxypropyl methylcellulose, hydroxyethyl methylcellulose, carboxymethylcellulose or salts thereof, Carbopol®, poly(hydroxyethylmethacrylate), poly(methoxyethylmethacrylate), poly(methoxyethoxy-ethylmethacrylate), polymethylmethacrylate (PMMA), methylmethacrylate (MMA), gelatin, polyvinyl alcohols, propylene glycol, or combinations thereof.

In various embodiments, the molecular weight of the polymer can be a wide range of values. The average molecular weight of the polymer can be from about 1000 to about 10,000,000; or about 1,000 to about 1,000,000; or about 5,000 to about 500,000; or about 10,000 to about 100,000; or about 20,000 to 50,000.

As described above, it may be desirable in certain clinical applications using depots for controlled delivery of therapeutic agents to use copolymers comprising at least two of PGA, PLA, PCL, PDO, and PVA. These include, for example, poly(lactide-co-caprolactone) (PLCL) (e.g. having a PLA to PCL ratio of from 90:10 to 60:40) or its derivatives and copolymers thereof, poly(DL-lactide-co-caprolactone) (DL-PLCL) (e.g. having a DL-PLA to PCL ratio of from 90:10 to 50:50) or its derivatives and copolymers thereof, poly(glycolide-co-caprolactone) (PGCL) (e.g. having a PGA to PCL ratio of from 90:10 to 10:90) or its derivatives and copolymers thereof, or a blend of PCL and PLA (e.g. a ratio blend of PCL and PLA having a wt:wt ratio of 1:9 to 9:1). In one preferred embodiment, the bioresorbable polymer comprises a copolymer of polycaprolactone (PCL), poly(L-lactic acid) (PLA) and polyglycolide (PGA). In such a preferred embodiment, the ratio of PGA to PLA to PCL of the copolymer may be 5-60% PGA, 5-40% PLA and 10-90% PCL. In additional embodiments, the PGA:PLA:PCL ratio may be 40:40:20, 30:30:50, 20:20:60, 15:15:70, 10:10:80, 50:20:30, 50:25:25, 60:20:20, or 60:10:30. In some embodiments, the polymer is an ester-terminated poly(DL-lactide-co-glycolide-co-caprolactone) in a molar ratio of 60:30:10 (DURECT Corporation).

In some embodiments, a terpolymer may be beneficial for increasing the degradation rate and ease of manufacturing, etc.

To minimize the size of a bioresorbable depot, it is generally preferred to maximize the loading of therapeutic agent in the polymer to achieve the highest possible density of therapeutic agent. However, polymer carriers having high densities of therapeutic agent are more susceptible to burst release kinetics and, consequently, poor control over time release. As described above, one significant benefit of the depot structure described herein, and particularly the control region feature of the depot, is the ability to control and attenuate the therapeutic agent release kinetics even with therapeutic agent densities that would cause instability in other carriers. In certain embodiments, the therapeutic agent loading capacity includes ratios (wt:wt) of the therapeutic agent to bioresorbable polymer of approximately 1:3, 1:2, 1:1, 3:2, 2:1, 3:1, 4:1, 5:1, 6:1, 7:1, 8:1, 9:1, 10:1, 12:1, 14:1, or 16:1. In some embodiments, it may be desirable to increase the therapeutic effect or potency of the therapeutic agent released from the depot described herein while still maintaining the same or similar polymer to therapeutic agent ratio. This can be accomplished by using an essentially pure form of the therapeutic agent as opposed to a salt derivative. Additionally or alternatively, the therapeutic agent can be mixed with clonidine or epinephrine, which are known to increase the therapeutic effect of certain drugs.

In some embodiments, the bioresorbable polymer used in various layers of the depot may manifest as a layer of electrospun microfibers or nanofibers. Biocompatible electrospun microfibers/nanofibers are known in the art and may be used, for example, to manufacture implantable supports for the formation of replacement organs in vivo (U.S. Patent Publication No. 2014/0272225; Johnson; Nanofiber Solutions, LLC), for musculoskeletal and skin tissue engineering (R. Vasita and D. S. Katti, Int. J. Nanomedicine, 2006, 1:1, 15-30), for dermal or oral applications (PCT Publication No. 2015/189212; Hansen; Dermtreat APS) or for management of postoperative pain (U.S. Patent Publication No. 2013/0071463; Palasis et al.). As a manufacturing technique, electrospinning offers the opportunity for control over the thickness and the composition of the nano- or micro-fibers along with control of the porosity of the fiber meshes (Vasita and Katti, 2006). These electrospun scaffolds are three-dimensional and thus provide ideal supports for the culture of cells in vivo for tissue formation. Typically, these scaffolds have a porosity of 70-90% (U.S. Pat. No. 9,737,632; Johnson; Nanofiber Solutions, LLC). Suitable bioresorbable polymers and copolymers for the manufacture of electrospun microfibers include, but are not limited to, natural materials such as collagen, gelatin, elastin, chitosan, silk fibrion, and hyaluronic acid, as well as synthetic materials such as poly(&-caprolactone) (PCL), poly(glycolic acid) (PGA), poly(lactic-co-glycolic acid) (PLGA), poly(l-lactide-co-ε-caprolactone), and poly(lactic acid) (PLA).

Electrospun microfibers that are made from a bioresorbable polymer or copolymer and have been used in conjunction with a therapeutic agent are known in the art. For example, Johnson et al. have disclosed the treatment of joint inflammation and other conditions with an injection of biocompatible polymeric electrospun fiber fragments along with a carrier medium containing chitosan (U.S. Published Application No. 2016/0325015; Nanofiber Solutions, LLC). Weldon et al. reported the use of electrospun bupivacaine-eluting sutures manufactured from poly(lactic-co-glycolic acid) in a rat skin wound model, wherein the sutures provided local anesthesia at an incision site (J. Control Release, 2012, 161:3, 903-909). Similarly, Palasis et al. disclosed the treatment of postoperative pain by implanting electrospun fibers loaded with an opioid, anesthetic or a non-opioid analgesic within a surgical site (U.S. Patent Publication No. 2013/0071463; Palasis et al.). Electrospun microfibers suitable for use in the present technology may be obtained by the methods disclosed in the above cited references, which are herein incorporated in their entirety.

When implanted in a patient's joint (for example, a knee joint), the bioresorbable depot described above may be positioned in the joint such that it will be articulating throughout the duration of release. So as to avoid premature release of the analgesic, it is desirable for the depot to have a threshold level of mechanical integrity and stability until most of the analgesic has been released. While it may be desirable to maximize the loading of therapeutic agent in the bioresorbable depot, as described above, such maximization can typically be at the expense of mechanical integrity and stability of the depot. Given the high dosage of anesthetic necessary to provide analgesia through both the acute and subacute postoperative pain periods and limited space in the knee, it is desirable for the depot described herein to have a high density loading of anesthetic while still maintaining sufficient mechanical integrity and stability in the knee. The layered structure and, particularly, the presence of the control region provide some safeguard against the premature release of anesthetic. Moreover, the use of heat compression in the manufacturing process enables substantial loading of anesthetic into the therapeutic region while creating a thermal bond between the therapeutic region and control region, thereby preventing delamination, and a consequent uncontrolled release of drug, when the depot is subjected to mechanical stress in the knee.

It is generally desirable that the implanted polymer fully degrade following complete delivery of the therapeutic agent. Full degradation is preferred because, unless the implanted polymer provides some structural function or support, the clinical practitioner would have to reconcile leaving in a foreign body with no functional purpose, which could be a source of inflammation or infection, or perform another surgery simply to remove the remaining polymer. As an alternative to full degradation, it would be desirable for any remaining polymer to be fully encapsulated by the body.

The degradation of an implanted polymer consists essentially of two sequential processes: diffusion of an aqueous solution (e.g., physiological fluids) followed by hydrolytic degradation. Degradation usually takes one of two forms: (1) surface erosion; and (2) bulk degradation. Surface erosion of a polymer occurs when the polymer erodes from the surface inward, where hydrolytic erosion at the surface is faster than the ingress of water into the polymer. Conversely, bulk degradation occurs throughout the entire polymer, where water penetrates and degrades the interior of the material faster than the surface can erode. Polymers such as PLA, PGA, PLGA and PCL all resorb into the body via bulk degradation.

The time necessary for complete degradation can vary greatly based on the material selected and the clinical performance requirements of the depot. For example, in the case of treating and managing postoperative pain, it may be desirable for the polymer depot to release therapeutic agent (i.e., an analgesic) for anywhere from 5 to 30 days. In the case of treating or preventing infection of a prosthetic joint (e.g., knee or hip implant), it may be desirable for the polymer depot to release an anti-infective agent for anywhere from 2 to 4 months. Alternatively, even if the entire amount of therapeutic agent loaded into the polymer has been released, it may be desirable for the polymer to degrade over a longer period than the duration of drug release. For example, rapid degradation can often make the polymer brittle and fragile, thereby compromising mechanical performance, or provoking an inflammatory response from the body. In particular, it may be desirable, in certain clinical applications, to have an embodiment wherein degradation of the polymer commenced only after release of substantially all of the therapeutic agent.

In certain embodiments of the present technology, it may be desirable for the polymer to fully resorb into the body after substantially all therapeutic agent loaded therein is released. In certain embodiments, this degradation can be as short as 1 month. Alternatively, in other embodiments, full degradation could take as long as 2 months, 3 months, 4 months, 6 months, 9 months or 12 months. In some embodiments, the bioresorbable polymer substantially degrades in vivo within about one month, about two months, about three months, about four months, about five months or about six months. In some embodiments, it may be desirable for full degradation to be 6 months such that the mechanical properties of the implanted polymer are preserved for the first 2 months following implantation.

Core Acidification

Degradation of certain polymers (for example, via hydrolysis) produces one or more acids. Examples of such polymers include, for example, polyesters such as polyhydroxyalkanoates (PHA) and polyalphahydroxy acids (AHA). Exemplary PHAs include, but are not limited to, polymers of 3-hydroxypropionate, 3-hydroxybutyrate, 3-hydroxyvalerate, 3-hydroxycaproate, 3-hydroxyheptanoate, 3-hydroxyoctanoate, 3-hydroxynonanoate, 3-hydroxydecanoate, 3-hydroxyundecanoate, 3-hydroxydodecanoate, 4-hydroxybutyrate and 5-hydroxyvalerate. Examples of AHAs include, but are not limited to, various forms of polylactide or polylactic acid including PLA, PLLA or PDLLA, polyglycolic acid and polyglycolide, poly(lactic-co-glycolic acid), poly(lactide-co-glycolide), poly(ε-caprolactone) and polydioxanone. Examples of acids include carboxylic acids, such as lactic acid and glycolic acid. The control region and/or therapeutic region of the depots of the present technology may include one or more of the foregoing polymers. In some embodiments, the control region and/or therapeutic region of the depots of the present technology may include a bioresorbable polymer that produces one or more carboxylic acids during degradation, the carboxylic acid(s) having a pKa less than about 7.4, less than about 7.3, less than about 7.2, less than about 7.1, or less than about 7.0.

The degradation of an implanted device comprising such acid-producing polymers may result in accumulation of acid degradation products within the interior of the device, a phenomenon referred to herein as "core acidification." Traditional biodegradable orthopedic implants often exhibit tissue inflammation and/or other detrimental effects due to core acidification, as discussed further below. For ease of explanation, the following discussion is made with reference specifically to degradation of polymers that include polylactic acid and/or polyglcolic acid. However, it will be appreciated that the following discussion equally applies to any bioresorbable polymer that produces one or more carboxylic acids during degradation, the carboxylic acid(s) having a pKa less than about 7.0.

The degree of core acidification undergone by an implanted device may be determined in large part by the geometry and dimensions of the device. (See, e.g., Grizzi et al., *Hydrolytic degradation of devices based on poly (dl-lactic acid) size-dependence*, BIOMATERIALS, 1995, Vol. 16 No. 4, pp. 305-11; Fukuzaki et al., *in vivo characteristics of high molecular weight copoly (l-lactide glycolide) with S-type degradation pattern for application in drug delivery systems*, BIOMATERIALS 1991, Vol. 12 May, pp. 433-37; Li et al., *Structure-property relationships in the case of degradation of massive alipathic poly-(a-hydroxy acids) in aqueous media*, JOURNAL OF MATERIALS SCIENCE: MATERIALS IN MEDICINE I (1990), pp. 123-130). The degradation profile of an implant and local toxicity resulting from degradation byproducts may mediate long-term biodegradable implant-induced inflammation, particularly in the case of biodegradable orthopedic implants. (See Amini, A. R., et al., *Short-term and long-term effects of orthopedic biodegradable implants*, JOURNAL OF LONG TERM EFFECTS OF MEDICAL IMPLANTS 2011; 21 (2): pp. 93-122).

Figure 17:
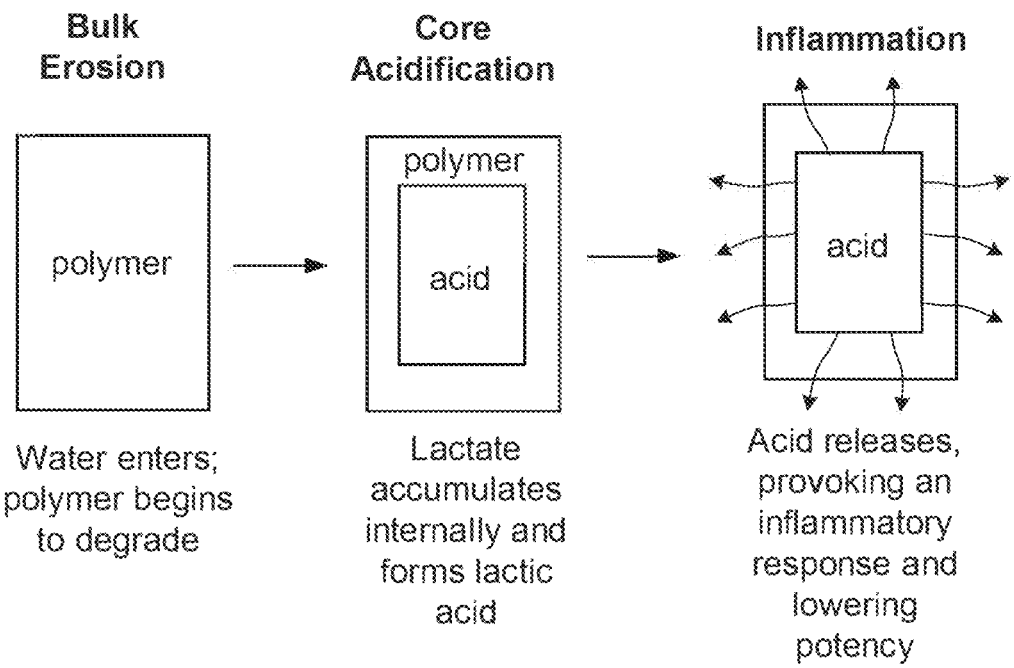
FIG. 17 is a schematic representation of core acidification of the prior art.

As shown schematically in FIG. 17, thick biodegradable polymer films (e.g., films having a volume with a minimum cross-sectional dimension greater than about 400-500 microns) degrade by bulk erosion (i.e., degradation occurs throughout the whole material equally; both the surface and the inside of the material degrade at substantially the same time). As the polymer degrades, lactic acid and/or glycolic acid degradation products are produced at an internal region of the film. If the film thickness is sufficiently high (e.g., greater than 1 mm), the lactic acid and/or glycolic acid is not immediately exposed to a pH 7.4 environment (e.g., the surrounding physiologic fluids), and therefore is not immediately converted to lactate and/or glycolate. Accordingly, the lactic acid and/or glycolic acid accumulates within the interior portion of the film (core acidification), which may cause detrimental effects such as a drop in local pH and local inflammation, as discussed below.

In contrast, thin biodegradable polymer films (e.g., having a minimum cross-sectional dimension less than about 400-500 microns) typically degrade by surface erosion. The buffering capacity of the body (e.g., due to the presence of physiologic fluids buffered to pH 7.4) is sufficient to nearly instantaneously convert any surface-generated lactic acid to lactate and/or glycolic acid to glycolate. Therefore, due to the high surface area to volume ratios of thin films, there is generally no core acidification, and therefore no drop in local pH or local inflammation. However, thin polymer films may be less suitable for certain applications, e.g., due to decreased structural integrity and/or therapeutic agent loading capacity. For example, it is generally understood that the release rate of therapeutic agent from within a polymer implant is proportional to the surface area of the polymer implant. More precisely, the release rate as a proportion of total drug payload is typically proportional to the implant's total surface area to total volume ratio. It may be challenging for a thin film polymer, which invariably has a high total surface area to total volume ratio, to carry a high payload of therapeutic agent and release that payload over a long duration. A traditional polymer film may have the thickness to be able to carry the desired payload of therapeutic agent and the lower total surface area to total volume ratio to achieve the desired dosage requirements over time, but this greater thickness and resulting low surface area to volume ratio may create a high risk of core acidification. In contrast, the embodiments described herein allow for a higher payload of therapeutic agent and a lower total surface area to total volume ratio to achieve drug release profile over a sustained period of time without the concomitant risk of core acidification.

Figure 18:
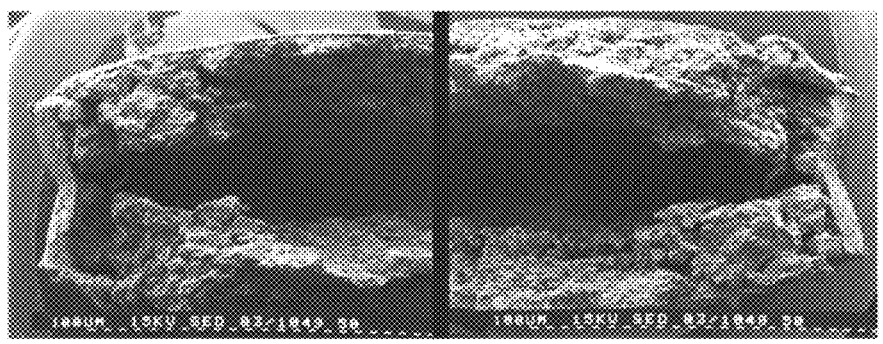
FIG. 18 is a scanning electron microscope image of a polymer tablet of the prior art after 20 days of degradation.

Core acidification may cause various detrimental effects. For example, the reduction in pH may autocatalyze degradation of the remaining polymer, thus increasing the degradation rate of the implant. This may cause premature release of therapeutic agent, reduce the structural integrity of the implant, and/or result in implant rupture. Additionally, if the accumulated lactic acid and/or glycolic acid is released into the body over a sufficiently short period of time (e.g., due to degradation or rupture of the implant), the sudden release of acid may overcome the buffering capacity of the surrounding physiologic environment, thereby producing a sudden decrease in local pH and provoking an inflammatory response. FIG. 18, for example, is a scanning electron microscope ("SEM") image of a polymer tablet of the prior art after 20 days of degradation. Inflammation in and around a prosthetic joint may be particularly concerning because of the risk of inflammation-induced osteolysis, which may cause a loosening of the newly implanted joint, and increased risk of infection. Inflammation may also prevent or reduce the effectiveness of analgesia.

Moreover, a decrease in local pH due to core acidification may detrimentally affect the activity of therapeutic agents that have a pKa greater than physiologic pH. For example, bupivacaine has a pKa of about 8.0, and is convertible between a free base form and a salt form (such as its hydrochloride salt form, bupivacaine HCl). Intracellular bupivacaine HCl produces analgesia by blocking sodium from entering the neuron; however, only the bupivacaine free base can cross the cell membrane into the neuron. Once the free base crosses into the intracellular space, it is at least partially converted into bupivacaine HCl due to the decreased pH of the intracellular environment (pH 7.2) relative to the extracellular environment (pH 7.4). If the extracellular pH is at or near physiologic pH, the ratio of bupivacaine free base to bupivacaine HCl is sufficiently high for effective intracellular uptake, thereby producing an analgesic effect. However, if the extracellular pH is reduced (e.g., due to core acidification), the ratio of bupivacaine free base relative to bupivacaine HCl decreases correspondingly, thus slowing intracellular uptake and thereby reducing or altogether eliminating the analgesic effect.

The depots 100 of the present technology surprisingly do not undergo core acidification, similar to a thin film, despite having a relatively high minimum cross-sectional dimension (e.g., greater than or equal to about 400 microns). As shown schematically in FIG. 19A, the depots of the present technology may shed up to 50%, 60%, 70%, or 80% of their individual mass (e.g., therapeutic agent and/or releasing agent) over the course of releasing the therapeutic agent (e.g., 5 days, 7 days, 10 days, 14 days, 20 days, 30 days, etc.), resulting in a highly porous, mesh-like system that—at least for the purpose of degradation—behaves like a thin film because of its high surface area to volume ratio. Without being bound by theory, it is believed that the polymer matrix of the therapeutic region becomes highly porous as degradation continues, allowing physiologic fluids to invade the highly porous polymer matrix to degrade the remaining polymer via surface erosion, thereby avoiding core acidification and the resulting inflammatory response.

Accordingly, the depots 100 of the present technology can be implanted in the body without exhibiting the detrimental effects attributed to core acidification, while still having sufficiently large dimensions to maintain structural integrity and/or accommodate relatively high loads of therapeutic agent. For example, a depot 100 can comprise a polymer matrix having a volume with a minimum cross-sectional dimension (e.g., minimum thickness) of at least 400 microns.

Several aspects of the technology are directed to polymer implants that are not configured for drug delivery and/or may not include any therapeutic agent. For example, the present technology includes biodegradable implants configured to support, repair, and/or provide access to one or more portions of the body. In some embodiments, the polymer implant may be an orthopedic implant. The implant may be selected from the group consisting of a pin, a screw, a plate, a rod, a tack, a suture anchor, a spine cage, a scaffold and a bone graft. For any of the foregoing embodiments, the implant may include a polymer matrix including a polymer having an acid as a degradation byproduct. For example, the polymer may be a polyhydoxyalkanoate (PHA). In such embodiments, at least a portion of the polymer matrix may have a volume with a minimum cross-sectional dimension of at least 400 μm before degradation of the polymer begins. In some embodiments, the polymer matrix has a minimum cross-sectional dimension of at least 500 μm, 600 μm, 700 μm, 800 μm, 900 μm, 1 mm, 2 mm, 3 mm, 4 mm, 5 mm, or 6 mm. When the implant is (a) submerged in aqueous media for a duration sufficient for a molecular weight of the polymer and/or a mass of the polymer matrix to decrease by about 25% to about 75%, and (b) subsequently submerged in a buffer solution and broken up such that an interior region of the implant is in fluid communication with the surrounding buffer solution, a pH of the surrounding buffer solution may be within about 0.5 units of the pH of the buffer solution before the implant is placed in the buffer solution.

EXAMPLES

Example 1

Core Acidification Testing of Depot Samples with Uniform Dimensions

This example describes preparation and testing of depot samples having the same dimensions (25 mm×15 mm×1.5 mm). Two depot samples were prepared. The first depot sample (or "Sample 1") represented the depot technology of the present application and was structured similarly to the embodiment of FIG. 5. Sample 1 had a therapeutic region sandwiched between two inner control layers (closest to the therapeutic region, such as 302b and 302c in FIG. 5) and two outer control layers (farthest from therapeutic region, such as 302a and 302d in FIG. 5). Within the therapeutic region, the ratio of releasing agent to polymer to therapeutic agent was 5:10:20. The inner control layers had a releasing agent to polymer ratio of 5:10. The outer control layers had a releasing agent to polymer ratio of 1:10. The releasing agent used in the therapeutic region and the control layers was Tween 20. The polymer used in the therapeutic region and the control layers was 50/50 PLGA. The therapeutic agent used in the therapeutic region was bupivacaine HCl.

Sample 1 was manufactured by heat compressing the therapeutic region and control layers 4 times for 2 minutes at a temperature of 80° C. and a pressure of 0.6 MPa to achieve final implant dimensions of 25 mm×15 mm×1.5 mm, then sterilized using e-beam (30 kGy).

The second depot sample (or "Sample 2") was a polymer-only sample. Sample 2 was manufactured by heat compressing a 50/50 PLGA polymer resin 5 times at a temperature of 155° C. and a pressure of 0.6 MPa for 2 minutes to achieve final implant dimensions of 25×15×1.5 mm, then sterilized using e-beam (30 kGy). No releasing agent, therapeutic agent, or solvent was used for the preparation of Sample 2.

Both samples were soaked for 3 weeks in 100 ml of water at 37° C. At the end of this period the samples were removed and placed into 20 ml PBS (pH=7.3) at an ambient temperature of 24° C. The samples were then sonicated to break the depots into multiple pieces at a frequency of 32-38 kHz for 10 minutes.

The pH of the PBS solution containing each of the samples was measured using a calibrated pH meter (Orion Star All1 pH meter from Thermo Scientific) before and after sonication. The pH meter was calibrated using standards at pH=1.68, 7.00 and 10.01. A drop in pH was considered indicative of a prior build-up of lactic acid and/or glycolic acid in the core of the sample.

TABLE 1

Example 1 Results

|  | pH before Sonication | pH after Sonication |
|---|---|---|
| Sample 1 (with therapeutic region) | 7.30 | 7.18 |
| Sample 2 (polymer only) | 7.32 | 3.98 |

FIGS. 19B and 19C are SEM images of the therapeutic region of Sample 1 pre- and post-elution, respectively.

The results make it clear that Sample 2 (the polymer-only monolith) had a buildup of acid in its core that was released after sonication, thus dropping the pH of the solution containing Sample 2 from 7.32 (prior to sonication) to 3.98 (after sonication), for a total pH drop of 3.34. In other words, the PBS solution in Sample 2 was more than 1,000 times more acidic after the contents of the Sample 2 depot was released than before. In contrast, the pH in the solution containing the sample in accordance with the present technology-Sample 1-dropped only approximately 0.12 units, and thus was only 1.2 times more acidic after the contents of Sample 1 was released than before. Thus, there was a prior build-up of lactic acid and/or glycolic acid in the core of Sample 2, but not of Sample 1.

Example 2

Preparation of Depot Samples with Uniform Polymer Mass

This example describes preparation of depot samples having substantially the same polymer mass. Three types of depot samples were used: test sample ("TKAine depot"), negative control, and positive control. Note that the samples were intentionally designed to be of different dimensions in order for the mass of polymer in all three groups of samples to be equivalent. This was based on the estimation of polymer in a single TKAine depot to be approximately one-third of its total mass.

TKAine Depot

This was a 26 mm×16 mm×1.5 mm-sized depot with control layers applied on both sides. This depot represented the depots of the present technology and was structured similarly to FIG. 4. Each TKAine depot was a compressed film comprising bupivacaine (BUP) (therapeutic agent), polysorbate 20 (Tween-20) (releasing agent), and a bioresorbable polymeric matrix (50/50 PLGA). The anticipated dose delivered from each TKAine depot over 14 days was 300 mg of bupivacaine HCl monohydrate (282 mg anhydrous bupivacaine HCl). As part of the dose escalation, up to 8 TKAine depots may be placed in a subject.

Each TKAine depot was fabricated with a drug-containing core layer (i.e., therapeutic region) that was sandwiched between non-drug-containing bioresorbable polymer layers (i.e., control layers). The depot was then compressed to yield a uniform, multi-layer depot. Each non-drug layer included a bioresorbable polymer and a non-ionic surfactant (polysorbate 20) (releasing agent). Each drug layer included a bioresorbable polymer, non-ionic surfactant (polysorbate 20) (releasing agent), and bupivacaine (therapeutic agent). The extended drug release characteristics of TKAine depots were controlled by the specific ratios of polymer, bupivacaine, and polysorbate 20 surfactant, and the formulation of each layer. The mass ratio of BUP:PLGA:Tween-20 in the therapeutic region was 20:10:1 and the ratio of PLGA:Tween-20 in the control layers was 5:10. Milled bupivacaine HCl monohydrate (10 μm diameter) from Cambrex was used.

The specific formulations of the core and control layers are provided in Tables 2 and 3 below:

TABLE 2

Formulation (core layer) information

Formulation Preparation
(Core Layer)

| Material | Mass (g) |
|---|---|
| Tween 20 | 0.6918 |
| 50/50 PLGA | 6.9200 |
| Bupivacaine HCl | 13.8674 |
| Acetone | 20.8493 |

TABLE 3

Formulation (control layer) information

Formulation Preparation
(Control Layer)

| Material | Mass (g) |
|---|---|
| Tween 20 | 3.4949 |
| 50/50 PLGA | 6.9999 |
| Acetone | 20.7790 |

Negative Control

This was a 16 mm×8 mm×1.5 mm-sized sample that was made wholly from polymer only (specifically, 50/50 Poly (DL-lactide-co-glycolide)). This was the negative control sample that was designed to intentionally experience core acidification.

The sample was prepared by compressing 50/50 PLGA resin in between two sheets of polyethylene terephthalate (PET) at 0.6 MPa with both the top and bottom plates powered on at 155° C. for 2 minutes to melt the resin, forming a polymer base film. The polymer base film was peeled off from the PET sheet and the thickness of the polymer base film measured. The polymer base film was folded and compressed for short amounts of time (10 seconds) until desired thickness of 1.5 mm was achieved. The samples were then cut to the desired dimensions (16 mm×8 mm×1.5 mm). The samples were sterilized using 1 e-beam at 30 kGy.

Positive Control

This was a 36 mm×35 mm×0.15 mm-sized sample that was made wholly from polymer only (specifically, 50/50 Poly(DL-lactide-co-glycolide)). This was the positive control sample that was designed to experience minimal core acidification.

The sample was prepared by compressing 50/50 PLGA resin in between two sheets of polyethylene terephthalate (PET) at 0.6 MPa with both the top and bottom plates powered on at 155° C. for 2 minutes to melt the resin, forming a polymer base film. The polymer base film was peeled off from the PET sheet and the thickness of the polymer base film measured. The polymer base film was folded and compressed for longer amounts of time (30 seconds) until desired thickness of 0.15 mm was achieved. The samples were then cut to the desired dimensions (36 mm×35 mm×0.15 mm). The samples were sterilized using 1 e-beam at 30 kGy.

The dimensions and masses of each sample are provided in Table 4 below:

TABLE 4

| Sample ID | B168-55-2.3 | B168-55-2.4 | B168-55-2.5 | B168-55-2.6 | B168-55-2.7 | B168-55-2.8 | B168-55-2.9 | B168-55-2.10 |
|---|---|---|---|---|---|---|---|---|
| Description | TKAine Depot | TKAine Depot | TKAine Depot | TKAine Depot | TKAine Depot | TKAine Depot | TKAine Depot | TKAine Depot |
| Length (mm) | 25.86 | 25.14 | 25.3 | 25.45 | 26.15 | 25.37 | 26.2 | 26.04 |
| Breadth (mm) | 15.9 | 15.77 | 16.74 | 15.32 | 16.62 | 16.61 | 16.77 | 16.72 |
| Thickness (mm) | 1.574 | 1.55 | 1.605 | 1.57 | 1.539 | 1.57 | 1.612 | 1.604 |
| Mass (g) | 0.7323 | 0.6727 | 0.7457 | 0.6816 | 0.7737 | 0.7439 | 0.7929 | 0.7839 |

| Sample ID | B168-55-NC3 | B168-55-NC4 | B168-55-NC5 | B168-55-NC6 | B168-55-NC7 | B168-55-NC8 | B168-55-NC9 | B168-55-NC10 |
|---|---|---|---|---|---|---|---|---|
| Description | Negative Control | Negative Control | Negative Control | Negative Control | Negative Control | Negative Control | Negative Control | Negative Control |
| Length (mm) | 16.61 | 15.99 | 16.2 | 15.25 | 16.67 | 17.23 | 16.45 | 15.83 |
| Breadth (mm) | 9.69 | 8.9 | 8.98 | 9.21 | 9.78 | 8.54 | 9.41 | 8.23 |
| Thickness (mm) | 1.665 | 1.657 | 1.873 | 1.579 | 1.66 | 1.73 | 1.637 | 1.534 |
| Mass (g) | 0.2786 | 0.2383 | 0.2574 | 0.2334 | 0.2782 | 0.24 | 0.2693 | 0.2269 |

| Sample ID | B168-55-PC3 | B168-55-PC4 | B168-55-PC5 | B168-55-PC6 | B168-55-PC7 | B168-55-PC8 | B168-55-PC9 | B168-55-PC10 |
|---|---|---|---|---|---|---|---|---|
| Description | Positive Control | Positive Control | Positive Control | Positive Control | Positive Control | Positive Control | Positive Control | Positive Control |
| Length (mm) | 36.66 | 36.62 | 33.83 | 36.28 | 36.38 | 36.25 | 36.81 | 37.36 |
| Breadth (mm) | 35.22 | 35.58 | 32.05 | 35.12 | 35.44 | 35.77 | 35.78 | 34.35 |
| Thickness (mm) | 0.149 | 0.155 | 0.216 | 0.14 | 0.164 | 0.149 | 0.143 | 0.145 |
| Mass (g) | 0.2307 | 0.2461 | 0.26 | 0.2164 | 0.2613 | 0.226 | 0.2342 | 0.2302 |

Example 3

Core Acidification Testing of Depot Samples with Uniform Polymer Mass

This example describes testing of the depot samples prepared in Example 2. The twenty-four samples were each placed in individual fabric bags (made from polyester-polyethylene blend or equivalent) and immersed in the degradation media (100 mL of PBS) at 37° C. A string was used to hold the fabric bags away from the glass surface of the bottle.

During the first two weeks of the degradation, the degradation media of all twenty-four samples was replaced every day with 100 mL of fresh PBS with the objective of removing any drug eluted from the TKAine depots while subjecting the other samples to the same test procedures. No measurement of the pH of the degradation media was taken during the first two weeks of the degradation period.

For the remainder of the degradation period, the degradation media of all twenty-four samples was left untouched. During this period, the pH of the degradation media was measured every day (ignoring weekends). The pH was measured when the degradation media was at ambient temperature.

At the end of two and four weeks, two TKAine depots, two negative control samples, and two positive control samples were retrieved from the degradation media and dried using Kimwipes prior to sonication. Sonication of samples was performed as follows: six glass bottles containing 20 mL of PBS were prepared. The pH of the six volumes of PBS at ambient temperature was measured and recorded. The six degraded samples were then placed in the glass bottles and sonicated for 20 minutes. The sonication media was left to cool down to ambient temperature prior to the measurement of pH of the sonication media. At t=2 weeks, the samples were sonicated a second time for 60 minutes, while at t=4 weeks, the samples were extremely degraded and thus were not sonicated a second time.

The pH measurements prior to and after sonication are provided in Table 5 below:

TABLE 5

| | | | Results | | | |
|---|---|---|---|---|---|---|
| | | | Sonication Rounds | | | |
| | | | 1 | | 2 | |
| t = (weeks) | Sample Type | Sample ID | pH before | pH after | pH before | pH after |
| 2 | TKAine | B168-55-2.3 | 7.61 | 7.55 | 7.48 | 6.92 |
| 2 | Depot | B168-55-2.4 | 7.61 | 7.54 | 7.47 | 6.82 |
| 4 | | B168-55-2.5 | 7.43 | 6.33 | NA | |
| 4 | | B168-55-2.6 | 7.32 | 6.07 | | |
| 2 | Negative | B168-55-NC3 | 7.53 | 7.24 | 7.48 | 3.61 |
| 2 | Control | B168-55-NC4 | 7.51 | 7.24 | 7.31 | 4.18 |
| 4 | | B168-55-NC5 | 7.39 | 6.64 | NA | |
| 4 | | B168-55-NC6 | 7.29 | 6.77 | | |
| 2 | Positive | B168-55-PC3 | 7.54 | 7.3 | 7.5 | 6.71 |
| 2 | Control | B168-55-PC4 | 7.59 | 7.14 | 7.5 | 6.21 |
| 4 | | B168-55-PC5 | 7.44 | 6.65 | NA | |
| 4 | | B168-55-PC6 | 7.34 | 6.66 | | |

Figure 66:
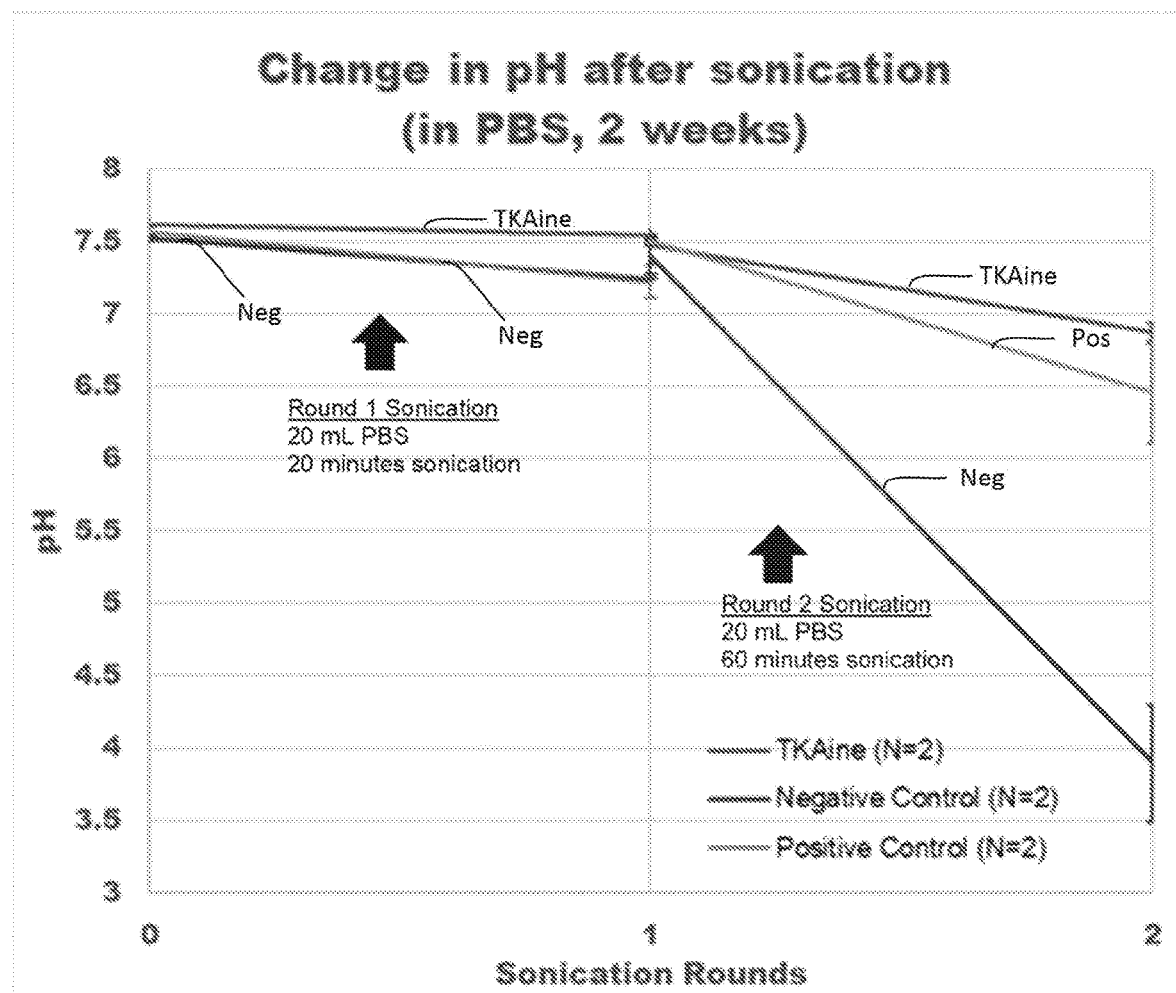
FIG. 66 is a graph showing the results of an experiment at 2 weeks.
Figure 67:
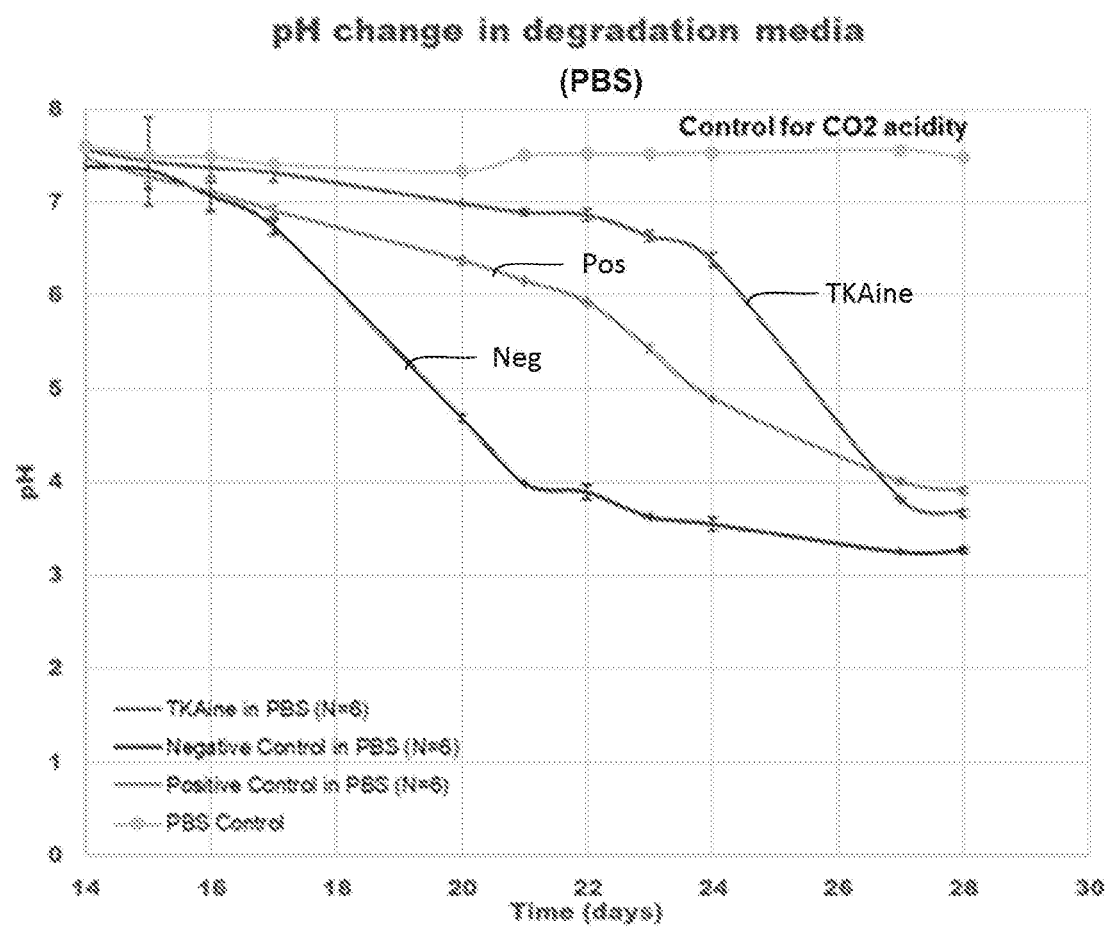
FIG. 67 is a graph showing the results of the experiment at 4 weeks.

As shown in FIG. 66, after two weeks of degradation, the negative control exhibited a sharp drop in pH following sonication, while both the positive control and the TKAine depot exhibited much more subdued drops in pH. As shown in FIG. 67, after four weeks of degradation, the samples were extremely degraded and the drop in pH was likely due to cleaving of ester linkages from the sonication rather than due to build-up of degradation products (for example, lactic acid and glycolic acid).

Note that all samples had an equivalent amount of PLGA, and therefore ester linkages, and thus would be expected to generate the same number of lactic acid and glycolic acid degradation products. However, the pH dropped much more rapidly for the negative control indicating that the rate of release of acid byproducts was sufficient to overcome the buffer capacity of the PBS. A similar phenomenon would be expected in vivo. In contrast, the pH drop associated with the TKAine depot was minimal out to 24 days, and thus minimal inflammatory response would be expected for implanted TKAine depots in vivo.

These results support the hypothesis that thicker samples (negative control) develop core acidification, as can be seen in the sharp drop in pH of the negative control samples, while thinner samples (positive control) develop minimal core acidification, which can be seen in a much smaller drop in pH of the positive control samples. The TKAine depot, being a relatively thick sample, might be expected to undergo core acidification similar to that of the negative control. However, because of the diffusion of drug out from the TKAine depot over the first two weeks, channels in the TKAine are created, allowing any degradation products (for example lactic acid and glycolic acid) to diffuse out as well. This can be seen in FIG. 66, where the TKAine depot behaved more like the positive control (thin monolith) rather than the negative control (thick monolith).

Figure 68:
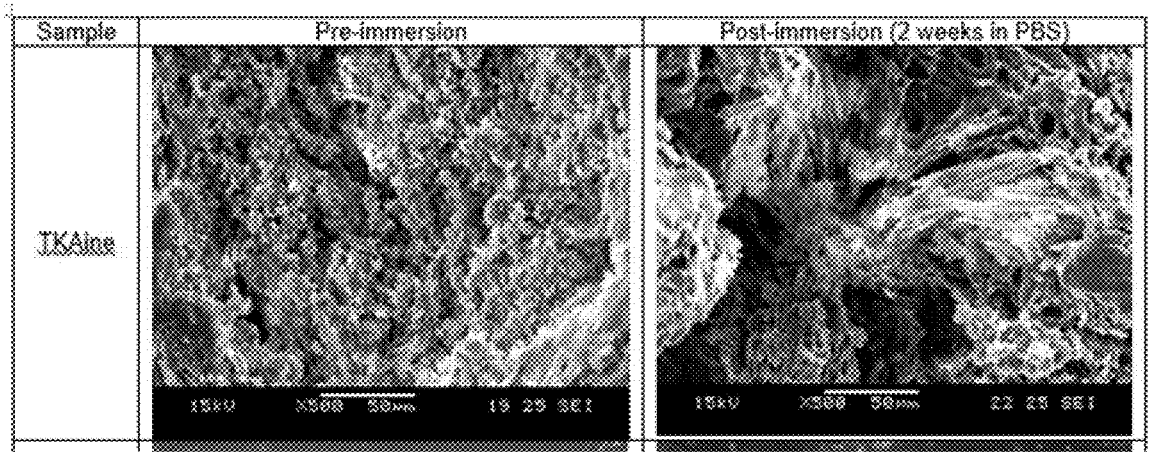
FIGS. 68-70 are SEM images of a depot of the present technology, a negative control, and a positive control, each pre-immersion and post-immersion.
Figure 69:
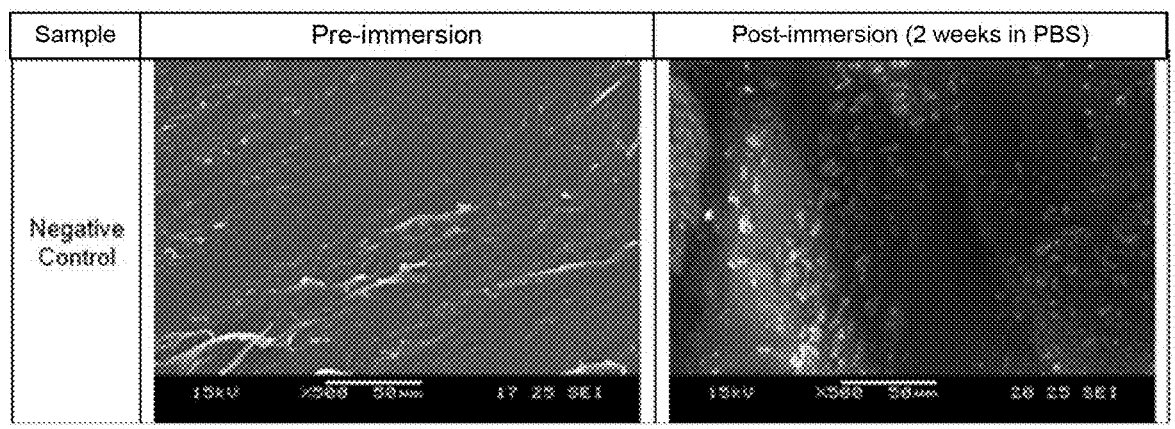
Figure 70:
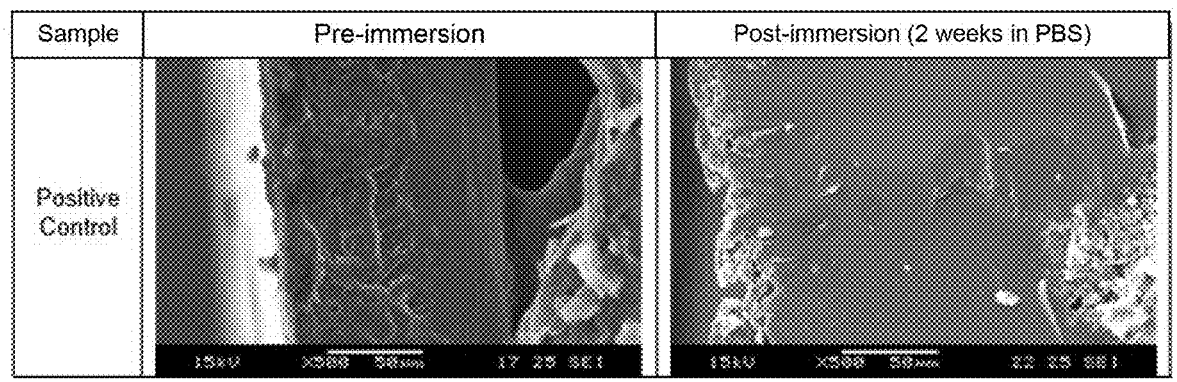

FIGS. 68-70 illustrate scanning electron microscope (SEM) images of the TKAine depots, negative and positive controls were taken both before and after immersion in PBS for two weeks at 500× magnification. The objective of taking such images was to show the presence of degradation products in the TKAine depot samples while showing a lack of degradation products in the positive and negative control samples.

As shown in FIGS. 68-70, after two weeks of immersion in PBS, the TKAine depot's cross-section appeared to have larger voids, due to release of drug after the immersion period. The negative control's cross-section appeared to have degraded significantly and appeared to have a more viscous, liquid-like consistency than the pre-immersion sample's cross-section. The positive control's cross-section did not appear to be any different when compared to the image of the pre-immersion sample's cross-section.

FIGS. 68-70, support the hypothesis by showing that the thicker negative control does experience core acidification (by developing a liquid-like consistency after two weeks of immersion in PBS) while the thinner positive control experiences minimal core acidification (as can be seen by the lack of change in the cross-section images after two weeks of immersion in PBS). FIGS. 68-70 also show that the TKAine depot does indeed become more porous over time due to the diffusion of drug out from the polymer matrix, which, when combined with the pH data obtained and shown in FIG. 66, is a strong indication that the TKAine depot design is able to eliminate core acidification.

In conclusion, the TKAine depot's design and drug release mechanics allow for it to be implanted without the associated inflammatory response from build-up of degradation products that typical thick bioresorbable polymer implants experience. This lowers the risk of implantation and improves TKAine depot's safety outcome.

E. Releasing Agent

In many implantable drug eluting technologies, the depot provides an initial, uncontrolled burst release of drug followed by a residual release. These drug release kinetics may be desirable in certain clinical applications, but may be unavoidable even when undesirable. Hydrophilic drugs loaded in a polymer carrier will typically provide a burst release when exposed to physiologic fluids. This dynamic may present challenges, particularly when it is desirable to load a large volume of drug for controlled, sustained in vivo administration. For example, although it may be desirable to implant several days or weeks' worth of dosage to achieve a sustained, durable, in vivo pharmacological treatment, it is imperative that the therapeutic agent is released as prescribed, otherwise release of the entire payload could result in severe complications to the patient.

To achieve finer control over the release of the therapeutic agent when exposed to fluids, the depots 100 of the present technology may include a releasing agent. In some embodiments, both the therapeutic region 200 and the control region 300 include a releasing agent (or mix of releasing agents), which can be the same or different releasing agent (or mix of releasing agents) in the same or different amount, concentration, and/or weight percentage. In some embodiments, the control region 300 includes a releasing agent and the therapeutic region 200 does not include a releasing agent. In some embodiments, the therapeutic region 200 includes a releasing agent and the control region 300 does not include a releasing agent. At least as used in this section, "the releasing agent" applies to a releasing agent that may be used in the therapeutic region 200 and/or in the control region 300.

The type and/or amount of releasing agent within the therapeutic region 200 and/or control region 300 may be varied according to the desired release rate of the therapeutic agent into the surrounding biological fluids. For example, choosing releasing agents with different dissolution times will affect the rate of release. Also, the weight percentage of releasing agent in a region of polymer will influence the number and the size of the diffusion openings subsequently formed in the polymer, thereby affecting the rate of therapeutic agent release from the depot 100 (e.g., the greater the weight percentage of releasing agent, the faster the release). The presence of releasing agent in select regions also influences the release rate of therapeutic agent. For example, a depot with releasing agent in the control region 300 and/or therapeutic region 200 will generally release therapeutic agent at a higher rate compared to a depot with no releasing agent. Similarly, releasing agent in both the control region 300 and the therapeutic region 200 will generally release therapeutic agent at a higher rate than when releasing agent is in the control region alone.

In certain embodiments of the present technology, the layer-by-layer ratio of releasing agent to bioresorbable polymer can be adjusted to control the rate of therapeutic agent released from the depot 100. For example, in many embodiments of the present technology, the depot 100 includes a therapeutic region 200 having a weight percentage of releasing agent that is different than the weight percentage of the releasing agent in the control region 200. For example, the therapeutic region 200 may have a greater or lesser weight percentage of releasing agent than the control region 300. In some embodiments, the control region 300 may have a weight percentage of releasing agent that is at least 2 times greater than the weight percentage of the releasing agent in the therapeutic region 200. In some embodiments, the control region 300 may have a weight percentage of releasing agent that is at least 3-20 times greater, at least 4 times greater, at least 5 times greater, at least 6 times greater, at least 7 times greater, at least 8 times greater, at least 9 times greater, at least 10 times greater, at least 11 times greater, at least 12 times greater, at least 13 times greater, at least 14 times greater, at least 16 times greater, at least 17 times greater, at least 18 times greater, at least 19 times greater, at least 20 times greater, at least 25 times greater, at least 30 times greater, about 5 to 10 times greater, about 10 to 15 times greater, about 5 to 15 times greater, or about 15 to 25 times greater than the weight percentage of the releasing agent in the therapeutic region 200.

In many embodiments of the present technology, the releasing agent is a surfactant. Unlike the use as a releasing agent as described herein, surfactants are usually used to control the dispersions, flocculation and wetting properties of a drug or polymer. Fundamentally, surfactants operate on the interface between the polymer and drug or the interface between the drug and biological membrane. Depending on the type of formulation, surfactants typically play a role in several aspects of drug delivery: (1) solubilization or stabilization of hydrophobic drugs by lowering the entropic cost of solvating hydrophobic drug through complexation with drug molecules in solution (C. Bell and K. A. Woodrow, ANTIMICROB. AGENTS CHEMOTHER., 2014, 58:8, 4855-65); (2) improvement of the wetting of tablet or polymer for fast disintegration (M. Irfan, et al., SAUDI PHARM. J., 2016, 24, 537-46); (3) formation of colloidal drug delivery systems, such as reverse micelles, vesicles, liquid crystal dispersions, nanoemulsions and nanoparticles (M. Fanun, Colloids in Drug Delivery, 2010, p. 357); and (4) improvement the bioperformance of drugs by altering the permeability of biological membrane and consequently drug penetration/permeation profile (S. Jain, et al., Lipid Based Vesicular Drug Delivery Systems, 2014, Vol. 2014, Article ID 574673).

In order to illustrate the unique aspects of using a releasing agent in the polymeric control region to form diffusion openings and/or microchannels in the present technology, it is helpful to explain the more common approach of using hydrophilic molecules to enhance drug release. Conventionally, drug release is enhanced by creating a larger surface area in order to increase contact between the drug and the bodily fluid, thereby accelerating drug release. The most common mechanism for forming pores prior to implantation is to use non-surfactant hydrophilic molecules as pore-forming agents in polymer layers, either as a coating layer or a free-standing film (Kanagale, P., et al., AAPS PHARM. SCI.TECH., 2007; 8 (3), E1-7). Usually, pores are preformed by blending hydrophilic molecules with polymer, then removing the hydrophilic molecules by contact with water. However, when hydrophilic molecules are blended with hydrophobic polymer, the molecules tend to form hydrophilic domains and hydrophobic domains, which are energetically favorable due to the increase in entropy. When the film contacts water, hydrophilic domains are removed and replaced with large pores. The rate of drug release in this case is solely controlled by the porosity of the film and the resulting increased total surface area. The typical drug release curve in this case has a high, uncontrolled initial burst followed with a very slow release of residual drug afterwards.

Previously, when non-surfactant hydrophilic molecules are mixed into the polymer and then removed, a film with a porous structure is created. This porous layer reduces mechanical strength and elasticity, making it less suitable for certain applications. Additionally, this structure does not withstand heat compression bonding of the film because the pores would collapse. The loss of porous structure during heat compression negates the original intent of using the hydrophilic molecule, thus resulting in a densely packed film without any enhanced therapeutic agent release capability.

Further, if the hydrophilic molecule remains in the polymer layer during heat compression, the dissolution of the hydrophilic molecule in vivo causes the formation of very large pores, approximately 3-10 μm in diameter. Such large pores provide a large surface area, thereby causing a burst release of drug. In contrast to the use of hydrophilic molecules, the use of a surfactant as a releasing agent in the present technology enables the formation of microchannels approximately 5-20 nanometers in diameter, which is two orders of magnitude smaller than the pores resulting from the use of hydrophilic molecules. This allows tight control of the drug release by diffusion and, if desirable, without an uncontrolled burst release upon implantation. Additionally, use of a surfactant as a releasing agent allows the agent to remain present in the polymer prior to use and no pre-formed pores are created. This approach is particularly advantageous because the polymer's mechanical properties are preserved, thereby allowing the polymer to be easily processed and worked into different configurations.

In the present technology, the releasing agent is pre-mixed into the bioresorbable polymer such that each layer of polymer is contiguous and dense. The depot 100 is then formed when these layers are bonded together via heat compression without any adverse impact to the functional capabilities of the film. When the densely packed film is ultimately implanted, the releasing agent dissolves to enable efficient, controlled release of the therapeutic agent.

In some embodiments, the releasing agent comprises a polysorbate. Polysorbate is commonly used in the pharmaceutical industry as an excipient and solubilizing agent. Polysorbate is a non-ionic surfactant formed by the ethoxylation of sorbitan followed by esterification by lauric acid. Polysorbate 20 [IUPAC name: polyoxyethylene (20) sorbitan monolaurate] contains a mixture of ethoxylated sorbitan with 20 repeat units of polyethylene glycol distributed among four different sites in the sorbitan molecule. Common commercial names include Tween™ and Tween 20™ (Croda International Plc, Goole, East Yorkshire, UK) and Alkest® TW 20 (Oxiteno, Houston, TX).

Polysorbate is often utilized to improve oral bioavailability of a poorly water-soluble/hydrophobic drug. For example, polysorbate was used to improve bioavailability of active molecules that possess low solubility and/or intestinal epithelial permeability and it was observed that the bioavailability of this poorly water-soluble drug was greatly enhanced in a formulation with polysorbate or similar surfactants. (WO2008/030425; Breslin; Merck.) Akbari, et al., observed that using the hydrophilic carrier polyethylene glycol (PEG) along with polysorbate leads to faster an oral enhanced drug release rate because the polysorbate brings the drug in close contact with the PEG. (Akbari, J., et al., ADV. PHARM. BULL., 2015, 5 (3): 435-41.)

Polysorbate also functions as a water-soluble emulsifier that promotes the formation of oil/water emulsions. For example, the drug famotidine is known to have high solubility in water but low in vivo permeability. Polysorbate was used in an oral microemulsion formulation for enhancing the bioavailability of famotidine. (Sajal Kumar Jha, et al., IJDDR, 2011, 3 (4): 336-43.) Polysorbate is also used as a wetting agent to achieve rapid drug delivery. For example, Ball et al., achieved rapid delivery of maraviroc via a combination of a polyvinylpyrrolidone (PVP) electrospun nanofiber and 2.5 wt % Tween 20, which allowed for the complete release of 28 wt % maraviroc in just six minutes. It was believed that use of Tween 20 as a wetting agent allowed water to penetrate the PVP nanofiber matrix more quickly, thereby increasing the rate of drug release. (Ball, C., et al., ANTIMICROB. AGENTS CHEMOTHERAPY, 2014, 58:8, 4855-65.)

As described above, in order to improve drug release in certain polymer carriers, hydrophilic polymers, such as polysorbate, have been added to these carriers to accelerate or to enhance drug release from biocompatible polymers such as polyethylene glycol (PEG) in oral formulations (Akbari, J., et al., ADV. PHARM. BULL., 2015, 5 (3): 435-441). However, these formulations are intended to provide an immediate release of a hydrophobic drug into a hydrophilic environment (the in vivo physiologic fluid), not a variable or sustained controlled release as part of a control region.

In some embodiments, the releasing agent is polysorbate 20, commercially known as Tween 20™. Other releasing agents suitable for use in the present technology include polysorbates, such as Polysorbate 80, Polysorbate 60, Polysorbate 40, and Polysorbate 20; sorbitan fatty acid esters, such as sorbitan monostearate (Span 60), sorbitan tristearate (Span 65), sorbitane trioleate (Span 85), sorbitan monooleate (Span 80), sorbitan monopalmitate, sorbitan monostearate, sorbitan monolaurate, sorbitan monopalmitate, sorbitan trioleate, and sorbitan tribehenate; sucrose esters, such as sucrose monodecanoate, sucrose monolaurate, sucrose distearate, and sucrose stearate; castor oils such as polyethoxylated castor oil, polyoxyl hydrogenated castor oil, polyoxyl 35 castor oil, Polyoxyl 40 Hydrogenated castor oil, Polyoxyl 40 castor oil, Cremophor® RH60, and Cremophor® RH40; polyethylene glycol ester glycerides, such as Labrasol®, Labrifil® 1944; poloxamer; polyoxyethylene polyoxypropylene 1800; polyoxyethylene fatty acid esters, such as Polyoxyl 20 Stearyl Ether, diethylene glycol octadecyl ether, glyceryl monostearate, triglycerol monostearate, Polyoxyl 20 stearate, Polyoxyl 40 stearate, polyoxyethylene sorbitan monoisostearate, polyethylene glycol 40 sorbitan diisostearate; oleic acid; sodium desoxycholate; sodium lauryl sulfate; myristic acid; stearic acid; vitamin E-TPGS (vitamin E d-alpha-tocopherol polyethylene glycol succinate); saturated polyglycolized glycerides, such as Gelucire® 44/14 and and Gelucire® 50/13; and polypropoxylated stearyl alcohols such as Acconon® MC-8 and Acconon® CC-6.

Diffusion Openings

The channels or voids formed within the therapeutic region 200 and/or control region 300 by dissolution of the releasing agent may be in the form of a plurality of interconnected openings or pores and/or a plurality of interconnected pathways, referred to herein as "diffusion openings." In some embodiments, one or more of the channels may be in the form of discrete pathways, channels, or openings within the respective therapeutic and/or control region. Depending on the chemical and material composition of the therapeutic and control regions, one or more of the formed channels may extend: (a) from a first end within the therapeutic region to a second end also within the therapeutic region; (b) from a first end within the therapeutic region to a second end at the interface of the therapeutic region and the control region; (c) from a first end within the therapeutic region to a second end within the control region; (d) from a first end within the therapeutic region through the control region to a second end at an outer surface of the control region; (e) from a first end at the interface between the therapeutic region and the control region through the control region to a second end within the control region; (f) from a first end at the interface between the therapeutic region and the control region to a second end at an outer surface of the control region; (g) from a first end within the control region to a second end also within the control region; and (h) from a first end within the control region to a second end at an outer surface of the control region. Moreover, one or more of the channels may extend between two or more microlayers of the therapeutic region and/or control region.

F Constituent Ratios

In some embodiments, the ratio of the polymer in the control region 300 to the releasing agent in the control region 300 is at least 1:1. In some embodiments, the ratio may be at least 1.5:1, at least 2:1, at least 2.5:1, or at least 3:1.

In some embodiments, a ratio of the mass of the therapeutic agent in the depot 100 to the polymer mass of the depot is at least 1:1, at least 2:1, at least 3:1, at least 4:1, at least 5:1, at least 6:1, at least 7:1, at least 8:1, at least 9:1, at least 10:1, at least 11:1, at least 12:1, at least 13:1, at least 14:1, at least 15:1, or at least 16:1.

In some embodiments, the ratio of releasing agent to polymer to therapeutic agent in the therapeutic region 200 is of from about 0.1:10:20 to about 2:10:20, and in some embodiments of from about 0.1:10:20 to about 1:10:20, and in some embodiments of from about 0.1:10:20 to about 0.5:10:20.

In some embodiments, the ratio of releasing agent to polymer in the control region 300 is of from about 1:2 to about 1:10. In some embodiments, one or more of the control regions may have a ratio of releasing agent to polymer of 1:2, and one or more of the other control regions may have a ratio of releasing agent to polymer of 1:10

G. Selected Depot Embodiments Including a Barrier Region

In some embodiments, the depot 100 may be configured to release the therapeutic agent in an omnidirectional manner. In other embodiments, the depot may include one or more barrier regions 400 covering one or more portions of the therapeutic region 200 and/or control region 300, such that release of the therapeutic agent is limited to certain directions. The barrier region 400 may provide structural support for the depot. The barrier region 400 may comprise a low porosity, high density of bioresorbable polymer configured to provide a directional release capability to the depot. In this configuration, the substantial impermeability of this low porosity, high density polymer structure in the barrier region 400 blocks or impedes the passage of agents released from the therapeutic region 200. Accordingly, the agents released from the therapeutic region 200 take a path of less resistance through the control region 300 opposite from the barrier region 400, particularly following the creation of diffusion openings in the control region 300.

Figure 16A:
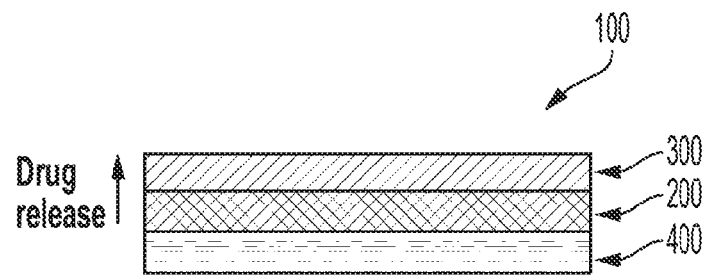
FIGS. 16A-16E depict various depot embodiments including a barrier region in accordance with the technology.

An example a depot 100 of the present technology having a barrier region 400 is shown in FIG. 16A. The barrier region 400 may comprise a low porosity, high density of bioresorbable polymer configured to provide a directional release capability to the multi-region depot. In this configuration, the low porosity, high density polymer structure in the barrier region 400 blocks or impedes passage of agents release from the therapeutic region 200. Accordingly, the agents released from the therapeutic region 200 take a path of lesser resistance through the control region opposite from the barrier region 400, particularly following the creation of channels in the control region. In an additional embodiment, the porosity of other regions of the multi-region depot can be varied to facilitate the release of therapeutic agent. For example, in this embodiment, the barrier region 400, the therapeutic region 200, and the control region 300 of the multi-region depot depicted in FIG. 16A may have different porosities ranging from low porosity in the barrier region 400 to higher porosities in the therapeutic agent and control regions to facilitate the release of therapeutic agent from the multi-region depot. In additional embodiments, the porosities of the edges of the multi-region depot, or within portions of any of the individual regions, can be varied to properly regulate or manipulate the release of therapeutic agent.

Figure 16B:
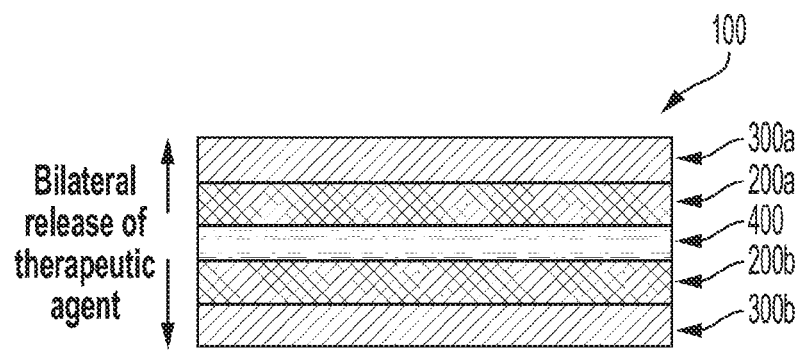
Figure 16C:
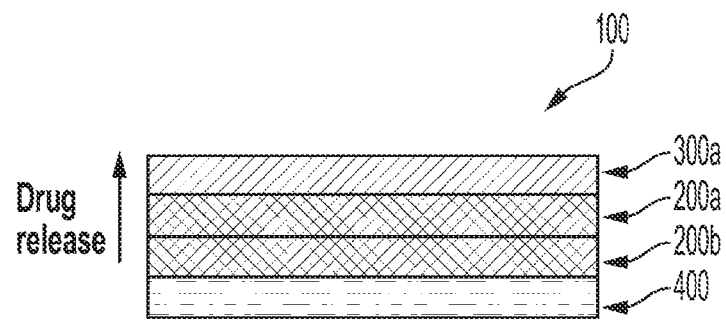

In the embodiment depicted in FIG. 16B, the multi-region depot provides for a bilateral or bidirectional release of therapeutic agent. This bidirectional release capability is accomplished through symmetric regioning about a high-density barrier region 400, wherein, as described above, the therapeutic agent releases along a path of less resistance, thereby releasing away from the high density barrier region 400. More specifically, disposed on one side of the barrier region 400 is a control region 300a and a therapeutic region 200a and, disposed on the other side of the barrier region 400, is a control region 300b and a therapeutic region 200b that are substantially similar to the pair on the other side. These pairs on either side of the barrier region 400 are configured to produce substantially equivalent, bidirectional release of therapeutic agent. In an alternate embodiment, a bidirectional release that is not equivalent (i.e., the therapeutic agent and/or rate of release in each direction is not the same) may be accomplished by asymmetric regioning, whereby the control region and therapeutic region pairs on either side of the barrier region 400 are substantially different.

In additional embodiments, it may be desirable for the multi-region depot to release multiple therapeutic agents. This capability can be particularly useful when multimodal pharmacological therapy is indicated. In the embodiment shown in FIG. 16C, the multi-region depot comprises a topmost or outermost control region 300a, a first therapeutic region 200a adjacent to the control region, a second therapeutic region 200b adjacent to the first therapeutic region 200a, and a barrier region 400 adjacent to the second therapeutic region 200b. In this embodiment, the first therapeutic region 200a and the second therapeutic region 200b comprise a first therapeutic agent and a second therapeutic agent, respectively. In certain embodiments, the first and second therapeutic agents are different. In one embodiment, the multi-region depot is configured to release the first and second therapeutic agents in sequence, simultaneously, or in an overlapping fashion to yield a complementary or synergistic benefit. In this configuration, the presence and function of the control region 300a may also ensure consistent and, if desired, substantially even release of multiple therapeutic agents residing beneath. Since many conventional drug delivery devices can fail to provide an even release of multiple drugs with different molecular weights, solubility, etc., the role of the control region in achieving a substantially even release of different therapeutic agents can be a significant advantage.

In some embodiments, the first therapeutic agent and second therapeutic agent are the same therapeutic agent but are present in the first and second therapeutic regions, respectively, in different relative concentrations to represent different dosages to be administered. In some embodiments, the first and second therapeutic agents of the first and second therapeutic regions, respectively, may have no clinical association or relationship whatsoever. For example, in an embodiment for use as part of a total joint replacement (e.g., total knee arthroplasty, total hip arthroplasty) or other surgical procedure, it may be clinically desirable to administer in the vicinity of the surgical site both an analgesic (e.g., local anesthetic) to treat and better manage postoperative pain for several days or weeks following the surgery and an antibiotic to treat or prevent surgical site infection associated with the surgery or implanted prosthesis (if any) for several weeks or months following the surgery. In this embodiment, the first therapeutic region 200a may comprise a therapeutically effective dose of local anesthetic to substantially provide pain relief for no less than 3 days and up to 15 days following the surgery and the second therapeutic region 200b may comprise a therapeutically effective dose of antibiotics to substantially provide a minimally effective concentration of antibiotic in the vicinity of the surgical site for up to three months following the surgery.

Figure 16D:
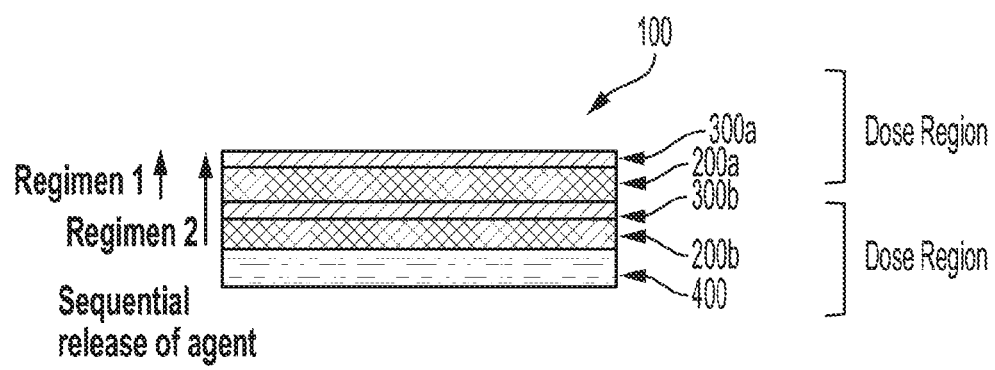

In some embodiments, as shown in FIG. 16D, the depot 100 comprises a first dosage region and a second dosage region, wherein the first and second dosage regions correspond to first and second dosage regimens. More specifically, each dosage region comprises a control region and therapeutic region pair, wherein each pair is configured for controlled release of a therapeutic agent from the therapeutic region 200a, 200b in accordance with a predetermined dosage regimen. For example, in treating and/or managing postoperative pain, it may be desirable for the multi-region depot to consistently release 50-400 mg/day of local anesthetic (e.g., bupivacaine, ropivacaine and the like) for at least 2-3 days following surgery (i.e., first dosage regimen) and then release a local anesthetic at a slower rate (e.g., 25-200 mg/day) for the next 5 to 10 days (i.e., second dosage regimen). In this exemplary embodiment, the first dosage region, and the control region and therapeutic region pair therein, would be sized, dimensioned, and configured such that the multi-region depot releases the first therapeutic agent in a manner that is consistent with the prescribed first dosage regimen. Similarly, the second dosage region, and the control region and therapeutic region pair therein, would be sized, dimensioned and configured such that the multi-region depot releases the second therapeutic agent in a manner that is consistent with the prescribed second dosage regimen. In another embodiment, the first and second dosage regions may correspond to dosage regimens utilizing different therapeutic agents. In one embodiment, the multi-region depot 100 is configured to administer the first and second dosage regimens in sequence, simultaneously, or in an overlapping fashion to yield a complementary or synergistic benefit. In an alternate embodiment of this scenario, the first and second dosage regimens, respectively, may have no clinical association or relationship whatsoever. For example, as described above with respect to the embodiment depicted in FIG. 16C, the first dosage regimen administered via the first dosage region may be treating or managing postoperative pain management and the second dosage regimen administered via the second dosage region may be treating or preventing infection of the surgical site or implanted prosthesis (if any).

Figure 16E:
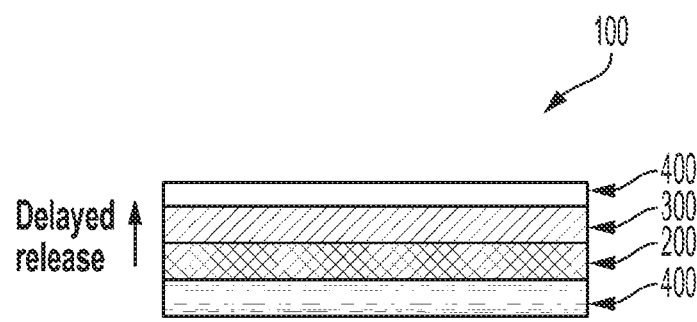

Certain embodiments of the present invention utilize delayed release agents. As illustrated in FIG. 16E, the depot 100 may include a barrier region 400 as the outermost (i.e., topmost) region to the multi-region depot and adjacent to a control region 300 comprising a releasing agent. The barrier region 400 presents a barrier to physiologic fluids from reaching and dissolving the releasing agent within the control region. In one embodiment, the barrier region 400 may comprise a delayed release agent mixed with a bioresorbable polymer, but without a releasing agent. Delayed release agents are different from the releasing agents used in the multi-region depot of the invention. Delayed release agents dissolve in physiological fluids more slowly than do releasing agents and thus provide the possibility for release of a therapeutic agent a defined amount of time following implantation of the multi-region depot. In embodiments where a delayed release agent is not present in the barrier region 400, it may take more time for the physiological fluids to traverse the barrier region 400 and contact the releasing agent. Only when the physiological fluids make contact with the control region will the releasing agent begin to dissolve, thus allowing the controlled release of the therapeutic agent. Delayed release agents may be advantageously used in the therapeutic methods of the invention wherein the therapeutic agent is not immediately required. For example, a nerve blocking agent may be injected prior to a surgical procedure, numbing the entire area around a surgical site. The controlled release of a local anesthetic is not required in such a surgery until the nerve block wears off.

Suitable delayed release agents for use in the present invention are pharmaceutically acceptable hydrophobic molecules such as fatty acid esters. Such esters include, but are not limited to, esters of myristoleic acid, sapienic acid, vaccenic acid, stearic acid, arachidic acid, palmitic acid, erucic acid, oleic acid, arachidonic acid, linoleic acid, linoelaidic acid, eicosapentaenoic acid, docosahexaenoic acid. Preferred esters include stearic acid methyl ester, oleic acid ethyl ester, and oleic acid methyl ester. Other suitable delayed release agents include tocopherol and esters of tocopherol, such as tocopheryl nicotinate and tocopheryl linolate.

H. Additional Depot Configurations

Figure 20:
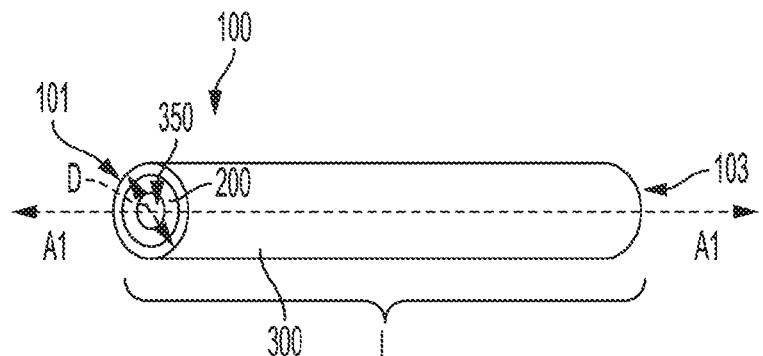
FIG. 20 is a perspective view of a depot in accordance with some embodiments of the present technology.

FIGS. 20-36 illustrate various examples of depots 100 having an elongated form. As depicted in FIG. 20, an "elongated depot" or an "elongated form" as used herein refers to a depot configuration in which the depot 100 has a length L between its ends along a first axis A1 (e.g., a longitudinal axis) that is at least 1.1, 1.2, 1.3, 1.4, 1.5, 1.6, 1.7, 1.8, 1.9, 2, 3, 4, 5, 6, 7, 8, 9, 10, 20, or 30 times greater than a maximum dimension D of a cross-sectional slice of the depot 100 within a plane orthogonal to the first axis A1. The elongated depots 100 described herein may include a therapeutic region 200 containing a therapeutic agent (such as any of the therapeutic agents described herein) and a control region 300 at least partially surrounding the therapeutic region 200 to control release of the therapeutic agent from the depot 100. The therapeutic region 200 may optionally include a bioresorbable polymer (such as any of the polymers described herein) and/or a releasing agent (such as any of the releasing agents described herein). The control region 300 may include a bioresorbable polymer (such as any of the polymers described herein) mixed with a releasing agent (such as any of the releasing agents described herein), but does not include any therapeutic agent at least prior to implantation. In some embodiments, the control region 300 may include some therapeutic agent prior to implantation, for example having a lower concentration of therapeutic agent than the therapeutic region 200. As discussed in greater detail below, the thickness of the control region 300, the concentration of releasing agent in the control region 300, the amount of exposed (uncovered) surface area of the therapeutic region 200, the shape and size of the depot 100, and other suitable parameters may be varied to achieve a desired release profile for the sustained, controlled release of the therapeutic agent from the depot 100.

In the embodiments shown in FIGS. 20-36, the elongated depot 100 has a cylindrical, columnar, and/or rod-like shape such that the cross-sectional shape is a circle and the cross-sectional dimension D is the diameter of the circle. In some embodiments, however, the elongated depot 100 may have another elongated configuration and/or cross-sectional shape along all or a portion of its length L. For example, the depot 100 may be in the form of a ribbon-like strip and thus have a square or rectangular cross-sectional shape. In other embodiments, the elongated depot 100 may have a circular, triangular, rhomboid, or other polygonal or non-polygonal cross-sectional shape based on the desired application. The elongated depot 100 may be a solid or semi-solid formulation with sufficient column strength to be pushed or pulled from a delivery device and sufficient durability and/or structural integrity to maintain its shape while the therapeutic agent is released into the surrounding anatomy for the desired duration of release.

A length L of the elongated depot 100 can be about 2 mm to about 300 mm, about 10 mm to about 200 mm, or about 10 mm to about 100 mm. In some embodiments, the maximum cross-sectional dimension D of the depot 100 can be between about 0.01 mm to about 5 mm, between about 0.1 mm to about 3 mm, or between about 0.5 mm to about 2 mm. The elongated form may be particularly well suited for injection or insertion to a subcutaneous, intramuscular, or other location through a needle or other suitable delivery device. Additionally or alternatively, the elongated depots 100 may be implanted using other techniques, for example surgical implantation through an open incision, a minimally invasive procedure (e.g. laparoscopic surgery), or any other suitable technique based on the application.

FIG. 20 illustrates an example of an elongated, generally cylindrical depot 100 comprising tubular, concentric therapeutic and control regions 200 and 300. The therapeutic region 200 comprises a tubular sidewall having an outer surface covered by the control region 300 and an exposed inner surface defining a lumen 350 that extends through the length L of the depot 100. The lumen 350 can be devoid of any material such that when the depot 100 is exposed to physiological fluid in vivo, the inner surface of the therapeutic region 200 is in direct contact with the fluid, thereby enhancing release of the therapeutic agent (relative to an elongated depot without a lumen through the therapeutic region). As shown in FIG. 20, the end surfaces of the therapeutic region 200 at the longitudinal ends 101, 103 of the depot 100 may also remain exposed/uncovered by the control region 300 (only one end surface is visible in FIG. 20). In some embodiments, the elongated depot 100 may include multiple, layered control regions 300 having the same composition or different compositions and/or the same thickness or different thicknesses. In these and other embodiments, the control region 300 may extend over one or both end surfaces of the therapeutic region 200. In particular embodiments, the lumen 350 extends through only a portion of the length L of the depot 100 and/or the tubular therapeutic region 200 is not concentric with the control region 300.

Figure 21:
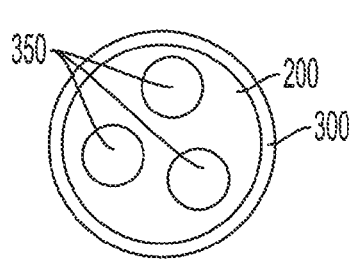
FIG. 21 is cross-sectional view of a depot in accordance with some embodiments of the present technology.

In some embodiments, the elongated depot 100 may include multiple lumens (e.g., two, three, four, five, six, etc.) extending through all or a portion of the length of the depot 100 and/or the length of the therapeutic region 200. For example, FIG. 21 is an end view of an elongated depot 100 having an inner therapeutic region 200 and an outer core region 300 covering an outer surface of the therapeutic region 200 along its length. In this particular example, the depot 100 includes three lumens 350 extending through the length of the therapeutic region 200. In the illustrated embodiment, each of the lumens 350 has a substantially circular cross-section and similar dimensions. In other embodiments, the lumens 350 may have other cross-sectional shapes, and/or the dimensions of each lumen 350 may vary from one another. In some embodiments, the elongated depot 100 may include multiple, layered control regions 300 having the same composition or different compositions and/or the same thickness or different thicknesses. In these and other embodiments, the control region 300 may extend over one or both end surfaces of the therapeutic region 200.

Figure 22:
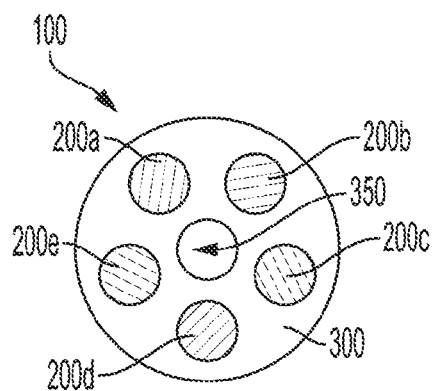
FIG. 22 is cross-sectional view of a depot in accordance with some embodiments of the present technology.

As shown in the end view of FIG. 22, the depot 100 can include a plurality of separate therapeutic regions 200 (labeled 200a-200e) extending longitudinally along the length of the depot 100. Although the depot 100 is shown having five therapeutic regions 200, in other embodiments the depot 100 may have more or fewer therapeutic regions 200 (e.g., two, three, four, six, seven, eight, etc.). The therapeutic regions 200 may be separated from one another by the control region 300. In the illustrated example, a central lumen 350 extends through the length of the control region 300, and the therapeutic regions 200 are distributed around the central lumen 350. In other embodiments, the elongated depot 100 may not include a lumen extending through any of its regions and may be solid across its cross-sectional dimension.

The therapeutic regions 200a-200e may have the same or different compositions, shapes, and/or dimensions. For example, the therapeutic regions 200a-200e may contain the same or different therapeutic agents, the same or different amount of therapeutic agent, the same or different polymers, and/or the same or different concentrations of releasing agents, depending on the desired release profile of each of the therapeutic regions 200a-200e. In the illustrated embodiment, each of the elongated therapeutic regions 200 has a substantially circular cross-section and similar dimensions. In other embodiments, the elongated therapeutic regions 200 may have other cross-sectional shapes and/or dimensions. In some embodiments, the elongated depot 100 may include one or more additional control regions 300 layered on top of the inner control region 300 surrounding the therapeutic regions 200a-200e. having the same composition or different compositions and/or the same thickness or different thicknesses. In these and other embodiments, the control region 300 may extend over one or both end surfaces of the therapeutic region 200.

Figure 23:
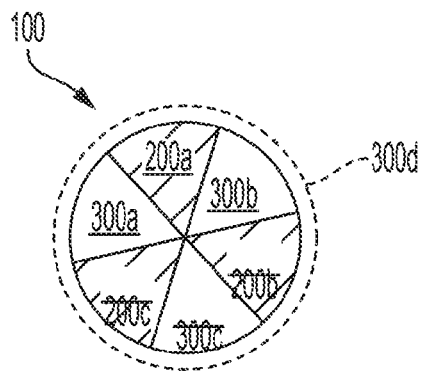
FIG. 23 is cross-sectional view of a depot in accordance with some embodiments of the present technology.

FIG. 23 illustrates another embodiment of an elongated depot 100 in which the cross-sectional area is composed of three elongated therapeutic regions 200a-200c separated radially from one another by three elongated control regions 300. In the illustrated embodiment, each of the separate regions intersects at a center in a pie-shaped configuration, however the constituent control regions 300a-300c and therapeutic regions 200a-200c can take any shape and form in different embodiments. Optionally, the depot 100 may include an additional control region 300d covering an outer surface of the more inner therapeutic regions 300a-300c and control regions 300a-300c to provide another layer of controlled release. In some embodiments, the elongated depot 100 may include multiple, layered control regions 300 having the same composition or different compositions and/or the same thickness or different thicknesses. In these and other embodiments, the control region 300 may extend over one or both end surfaces of the therapeutic region 200.

In certain instances, it may be beneficial to provide an elongated depot 100 having an inner therapeutic region 200 and an outer control region 300 of variable thickness and/or non-uniform coverage. Several examples of such depots 100 are shown FIGS. 24A-28. As depicted in FIGS. 24A-24C, the depot 100 can include an elongated therapeutic region 200 having a substantially uniform cross-sectional profile. The outer control region 300 radially surrounds the therapeutic region 200 along the length of the depot 100 and has a thickness that varies along the length of the depot 100. As shown in FIG. 24A, the control region 300 may have alternating first and second portions 305, 307 along its length. The first portions 302 can have a first thickness and the second portions 304 can have a second thickness greater than the first thickness. As such, the first portions 302 form annular grooves within the control region 300 at the outer surface of the depot 100. When implanted, the thinner first portions 302 may release the therapeutic agent more quickly than the thicker second portions 304, as the therapeutic agent has less control region to travel through before leaving the depot 100. By separately providing for faster-releasing portions and slower-releasing portions of the depot 100, the overall release rate of therapeutic agent from the therapeutic region 200 to a treatment site can be precisely tailored to a desired application. In addition to controlling the overall release rate, the release of therapeutic agent(s) can be spatially controlled, for example by directing a first therapeutic agent towards a first portion of the treatment site and a second therapeutic agent towards a second portion of the treatment site.

Figure 24D:
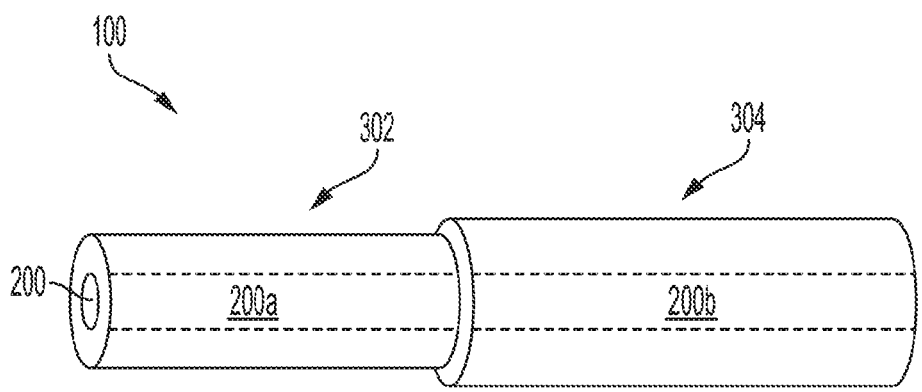
FIG. 24D is a perspective view of a depot in accordance with some embodiments of the present technology.

As shown in FIG. 24D, in some embodiments the elongated therapeutic region 200 may have different therapeutic agents disposed at different sections 200a, 200b along the length of the therapeutic region 200, where each section having a different therapeutic agent is axially aligned with a corresponding section of the control region 300 that has a thickness that is specific to the desired release profile of the underlying therapeutic agent. For example, in some applications it may be beneficial to release a first therapeutic agent at a faster rate and shorter duration and a second therapeutic agent at a slower rate for a longer duration. In such instances, the elongated therapeutic region 200 may have a first section 200a containing the first therapeutic agent (and optionally a polymer and/or releasing agent) and a second section 200b adjacent the first section 200a along the length of the therapeutic region 200 that has a second therapeutic agent (and optionally a polymer and/or releasing agent). The first section 302 of the control region 300 surrounding the first section 200a may have a thickness that is less than a thickness of the second section 304 of the control region 300 surrounding the second section 200b. As such, the first therapeutic agent contained in the first section 200a may release at a faster rate than the second therapeutic agent contained in the second section 200b. In some embodiments, a depot 100 can be configured to deliver two, three, four, five, or more different therapeutic agents, any or all of which can have different rates and times of release from the depot 100.

Figure 25:
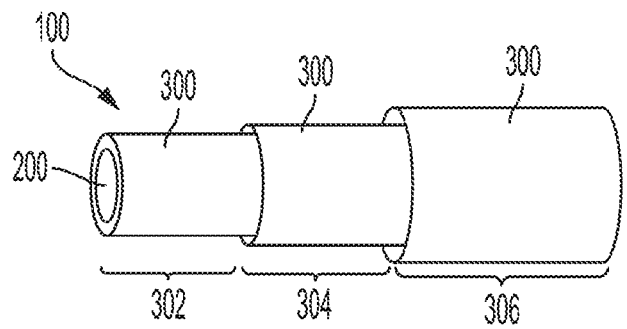
FIG. 25 is a perspective view of a depot in accordance with some embodiments of the present technology.

FIG. 25 illustrates another embodiment of an elongated depot 100 comprising an inner therapeutic region 200 radially surrounded by an outer control region 300. In the illustrated embodiment, the control region 300 includes three discrete sections 302, 304, 306 having increasing thickness. Although these increases in thickness are shown as step-changes between discrete sections, in other embodiments there may be a gradual taper or change in thickness of the control region 300 over the length of the depot 100. In some embodiments, the number of discrete sections may be varied as desired (e.g., two, four, five, six, seven, eight, nine, ten, or more discrete sections), and each discrete section may have an increased or decreased thickness and/or length relative to adjacent discrete sections. Each discrete section may be positioned around a corresponding section of the therapeutic region 200, and each section of the therapeutic region may include the same therapeutic agent, or may include different therapeutic agents as described with respect to FIG. 24D.

Figure 26:
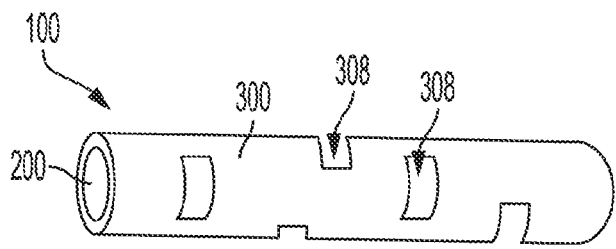
FIG. 26 is a perspective view of a depot in accordance with some embodiments of the present technology.
Figure 27:
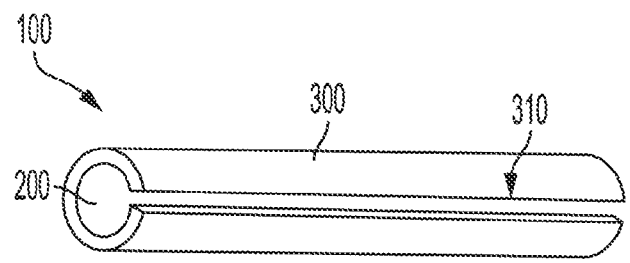
FIG. 27 is a perspective view of a depot in accordance with some embodiments of the present technology.
Figure 28:
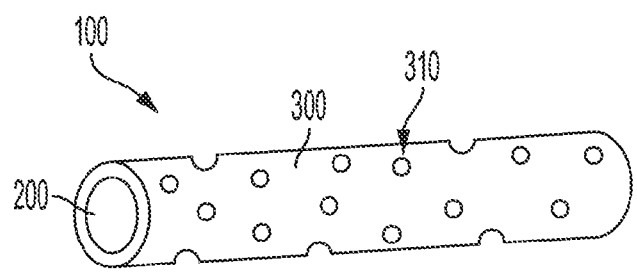
FIG. 28 is a perspective view of a depot in accordance with some embodiments of the present technology.

FIGS. 26-28 depict examples of elongated depots 100 comprising an inner therapeutic region 200 radially surrounded by an outer control region 300, where the outer control region 300 has one or more windows or openings extending through the entire thickness of the control region 300 to expose the underlying therapeutic region 200 through the opening(s). The openings can be notched into or laser cut from the control region 300, or the therapeutic region 200 can be masked while the control region 300 is applied (e.g., via spray- or dip-coating) to achieve the desired openings. The opening(s) provide a more rapid release route for the therapeutic agent to operate in concert with the more gradual release of therapeutic agent through the covered portions of the therapeutic region. The geometry of the opening(s) may be varied as desired, and can include squares, rectangles, circles, ellipses, slits, polygonal shapes, linear shapes, non-linear shapes, or combinations thereof.

As shown in FIG. 26, in some embodiments the openings may comprise a plurality of windows 308, some or all of which may extend around all or a portion of the circumference of the depot 100 and may be spaced apart along the length of the depot 100. FIG. 27 illustrates another embodiment of an elongated depot 100 in which the control region 300 is provided with a single elongated slit or opening 310. The opening 310 extends along the entire length of the control region 300 and/or depot 100 such that the control region 300 has a C-shape in cross-section. In the illustrated embodiment, the opening 310 extends substantially straight along a path parallel to the long axis of the depot 100, however in other embodiments the opening 310 may be curved, wind helically around the depot 100, or take any other suitable shape. The depot 100 shown in FIG. 28 is similar to that of FIGS. 26 and 27 except that the openings 350 are a plurality of circular holes or apertures extending through the thickness of the control region 300.

Figure 29A:
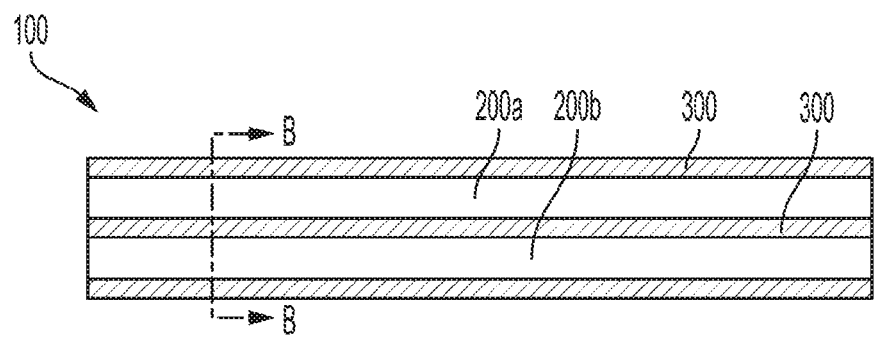
FIG. 29A is a side cross-sectional view of a depot in accordance with some embodiments of the present technology.
Figure 29B:
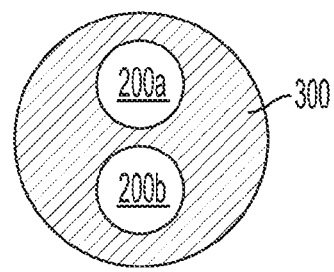
FIG. 29B is a cross-sectional view of the depot shown in FIG. 29A taken along line B-B.

FIGS. 29A and 29B are side and end cross-sectional views, respectively, of an elongated depot 100 comprising first and second elongated therapeutic regions 200a and 200b extending longitudinally within a surrounding control region 300. In the depicted embodiment, the central longitudinal axes of first and second therapeutic regions 200a and 200b are offset from each other and from the central longitudinal axis of the control region 300. In some embodiments, the first therapeutic region 200a can be configured to release the therapeutic agent more quickly than the second therapeutic region 200b, for example by varying the releasing agent concentration (if present), the therapeutic agent concentration, the polymer composition (if present), or other properties of the respective therapeutic regions 200a and 200b. The first and second therapeutic regions 200a and 200b can contain the same or different therapeutic agents.

Figure 30:
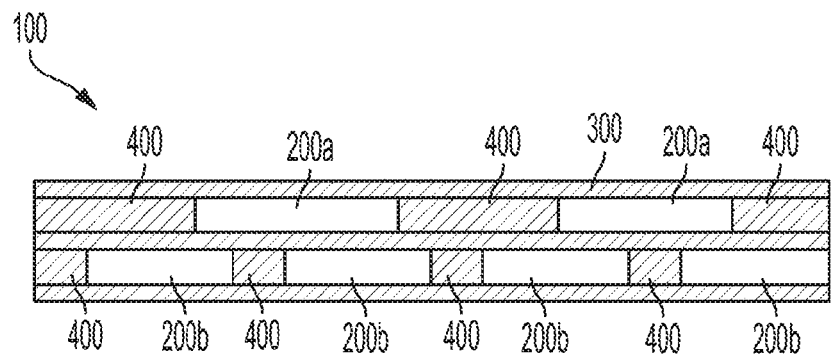
FIG. 30 is a side cross-sectional view of a depot in accordance with some embodiments of the present technology.

The depot 100 shown in FIG. 30 is similar to that of FIG. 29A except that each therapeutic region 200a is interspersed along its length by barrier regions 400. As noted previously, certain embodiments of the depots 100 described herein employ barrier regions that present a barrier to physiologic fluids. In one embodiment, one or more of the barrier regions 400 may comprise a bioresorable polymer without any releasing agent. In another embodiment, one or more of the barrier regions 400 can include a delayed release agent mixed with a bioresorbable polymer, but without a releasing agent.

As depicted in FIG. 30, the first therapeutic region 400a is interspersed with three barrier regions 400 of a first length, while the second therapeutic region 200b is interspersed with four delayed release regions 400 having a shorter length. The relative lengths, number, composition, and spacing of the barrier regions 400 can be selected to achieve the desired release profiles. In operation, an exposed portion of the first or second therapeutic regions 200a or 200b may release therapeutic agent relatively quickly. However, once the therapeutic region 200a or 200b has been eroded and the exposed face of the depot 100 is a barrier region 400, the release of therapeutic agent from that particular therapeutic region may drop significantly. Accordingly, the use of such barrier regions 400 can allow for highly controlled release, with multiple periods of relatively steady release of therapeutic agent punctuated by periods in which little or no therapeutic agent is released due to the presence of the barrier regions 400.

Figure 31:
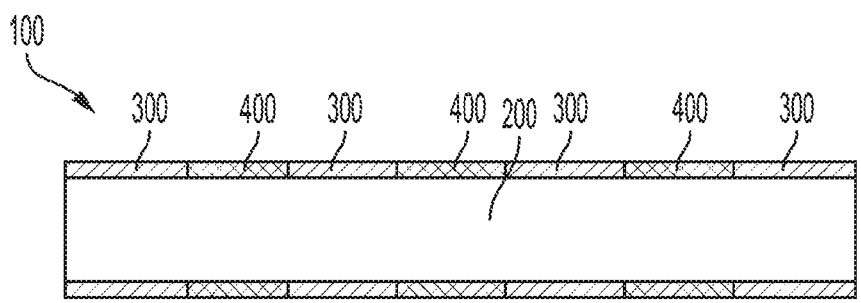
FIG. 31 is a side cross-sectional view of a depot in accordance with some embodiments of the present technology.

FIG. 31 illustrates a depot 100 in which the inner therapeutic region 200 is continuous along the length of the depot 100, while the control region 300 is punctuated by barrier regions 400. The incorporation of these barrier regions 400 reduces the exposed surface area of the control region 300 and thereby decreases the rate of release of therapeutic agent from the depot 100.

Figure 32:
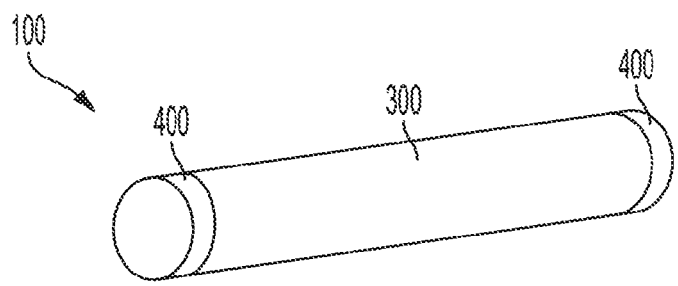
FIG. 32 is a perspective view of a depot in accordance with some embodiments of the present technology.
Figure 33:
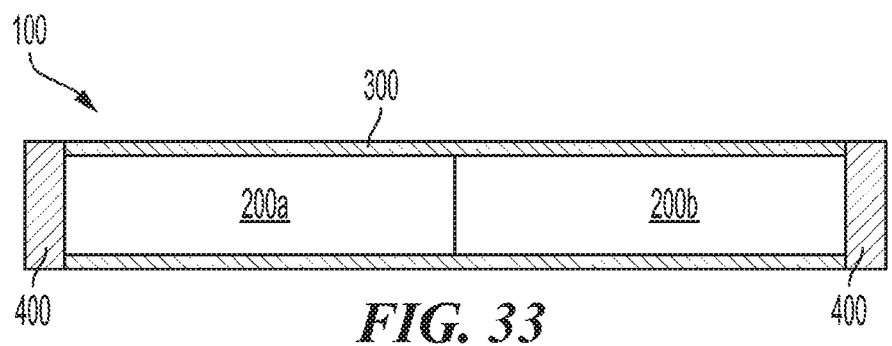
FIG. 33 is a side cross-sectional view of a depot in accordance with some embodiments of the present technology.

In the embodiments shown in FIG. 32-35, the elongated, columnar depot 100 includes first and second end caps formed of barrier regions 400. This configuration can eliminate the exposed surface at the ends of the columnar structure, thereby reducing the rate of release of therapeutic agent from the therapeutic region 200. As seen in FIGS. 32 and 33, the end caps formed of barrier regions 400 can have a diameter or cross-sectional transverse dimension substantially similar to that of the control region 300, such that the outer surface of the control region 300 is coplanar with a radially outermost surface of the barrier regions 400 forming the end caps.

Figure 34:
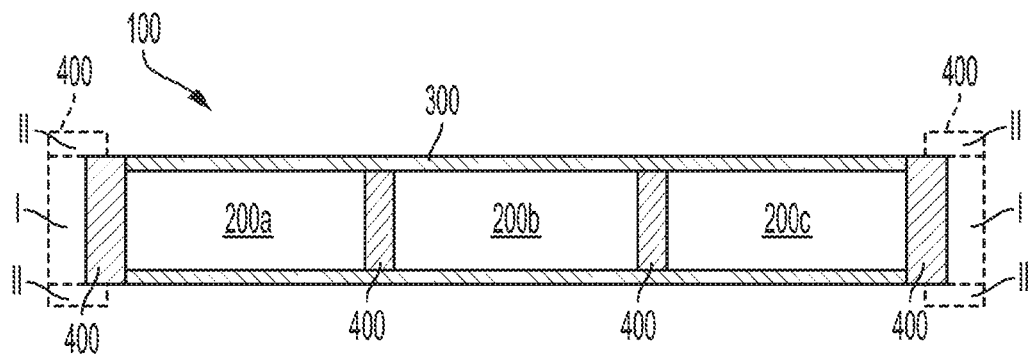
FIG. 34 is a side cross-sectional view of a depot in accordance with some embodiments of the present technology.
Figure 35:
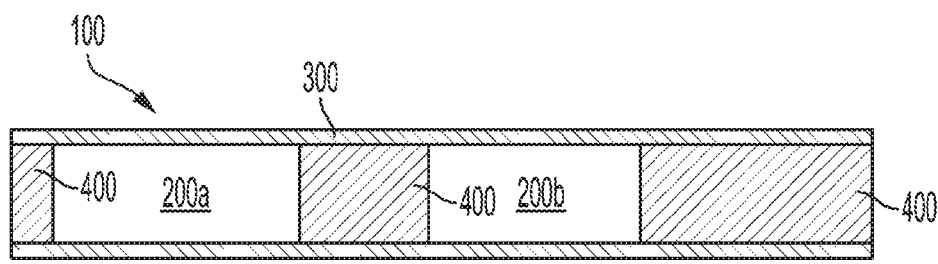
FIG. 35 is a side cross-sectional view of a depot in accordance with some embodiments of the present technology.

In the embodiment shown in FIG. 33, the depot 100 includes first and second therapeutic regions 200a and 200b that are coaxially aligned and directly adjacent to one another (e.g., arranged in an end-to-end fashion along their longitudinal axes), while in FIGS. 34 and 35 the adjacent therapeutic regions 200a-200c are separated from one another by intervening barrier regions 400. FIG. 34 additionally shows optional end caps 400 that extend further radially, for example as shown in Section I, the end caps formed by barrier regions 400 can have the same diameter or transverse dimension as the control region 300, or alternatively as shown in section II, the barrier regions 400 forming the end caps can project radially beyond the control region 300. In some embodiments, as best seen in FIG. 35, the thickness of the barrier regions 400 can vary across the depot 100 in order to achieve the desired release profile.

FIGS. 36A-39B illustrate various configurations of a depot 100 containing one or more therapeutic regions 200 that are at least partially surrounded by one or more control regions 300 and/or one or more barrier regions 400, with a form factor configured to provide the desired release profile. As noted previously, different therapeutic regions 200 can vary from one another in the composition of therapeutic agent(s) contained therein, the concentration of therapeutic agent(s) contained therein, polymer composition, or any other parameter that can vary the release profile. Similarly, in some embodiments the depot 100 may include multiple, layered control regions 300 and/or barrier regions 400 having the same composition or different compositions and/or the same thickness or different thicknesses. These depots 100 that include a plurality of different therapeutic regions 200, a plurality of different control regions 300, and/or a plurality of different barrier regions 400 can allow for controlled release of a single therapeutic agent or multiple different therapeutic agents according to a desired release profile. For example, in some applications it may be beneficial to release a first therapeutic agent at a faster rate and shorter duration and a second therapeutic agent at a slower rate for a longer duration. As described in more detail below, by varying the configuration and composition of the depots 100, the release profile of therapeutic agent(s) can be sequential (in the case of multiple therapeutic agents), delayed, zero-order, or otherwise.

In some embodiments, a plurality of depots can be provided together (for example as a kit, an assembly, pre-loaded into a delivery device such as a syringe, etc.). In some embodiments, the depots can have a variety of different release profiles. For example, a system can include a plurality of depots selected from at least two of the following groups: (1) depots configured to provide for a substantially immediate burst release of therapeutic agent, (2) depots configured to provide for a substantially first-order release of therapeutic agent, (3) depots configured to provide for a substantially zero-order release of therapeutic agent, and (4) depots configured to exhibit delayed release of therapeutic agents (as discussed below with respect to FIGS. 39A-39B).

Figure 36B:
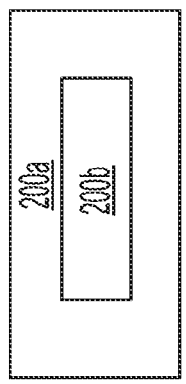
FIG. 36B is a cross-sectional view of the depot shown in FIG. 36A taken along line B-B.
Figure 36D:
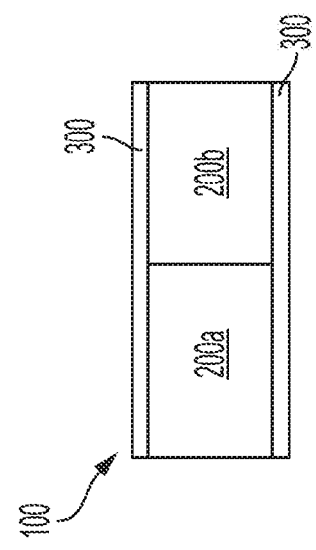
FIG. 36D is a side cross-sectional view of a depot in accordance with some embodiments of the present technology.
Figure 36A:
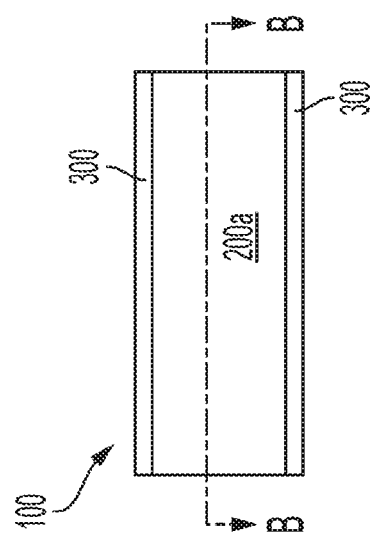
FIG. 36A is a side cross-sectional view of a depot in accordance with some embodiments of the present technology.

FIG. 36A shows a side view of a depot 100, and FIG. 36B shows a cross-sectional view taken along line B-B in FIG. 36A. As seen in FIGS. 36A-36B, in some embodiments the first therapeutic region 200a can envelop or at least partially or completely surround the second therapeutic region 200b. As a result, the first therapeutic region 200a will release its therapeutic agent(s) first, and release of therapeutic agent(s) from the second therapeutic region 200b will be relatively delayed. In some embodiments, the first therapeutic region 200a completely encapsulates the second therapeutic region 200b, such that no surfaces of the second therapeutic region 200b are directly exposed to physiologic fluids upon implantation in a patient's body. In other embodiments, the second therapeutic region 200b can be exposed along at least one face, thereby allowing more immediate release of therapeutic agent from the second therapeutic region 200b. In the illustrated embodiment, the first and second therapeutic regions 200a and 200b are arranged concentrically around the long axis of the depot 100, however in other embodiments the second therapeutic region 200b may be off-center, such that the first therapeutic region 200a is thicker along one side of the second therapeutic region 200b than along another side.

Figure 36C:
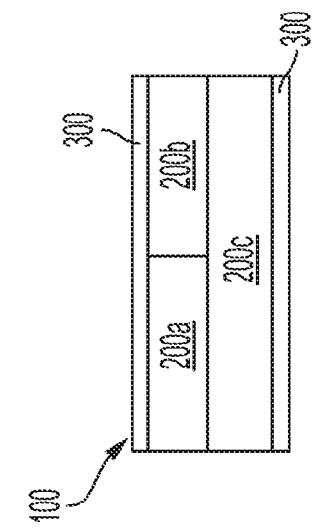
FIG. 36C is a side cross-sectional view of a depot in accordance with some embodiments of the present technology.

In the embodiment shown in FIG. 36C, first and second therapeutic regions 200a and 200b are arranged in an end-to-end fashion (e.g., in direct contact with one another), while a parallel third therapeutic region 200c extends along the length of the depot 100 and contacts both the first and second therapeutic regions 200a and 200b. FIG. 36D illustrates another embodiment in which first and second therapeutic regions 200a and 200b are arranged end-to-end and aligned along the length of the depot 100. These embodiments may be used to achieve directional release of therapeutic agents, e.g., the therapeutic agent of the first therapeutic region 200a is primarily released from a first end of the depot 100, and the therapeutic agent of the second therapeutic region 200b is primarily released from a second, opposite end of the depot 100, while the therapeutic agent of the third therapeutic region 200c releases from both ends of the depot 100.

Figure 37A:
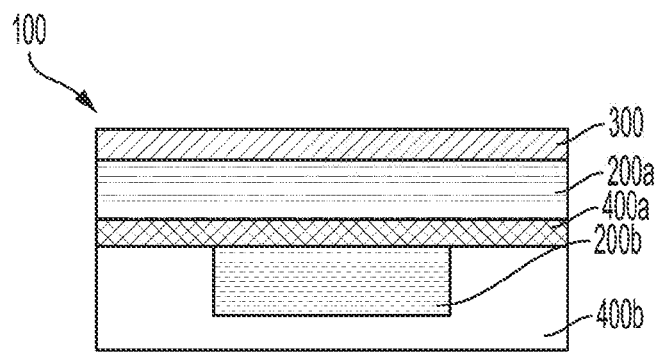
FIG. 37A is a side cross-sectional view of a depot in accordance with some embodiments of the present technology.

FIG. 37A illustrates a depot 100 configured to release therapeutic agent(s) from first and second therapeutic regions 200a and 200b in a sequential manner. As seen in FIG. 37A, the first therapeutic region 200a is partially covered by an overlying control region 300. The first therapeutic region 200a in turn overlies a first barrier region 400a. In the illustrated embodiment, the first therapeutic region 200a, the control region 300, and the first barrier region 400a each extend the entire length of the depot 100 and are each exposed along the side surfaces of the depot 100, however in other embodiments side surfaces may be covered completely or partially by a control region 300 and/or a barrier region 400. Beneath the first barrier region 400a is the second therapeutic region 200b, which may contain the same or different polymer composition and/or therapeutic agent as the first therapeutic region 200a. The second therapeutic region 200b is surrounded laterally by a second barrier region 400b, which also extends beneath the second therapeutic region 200b. As a result, the second therapeutic region 200b has at least one surface in contact with the first barrier region 400a and one or more remaining surfaces in contact with the second barrier region 400b, such that the second therapeutic region 200b is completely encapsulated by the first and second barrier regions 400a, 400b. In some embodiments, one or both of the barrier regions 400a and 400b can be substituted for control regions having a lower concentration of release agent than the control region 300.

As noted previously, barrier regions may present a barrier to physiologic fluids, for example by comprising a bioresorbable polymer without any releasing agent, or a delayed release agent mixed with a bioresorbable polymer, but without a releasing agent. The first barrier region 400a and the second barrier region 400b may differ from one another in composition, thickness, or any other parameters affecting dissolution of the barrier regions 400a and 400b. In some embodiments, the second barrier region 400b can be configured to dissolve more slowly than the first barrier region 400a, such that, after the first barrier region 400a has partially or completely dissolved, the second barrier region 400b remains intact and continues to block or delay passage of physiologic fluids therethrough.

In operation, the first barrier region 400a dissolves more slowly than either the control region 300 or the first and second therapeutic regions 200a and 200b, and therefore presents a barrier to physiological fluids passing through the first barrier region 400a. As a result, when the depot 100 is first placed into contact with physiologic fluids, the release agent of the control region 300 may begin to dissolve, thereby creating diffusion openings for the therapeutic agent(s) in the first therapeutic region 200a to escape therethrough. The therapeutic agent(s) in the first therapeutic region 200a may also escape directly through the exposed surfaces of the first therapeutic region 200a. However, at least in the initial period following implantation, the first barrier region 400a may stop or slow the passage of physiologic fluids through the barrier region 400a and to the underlying second therapeutic region 200b, such that the therapeutic agent(s) within the second therapeutic region 200b exhibits minimal or no release in the initial period. After a first period of time, the control region 300, first therapeutic region 200a and/or the first barrier region 400a may be partially or completely dissolved, thereby allowing at least some physiologic fluid to pass therethrough and come into contact with the second therapeutic region 200b. At this point, therapeutic agent(s) contained within the second therapeutic region 200b may begin to be released from the depot 100, for example by passing through openings formed in the first or second barrier regions 400a and 400b. Accordingly, the depot 100 can be configured such that all or substantially all (e.g., more than 80%, more than 90%) of the therapeutic agent(s) from the first therapeutic region 200a are released from the depot 100 before the therapeutic agent(s) from the second therapeutic region 200b are released in any substantial quantity (e.g., more than 1%, more than 5%, more than 10% of the therapeutic agent(s) contained within the second therapeutic region 200b). In some embodiments, the therapeutic agent(s) from the second therapeutic region 200b are not released in any substantial quantity until at least 12 hours, at least 18 hours, at least 24 hours, at least 36 hours, at least 48 hours, at least 3 days, at least 4 days, at least 5 days, at least 6 days, at least 7 days, at least 8 days, at least 9 days, at least 10 days, at least 11 days, at least 12 days, at least 13 days, at least 2 weeks, at least 3 weeks, at least 4 weeks, at least 5 weeks, at least 6 weeks, at least 7 weeks, at least 8 weeks, at least 9 weeks, at least 10 weeks, at least 11 weeks, or at least 12 weeks after implantation of the depot 100 and/or after release of substantially all of the therapeutic agent(s) from the first therapeutic region 200a.

In one example, the control region 300 is a PLGA film with a releasing agent, the first therapeutic region 200a is a PLGA film loaded with a first therapeutic agent (e.g., bupivacaine), the first barrier region 400a is a PLGA film with no releasing agent, the second therapeutic region 200b is a PLCL film loaded with a second therapeutic agent (e.g., 5-fluorouracil), and the second barrier region 400b is a PLCL film with no releasing agent. As will be understood, the particular polymers, therapeutic agents, releasing agents, concentrations thereof, and dimensions can be selected to achieve the desired release profiles of the first and second therapeutic agents and to achieve the desired total erosion of the depot 100 after a predetermined period of time.

Figure 37B:
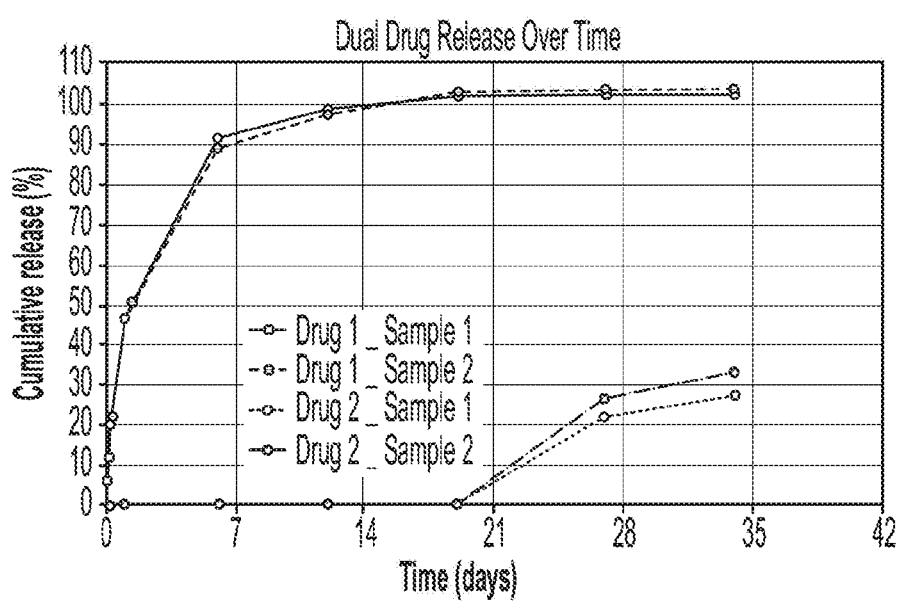
FIG. 37B depicts example release profiles over time of the depot shown in FIG. 37A.

Examples of the release profile from the depot 100 of FIG. 37A are illustrated in FIG. 37B. In this example, Samples 1 and 2 were each prepared with a configuration as shown in FIG. 37A with a thickness of approximately 1.8 mm and a length and width of approximately 20 mm. The control region 300 includes PLGA with polysorbate 20, commercially known as Tween 20™ as a releasing agent, with the ratio of Tween to polymer of 5:10. The first therapeutic region 200a includes a PLGA polymer with Tween 20 and bupivacaine HCl, with the ratio of tween to polymer to bupivacaine of 1:10:20. The first barrier region 400a includes a PLGA film with no releasing agent or therapeutic agent, and the second barrier region 400b includes a PLCL film with no releasing agent or therapeutic agent. The second therapeutic region 200b includes a PLCL polymer with 5-FU and no releasing agent, with a polymer to 5-FU ratio of 1:1.

Referring to FIG. 37B, the "Drug 1" lines illustrate release of a first therapeutic agent from the first therapeutic region 200a. The "Drug 2" lines illustrate release of a second therapeutic agent from the second therapeutic region 200b, which is not released in any substantial amount until a first period has passed (approximately 19 days in the embodiment of FIG. 37B), after which the second therapeutic agent begins to release from the depot 100. The result is a sequential release in which the first therapeutic agent is substantially completely released (e.g., more than 80%, more than 90%, more than 95%, more than 99% of the first therapeutic agent is released from the depot 100) before the second therapeutic agent begins to be released in any significant amount (e.g., more than 1%, more than 5%, or more than 10% of the second therapeutic agent is released from the depot 100).

Figure 38A:
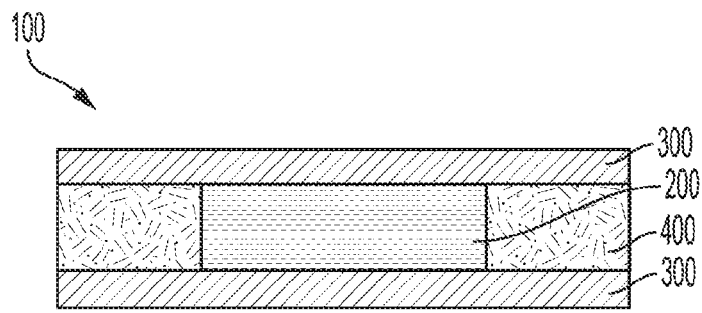
FIG. 38A is a side cross-sectional view of a depot in accordance with some embodiments of the present technology.

FIG. 38A illustrates a depot 100 configured to release a therapeutic agent from a therapeutic region 200 in accordance with a substantially zero-order release profile. In the illustrated embodiment, the depot 100 includes a therapeutic region 200 that is laterally surrounded by one or more barrier regions 400. In some embodiments, the therapeutic region 200 and the barrier region 400 can have a substantially similar thickness such that upper and lower surfaces of the therapeutic region and the barrier region 400 are substantially coplanar. First and second control regions 300 can be disposed over upper and lower surfaces of both the therapeutic region 200 and the barrier region 400, such that the therapeutic region 200 is completely encapsulated by the first and second control regions 300 and the barrier region 400.

When the depot 100 is placed in contact with physiological fluids (e.g., when implanted at a treatment site in vivo), the release agent in the control regions 300 will begin to dissolve to form diffusion openings therein, after which therapeutic agent(s) contained within the therapeutic region 200 may begin to pass through to be released from the depot 100. By virtue of the laterally disposed barrier regions 400, little or no therapeutic agent may pass from the therapeutic region 200 through the barrier regions 400 for at least a period of time (e.g., at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 2 weeks, at least 3 weeks, at least 4 weeks, at least 5 weeks, at least 6 weeks, at least 7 weeks, at least 8 weeks, at least 9 weeks, at least 10 weeks, at least 11 weeks, or at least 12 weeks). As a result, substantially linear release of therapeutic agent can be achieved by controlling the dimensions and composition of the control regions 300 and the therapeutic region 200. As used herein, "substantially linear" includes a release profile in which the rate of release over the specified time period does not vary by more than 5%, or more than 10% from the average release rate over the time period. The substantially linear release profile can be maintained over a desired period of time, e.g., over at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 2 weeks, at least 3 weeks, at least 4 weeks, at least 5 weeks, at least 6 weeks, at least 7 weeks, at least 8 weeks, at least 9 weeks, at least 10 weeks, at least 11 weeks, or at least 12 weeks.

In one example, the control region 300 can be a PLCL or PLGA film containing a releasing agent, the therapeutic region can be a PLCL film loaded with a therapeutic agent (e.g., bupivacaine; 5-fluorouracil, etc.), and the barrier region 400 can be a PLCL film with no releasing agent. As will be understood, the particular polymers, therapeutic agents, releasing agents, concentrations thereof, and dimensions can be selected to achieve the desired release profiles of the therapeutic agent(s) and to achieve the desired total erosion of the depot 100 after a predetermined period of time (e.g., approximately 40 days).

Figure 38B:
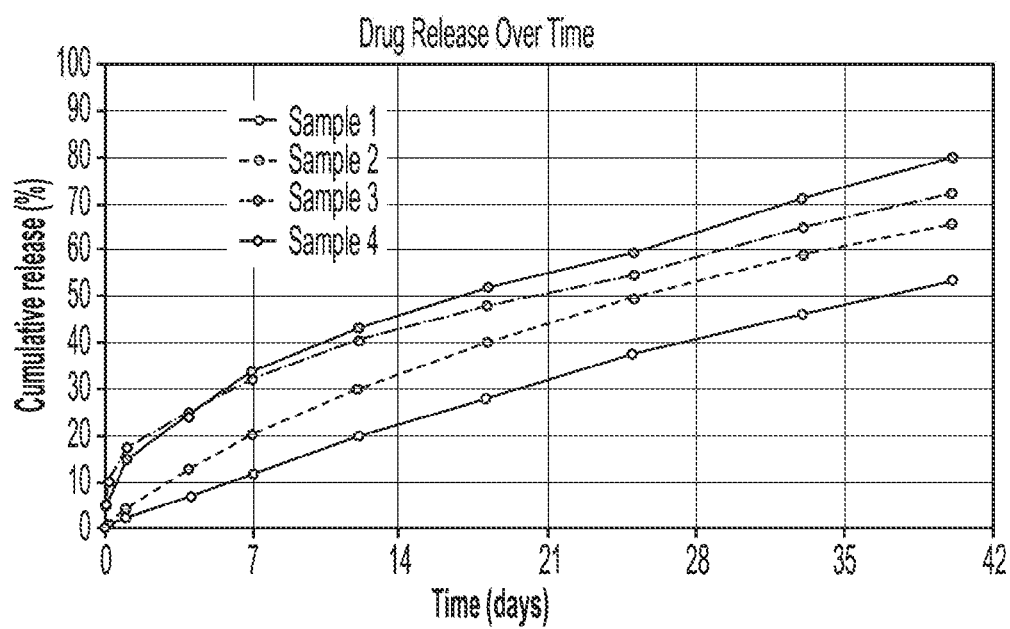
FIG. 38B depicts example release profiles over time of the depot shown in FIG. 38A.

Examples of the release profile from the depot 100 of FIG. 38A are illustrated in FIG. 38B, with four samples with varying polymer configurations illustrated. In this example, Samples 1-4 were each prepared with a configuration as shown in FIG. 38A with a thickness of approximately 0.8 mm and a length and width of approximately 20 mm.

Samples 1 and 2 were prepared using the same configuration, in which the control region 300 includes a PLCL polymer and Tween as a releasing agent with a Tween to polymer ratio of 1:2. The therapeutic region 200 includes a PLCL polymer with 5-FU and no releasing agent, with a polymer to 5-FU ratio of 1:1, and the barrier region 400 includes a PLCL polymer with no releasing agent. Samples 3 and 4 were prepared using the same configuration, in which the control region 300 includes a PLGA polymer and Tween as a releasing agent with a Tween to polymer ratio of 1:2. The therapeutic region 200 includes a PLCL polymer with 5-FU and no releasing agent, with a polymer to 5-FU ratio of 1:1, and the barrier region 400 includes a PLGA polymer with no releasing agent.

As seen in FIG. 38B, by varying the polymer configurations (e.g., composition, release agent, thickness, etc.), the zero-order release profile can be tuned to release at different rates. In some embodiments, there is an initially higher rate of release for a first short period (e.g., approximately 1 day in the illustrated examples), followed by a substantially linear release for the remaining period of time.

Figure 39A:
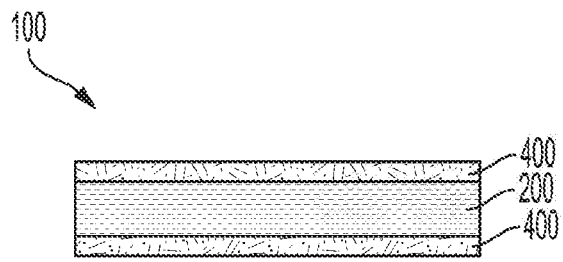
FIG. 39A is a side cross-sectional view of a depot in accordance with some embodiments of the present technology.

FIG. 39A illustrates a depot 100 configured to release a therapeutic agent from a therapeutic region 200 in accordance with a delayed release profile, in which little or none of the therapeutic agent(s) are released in a first period (e.g., less than 10%, less than 20% of the therapeutic agent(s) are released), followed by a rapid increase in release rate during a second period in which the therapeutic agent is released from the depot 100. In the illustrated embodiment, the depot 100 includes a therapeutic region 200 that is at least partially surrounded on opposing sides (e.g., over top and bottom surfaces) by barrier regions 400. In some embodiments, the therapeutic region 200 and the barrier region 400 can have a substantially similar length and width such that the therapeutic region 200 is exposed at one or more side surfaces of the depot 100.

When the depot 100 is placed in contact with physiological fluids (e.g., when implanted at a treatment site in vivo), the therapeutic agent(s) contained within the therapeutic region 200 will pass from the therapeutic region 200 into the surrounding environment through the exposed side surface (s) of the therapeutic region 200. In some embodiments, little or none of the therapeutic agent passes through the barrier regions 400 during an initial period. During this period, a relatively small portion of the therapeutic agent may be released through the exposed side surfaces (e.g., less than 20%, less than 15%, less than 10%, or less than 5% of the therapeutic agent may be released). After the first time period, the barrier regions 400 may begin to degrade, after which the therapeutic agent begins to be released through openings formed in the barrier regions 400. As a result, the depot 100 achieves a delayed release in which little or none of the therapeutic agent is released over a first time period (e.g., more than 1 week, more than 2 weeks, more than 3 weeks, more than 4 weeks, more than 5 weeks, more than 6 weeks, more than 7 weeks, more than 8 weeks, more than 9 weeks, more than 10 weeks), after which the therapeutic agent is released from the depot 100 at an increased rate. In some embodiments, the exposed side surfaces of the therapeutic region 200 can be partially or completely covered by one or more control regions 300 and/or by one or more barrier regions 400, which can further delay release of the therapeutic agent from the therapeutic region 200.

In one example, the therapeutic region 200 can be a PLCL film loaded with a therapeutic agent (e.g., bupivacaine; 5-fluorouracil, etc.), and the barrier regions 400 can be PLGA film with no release agent or PLCL film with no release agent. As will be understood, the particular polymers, therapeutic agents, concentrations thereof, and dimensions can be selected to achieve the desired release profiles of the therapeutic agent and to achieve the desired total erosion of the depot 100 after a predetermined period of time.

Figure 39B:
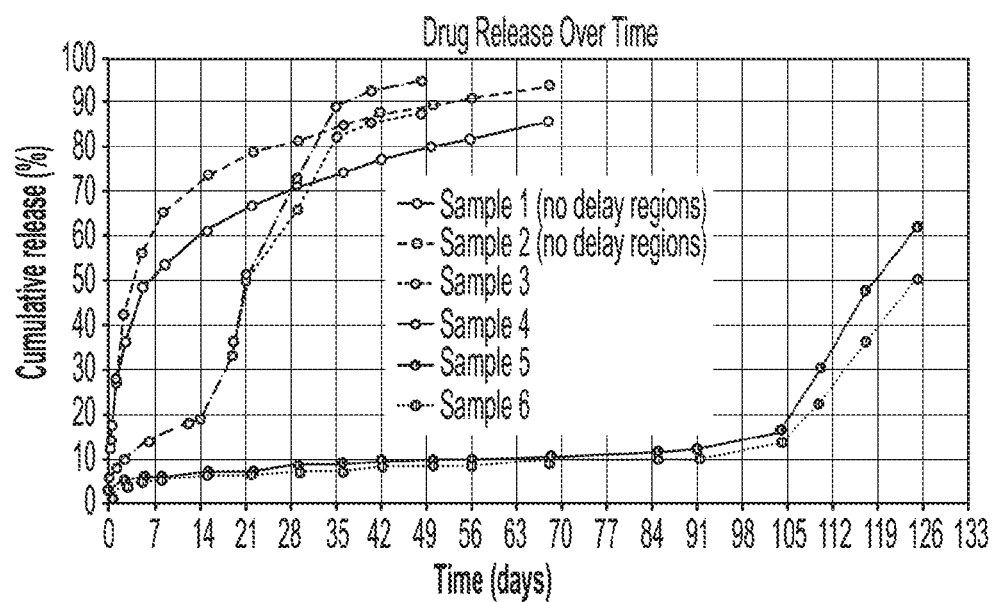
FIG. 39B depicts example release profiles over time of the depot shown in FIG. 39A.

Examples of the release profile from the depot 100 of FIG. 39A are illustrated in FIG. 39B. Samples 1 and 2 illustrate a release profile for a bare therapeutic region with no surrounding barrier regions. In samples 1 and 2, release of the therapeutic agent commences immediately after exposure to fluid. Samples 3-6 were each prepared with a configuration as shown in FIG. 39A. Samples 3 and 4 were prepared using the same configuration, in which the control region 300 includes a PLCL polymer and Tween as a releasing agent with a Tween to polymer ratio of 1:2. The therapeutic region 200 includes a PLCL polymer with 5-FU and no releasing agent, with a polymer to 5-FU ratio of 1:1, and the barrier region 400 includes a PLCL polymer with no releasing agent.

Samples 3-6 illustrate different examples of release profiles for the depot 100 of FIG. 39B with varying polymer configurations illustrated. In samples 3 and 4, the barrier regions 400 are made of a PLGA polymer, while in samples 5 and 6, the barrier regions 400 are made of a PLCL polymer. In samples 3 and 4, release of the therapeutic agent is delayed for approximately 2 weeks (e.g., less than 20%, less than 15%, less than 10%, or less than 5% of the therapeutic agent is released from the depot 100), after which the therapeutic agent is released from the depot 100 at an increased rate (e.g., at least 2 times, at least 3 times, at least 4 times, at least 5 times, or at least 10 times of the initial release rate). In samples 5 and 6, release of the therapeutic agent delayed for approximately 15 weeks (e.g., less than 20%, less than 15%, less than 10%, or less than 5% of the therapeutic agent is released from the depot 100), after which the therapeutic agent is released at an increased rate (e.g., at least 2 times, at least 3 times, at least 4 times, at least 5 times, or at least 10 times of the initial release rate). The barrier regions 400 in samples 3 and 4 are configured to degrade more quickly than the barrier regions 400 in samples 5 and 6, because PLGA degrades more quickly than PLCL. As a result, the delay period in samples 3 and 4 is shorter than the delay period in samples 5 and 6. In various embodiments, the degradation rate of the barrier regions 400 can be tuned by varying dimensions, selecting different polymers, or making any other suitable modifications to the barrier regions 400. By varying the polymer configurations (e.g., composition, thickness, etc.), the delayed release profile can be tuned to have different delay periods (e.g., an initial period during which little or none of the therapeutic agent is released) and to release the therapeutic agent at different rates following the delay period.

In some embodiments, it can be beneficial to provide a plurality of pre-formed openings or apertures extending through the depot 100, either in a regular or irregular pattern. Such openings can provide additional pathways for a therapeutic agent to pass from the therapeutic region to the treatment site, and as such can be controlled to vary the desired release profile. For example, in some embodiments the openings or apertures permit at least some of the therapeutic agent to be released directly from the therapeutic region 200 to the surrounding area, without passing through any overlying control region 300. These pre-formed openings or apertures may differ from diffusion openings formed by dissolution of releasing agent in that the openings or apertures are formed in the depot 100 prior to implantation in the patient's body. The openings or apertures may be used in combination with diffusion openings formed by dissolution of releasing agent to modulate the release profile of therapeutic agent. For example, a depot 100 having openings or apertures may release therapeutic agent at a higher rate than a depot 100 without openings or apertures.

Figure 40A:
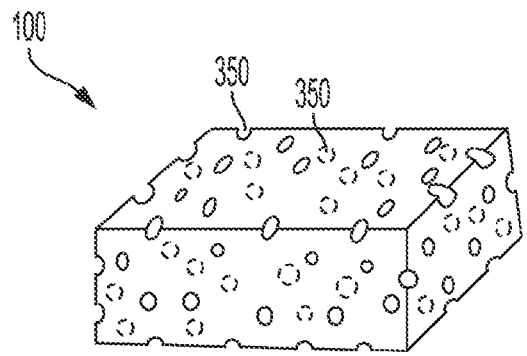
FIG. 40A is a perspective view of a depot in accordance with some embodiments of the present technology.

FIG. 40A illustrates a depot 100 with a sponge-like configuration in which a plurality of irregular openings 350 are formed through the depot 100. In some embodiments, such a depot 100 may be formed by introducing air or otherwise agitating the polymer composition during formation of the depot 100 and while encouraging the solvent to evaporate, resulting in a porous depot 100 with a plurality of openings therein. Such a depot 100 can be substantially uniform in its composition or can include an outer control region and an inner therapeutic region, one or both of which are permeated by some or all of the openings formed in the depot 100.

Figure 40B:
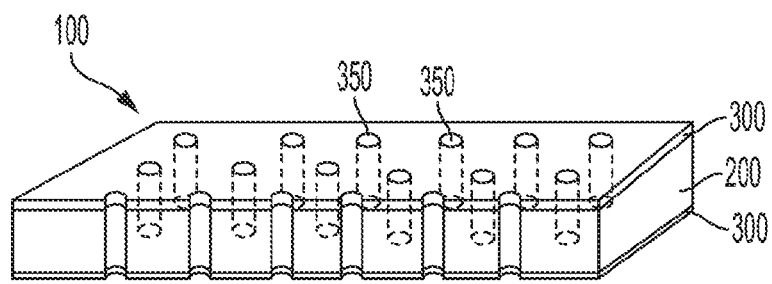
FIG. 40B is a perspective view of a depot in accordance with some embodiments of the present technology.

FIG. 40B illustrates a depot 100 in which a plurality of openings 350 extend through a thickness of the depot 100. In the illustrated embodiment, the openings 350 are substantially cylindrical and pass through upper and lower control regions 300 as well as an inner therapeutic region 200 along substantially parallel trajectories. In other embodiments, the openings 350 can assume other cross-sectional shapes, extend along other axes, and/or vary among one another in orientation, size, shape, etc.

In some instances, it can be useful to provide a depot that has a curved, bent, or rounded configuration. For example, such curved depots can beneficially provide adequate contact with a curved surface area of a treatment site, such as the interior of a bladder, an abdominal wall, a surface of a tumor, or any other suitable treatment site. In some embodiments, the depot can have a substantially straight configuration prior to being deployed in vivo and the curved configuration can be achieved after the depot 100 is deployed in vivo in the presence of physiological fluids, while in other embodiments the depot 100 can have maintain the curved configuration both prior to and after being deployed in vivo. FIGS. 41A-44 illustrate various examples of depots 100 having curved configurations. With reference to FIGS. 41A-B, the depot 100 can have an actuating region 320 that is less elastic than a therapeutic region 200. For example, the actuating region 320 can have a different composition, different dimensions, and/or can be manufactured according to different processes than the therapeutic region 200. By stretching the depot 100 beyond the elastic hysteresis point of the less elastic actuating region 320, the depot 100 can transition from the substantially straightened configuration (shown in FIG. 41A) to the curved configuration (shown in FIG. 41B), in which the less elastic actuating region 320 pulls the depot 100 into the curved shape. In some embodiments, this stretching can occur after implantation, while in other instances the stretching is performed during manufacturing or by a surgeon before implantation. In some embodiments, this transition involves plastic deformation of the depot 100, such that the depot 100 maintains the curved shape even after the stretching force has been removed.

A similar result can be achieved by varying the polymer compositions of different layers or regions as in FIGS. 42A-42B. For example a first region 322 may have a polymer composition that is more hydrophilic than a second region 324, and accordingly the first region 322 may absorb more water or other fluids when implanted in vivo than the second region 324. In various embodiments, either or both of the first and second regions 322, 324 can carry a therapeutic agent. In the embodiment illustrated in FIGS. 42A-42B, the second region 324 is made of poly(L-lactic acid) (PLLA) and the first region 322 is made of polycaprolactone (PCL). In the presence of water, the PCL will experience a higher water uptake than the PLLA when placed in the presence of fluids. As a result, the PCL expands to a greater degree than the PLLA, resulting in a transition from the straightened state (shown in FIG. 42A) to the curved state (shown in FIG. 42B). In this embodiment, the depot 100 may advantageously retain the straightened state until it is deployed in vivo at the treatment site, at which point the depot 100 will begin to absorb water, resulting in a transition to the curved state.

FIGS. 43A-43C illustrate another mechanism for achieving a curved depot. As shown in FIGS. 43A and 43B, the depot 100 may include an outer region B and an axially offset inner region A. The inner region A can have a different composition (e.g., different polymer, the presence of therapeutic agent, etc.) compared to the outer region B. Because the inner region A if offset from the axial centerline of the depot 100, a difference in elasticity or expansion between the inner region A and the outer region B can result in curvature of the depot 100. In one example, the inner region A may include PLLA and the outer region B may include PCL, such that when exposed to water, outer region B expands more than the inner region A, resulting in a curved state.

As noted previously, a curved depot 100 may advantageously be deployed against a curved treatment site, for example in apposition with a concavely curved tissue surface (e.g., the interior of the bladder) as shown in FIG. 44, or in apposition with a convexly curved tissue surface (e.g., over a surface of a protruding tumor) as shown in FIG. 45. In other embodiments, the depot 100 may be configured to have a more complex curvature, for example at least one concave region and at least one convex region, or having different regions with different degrees of curvature. Such complex curvature can be tailored to achieve tissue apposition at a desired treatment site, and can improve delivery of therapeutic agent to the treatment site.

Figure 46:
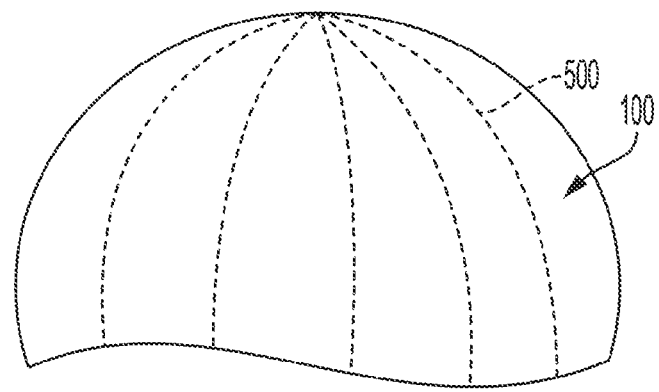
FIG. 46 is a side view of a depot in accordance with some embodiments of the present technology.
Figure 47:
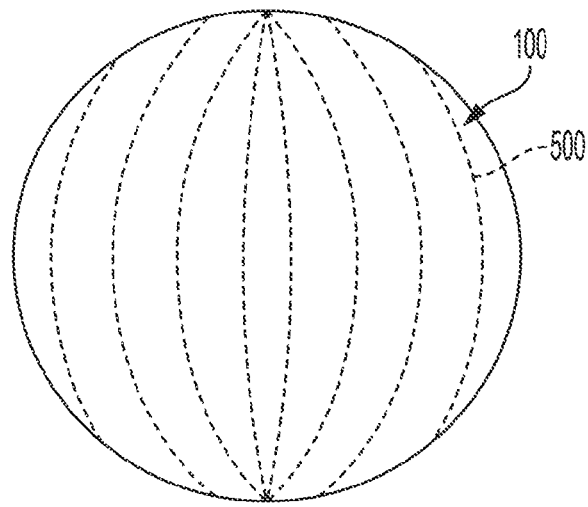
FIG. 47 is a side view of a depot in accordance with some embodiments of the present technology.

As shown in FIGS. 46 and 47, in some embodiments a treatment device can include an anchoring member 500 and a depot 100 carried on a surface of the anchoring member 500. The anchoring member 500 may be a generally hemispherical (as in FIG. 46), spherical (as in FIG. 47), or other suitable structure configured to expand from a low-profile state to a deployed state in apposition with a treatment site. The anchoring member 500 is configured to provide structural support to the treatment device, engage the adjacent anatomy (e.g., a bladder, etc.) to secure the treatment device to a selected treatment site.

In some embodiments, the depot 100 is bonded or otherwise adhered to the surface of the anchoring member 500. In other embodiments, the treatment device may include a depot 100 without an anchoring member 500. The depot 100 may comprise a biocompatible carrier loaded with one or more therapeutic agents and configured for a controlled, sustained release of the therapeutic agent(s) following in vivo placement of the depot. In some embodiments, the depot may be a thin, multilayer film loaded with a therapeutic agent, wherein, as described herein, the depot 100 is configured to release the therapeutic agent(s) at the treatment site.

In some embodiments the structure forming the anchoring member 500 may be a mesh structure. As used herein, "mesh" or "mesh structure" refers to any material (or combination of materials) having one or more openings extending therethrough. For example, in some embodiments, the anchoring member 500 comprises a plurality of filaments (e.g., wires, threads, sutures, fibers, etc.) that have been braided or woven into a tubular shape and heat set. In some embodiments, the mesh structure may be a stent formed of a laser-cut tube or laser-cut sheet, or the mesh structure may be a stent formed via thin film deposition. The anchoring member 500 may be in the form of a flat wire coil attached to a single longitudinal strut, a slotted tube, a helical band that extends circumferentially and longitudinally along the length of the anchoring member, a modular ring, a coil, a basket, a plurality of rings attached by one or more longitudinal struts, a braided tube surrounding a stent, a stent surrounding a braided tube, and/or any suitable configuration or embodiment disclosed herein.

In some embodiments, the anchoring member 500 may be formed of a superelastic material (e.g., nickel-titanium alloys, etc.) or other resilient materials such as stainless steel, cobalt-chromium alloys, etc. configured to self-expand when released from a delivery catheter. For example, the anchoring member may self-expand when pushed through the distal opening of the catheter, or by the delivery catheter being pulled proximally of the anchoring member. In some embodiments the anchoring member 500 may self-expand upon release from other constraining mechanisms (e.g., removable filaments, etc.). In some embodiments, the anchoring member 500 may be expanded manually (e.g., via balloon expansion, a push wire, a pull wire, etc.).

In some embodiments, the anchoring member 500 includes gold, magnesium, iridium, chromium, stainless steel, zinc, titanium, tantalum, and/or alloys of any of the foregoing metals or including any combination of the foregoing metals. In some embodiments, the anchoring member 500 may include collagen or other suitable bioresorbable materials such as PLA, PLG, PLGA etc. In certain embodiments, the metal comprising the mesh structure may be highly polished and/or surface treated to further improve its hemocompatibility. The anchoring member 500 may be constructed solely from metallic materials without the inclusion of any polymer materials, or may include a combination of polymer and metallic materials. For example, in some embodiments the anchoring member 500 may include silicone, polyurethane, polyethylene, polyesters, polyorthoesters, polyanhyrides, and other suitable polymers. This polymer may form a complete sphere or hemisphere to block passage of tumor or drug though the anchoring member 500, or it may have microscopic pores to allow passage of drug but not tumor cells, or it may have small or large openings. In addition, all or a portion of the anchoring member may include a radiopaque coating to improve visualization of the device during delivery, and/or the anchoring member 500 may include one or more radiopaque markers.

In some embodiments, the anchoring member 500 may have other suitable shapes, sizes, and configurations. To improve fixation, in some embodiments the anchoring member 500 may have one or more protrusions extending radially outwardly from the mesh structure along all or a portion of its length, the one or more protrusions being configured to engage with tissue at the treatment site. For example, the anchoring member 500 may include one or more barbs, hooks, ribs, tines, and/or other suitable traumatic or atraumatic fixation members.

As previously mentioned, the depot 100 may be bonded or otherwise adhered to an outer surface of the anchoring member 500. For example, the depot 100 may be bonded to the anchoring member 500 by adhesive bonding, such as cyanoacrylate or UV curing medical grade adhesive, chemical or solvent bonding, and/or thermal bonding, and other suitable means. The depot 100 may also be sewn or riveted to the anchoring member 500. In some embodiments, the depot 100 may be woven into the anchoring member 500 at one or more sections of the anchoring member 500. In some embodiments, the anchoring member 500 may be dip coated in a solution comprising the material elements of the depot 100, and/or the anchoring member 500 may be spray coated with the depot 100. Sections of the anchoring member 500 may be selectively masked such that only certain portions of the anchoring member 500 may be coated with the depot 100. In some embodiments, the anchoring member 500 may be originally in the form of a sheet, and the sheet may be embedded into the depot 100 (for example, with the depot 100 as a multilayer film construction.) The resulting sheet structure (i.e., the anchoring member 500 embedded within the depot 100) may be rolled into a tubular structure (with or without the adjacent ends attached) for delivery into the body. In some embodiments, the depot may be coated with a bioresorbable adhesive derived from polyethylene glycol (PEG or PEO), for example, or from other hydrogels. The PEG or hydrogel may also be integral to the depot 100 via mixing in solution with the depot materials and not a separate coating.

The depot 100 may be disposed along all or a portion of the surface of the anchoring member 500, all or a portion of the circumference of the mesh structure, and/or cover or span all or some of the openings in the mesh structure depending on the local anatomy of the treatment site. For example, the volume, shape, and coverage of the tumor may vary patient-to-patient. In some cases, it may be desirable to use a treatment device having a depot 100 extending around the entire outer surface and/or inner surface of the anchoring member 500. In other cases, it may be desirable to use a treatment device having a depot 100 extending around less than the entire outer surface and/or inner surface of the anchoring member 500 to reduce exposure of potentially healthy tissue to the chemotherapeutic agents.

In some cases, the depot 100 may be elastically expandable, such that the depot 100 expands with the anchoring member 500 as it is deployed. The depot 100 may also be less elastic but can be folded for delivery in a compact form. Alternatively, the depot 100 could be configured to change shape as it is expanded. For example, a tubular depot could have a pattern of overlapping longitudinal slots, so that it expands into a diamond-shaped pattern as it is expanded. The expanded pattern of the depot 100 may align with the pattern of the anchoring member 500, or it may be totally independent of the anchoring member 500. This approach may enable the highest volume of therapeutic agent to be delivered in the most compact delivery format, while still enabling expansion on delivery and flexion, compression and expansion while positioned at the treatment site.

Figure 48A:
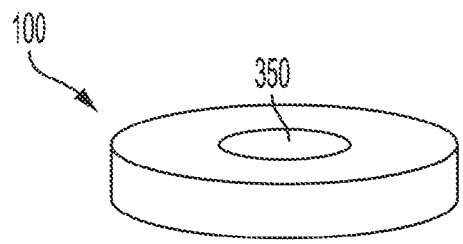
FIGS. 48A and 48B are perspective views of depots in accordance with some embodiments of the present technology.
Figure 48B:
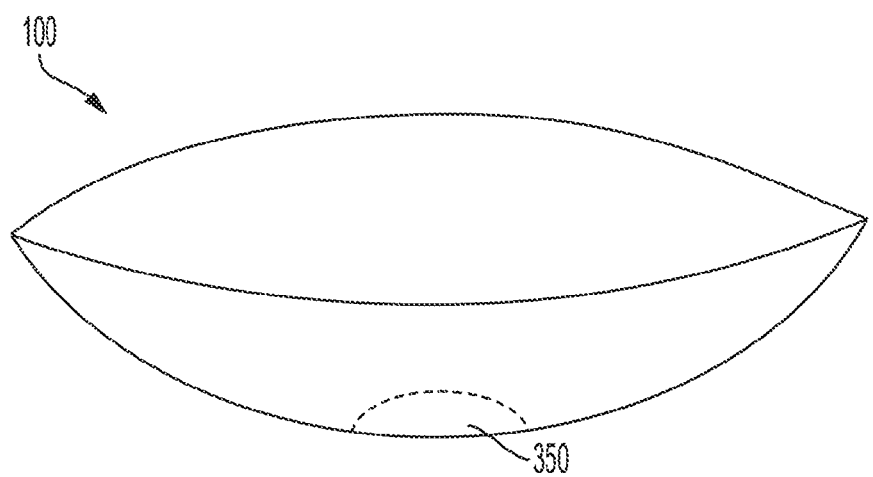

In certain cases, it can be useful to provide a depot 100 with a larger opening or lumen 350 therethrough. For example, a depot 100 deployed in a bladder may benefit from a relatively large opening that allows urine to pass therethrough. Such an opening can reduce the risk of the depot 100 interfering with normal physiological function. FIGS. 48A and 48B illustrate two different embodiments of such depots 100. As seen in FIG. 48A, the depot 100 can be substantially annular or ring-like structure with a central opening 350. For example, the central opening 350 can have a greatest transverse dimension that is more than 10%, more than 20%, more than 30%, more than 40%, or more than 50% of the length of a maximum transverse dimension and the annular depot 100. In the embodiment shown in FIG. 48B, the depot 100 can be a curved (e.g., semi-spherical or semi-ellipsoid) structure with a central opening 350 configured to allow fluid to pass therethrough. Although single openings 350 are illustrated in these embodiments, in other embodiments there may be two or more openings 350 configured to facilitate normal physiological function when the depot 100 is implanted at a treatment site.

FIGS. 49A-C illustrate perspective, top, and cross-sectional views, respectively, of a depot 100 having an annular semi-annular shape. As illustrated, the depot 100 is an elongated strip, ribbon, or band that curls about an axis A. The depot 100 in the form of an elongated strip has an inwardly facing lateral surface 144a and an outwardly facing lateral surface 144b each having a width W. First and side second surfaces 144c and 144d can extend between the lateral surfaces 144a and 144b, defining a thickness T, such that the depot has a substantially rectangular cross-section as seen in FIG. 49C. In some embodiments, the band can have a thickness T of between about 0.1 mm and about 10 mm, or between about 0.5 mm and about 5 mm, or about 2 mm. In some embodiments, the depot 100 can have a height H of between about 0.1 mm and about 10 mm, or between about 0.5 mm and about 5 mm, or about 1 mm. The depot 100 can be curled about the axis A such that first and seconds ends are adjacent to one another, while leaving a gap 145 therebetween. In this curled configuration, the depot 100 is characterized by an inner diameter D. In some embodiments, for example for use in a bladder, the diameter D can be between about 2 cm and about 20 cm, for example between about 2 cm and about 10 cm, or between about 4 cm and about 8 cm, or approximately 6 cm. In some embodiments, the depot 100 can have a length of between about 20 cm and about 100 cm, for example between about 30 cm and about 50 cm, or approximately 38 cm.

In some embodiments, the ends can be joined together, creating a closed annular shape. As seen in FIG. 49C, in some embodiments the depot 100 includes a control region 300 disposed on the inwardly facing lateral surface 144a and another control region 300b disposed on the outwardly facing lateral surface 144b. In some embodiments, a therapeutic region 200 disposed between the two control regions 200 can be partially or completely exposed along the side surface 144c. Optionally, the therapeutic region 200 can also be partially or completely exposed along an opposing side surface 144d disposed opposite the first side surface 144c.

In some embodiments, the depot 100 of FIGS. 49A-49C can be delivered to the treatment site in a compressed configuration, either straightened longitudinally, or curled tightly about a central axis, or other compressed state. When delivered, the depot 100 can expand into the annular or semi-annular configuration as shown in FIG. 49A. In some embodiments, the depot 100 can be positioned such that the outwardly facing lateral surface 144b is in apposition with tissue along at least a portion of its length.

FIG. 50A shows an end view of a depot 100 in a spirally curled state and FIG. 50B shows a side view of the depot 100 in an uncurled state. The depot 100 includes a plurality of segments I-IV having different structural and mechanical properties that cause the depot 100 to assume the spirally curled configuration shown in FIG. 50A when placed in the presence of physiological fluids in vivo at a treatment site. For example, the different segments I-IV can vary in polymer composition, therapeutic agent, concentration of therapeutic agent, concentration of release agent, or any other parameter that affects the mechanical and structural properties of the depot 100, resulting in a spirally wound depot 100 as seen in FIG. 50A. In some embodiments, the spiral winding can facilitate placement of the depot 100 at a treatment site, and/or improve attachment to anatomical tissue at the treatment site.

Figure 51:
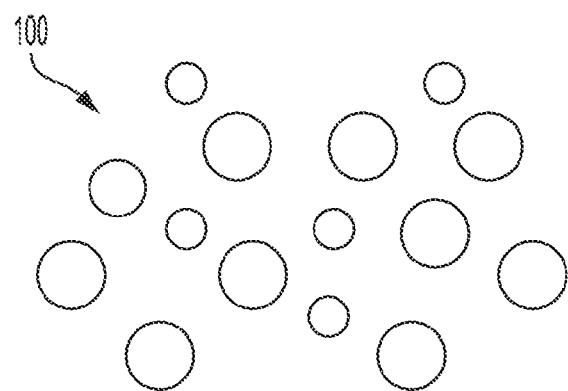
FIG. 51 illustrates a plurality of depots in accordance with some embodiments of the present technology.

FIG. 51 illustrates a plurality of depots 100 in the form of microbeads, microspheres or particles. In various embodiments, each microbead can include a therapeutic region at its core and one or more control regions partially, substantially, or completely surrounding the therapeutic region. In some embodiments, the microbead may include multiple, layered control regions and/or therapeutic regions having the same composition or different compositions and/or the same thickness or different thicknesses. The release profile of any particular microbead is determined by its size, composition, and the thickness of the control region and therapeutic region. In some embodiments, a plurality of microbeads are provided having varying dimensions, varying shapes (e.g. spherical, ellipsoid, etc.), varying polymer compositions, varying concentration of therapeutic agent in the therapeutic region, varying concentration of releasing agent in the control region, or variation of any other parameters that affect the release profile. As a result, the composite release profile of the plurality of microbeads can be finely tuned to achieve the desired cumulative release of therapeutic agent to the treatment site. In various embodiments, some or all of the microbeads can have a diameter or largest cross-sectional dimension of between about 0.01 to about 5 mm, or between about 0.1 mm to about 1.0 mm. In some embodiments, some or all of the microbeads can have a diameter or largest cross-sectional dimension that is less than about 5 mm, less than about 2 mm, less than about 1.0 mm, less than about 0.9 mm, less than about 0.8 mm, less than about 0.7 mm, less than about 0.6 mm, less than about 0.5 mm, less than about 0.4 mm, less than about 0.3 mm, less than about 0.2 mm, or less than about 0.1 mm.

Figure 52A:
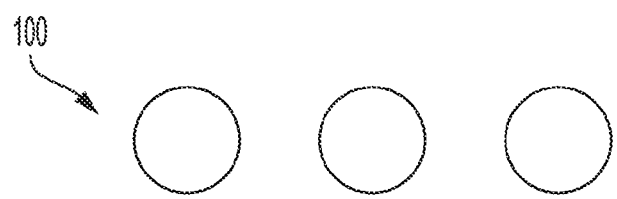
FIG. 52A is an end view of a plurality of depots in accordance with some embodiments of the present technology.
Figure 52B:
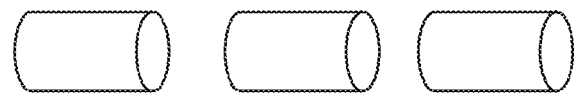
FIG. 52B is a side view of the depots shown in FIG. 52A.

FIGS. 52A and 52B illustrate end and side views, respectively, of a plurality of depots 100 in the form of pellets. In the illustrated embodiment, the pellets are substantially cylindrical, however the particular shape and dimensions of the pellets may vary to achieve the desired release kinetics and form factor. For example, the pellets can have rounded ends (e.g., ellipsoid), and/or can have a cross-sectional shape that is circular, elliptical, square, rectangular, regular polygonal, irregular polygonal, or any other suitable shape. In some embodiments, each pellet can include an inner therapeutic region at least partially surrounded by an outer control region. In some embodiments, the pellet may include multiple, layered control regions and/or therapeutic regions having the same composition or different compositions and/or the same thickness or different thicknesses. As with the microbeads shown in FIG. 51, individual pellets of the plurality can vary from one another in one or more of shape, polymer composition, concentration of therapeutic agent in the therapeutic region, concentration of the releasing agent in the control region, thickness of the control region, thickness of the therapeutic region, and any other parameter that affect the release profile. As a result, the composite release profile of the plurality of pellets can be finely tuned to achieve the desired cumulative release of therapeutic agent to the treatment site.

In various embodiments, the depot can be different sizes, for example, the depot may be a length of from about 0.4 mm to 100 mm and have a diameter or thickness of from about 0.01 to about 5 mm. In various embodiments, the depot may have a layer thickness of from about 0.005 to 5.0 mm, such as, for example, from 0.05 to 2.0 mm. In some embodiments, the shape may be a rectangular or square sheet having a ratio of width to thickness in the range of 20 or greater, 25 or greater, 30 or greater, 35 or greater, 40 or greater, 45 or greater, or 50 or greater.

In some embodiments, a thickness of the control region (a single sub-control region or all sub-control regions combined) is less than or equal to 1/10, 1/15, 1/20, 1/25, 1/30, 1/35, 1/40, 1/45, 1/50, 1/75, or 1/100 of a thickness of the therapeutic region. In some embodiments, the depot 100 has a width and a thickness, and a ratio of the width to the thickness is 21 or greater. In some embodiments, the ratio is 22 or greater, 23 or greater, 24 or greater, 25 or greater, 26 or greater, 27 or greater, 28 or greater, 29 or greater, 30 or greater, 35 or greater, 40 or greater, 45 or greater, or 50 or greater. In some embodiments, the depot 100 has a surface area and a volume, and a ratio of the surface area to volume is at least 1, at least 1.5, at least 2, at least 2.5, or at least 3.

I. Example Methods of Manufacture

The depots of the present technology may be constructed using various combinations of bioresorbable polymer layers, wherein these layers may include therapeutic agents, releasing agents, delayed release agents, etc., in varying combinations and concentrations in order to meet the requirements of the intended clinical application(s). In some embodiments, the polymer regions or layers may be constructed using any number of known techniques to form a multilayer film of a particular construction. For example, a bioresorbable polymer and a therapeutic agent can be solubilized and then applied to the film via spray coating, dip coating, solvent casting, and the like. In an alternative embodiment, a polymer layer for use as a control region and/or a therapeutic region can be constructed from electrospun nanofibers.

The depots 100 described herein may be constructed by placing therapeutic regions (and/or sub-regions) and/or control regions (and/or sub-regions) on top of one another in a desired order and heat compressing the resulting multilayer configuration to bond the layers together. Heat compression may be accomplished using any suitable apparatus known in the art. In one embodiment, the heat compression process consists of utilizing a heat compressor (Kun Shan Rebig Hydraulic Equipment Co. Ltd., China), and heat compressing the stacked assembly of therapeutic 200 and/or control regions 300 at a temperature that is above room temperature (e.g., at least 30° C., 35° C., 40° C., 45° C., 50° C., 55° C., 60° C., 65° C., 70° C., 75° C., 80° C., 85° C., 90° C., 95° C., 100° C., 105° C., 110° C., 115° C., or 120° C., etc.) and a pressure of from about 0.01 MPa to about 1.0 MPa, or about 0.10 MPa to about 0.8 MPa, or about 0.2 MPa to about 0.6 MPa. The inventors have discovered that heating the therapeutic and control regions during compression (separately or after stacking) increases the therapeutic agent density in the depot 100. The inventors have also discovered that heat compression at lower pressures enable higher drug densities.

Depending on the therapeutic dosage needs, anatomical targets, etc., the depot 100 can be processed, shaped and otherwise engineered to produce form factors that can be administered to the patient by implantation in the body by a clinical practitioner. For example, various configurations of the film may be achieved by using a jig with a pre-shaped cutout, hand cutting the desired shape or both. Some of the form factors producible from the multilayer film for implantation into the body include: strips, ribbons, hooks, rods, tubes, patches, corkscrew-formed ribbons, partial or full rings, nails, screws, tacks, rivets, threads, tapes, woven forms, t-shaped anchors, staples, discs, pillows, balloons, braids, tapered forms, wedge forms, chisel forms, castellated forms, stent structures, suture buttresses, coil springs, and sponges. As described below with respect to FIG. 52C, in some embodiments a pellet-like or mini-cylindrical depot 100 can be punched or otherwise cut out of a sheet of a multilayer film. A depot 100 may also be processed into a component of the form factors mentioned above. For example, the depot 100 could be rolled and incorporated into tubes, screws tacks or the like. In the case of woven embodiments, the depot 100 may be incorporated into a multi-layer woven film wherein some of the filaments used are not the inventive device. In one example, the depot 100 is interwoven with Dacron, polyethylene or the like.

In some embodiments, one or more depots 100 can be cut into a desired shape or form factor using precision laser cutting. Various laser modalities may be used, for example infrared lasers, near-infrared lasers, deep ultraviolet lasers, or other suitable lasers for cutting depots 100 to the desired configurations. Such laser cutting can use continuous or pulsed, and the operating parameters (e.g., intensity, frequency, polarization, etc.) may be selected to achieve the desired cut. Using computer-controller laser-cutting can provide for a precise, repeatable manufacturing process that achieves consistent dimensions and release profiles. In some embodiments, the cut surfaces resulting from the laser-cut can be significantly smoother than those achieved using a mechanical stamp, jig, or punch to cut depots from a sheet of a multi-layer film. In some instances, the smoother cut surfaces can provide for improved release profiles, for example with more consistency among depots 100 manufactured according to this process.

In some embodiments, the therapeutic region 200 can be extruded into an elongated form (e.g., a cylindrical rod), after which the control region 300 may be spray- or dip-coated over the extruded therapeutic region 200. Portions of the extruded therapeutic region 200 may be masked to leave gaps in the control region 300, or alternatively portions of the control region 300 may be removed via etching, scraping, or other techniques to achieve any desired openings or thinning of the control region 300 in any desired portions. In some embodiments, an extruded cylinder having a lumen extending therethrough can be selectively filled with a therapeutic region 200 and/or a control region 300 along its length to form an elongated depot 100.

In some embodiments, a therapeutic region 200 in the shape of a cylindrical rod is formed by dissolving the therapeutic region composition (e.g., a mixture of polymer (s) and therapeutic agent) into acetone, and then loading the dissolved therapeutic region composition into a syringe (e.g., a 1 ml syringe) and attaching a needle thereto (e.g., a 19G needle). The therapeutic region solution is then injected into ethanol for polymer solidification. After waiting for the solution to harden (e.g., approximately 90 seconds), the resulting rod can be removed from the ethanol and air-dried. In another embodiment, the therapeutic region composition can be injected into a cross-linking solution to solidify the polymer.

The therapeutic region 200 may be spray- or dip-coated with a surrounding control region 300. Alternatively, in some embodiments, the therapeutic region 200 in elongated cylindrical form can be inserted into an inner lumen of a coaxial needle. The coaxial needle can include an inner needle disposed coaxially within the lumen of an outer needle. In one example, the inner needle can have an inner diameter of approximately 0.84 mm and an outer diameter of approximately 1.24 mm, and the outer needle can have an inner diameter of approximately 1.6 mm and an outer diameter of approximately 2.11 mm, though these dimensions can vary and be tailored to the desired dimensions of the therapeutic region 200 and control region 300. A control region composite (e.g., a mixture of polymer and releasing agent) can be dissolved in acetone, and then loaded into a syringe (e.g., a 1 mL syringe). The control region solution is then injected through the outer needle, surrounding the cylindrical therapeutic region disposed within the inner needle. The resulting depot 100 is a cylindrical form with a control region 300 substantially uniformly surrounding the inner cylindrical therapeutic region 200. In some embodiments, the resulting cylindrical form can be suitable for injecting using a needle, thereby providing for a convenient mechanism to deliver the depot to any number of different treatment sites. In other embodiments, a coaxial needle having three or more coaxial lumens can be used for the formation of multiple therapeutic and/or control regions, for example having a plurality of different therapeutic agents that can be configured to be released sequentially from the depot 100.

In some embodiments, an extruded depot 100 in the form an elongated columnar structure (e.g., a cylindrical rod, strip, etc.) can be pinched down at one or more positions along its length to be subdivided into discrete portions. For example, an elongated depot 100 may be pinched such that the depot is completely severed into discrete sections, or to provide a narrowed, weakened portion that can be susceptible to flexing and/or breaking.

Figure 52C:
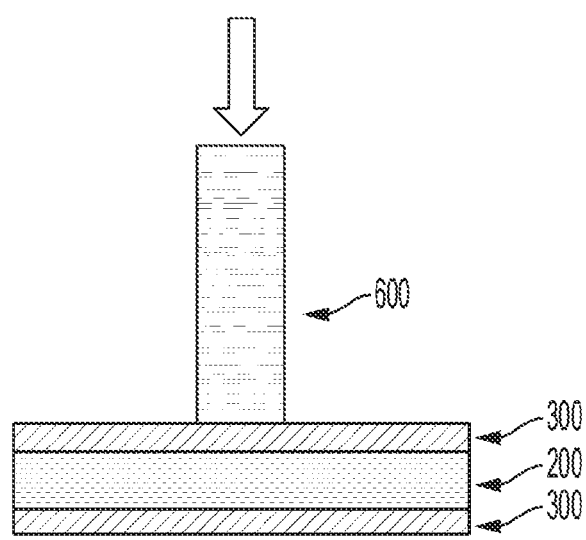
FIG. 52C illustrates a method of manufacturing the depots shown in FIGS. 52A and 52B.

FIG. 52C illustrates one method of manufacturing depots in the form of pellets as shown in FIGS. 52A and 52B. A sheet including a plurality of layered regions such as outer control regions 300 at least partially surrounding an inner therapeutic region 200 is provided. A punch 600 with a hollow blade can be used to cut out individual pellets from the sheet, for example by pressing the punch 600 through the sheet along an axis orthogonal to the surface of the sheet. In some embodiments, the resulting pellets each retain the layered regions of the sheet (e.g., a therapeutic region 200 sandwiched between first and second control regions 300). In such embodiments, the resulting pellet can have at least a portion of the therapeutic region 200 exposed through the control region(s) 300, for example with lateral sides of the pellet having exposed portions of the therapeutic region 200. Such exposed portions of the therapeutic region 200 can contribute to a higher initial release rate of the therapeutic agent.

In some embodiments, the punch 600 is heated before cutting the pellets from the sheet, for example by being heated in an oven to approximately 80° C., or to a suitable temperature to at least partially melt or deform the control region 300. The heated punch 600 can at least partially deform the top layer (e.g., partially melting the upper control region 300) causing it to wrap around the lateral edges of the therapeutic region 200. The resulting depot 100 may then take the form of a pellet 100 in which the inner therapeutic region 200 is completely or substantially completely surrounded by the control region(s) 300. In some embodiments, the motion of pressing the punch 600 can be varied to achieve the desired coverage of the control region(s) 300 over the therapeutic region 200. For example, in some embodiments, the punch 600 can be rotated while being pressed through the sheet, and in some embodiments the punch 600 can be moved more slowly or move quickly to allow varying degrees of deformation and flow of the control region(s) 300. In other embodiments, the punch 600 is not heated before being pressed through the sheet.

The dimensions of the depots 100 in the form of pellets or mini-cylinders can be controlled by varying the thickness of the sheet and by selecting the diameter or lumen cross-sectional dimensions of the punch 600. In some embodiments, the sheet can have a thickness of between about 0.5 and 2 mm (e.g., approximately 0.85 mm), and the punch 600 can have a circular lumen with a diameter of between about 0.5 mm and about 3 mm (e.g., approximately 1 mm). In other embodiments, the punch 600 can cut out depots 100 in other shapes, for example, square, rectangular, elliptical, star-shaped, wavy, irregular polygonal, or any other suitable cross-sectional shape. In some embodiments, a wavy or jagged shape can provide a larger surface area for the resulting pellets, thereby increasing a rate of release of therapeutic agent from the pellets. In some embodiments, the resulting depots 100 in the form of pellets or mini-cylinders are insertable through a needle or other suitable delivery shaft. For example, a plurality of approximately pellets having 1 mm diameters may be loaded coaxially into a 17-gauge needle and inserted subcutaneously to a treatment site in a patient. Smaller pellet-like depots 100 could be inserted through even smaller needles, for example 18- to 22-gauge needles. Such pellets or mini-cylinders can achieve a considerably high drug loading, as described elsewhere herein, for example at least 50% by weight of the therapeutic agent or more.

In some embodiments, microbead and/or pellet-like depots (e.g., as in FIGS. 51-52) can be formed by providing an elongated structure (e.g., a cylindrical, columnar, or rod-shaped structure) having a therapeutic region 200 at least partially surrounded by a control region 300, and then cutting or otherwise dividing the structure into a plurality of pellets, particles, or microbeads along its length.

II. Examples

The following examples are offered by way of illustration and not by way of limitation.

Example 1

Preparation of bioresorbable polymer/drug films. Two depots of the present technology containing a high payload the local anesthetic bupivacaine were prepared according to the following procedures.

Each of the sample depots consisted of a heat compressed, multi-layer film having the configuration shown in FIG. 5. The therapeutic region consisted of a single layer and was sandwiched between two inner control layers (closest to the therapeutic layer, such as 302b and 302c in FIG. 5, and referred to as "Control Layer A" in Table 4 below) and two outer control layers (farthest from therapeutic region, such as 302a and 302d in FIG. 5, and referred to as "Control Layer B" in Table 4). The constituents of the therapeutic region and the control region are detailed in Table 4.

TABLE 4

| | |
|---|---|
| Therapeutic Region Polymer | Single layer Poly(L-lactide-co-glycolic-co-ε-caprolactone) (1760 mg) (Durect Corp, Birmingham) PLA to PGA to PCL ratio of from 90:5:5 to 60:30:10 |

TABLE 4-continued

| Releasing Agent | Tween 20 (860 mg) (Sigma-Aldrich Pte Ltd; Singapore) |
|---|---|
| Anesthetic | bupivacaine hydrochloride (3520 mg) (Xi'an Victory Biochemical Technology Co., Ltd.; Shaanxi, People's Republic of China) |
| Anesthetic:Polymer | 2:1 |
| Releasing Agent:Polymer:Anesthetic | 5:10:20 |
| Control Region | |
| Control Layer A | innermost layer on top and bottom |
| Polymer | PLGACL (1056 mg) |
| Releasing Agent | Tween 20 (517 mg) |
| Control Layer B | outermost layer on top and bottom |
| Polymer | PLGACL (1056 mg) |
| Releasing Agent | Tween 20 (103 mg) |

Therapeutic region components. The therapeutic region was prepared by combining the polymer, releasing agent, anesthetic, and 3.15 mg of acetone (Merck; Kenilworth, NJ) in a glass vial and mixing thoroughly. The resulting blend was poured onto a flat plate and compressed multiple times to form a thick film (about 1 mm thick) upon drying.

Control region components. The control region was prepared by combining the polymer, releasing agent, and 4.7 mg of acetone (Merck; Kenilworth, NJ) in a glass vial and mixing thoroughly. The resulting blend was poured onto a flat plate and drawn by a film applicator to form a thin film (<200 μm thickness) upon drying.

For the sample depot, the single layer therapeutic region and the four layers comprising the control region were aligned and compressed by a heat compressor. The thin film was cut to form a 25 mm×15 mm sample with overall film thickness <1.2 mm.

in vitro drug release testing of bupivacaine depot. The purpose of this procedure was to measure the release of bupivacaine from a bioresorbable polymer depot into a receiving fluid of 1×PBS. Each release experiment was conducted in duplicate. The in vitro release procedure consisted of placing a known size of film into an apparatus containing the receiving fluid. The in vitro release apparatus consisted of a 200 mL glass bottle. A receiving fluid in the amount of 100 mL was added to each sample bottle. During the release study, the apparatus was placed in a water bath maintained at 37±2° C. At predetermined intervals, samples of the receiving fluid were removed and analyzed for bupivacaine concentration by UV-Visible Spectrophotometer.

Figure 53:
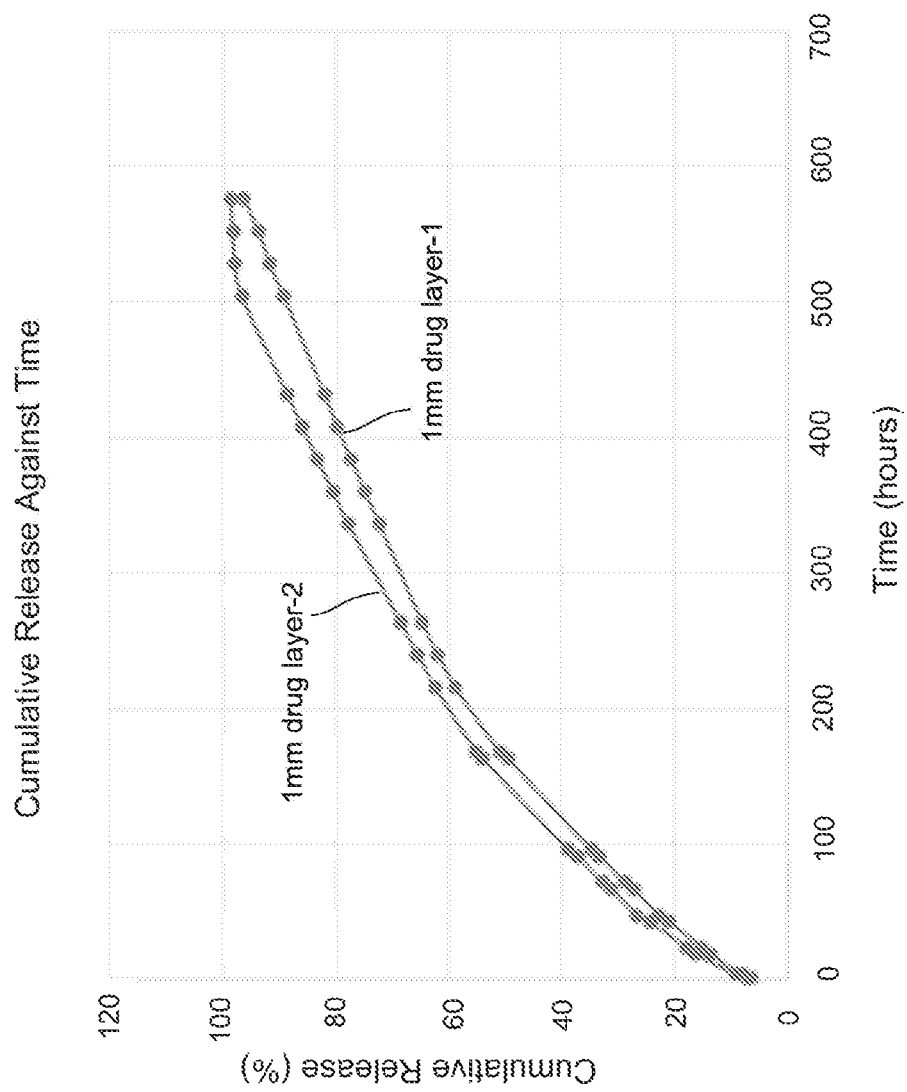
FIG. 53 depicts the in vitro release profile for the depots as described in Example 1, in accordance with the present technology.

FIG. 53 shows the drug release profile for the depots with effectively reduced initial burst effect and demonstrated a desirable consistent controlled release of drug.

Example 2A

Preparation of bioresorbable polymer drug films. Two depots of the present technology comprising the local anesthetic bupivacaine were prepared as described in Example 1, except the depots of the present example comprised two of the depots of Example 1 stacked on top of one another and heat compressed to form a new, thicker sample having an overall film thickness of about 2 mm (for example, see the configuration shown in FIG. 6).

in vitro drug release testing of bupivacaine depot. in vitro drug release testing of the depots was performed as described in Example 1.

Figure 54:
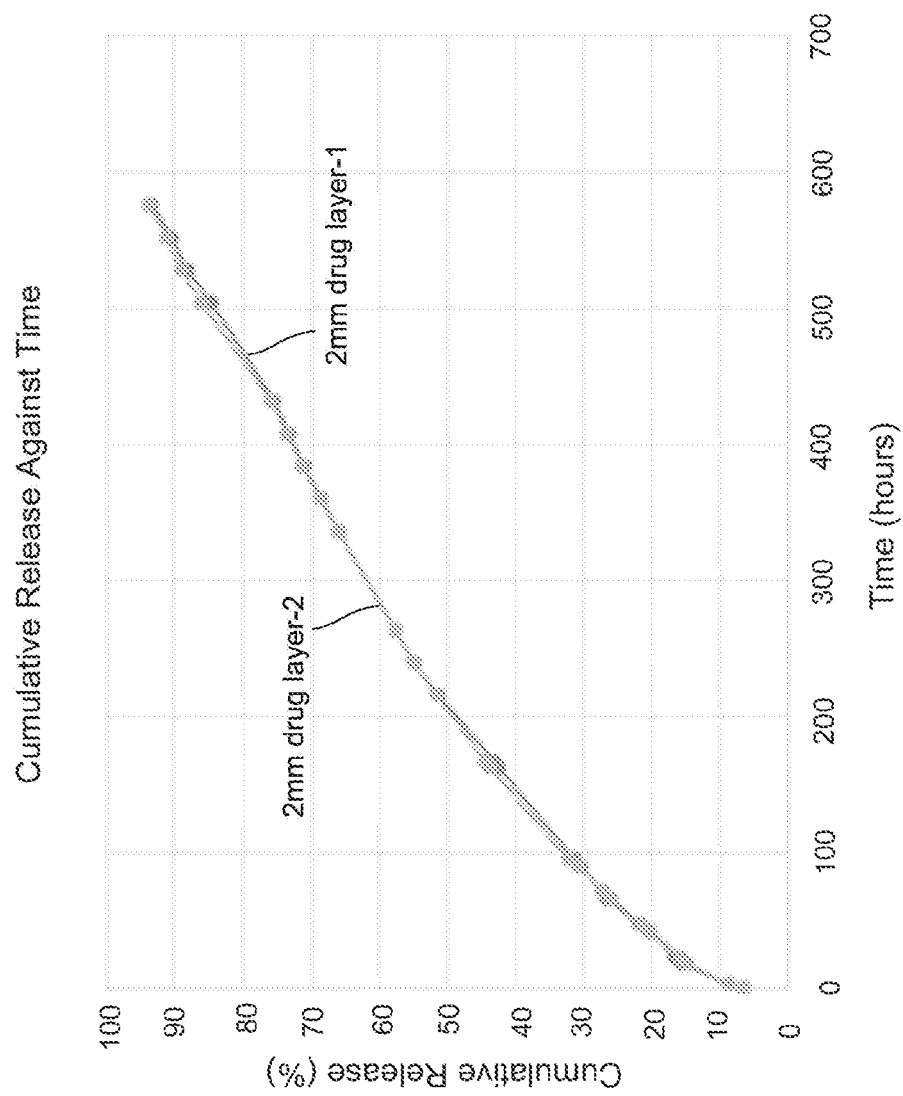
FIG. 54 depicts the in vitro release profile for the depots as described in Example 2A, in accordance with the present technology.

Release profiles. FIG. 54 shows the average cumulative dose profiles of the bupivacaine films. The graph shows controlled release of over 500 hours with the initial 24-hour release of about 20%.

Example 2B

Preparation of bioresorbable polymer drug films. Two depots of the present technology comprising the local anesthetic bupivacaine were prepared as described in Example 1, except the depots of the present example comprised three of the depots of Example 1 stacked on top of one another and heat compressed to form a new, thicker sample having an overall film thickness of about 3 mm (for example, see the configuration shown in FIG. 7).

In vitro drug release testing of bupivacaine depot. in vitro drug release testing of the depots was performed as described in Example 1.

Figure 55:
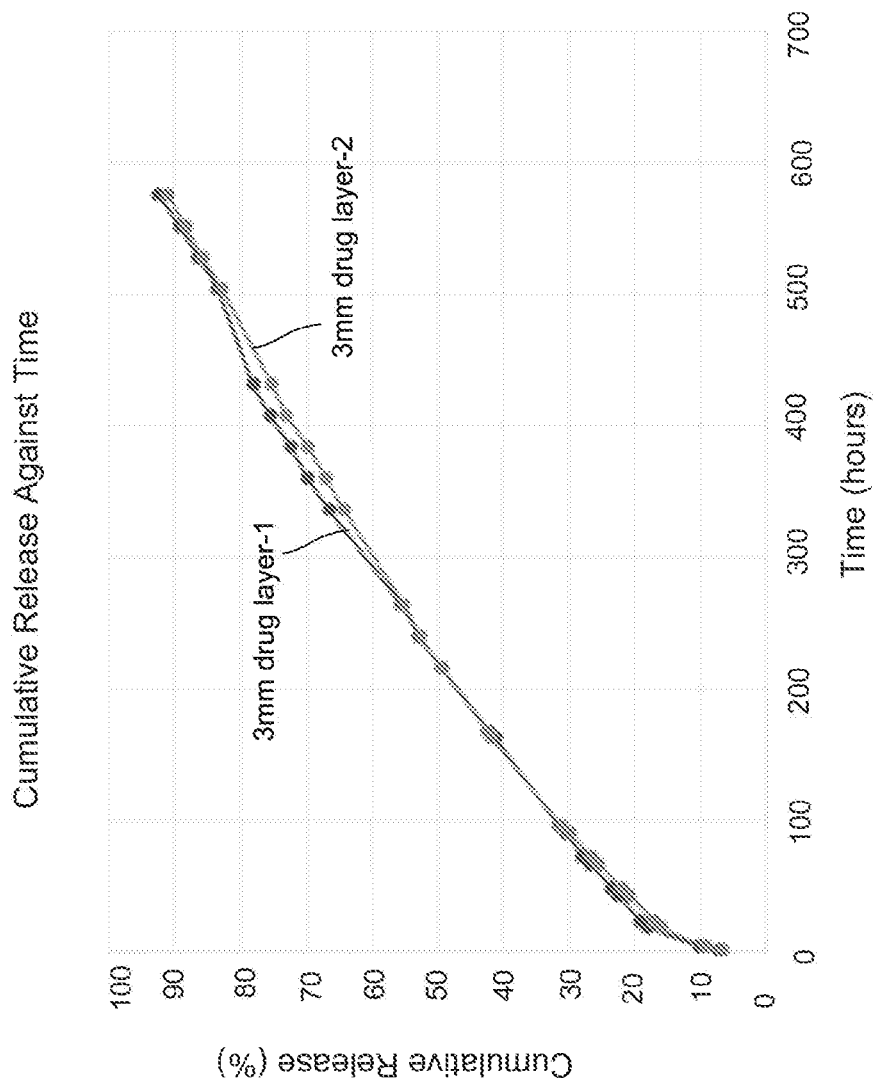
FIG. 55 depicts the in vitro release profile for the depots as described in Example 2B, in accordance with the present technology.

Release profiles. FIG. 55 shows the average cumulative dose profiles of the bupivacaine films. The graph shows controlled release of over 500 hours with the initial 24-hour release of about 20%.

Example 3

Preparation of bioresorbable polymer drug films. Four depots of the present technology comprising the local anesthetic bupivacaine were prepared as described below.

Each of the sample depots consisted of a heat compressed, multi-layer film formed of an inner depot similar to that shown in FIG. 5 encapsulated by a different control region (described below). The inner depot of each sample depot consisted of a therapeutic region (formed of 10 heat-compressed therapeutic layers) sandwiched between two inner control layers (closest to the therapeutic region, such as 302b and 302c in FIG. 5, and referred to as Control Layer A in Table 5 below) and two outer control layers (farthest from therapeutic region, such as 302a and 302d in FIG. 5), and referred to as Control Layer B in Table 5). The constituents of the therapeutic region and the control region are detailed in Table 5.

TABLE 5

| Therapeutic Region | 10 heat-compressed microlayers |
|---|---|
| Polymer | Poly(L-lactide-co-ε-caprolactone)(PLCL) (Corbion; Lenexa, KS) having a PLA to PCL ratio of from 90:10 to 60:40 (880 mg) |
| Releasing Agent | Tween 20 (440 mg) (Sigma-Aldrich Pte Ltd; Singapore) |
| Anesthetic | bupivacaine hydrochloride (1760 mg) (Xi'an Victory Biochemical Technology Co., Ltd.; Shaanxi, People's Republic of China) |
| | DCM 13.33 g |
| Anesthetic:Polymer | 2:1 |
| Control Region | |
| Control Layer A | |
| Polymer | PLCL (352 mg) |
| Releasing Agent | Tween 20 (172 mg) |
| DCM | 5.3 g |
| Control Layer B | |
| Polymer | PLCL (352 mg) |
| Releasing Agent | Tween 20 (35 mg) |
| DCM | 5.3 g |

Therapeutic region. The therapeutic region constituents (see Table 5 above) were added to a glass vial and mixed thoroughly. The resulting blend was poured onto a flat plate and drawn by a film applicator to form a thin film upon drying (<200 μm thickness).

Control region. The control region constituents (see Table 5 above) were added to a glass vial and mixed thoroughly. The resulting blend was poured onto a flat plate and drawn by a film applicator to form a thin film upon drying (<200 µm thickness).

For each sample film, 10 drug layers (each initially <200 µm thickness) and 4 control layers were aligned (Control B-Control A-10 therapeutic layers-Control A-Control B) and compressed by a heat compressor (Kun Shan Rebig Hydraulic Equipment Co. Ltd.; People's Republic of China). The resulting thin film was cut to form a 20 mm×20 mm triangle sample with an overall film thickness of <0.2 mm. The triangle samples were further aligned, and fully encapsulated, with (a) a Control Layer A on both sides (i.e., two additional control layers), (b) a Control Layer B on both sides (i.e., two additional control layers), (c) two of Control Layer A on both sides (i.e., four additional control layers), (d) two of Control Layer B on both sides (i.e., four additional control layers). The resulting assembly was then compressed by a heat compressor (Kun Shan Rebig Hydraulic Equipment Co. Ltd.; People's Republic of China).

in vitro drug release testing of bupivacaine depot. The purpose of this procedure was to measure the release of bupivacaine, from a bioresorbable polymer depot into a receiving fluid of 1×PBS. Each release experiment was conducted in duplicate. The in vitro release procedure consisted of placing a known size of film into an apparatus containing the receiving fluid. The in vitro release apparatus consisted of either a 20 mL or a 100 mL glass bottle. A receiving fluid in the amount of 12 mL or 50 mL was added to each sample bottle. During the release study, the apparatus was placed in a water bath maintained at 37±2° C. At predetermined intervals, samples of the receiving fluid were removed and analyzed for bupivacaine concentration by a UV-Visible Spectrophotometer.

Figure 56:
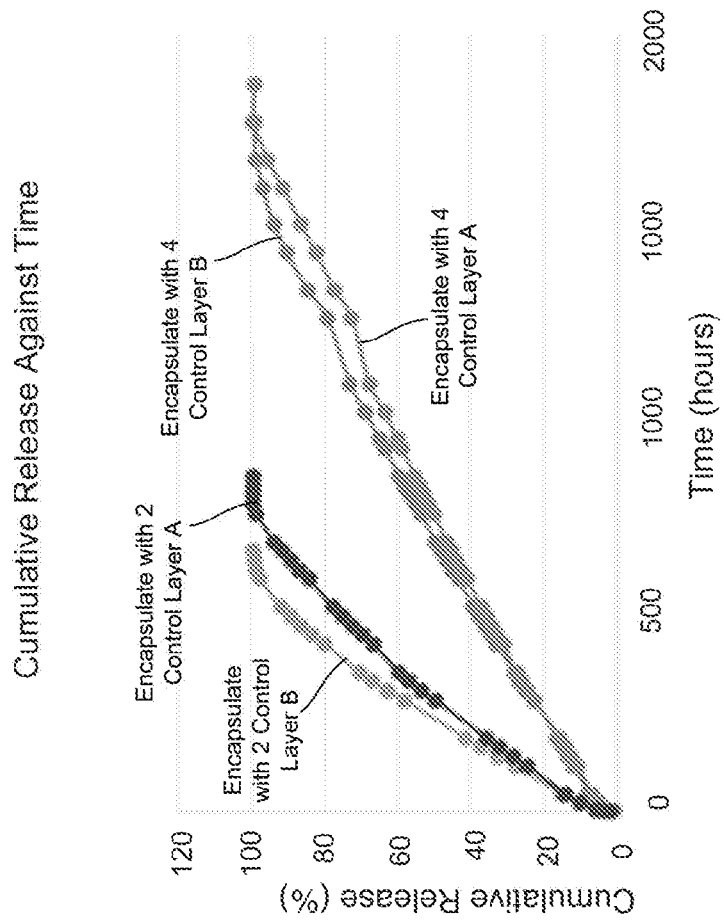
FIG. 56 depicts the in vitro release profile for the depots as described in Example 3, in accordance with the present technology.

Release profiles. FIG. 56 shows the average cumulative dose profiles of the bupivacaine films. The graph shows controlled release of over 1500 hours for some of the configurations.

Example 4

Sample depots of the present technology were implanted subcutaneously in living rabbits (one depot per rabbit). The depots were placed in a subcutaneous pocket.

Each of the sample depots consisted of a heat compressed, multi-layer film having the configuration shown in FIG. 5. The therapeutic region consisted of a single layer and was sandwiched between two inner control layers (closest to the therapeutic layer, such as 302b and 302c in FIG. 5) and two outer control layers (farthest from therapeutic region, such as 302a and 302d in FIG. 5).

The present example tested two groups of depots, each utilizing a different polymer. The depots in Group A included Poly(DL-lactide-glycolide-&-caprolactone) in a molar ratio of 60:30:10, and the depots in Group B included Poly(DL-lactide-co-glycolide) in a molar ratio of 50:50. Each group included a depot having a low, medium, or high dose of bupivacaine HCl.

For the depots of Group A, each inner control layer consisted of 3.9 mg, 4.0 mg, or 4.7 mg of the polymer (for Low, Med, and High dose groups, respectively) and 1.9 mg, 2.0 mg, or 2.3 mg of a releasing agent (polysorbate 20) (for Low, Med, and High dose groups, respectively). Each outer control layer consisted of 5.3 mg, 5.5 mg, or 6.3 mg of the polymer (for Low, Med, and High dose groups, respectively) and 1.9 mg, 2.0 mg, or 2.3 mg of a releasing agent (polysorbate 20) (for Low, Med, and High dose groups, respectively).

For the depots of Group A, the therapeutic region consisted of 71.5 mg, 152.6 mg, or 269 mg of the polymer (for Low, Med, and High dose groups, respectively), 34.9 mg, 74.6 mg, or 131.5 mg of a releasing agent (polysorbate 20) (for Low, Med, and High dose groups, respectively), and 142.9 mg, 305.2 mg, or 538.1 mg of a local anesthetic (bupivacaine HCl).

For the depots of Group B, each inner control layer consisted of 4.7 mg, 5.1 mg, or 5.3 mg of the polymer (for Low, Med, and High dose groups, respectively) and 2.3 mg, 2.5 mg, or 2.6 mg of a releasing agent (polysorbate 20) (for Low, Med, and High dose groups, respectively). Each outer control layer consisted of 6.4 mg, 6.9 mg, or 7.3 mg of the polymer (for Low, Med, and High dose groups, respectively), and 0.6 mg, 0.7 mg, or 0.7 mg of a releasing agent (polysorbate 20) (for Low, Med, and High dose groups, respectively).

For the depots of Group B, the therapeutic region consisted of 87.0 mg, 171.1 mg, or 317.7 mg of the polymer (for Low, Med, and High dose groups, respectively), 42.5 mg, 83.6 mg, or 155.2 mg of a releasing agent (polysorbate 20) (for Low, Med, and High dose groups, respectively), and 173.9 mg, 342.2 mg, or 635.4 mg of a local anesthetic (bupivacaine HCl).

Within each of Group A and Group B, the low dose depots were about 20 mm×20 mm×<1 mm (e.g., 0.89 mm and 0.9 mm), the medium dose depots were about 20 mm×20 mm×<2 mm (e.g., 1.8 mm and 1.6 mm), and the high dose depots were about 20 mm×20 mm×<3 mm (e.g., about 2.7 mm and about 2.8 mm).

Blood draws for bupivacaine concentration analysis were collected through Day 28.

Group A

The Group A depots were administered to 3 rabbits/dose group and PK samples were collected to day 28. The semi-log plot of the group mean data for each dose is shown in FIG. 57. The product, regardless of dose, exhibits peak exposure within the first 72 hours and then a plateau of exposure that is determined by the dose (the higher the dose the longer the plateau) followed by more rapid terminal clearance. The release of bupivacaine is rapid with a consistent similar profile for each rabbit with moderate variability over the first 72 hours.

Figure 57A:
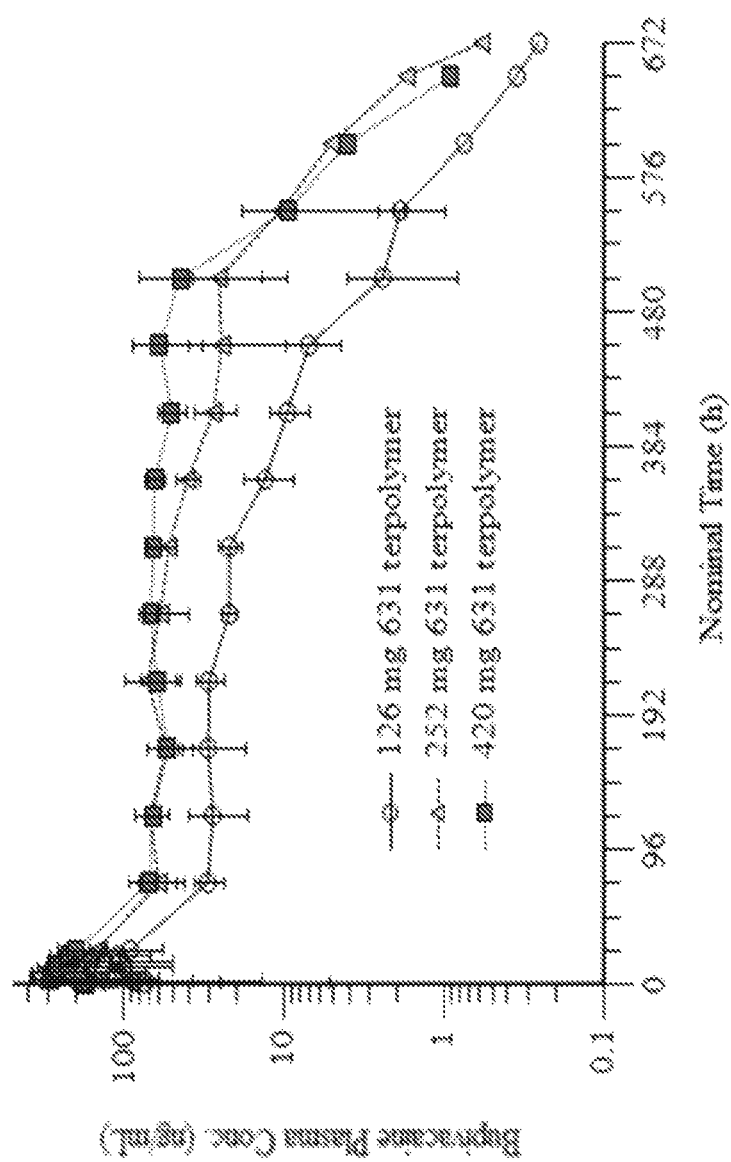
FIG. 57A shows the in vivo blood plasma bupivacaine concentration over time for a rabbit implanted with the depots as described in Example 4, in accordance with the present technology.
Figure 57B:
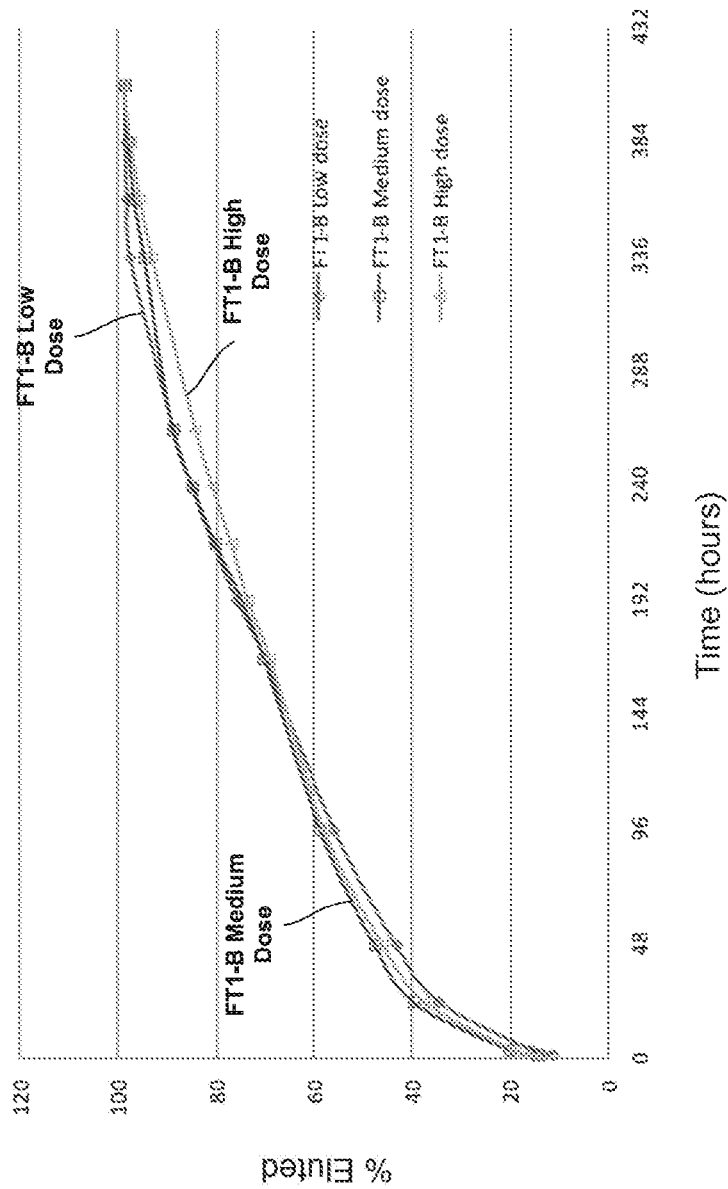
FIG. 57B depicts the in vitro release profile over time for the sample depots as described in Example 4, in accordance with the present technology.

The in vitro pharmacokinetic ("PK") profile for Group A is shown in FIG. 57B. The half-life of the initial distribution phase through the first 72-96 hours was generally consistent through the three dose strengths (implant sizes) and $T_{max}$ occurred within the first 24 hours for all rabbits, with a median $T_{max}$ between 4-8 hours. The peak exposure ($C_{max}$) for the high dose exhibited a low CV % of 17.6%. This data would indicate a controlled initial rapid release of bupivacaine during the period of greatest discomfort post TKA surgery. The exposure profile was stable from 72 hours through at least 436 hours. The terminal phase half-life started to exhibit the more innate half-life of bupivacaine, particularly in the high dose where the terminal phase $t_{1/2}$ was 17.4 hours. This would suggest that the depot had almost completely released the drug by Day 21.

The high dose, Group A depot was consistent in average exposure from Day 3 to Day 18, while the mid and low dose depots were consistent from Day 3 to Day 14. There was not a significant difference in exposure between the Mid and High dose groups from Day 3-14, while the Low dose was approximately half the exposure level during this time period.

Group B

Figure 57C:
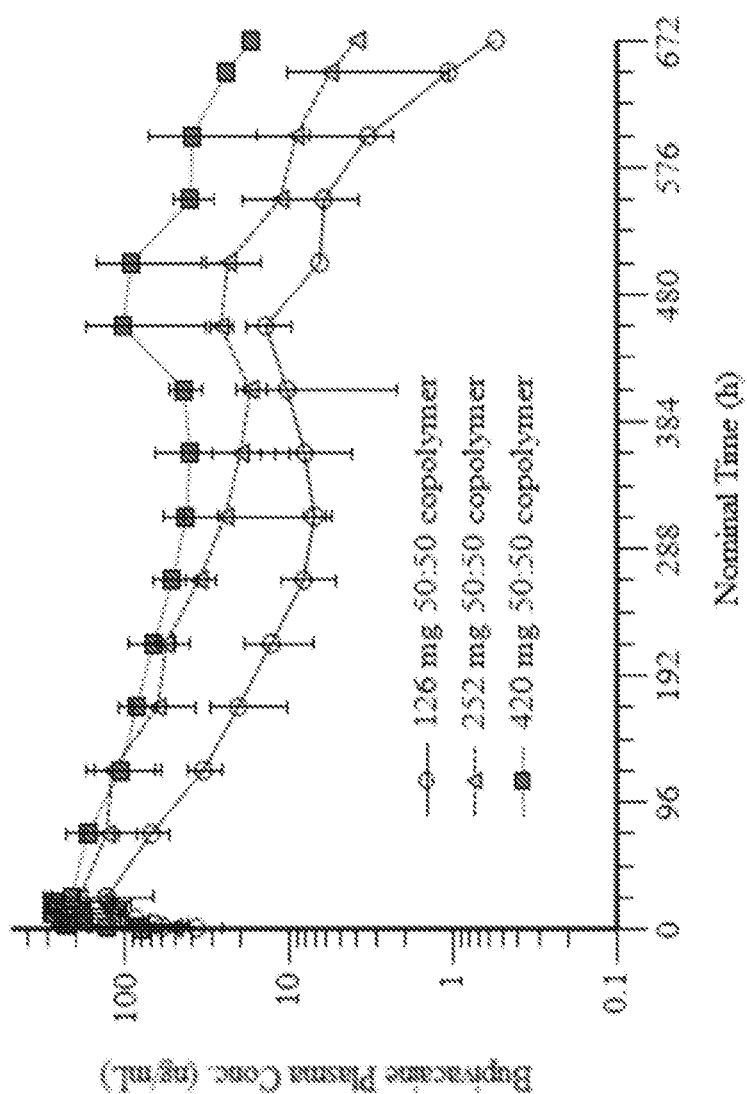
FIG. 57C shows the in vivo blood plasma bupivacaine concentration over time for a rabbit implanted with the depots as described in Example 4, in accordance with the present technology.

Formulation 50:50 copolymer was administered to 3 rabbits/dose group and PK samples were collected to hour 672 (Day 28). The semi-log plot of the group mean data for each dose is presented in FIG. 57C. The product, regardless of dose, exhibits peak exposure within the first 72 hours and then a gradual decline in exposure followed by a secondary faster release coupled with a secondary peak in exposure at approximately Day 19-21. After the secondary peak, bupivacaine exposure declined with different rates dependent on dose (lower the dose the faster the clearance). FIG. 57C highlights the group mean (SD) and individual rabbits for Low Dose (126 mg) in Panel A, Mid Dose (252 mg) in Panel B and High Dose (420 mg) in Panel C through the first 96 hours. The release of bupivacaine is rapid with a consistent and similar profile for each rabbit with moderate variability over the first 72 hours.

Figure 57D:
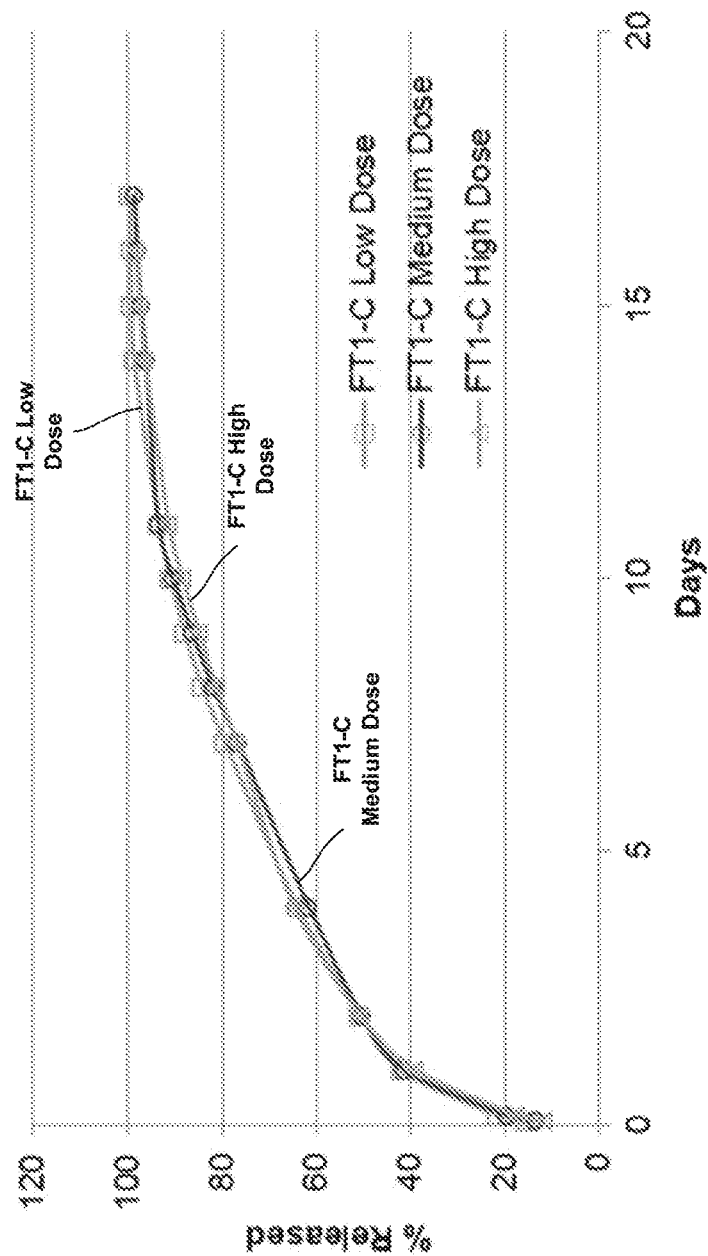
FIG. 57D depicts the in vitro release profile over time of the sample depots as described in Example 4, in accordance with the present technology.

The in vitro pharmacokinetic profile is shown in FIG. 57D. The 50:50 copolymer did not exhibit an initial distribution half-life like the 631 terpolymer, however $T_{max}$ occurred within the first 24 h for all rabbits, with a median $T_{max}$ that was slightly further out in time, between 16-20 hours. The peak exposure ($C_{max}$) exhibited a very low CV % of 5.99%. This data would indicate a controlled initial rapid release of bupivacaine during the acute postoperative pain period (i.e., period of greatest discomfort post TKA surgery) followed by a more gradual decline in release rate through the subacute postoperative pain period, which is consistent with the presumed steady decline in pain during that same period. This release profile having the steady decline in release rate during the acute postoperative pain period is in contrast with the release rate of the 631 polymer formulation, where the release rate states substantially constant throughout the postoperative pain period.

All three dose levels slowly decreased exposure over the Day 3 to Day 18 time period.

Example 5

Two sample depots of the present technology were implanted in the intraarticular space of a knee joint of a living canine. The surgeon performed a medial and lateral parapatellar arthrotomy to insert one sample depot in the medial gutter and one sample depot in the lateral gutter. The depots were anchored in place by 4-0 PDS II suture. Two canines were the subject of the present study.

Each of the sample depots consisted of a heat compressed, multi-layer film having the configuration shown in FIG. 5. The therapeutic region consisted of a single layer and was sandwiched between two inner control layers (closest to the therapeutic layer, such as 302b and 302c in FIG. 5) and two outer control layers (farthest from therapeutic region, such as 302a and 302d in FIG. 5). Each inner control layer consisted of 5.7 mg of a bioresorbable polymer (60:30:10 terpolymer Poly(DL-lactide-glycolide-ε-caprolactone)) and 2.8 mg of a releasing agent (polysorbate 20). Each outer control layer consisted of 7.7 mg of a bioresorbable polymer (60:30:10 terpolymer Poly(DL-lactide-glycolide-ε-caprolactone)) and 0.8 mg of a releasing agent (polysorbate 20).

The therapeutic region comprised a single layer consisting of 118 mg of a bioresorbable polymer (60:30:10 terpolymer Poly(DL-lactide-glycolide-ε-caprolactone)), 57.6 mg of a releasing agent (polysorbate 20), and 235.9 mg of a local anesthetic (bupivacaine HCl).

Each of the depots was about 15 mm×about 25 mm×about 1 mm.

Following implantation, the canines were evaluated at predetermined intervals to determine the post-operative pharmacokinetic (PK) profile of bupivacaine in synovial fluid and blood plasma. For PK values of bupivacaine in the blood plasma (i.e., representing systemic bupivacaine levels), blood was drawn at scheduled intervals after implantation of the depots. The PK results for the plasma fluid samples are shown at FIG. 58.

Figure 58:
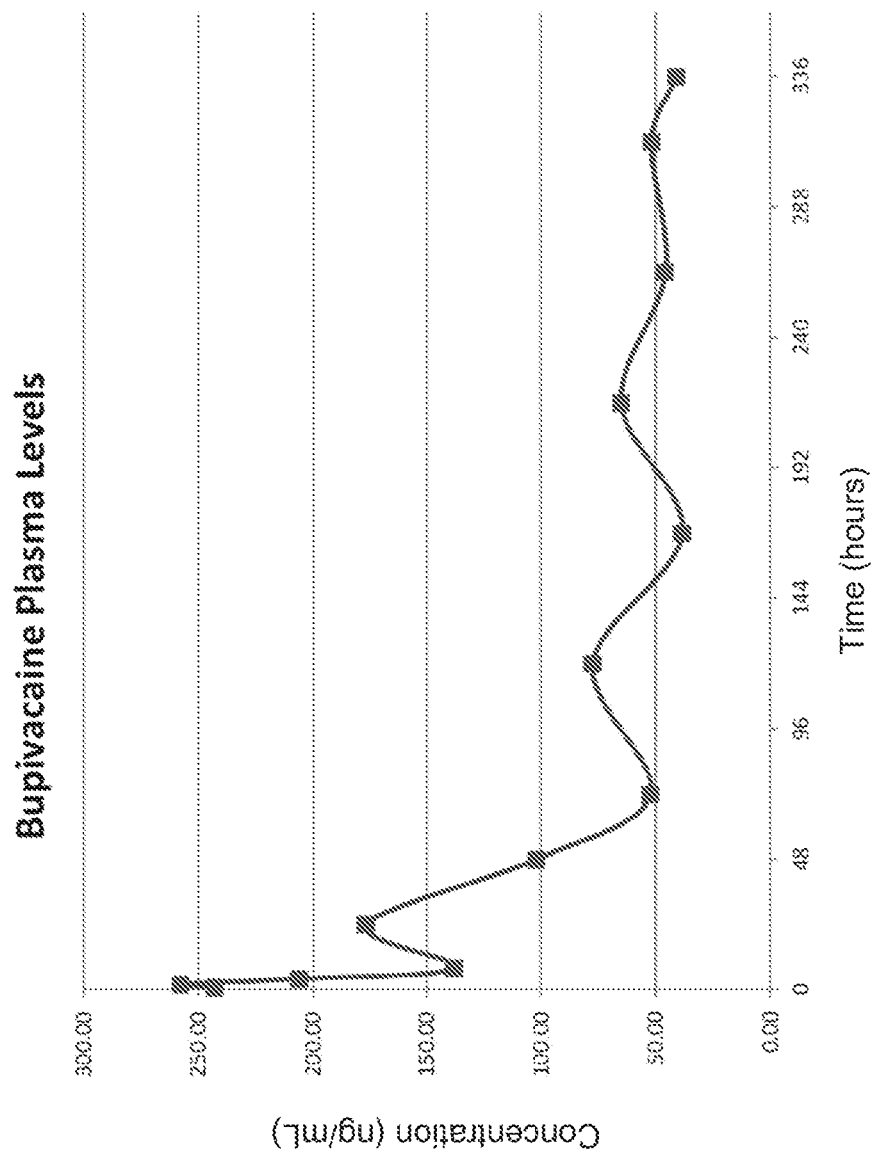
FIG. 58 shows the in vivo blood plasma bupivacaine concentration over time for a canine implanted with the depots as described in Example 5, in accordance with the present technology.

As shown in FIG. 58, the depot 100 released an initial, controlled burst over about the first three days, followed by a tapering release for the remaining 11 days.

Example 6

Three sample depots of the present technology were implanted in the intraarticular space of a knee joint of a living sheep. The surgeon performed a medial and lateral parapatellar arthrotomy to insert one sample depot in the medial gutter and two sample depots in the lateral gutter. The lateral gutter depots were sutured side-by-side prior to implantation to keep the depots in place relative to each other in the gutter. The depots were then anchored in place to the capsular tissue by 4-0 PDS II suture.

Each of the sample depots consisted of a heat compressed, multi-layer film having the configuration shown in FIG. 5. The therapeutic region consisted of a single layer and was sandwiched between two inner control layers (closest to the therapeutic layer, such as 302b and 302c in FIG. 5) and two outer control layers (farthest from therapeutic region, such as 302a and 302d in FIG. 5). Each inner control layer consisted of 5.3 mg of a bioresorbable polymer (Poly(DL-lactide-co-glycolide) in a molar ratio of 50:50)) and 2.6 mg of a releasing agent (polysorbate 20). Each outer control layer consisted of 7.2 mg of a bioresorbable polymer (Poly (DL-lactide-co-glycolide) in a molar ratio of 50:50)) and 0.7 mg of a releasing agent (polysorbate 20).

The therapeutic region comprised a single layer consisting of 118.1 mg of a bioresorbable polymer (Poly(DL-lactide-co-glycolide) in a molar ratio of 50:50), 57.7 mg of a releasing agent (polysorbate 20), and 236.3 mg of a local anesthetic (bupivacaine HCl).

Each of the depots was about 15 mm×about 25 mm×about 1 mm.

Following implantation, the sheep was evaluated at 1, 4, 8, 15, and 30 days to determine the post-operative pharmacokinetic (PK) profile of bupivacaine in synovial fluid and blood plasma.

Figure 59A:
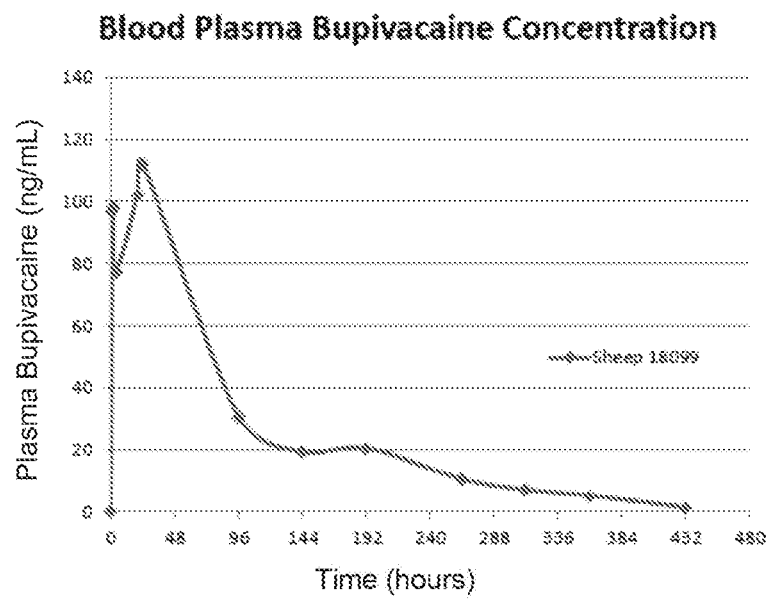
FIG. 59A shows the in vivo blood plasma bupivacaine concentration over time for a sheep implanted with the depots as described in Example 6, in accordance with the present technology.

For PK values of bupivacaine in the blood plasma (i.e., representing systemic bupivacaine levels), 1 mL of blood was drawn 1, 2, 4, 8, 12, 16, 20, 24 and 48 hours after implantation of the depots, then every 48 hours (at the same time as was drawn on previous days, +/−1 hr) in all animals until day 28 prior to sacrifice. The PK results for the plasma fluid samples are shown in FIG. 59A. As shown, the systemic plasma bupivacaine concentration showed an initial, controlled burst over the first 2-4 days, followed by a tapering release for the remaining period.

Figure 59B:
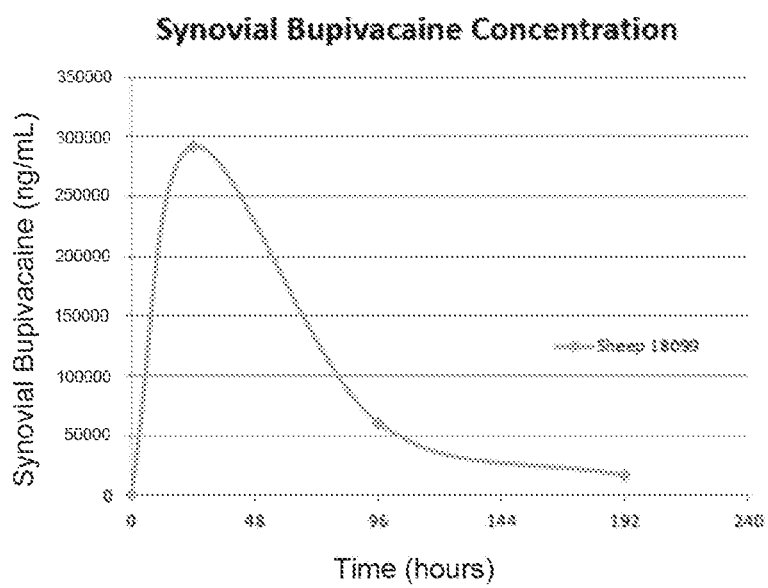
FIG. 59B shows the in vivo synovial bupivacaine concentration over time for a sheep implanted with the depots as described in Example 6, in accordance with the present technology.

For PK values of bupivacaine in the synovial fluid (i.e., representing local bupivacaine levels), a minimum of 0.5 mL of synovial fluid was aspirated from the joint at 0 hours (i.e., just prior to surgery), 24 hours, 96 hours, and 192 hours. The PK results for the synovial fluid samples are shown in FIG. 59B. As shown, the local synovial concentration showed an initial, controlled burst over the first 2-4 days, followed by a tapering release for the remaining period.

Figure 59C:
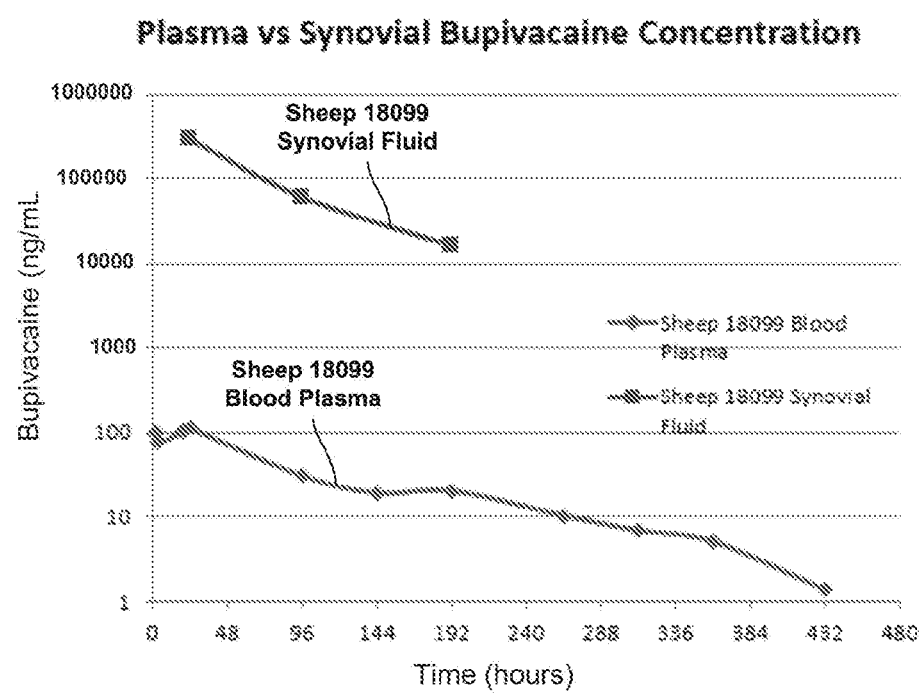
FIG. 59C is a plot depicting the blood plasma bupivacaine concentration versus the synovial bupivacaine concentration over time for a sheep implanted with the depots as described in Example 6, in accordance with the present technology.

FIG. 59C is a plot depicting the blood plasma bupivacaine concentration versus the synovial bupivacaine concentration over time. As demonstrated in FIG. 59C, the PK values are illustrative of a release profile achieved in prior in vitro and in vivo studies, wherein the initial, controlled burst over the first 2-4 days provides a substantial dosage of bupivacaine during the acute postoperative pain period and the tapering release that follows provides a therapeutic dosage during the subacute postoperative pain period. As shown, local bupivacaine levels were an order of magnitude greater than systemic bupivacaine levels. Achieving a high local concentration of bupivacaine without correspondingly high systemic levels allows for optimized analgesia without the risk of systemic toxicity.

III. Selected Systems and Methods for Treating Postoperative Pain Associated with Orthopedic Surgery The depots 100 of the present technology may be used to treat a variety of orthopedic injuries or diseases depending upon the nature of the therapeutic agent delivered as described above. The therapeutic agent may be delivered to specific areas of the patient's body depending upon the medical condition being treated. The depots 100 of the present technology may be positioned in vivo proximate to the target tissue (i.e., bone, soft tissue, etc.) in the patient's body to provide a controlled, sustained release of a therapeutic agent for the treatment of a particular condition. This implantation may be associated with a surgery or intervention for acutely treating the particular condition, whereby the depot enables chronic, sustained pharmacological treatment following completion of the surgery or intervention. The depot may be a standalone element, or may be coupled to or integrated as part of an implantable device or prosthesis associated with the intervention or surgery.

The amount of the therapeutic agent that will be effective in a patient in need thereof will depend on the specific nature of the condition, and can be determined by standard clinical techniques known in the art. In addition, in vitro or in vivo assays may optionally be employed to help identify optimal dosage ranges. The specific dose level for any particular individual will depend upon a variety of factors including the activity of the drug, the age, body weight, general physical and mental health, genetic factors, environmental influences, sex, diet, time of administration, location of administration, rate of excretion, and the severity of the particular problem being treated.

Some aspects of the present technology include a system comprising a plurality of depots (each of which could be any of the depots described herein) provided for implantation by a clinical practitioner. In this system, each depot may be configured for controlled release of therapeutic agent to tissue proximate to the implantation site of the depot. The depots in the system may be identical or may vary in several respects (e.g., form factor, therapeutic agent, release profile, etc.). For example, the system may be comprised of a depot having a release profile that provides for an immediate release of therapeutic agent and other depots comprised of a depot having a release profile that provides for a delayed release of therapeutic agent.

Many depots of the present technology are configured to be implanted at a surgical site to treat postoperative pain at or near the site. As used herein, the term "pain" includes nociception and the sensation of pain, both of which can be assessed objectively and subjectively, using pain scores and other methods well-known in the art, such as opioid usage. In various embodiments, pain may include allodynia (e.g., increased response to a normally non-noxious stimulus) or hyperalgesia (e.g., increased response to a normally noxious or unpleasant stimulus), which can in turn be thermal or mechanical (tactile) in nature. In some embodiments, pain is characterized by thermal sensitivity, mechanical sensitivity and/or resting pain. In other embodiments, pain comprises mechanically-induced pain or resting pain. In still other embodiments, the pain comprises resting pain. The pain can be primary or secondary pain, as is well-known in the art. Exemplary types of pain reducible, preventable or treatable by the methods and compositions disclosed herein include, without limitation, include post-operative pain, for example, from the back in the lumbar regions (lower back pain) or cervical region (neck pain), leg pain, radicular pain (experienced in the lower back and leg from lumbar surgery in the neck and arm from cervical surgery), or abdominal pain from abdominal surgery, and neuropathic pain of the arm, neck, back, lower back, leg, and related pain distributions resulting from disk or spine surgery. Neuropathic pain may include pain arising from surgery to the nerve root, dorsal root ganglion, or peripheral nerve.

In various embodiments, the pain results from "post-surgical pain" or "post-operative pain" or "surgery-induced pain", which are used herein interchangeably, and refer to pain arising in the recovery period of seconds, minutes, hours, days or weeks following a surgical procedure (e.g., hernia repair, orthopedic or spine surgery, etc.). Surgical procedures include any procedure that penetrates beneath the skin and causes pain and/or inflammation to the patient. Surgical procedure also includes arthroscopic surgery, an excision of a mass, spinal fusion, thoracic, cervical, or lumbar surgery, pelvic surgery or a combination thereof.

Figure 60A:
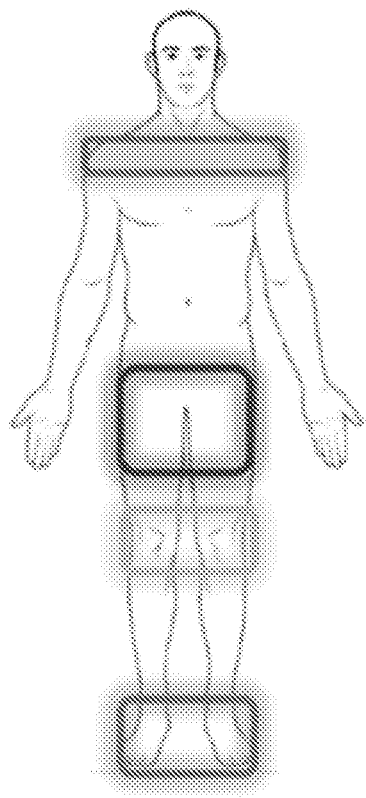
FIGS. 60A and 60B illustrate common locations within a patient that may be sites where surgery is conducted and locations where the depot can be administered.
Figure 60B:
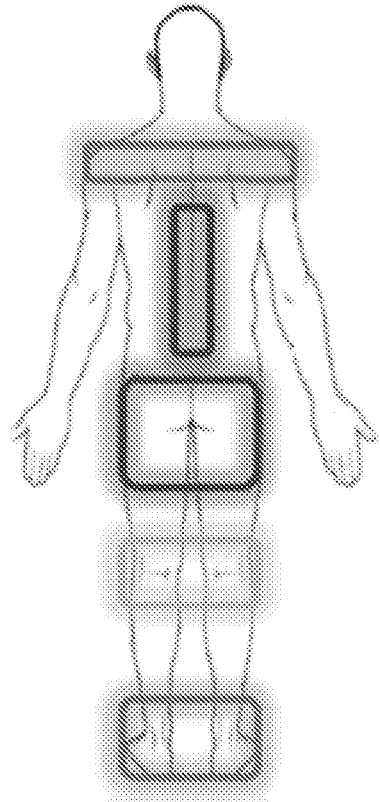

FIGS. 60A and 60B illustrate common locations within a patient that may be sites where surgery is conducted and locations where the depots of the present technology can be administered. It will be recognized that the locations illustrated in FIGS. 60A and 60B are merely exemplary of the many different locations within a patient where a surgery may take place. For example, surgery may be required at a patient's knees, hips, upper extremities, lower extremities, neck, spine, shoulders, abdomen and pelvic region. FIG. 61 is a table showing common surgical procedures for which the depots 100 of the present technology may be utilized for treating postoperative pain.

Many embodiments of the present technology include one or more depots, having the same or different configuration and/or dosing, that are configured to be positioned at or near a surgical site of a knee joint to treat pain associated with a total knee replacement surgery. As previously described, the depots of the present technology may be solid, self-supporting, flexible thin films that is structurally capable of being handled by a clinician during the normal course of a surgery without breaking into multiple pieces and/or losing its general shape. This way, the clinician may position one or more of the depots at various locations at or near the intracapsular and/or extracapsular space of the knee joint, as necessary to address a particular patient's needs and/or to target particular nerves innervating the knee.

FIGS. 62A-62C, for example, are front, lateral, and medial views of a human knee, showing the location of the nerves innervating the extra- and intracapsular portion of a knee joint. In some embodiments, the depots may be implanted adjacent to one or more nerves (such as the nerves shown in FIGS. 62A-62C) innervating the knee.

Figure 63A:
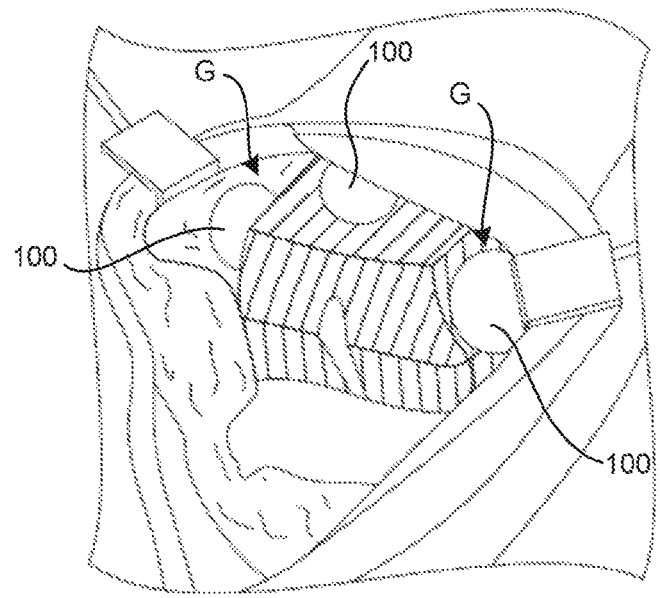
FIG. 63A is a splayed view of a human knee exposing the intracapsular space and identifying potential locations for positioning one or more depots.
Figure 63B:
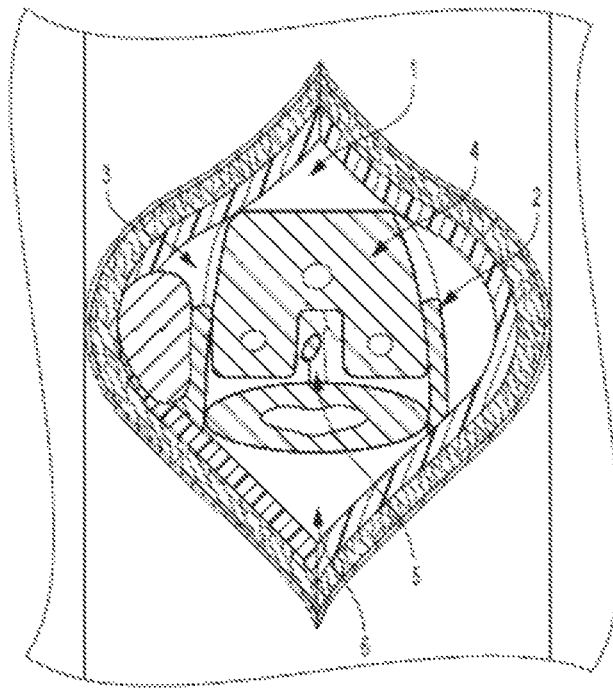
FIG. 63B is a splayed view of a human knee exposing the intracapsular space and showing several depots positioned within for treating postoperative pain.

In some instances, it may be beneficial to position one or more of the depots within the joint capsule. For example, FIG. 63A is a splayed view of a human knee exposing the intracapsular space and identifying potential locations for positioning one or more depots, and FIG. 63B is a splayed view of a human knee exposing the intracapsular space and showing several depots 100 positioned within for treating postoperative pain. As shown in FIGS. 63A and 63B, in some instances, one or more depots may be positioned at or near the suprapatellar pouch SPP, specifically under the periosteum and attached to the quadriceps tendon. Additional areas for placement of one or more depots 100 may include generally the medial and lateral gutters MG, LG (including optional fixation to tissue at the medial or lateral side of the respective gutter), on the femur F, on the tibia T (e.g., posterior attachment to the tibial plateau, at or near the anterior tibia to anesthetize infrapatellar branches of the saphenous nerve). In some embodiments, one or more depots may be positioned adjacent to at least one of a posterior capsule PC of the knee, a superior region of the patella P, and/or the arthrotomy incision into the knee capsule. In some embodiments, one or more depots 100 may be positioned at or near the saphenous nerve, the adductor canal, and/or the femoral nerve. In some embodiments, one or more of the depots may be configured to be positioned at or near an infrapatellar branch of the saphenous nerve, one or more genicular nerves of the knee, a superior region of the patella P. It may be desirable to position the depot within the knee capsule but away from any articulating portions of the knee joint itself.

Figure 64B:
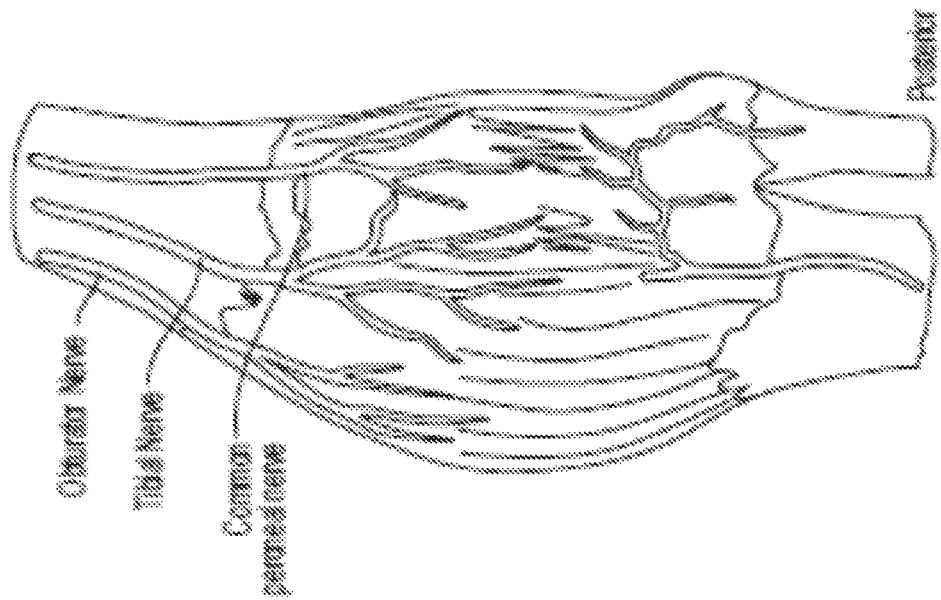
FIGS. 64A and 64B show anterior and posterior, extracapsular views of a human knee, showing the location of the nerves innervating the knee at an extracapsular location.
Figure 64A:
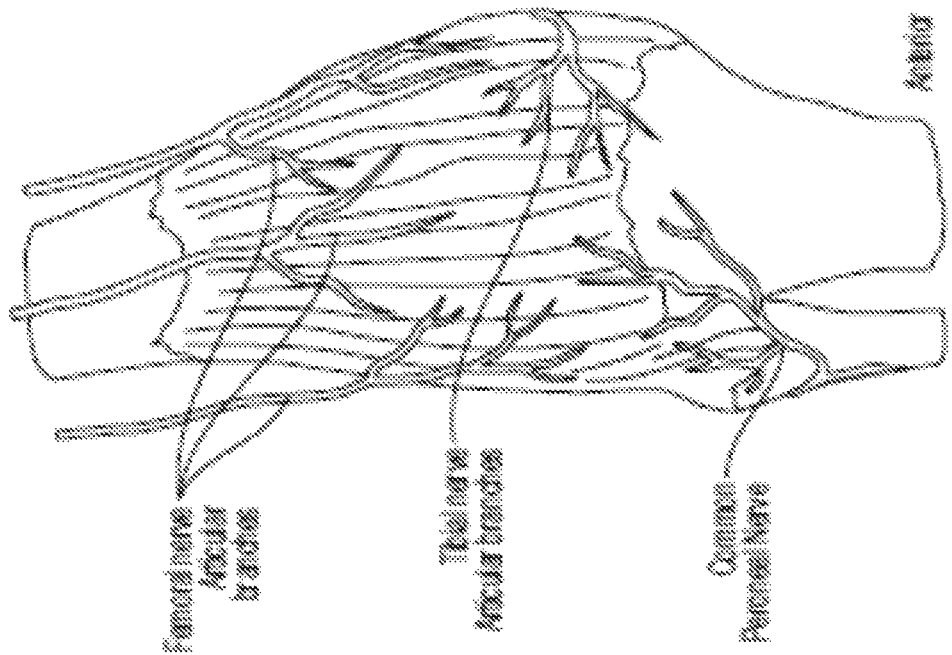
Figure 65:
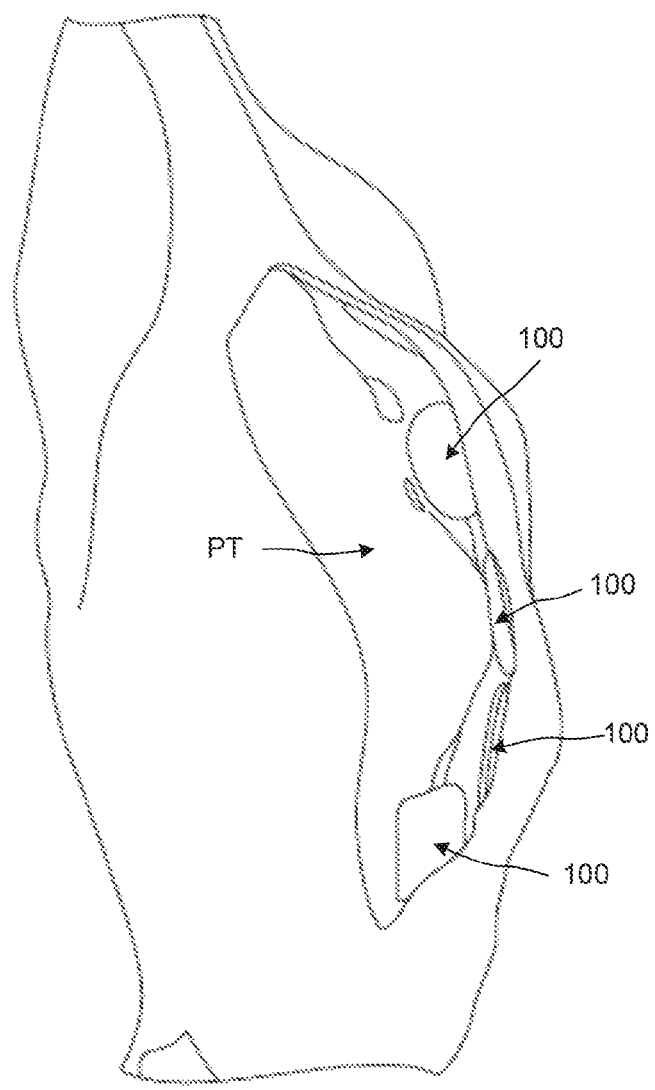
FIG. 65 is an anterior view of a partially-splayed human knee, showing an extracapsular space and showing several depots of the present technology positioned at the extracapsular space for treating postoperative pain.

Instead of or in addition to the placement of depots within the intracapsular space, one or more depots may be placed at an extracapsular position. FIGS. 64A and 64B, for example, show anterior and posterior views, respectively, of the nerves as positioned at an extracapsular location. In some embodiments, the depots may be implanted adjacent to one or more extracapsular nerves (such as the nerves shown in FIGS. 64A and 64B). As shown in FIG. 65, in some embodiments one or more depots 100 may be positioned along or adjacent the subcutaneous skin incision.

In some embodiments, the system includes a first depot (or plurality of depots) and a second depot (or plurality of depots), all of which are configured to be implanted at or near the knee joint. The first depot(s) may have the same or different release profile, rate of release, therapeutic agent (such as non-anesthetic analgesics, NSAIDs, antibiotics, etc.), duration of release, size, shape, configuration, total payload, etc. as the second depot(s).

So as not to interfere or overlap with a peripheral nerve block administered perioperatively to the patient, one or more of the depots may optionally include a delay release capability for 6 to 24 hours following implantation. In some embodiments, one or more depots placed in the adductor canal and knee capsule may be configured to have a delay in the release of therapeutic agent that may exceed 24 hours.

The depots 100 disclosed herein may be used to treat postoperative pain associated with other knee surgeries. For example, one or more depots may be used to treat postoperative pain associated with an ACL repair surgery, a medial collateral ligament ("MCL") surgery, and/or a posterior cruciate ligament ("PCL") surgery. For ACL repair, one or more depots may be positioned to delivery analgesic to the femoral and/or sciatic nerves, while for PCL repair surgery, one or more depots may be positioned parasacral to deliver analgesic to the sciatic nerve. The one or more depots may be used to treat postoperative pain associated with a partial knee replacement surgery, total knee replacement surgery, and/or a revision surgery of a knee replacement surgery. In such procedures, one or more depots can be placed contiguous to the joint or repair site to provide a local block, or else may suitably positioned to provide a regional block by delivering an analgesic to one or more of the femoral nerve or the sciatic nerve, for example via placement in the adductor canal.

In addition to the knee-related surgeries described above, embodiments of the depots disclosed herein can be used to treat postoperative pain associated with other orthopedic surgeries as described in more detail below and as summarized in part in FIG. 61. Examples include surgical procedures involving the ankle, hip, shoulder, wrist, hand, spine, legs, or arms. For at least some of these surgical procedures, analgesic can be provided to deliver a local block or a regional block to treat postoperative pain. For a local block, one or more depots can be attached under direct vision in open surgery, for example during joint arthroplasty, open reduction and internal fixation (ORIF) surgery, ligament reconstruction, etc. In such procedures involving a joint, one or more depots can be positioned at the joint capsule (e.g., at or near the intracapsular and/or extracapsular space of the joint) or adjacent soft tissues spaced apart from articulating surfaces to avoid the depot interfering with joint movement or being damaged by contact with articulating surfaces. In cases involving fracture repair or ligament repair, one or more depots can be positioned at or adjacent to the repair site to provide a local block. For a regional block, one or more depots can be deposited at a treatment site adjacent to the target nerve via ultrasound guidance using a blunt trocar catheter or other suitable instrument. In at least some embodiments, it can be beneficial to combine delivery of analgesic or other therapeutic agents via the depot(s) with delivery of NSAIDs, a long-acting narcotic delivered preoperatively, and/or acetaminophen. The sustained, controlled, release of an analgesic via the one or more depots may work in concert with these other therapeutic agents to provide a reduction in postoperative pain associated with orthopedic and other surgical procedures.

In one example, one or more depots as described herein can be used to treat postoperative pain associated with foot and ankle surgeries such as ankle arthroplasty (including ankle revision, ankle replacement, and total ankle replacement), ankle fusion, ligament reconstruction, corrective osteotomies (e.g., bunionectomy, pes planus surgery), or open reduction and internal fixation (ORIF) of ankle or foot fractures. In treating postoperative pain associated with such surgeries, one or more depots can be configured and positioned adjacent to the joint or repair site to provide a local block. Additionally or alternatively, one or more depots can be placed parasacral or at another suitable location to target one or more of the subgluteal sciatic nerve, popliteal sciatic nerve, deep peroneal nerve, or the superficial peroneal nerve. In some embodiments, depots positioned to treat postoperative pain associated with ankle or foot surgeries can have a release profile configured to deliver therapeutically beneficial levels of analgesic for a period of between 3-7 days.

In another example, one or more depots as described herein can be used to treat postoperative pain associated with hip surgeries such as hip arthroplasty (including hip revision, partial hip replacement, and total hip replacement) or open reduction and internal fixation (ORIF) of hip fractures. In treating postoperative pain associated with such surgeries, one or more depots can be configured and positioned adjacent to the joint or repair site to provide a local block. Additionally or alternatively, a regional block can be provided by placing depots in the psoas compartment, lumbar paravertebral space, fascia iliaca, or other suitable location to target one or more of the lumbar plexus, sacral plexus, femoral nerve, sciatic nerve, superior gluteal nerve, or obturator nerve. In some embodiments, it may be beneficial to secure the one or more depot(s) (e.g., using a fixation mechanism as described herein) to maintain an anterior position of the depot, thereby preventing or reducing exposure of analgesic to motor nerves (e.g., sciatic or femoral nerves). In some embodiments, depots positioned to treat postoperative pain associated with hip surgeries can have a release profile configured to deliver therapeutically beneficial levels of analgesic for a period of 5-7 or 7-10 days depending on the particular surgical procedure.

Post-operative pain associated with shoulder and upper-arm surgeries can likewise be treated using one or more depots as disclosed herein. Examples of such surgeries include shoulder arthroplasty (including shoulder revision, partial shoulder replacement, and total shoulder replacement), upper-arm fracture repair (scapular, humerus), ligament/tendon repair (e.g., rotator cuff, labrum, biceps, etc.), or open reduction and internal fixation (ORIF) of fractures of the shoulder or upper arm. In treating postoperative pain associated with such surgeries, one or more depots can be configured and positioned adjacent to the joint or repair site to provide a local block. Additionally or alternatively, one or more depots can be configured and positioned to target the brachial plexus by placing one or more depots in the cervical paravertebral space, interscalene, or supraclavicular space. In some embodiments, interscalene placement of the depots can avoid exposure of analgesic to native cartilage, thereby reducing the risk of chondrotoxicity. In some embodiments, depots positioned to treat postoperative pain associated with shoulder or upper-arm related surgeries can have a release profile configured to deliver therapeutically beneficial levels of analgesic for a period of 3-7 days.

In another example, one or more depots as described herein can be used to treat postoperative pain associated with elbow surgeries such as elbow arthroplasty (including elbow revision, partial elbow replacement, and total elbow replacement), ligament reconstruction, or open reduction and internal fixation (ORIF) of fractures of the elbow. In treating postoperative pain associated with such surgeries, one or more depots can be positioned adjacent to the joint or repair site to provide a local block. Additionally or alternatively, one or more depots can be configured and positioned to target the brachial plexus nerves, for example by being placed at or near the cervical paravertebral space, infraclavicular, or axillary position, or other suitable location. In some embodiments, depots positioned to treat postoperative pain associated with elbow surgeries can have a release profile configured to deliver therapeutically beneficial levels of analgesic for a period of 3-7 days.

Post-operative pain associated with wrist and hand surgeries can also be treated using one or more depots as described herein. Examples of wrist and hand surgeries include wrist arthroplasty (including wrist revision, partial wrist replacement, and total wrist replacement), wrist fusion, and open reduction and internal fixation (ORIF) of fractures of the wrist. In treating postoperative pain associated with such surgeries, one or more depots can be configured and positioned adjacent to the wrist joint or repair site to provide a local block. Additionally or alternatively, one or more depots can be configured and positioned to target the target the ulnar, median, radial, and cutaneous forearm nerves, for example via placement at the antecubital fossa, cervical paravertebral space, infraclavicular, or axillary position. In some embodiments, depots positioned to treat postoperative pain associated with wrist and hand surgeries can have a release profile configured to deliver therapeutically beneficial levels of analgesic for a period of 3-7 days.

The depots disclosed herein may likewise be used to treat postoperative pain from other orthopedic surgeries. For example, post-operative pain associated with spinal fusion can be treated via placement of one or more depots subcutaneously or in the paravertebral space. In treatment of post-operative pain associated with fibular fracture repair, one or more depots can be configured and placed to target the sciatic nerve and/or the popliteal sciatic nerve, for example being placed parasacral. Various other placements and configurations are possible to provide therapeutic relief from post-operative pain associated with orthopedic surgical procedures.

IV. Selected Systems and Methods for Treating Postoperative Pain Associated with Non-orthopedic Surgery The depots 100 of the present technology may be used to treat a variety of medical conditions depending upon the nature of the therapeutic agent delivered as described above. The therapeutic agent may be delivered to specific areas of the patient's body depending upon the medical condition being treated. The depots 100 of the present technology may be positioned in vivo proximate to the target tissue in the patient's body to provide a controlled, sustained release of a therapeutic agent for the treatment of a particular condition. This implantation may be associated with a surgery or intervention for acutely treating the particular condition, whereby the depot enables chronic, sustained pharmacological treatment following completion of the surgery or intervention. The depot 100 may be a standalone element, or may be coupled to or integrated as part of an implantable device or prosthesis associated with the intervention or surgery.

The amount of the therapeutic agent that will be effective in a patient in need thereof will depend on the specific nature of the condition, and can be determined by standard clinical techniques known in the art. In addition, in vitro or in vivo assays may optionally be employed to help identify optimal dosage ranges. The specific dose level for any particular individual will depend upon a variety of factors including the activity of the drug, the age, body weight, general physical and mental health, genetic factors, environmental influences, sex, diet, time of administration, location of administration, rate of excretion, and the severity of the particular problem being treated.

Some aspects of the present technology include a system comprising a plurality of depots (each of which could be any of the depots described herein) provided for implantation by a clinical practitioner. In this system, each depot may be configured for controlled release of therapeutic agent to tissue proximate to the implantation site of the depot. The depots in the system may be identical or may vary in several respects (e.g., form factor, therapeutic agent, release profile, etc.). For example, the system may be comprised of a depot having a release profile that provides for an immediate release of therapeutic agent and other depots comprised of a depot having a release profile that provides for a delayed release of therapeutic agent.

Many depots of the present technology are configured to be implanted at a surgical site to treat postoperative pain at or near the site. As used herein, the term "pain" includes nociception and the sensation of pain, both of which can be assessed objectively and subjectively, using pain scores and other methods well-known in the art, such as opioid usage. In various embodiments, pain may include allodynia (e.g., increased response to a normally non-noxious stimulus) or hyperalgesia (e.g., increased response to a normally noxious or unpleasant stimulus), which can in turn be thermal or mechanical (tactile) in nature. In some embodiments, pain is characterized by thermal sensitivity, mechanical sensitivity and/or resting pain. In other embodiments, pain comprises mechanically-induced pain or resting pain. In still other embodiments, the pain comprises resting pain. The pain can be primary or secondary pain, as is well-known in the art. Exemplary types of pain reducible, preventable or treatable by the methods and compositions disclosed herein include, without limitation, include post-operative pain and neuropathic pain of the arm, neck, back, lower back, leg, and related pain distributions. Neuropathic pain may include pain arising from surgery to the nerve root, dorsal root ganglion, or peripheral nerve.

In various embodiments, the pain results from "post-surgical pain" or "post-operative pain" or "surgery-induced pain," which are used herein interchangeably, and refer to pain arising in the recovery period of seconds, minutes, hours, days or weeks following a surgical procedure. Surgical procedures include any procedure that penetrates beneath the skin and causes pain and/or inflammation to the patient. Surgical procedure also includes arthroscopic surgery, an excision of a mass, spinal fusion, thoracic, cervical, or lumbar surgery, pelvic surgery, chest-related surgery, breast-related surgery, gynecological or obstetric surgery, general, abdominal, or urological surgery, ear, nose, and throat (ENT) surgery, oral and maxillofacial surgery, oncological surgery, cosmetic surgery, or a combination thereof. FIG. 61 is a table showing common surgical procedures for which the depots 100 of the present technology may be utilized for treating postoperative pain.

Many embodiments of the present technology include one or more depots, having the same or different configuration and/or dosing, that are configured to be positioned at or near a surgical site to treat pain associated with recovering from a surgical procedure. As previously described, the depots of the present technology may be solid, self-supporting, flexible thin films that is structurally capable of being handled by a clinician during the normal course of a surgery without breaking into multiple pieces and/or losing its general shape. This way, the clinician may position one or more of the depots at various locations at or near the treatment site, as necessary to address a particular patient's needs and/or to target particular nerves innervating the surgical site.

In some embodiments, the system includes a first depot (or plurality of depots) and a second depot (or plurality of depots), all of which are configured to be implanted at or near the treatment site. The first depot(s) may have the same or different release profile, rate of release, therapeutic agent contained (such as non-anesthetic analgesics, NSAIDs, antibiotics, etc.), duration of release, size, shape, configuration, total payload, etc. as the second depot(s).

So as not to interfere or overlap with a peripheral nerve block administered perioperatively to the patient, one or more of the depots may optionally include a delay release capability for 6 to 24 hours following implantation. In some embodiments, one or more depots placed at the treatment site may be configured to have a delay in the release of therapeutic agent that may exceed 24 hours.

The depots disclosed herein may be used to treat postoperative pain associated with a wide variety of surgeries. For example, as summarized in FIG. 61, the depots may be used to treat postoperative pain for chest-related surgery, breast-related surgery, gynecological or obstetric surgery, general, abdominal, or urological surgery, ear, nose, and throat (ENT) surgery, oral and maxillofacial surgery, oncological surgery, or cosmetic surgery). For particular surgeries or classes of surgeries, one or more depots can be positioned at a treatment site to treat postoperative pain. The treatment site may be at or near the surgical site, or in some embodiments may be separated from the surgical site and proximate to a target nerve or nerve bundle that innervates the surgical site.

In one example, one or more depots as described herein can be used to treat postoperative pain associated with chest-related surgeries such as a thoracotomy, esophageal surgery, cardiac surgery, lung resection, thoracic surgery, or other such procedure. In treating postoperative pain associated with such surgeries, one or more depots can be configured and positioned to target the intercostal nerves, for example by being placed at or near the thoracic paravertebral space or other suitable location. Analgesics delivered to the intercostal nerves can reduce pain in a patient's chest area, thereby relieving postoperative pain associated with the above-noted chest-related surgical procedures.

In another example, one or more depots disclosed herein can be used to treat postoperative pain associated with breast-related surgeries such as a mastectomy, breast augmentation, breast reduction, breast reconstruction procedure, or other such procedure. To treat postoperative pain from such procedures, one or more depots can be positioned and configured to deliver analgesics or other therapeutic agents to the intercostal nerves, for example via placement at or near the patient's infraclavicular space or other suitable location. Additionally or alternatively, one or more depots can be positioned and configured to deliver analgesics or other therapeutic agents to the lateral pectoral nerve and/or the medial pectoral nerve, for example via placement between the serratus anterior muscle and the latissimus dorsi muscle or other suitable location. As noted above, analgesics delivered to the intercostal nerves can reduce pain in a patient's chest area, while analgesics delivered to the lateral and/or medial pectoral nerves can reduce pain in the pectoralis major and pectoralis minor, thereby reducing postoperative pain associated with the above-noted chest-related surgical procedures.

As another example, one or more depots can be used to treat postoperative pain associated with general, abdominal, and/or urological procedures. Examples of such procedures include proctocolectomy, pancreatectomy, appendectomy, hemorrhoidectomy, cholecystectomy, kidney transplant, nephrectomy, radical prostatectomy, nephrectomy, gastrectomy, small bowel resection, splenectomy, incisional hernia repair, inguinal hernia repair, sigmoidectomy, liver resection, enterostomy, rectum resection, kidney stone removal, and cystectomy procedures. For such operations, postoperative pain can be treated by placing one or more depots to target nerves at the transverse abdominis plane (TAP). Analgesics delivered to the TAP can anesthetize the nerves that supply the anterior abdominal wall, thereby reducing postoperative pain in this region. In some embodiments, one or more depots are disposed between the internal oblique and transverse abdominis muscles. In some embodiments, one or more depots can be disposed at or adjacent to the abdominal wall, for example being secured in place via fixation mechanisms as described in more detail below.

In some embodiments, one or more depots are used to treat postoperative pain associated with gynecological and obstetric surgeries, for example a myomectomy, Caesarian section, hysterectomy, oophorectomy, pelvic floor reconstruction, or other such surgical procedure. For such procedures, the depot(s) can be configured and positioned to deliver analgesics or other therapeutic agents to one or more of the nerves innervating the pelvic and/or genital area, for example the pudendal nerve, intercostal nerve, or other suitable nerve.

In some embodiments, one or more depots can be used to treat postoperative pain associated with ear, nose, and threat (ENT) surgical procedures, for example tonsillectomy, submucosal resection, rhinoplasty, sinus surgery, inner ear surgery, parotidectomy, submandibular gland surgery, or other such operation. Similarly, one or more depots can be used to treat postoperative pain associated with oral and maxillofacial surgeries, for example dentoalveolar surgery, dental implant surgery, orthognathic surgery, temporomandibular joint (TMJ) surgery, dental reconstruction surgeries, or other such operations. For ENT surgical procedures and oral and maxillofacial surgical procedures, the depot(s) can be configured and positioned to deliver analgesics or other therapeutic agents to one or more of the nerves innervating regions affected by the surgical procedure, for example the mandibular nerve, the mylohyoid nerve, lingual nerve, inferior alveolar nerve, buccal nerve, auriculotemporal nerve, anterior ethmoidal nerve, or other suitable nerve.

One or more depots 100 can also be used to treat postoperative pain for other surgical procedures, for example oncological surgeries (e.g., tumor resection), cosmetic surgeries (e.g., liposuction), or other surgical procedure resulting in postoperative pain. For treatment of postoperative pain associated with any particular surgery, the number of depots and the characteristics of individual depots can be selected to deliver the desired therapeutic benefits. For example, the dimensions of the depot(s), the amount of therapeutic agent per depot, the release profile, and other characteristics can be tuned to provide the desired treatment of postoperative pain. For example, while a patient recovering from a knee-replacement surgery may benefit from delivery of analgesics for at least 14 days, a patient recovering from a tonsillectomy may not require the same level or duration of analgesic drug delivery. As such, depots delivered to a patient for treatment of postoperative pain following a tonsillectomy may require fewer depots, or depots having a smaller payload of therapeutic agent, or depot(s) having a steeper release profile, etc. Additionally, the number and characteristics of the depot(s) selected for implantation can be tailored to accommodate the target anatomical region for placement in the patient's body.

V. Selected Examples of Treatment Members of the Present Technology

In some embodiments, the depot may not include a therapeutic agent and thus may not be drug-eluting. Rather, the depot may be a treatment member configured to be implanted in a mammalian body for at least 7 days without undergoing core acidification. The treatment member may comprise a polymer (such as any of the polymers disclosed here) mixed with a releasing agent (such as any of the releasing agents disclosed herein) and having a minimum cross-sectional dimension of 400 μm. The treatment member may be configured to provide structural support for tissue, such as bone, ligaments, tendons, cartilage, and other connective tissue. Additionally or alternatively, the treatment member may be configured as an implant for cosmetic procedures. The treatment member may be an implant configured to be positioned at the head or neck region of the patient (for example for ear, nose, and throat (ENT) surgical procedures, such as rhinoplasty or sinus surgery). The treatment member may be configured for use in oral and maxillofacial surgeries, for example dentoalveolar surgery, dental implant surgery, orthognathic surgery, temporomandibular joint (TMJ) surgery, dental reconstruction surgeries, or other such operations (for example, the treatment member may be an oral and/or dental implant). The treatment member may also be configured for implantation as part of an orthopedic surgery. For example, the treatment member may be configured to be positioned at a joint of a patient, such as a shoulder, knee, elbow, ankle, wrist, or knee (such as a bone or connective tissue screw, anchor, etc. and/or all or a part of a prosthetic joint), and/or at an extremity of the patient. In some embodiments, the treatment member may comprise all or a portion of an implant configured to treat a fracture or other connective tissue trauma. In some embodiments, the treatment member may comprise all or a portion of an implantable stent, valve, or other device implanted during interventional procedures.

VI. Conclusion

Although many of the embodiments are described above with respect to systems, devices, and methods for treating postoperative pain, the technology is applicable to other applications and/or other approaches. For example, the depots of the present technology may be used to treat postoperative pain associated with a veterinary procedure and/or surgery. Moreover, other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described above with reference to FIGS. 2-70.

The above detailed descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

Unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present technology. At the very least, and not as an attempt to limit the application of the doctrine of equivalents to the scope of the claims, each numerical parameter should at least be construed in light of the number of reported significant digits and by applying ordinary rounding techniques. Additionally, all ranges disclosed herein are to be understood to encompass any and all subranges subsumed therein. For example, a range of "1 to 10" includes any and all subranges between (and including) the minimum value of 1 and the maximum value of 10, i.e., any and all subranges having a minimum value of equal to or greater than 1 and a maximum value of equal to or less than 10, e.g., 5.5 to 10.

It is noted that, as used in this specification and the appended claims, the singular forms "a," "an," and "the," include plural referents unless expressly and unequivocally limited to one referent. For example, reference to "a therapeutic agent" includes one, two, three or more therapeutic agents.

The headings above are not meant to limit the disclosure in any way. Embodiments under any one heading may be used in conjunction with embodiments under any other heading.

We claim:

1. A depot comprising:
    a polymer matrix including a polyalphahydroxy acid (AHA) having an acid as a degradation byproduct and a therapeutic agent, wherein the therapeutic agent comprises at least 50% of the total weight of the depot, and wherein at least a portion of the polymer matrix has a volume with a minimum cross-sectional dimension of at least 400 µm before degradation of the AHA begins;
    wherein, when implanted in vivo, the depot is configured to release the therapeutic agent such that a plurality of pores are formed in the polymer matrix, and
    wherein, when the depot is (a) submerged in aqueous media for a duration sufficient for a molecular weight of the AHA and/or a mass of the polymer matrix to decrease by about 25% to about 75%, and (b) subsequently submerged in a buffer solution and broken up such that an interior region of the depot is in fluid communication with the surrounding buffer solution, a pH of the surrounding buffer solution is within about 0.5 units of the pH of the buffer solution before the depot is placed in the buffer solution.

2. The depot of claim 1, wherein the depot is configured to be implanted at a treatment site in vivo and, while implanted, release the therapeutic agent at the treatment site for no less than 7 days.

3. The depot of claim 1, wherein the therapeutic agent comprises at least 60% of the total weight of the depot.

4. The depot of claim 1, wherein the therapeutic agent includes a local anesthetic.

5. The depot of claim 1, wherein the polymer matrix includes a therapeutic region and a control region, wherein the therapeutic region includes the therapeutic agent and the control region does not include the therapeutic agent.

6. The depot of claim 5, wherein the therapeutic region includes a releasing agent.

7. The depot of claim 1, wherein the AHA is poly(lactide-co-glycolide).

8. The depot of claim 1, wherein the buffer solution is buffered to a pH of about 7.4.

9. The depot of claim 1, wherein the AHA includes one or more of poly(lactide) or poly(glycolic acid).

10. The depot of claim 1, wherein the degradation byproduct is a carboxylic acid.

11. The depot of claim 10, wherein the carboxylic acid has a pKa less than or equal to 7.0.

12. The depot of claim 1, wherein the cross-sectional dimension is at least 1 mm.

13. A biodegradable implant, the implant comprising:
    a polymer matrix including a polyalphahydroxy acid (AHA) having an acid as a degradation byproduct and a therapeutic agent, wherein the therapeutic agent comprises at least 50% of the total weight of the implant, and wherein at least a portion of the polymer matrix has a volume with a minimum cross-sectional dimension of at least 400 µm before degradation of the AHA begins;
    wherein the implant is configured to release the therapeutic agent over a period of at least 14 days such that a plurality of pores are formed within the polymer matrix, and
    wherein, when the implant is (a) submerged in aqueous media for a duration sufficient for a molecular weight of the AHA and/or a mass of the polymer matrix to decrease by about 25% to about 75%, and (b) subsequently submerged in a buffer solution and broken up such that an interior region of the implant is in fluid communication with the surrounding buffer solution, a pH of the surrounding buffer solution is within about 0.5 units of the pH of the buffer solution before the implant is placed in the buffer solution.

14. The implant of claim 13, wherein the therapeutic agent includes a local anesthetic.

15. The implant of claim 14, wherein the local anesthetic is bupivacaine.

16. The implant of claim 13, wherein the therapeutic agent comprises at least 60% of the total weight of the implant.

17. The implant of claim 13, wherein the polymer matrix includes a therapeutic region and a control region covering at least a portion of the therapeutic region, wherein the therapeutic region includes the therapeutic agent and the control region is substantially impermeable to diffusion.

18. The implant of claim 13, wherein the cross-sectional dimension is at least 1 mm.

19. The implant of claim 13, wherein the AHA includes one or more of poly(lactide) or poly(glycolic acid).

20. The depot of claim 1, wherein the polymer matrix comprises:
    a therapeutic region having a first surface and a second surface;
    a first control region disposed at the first surface of the therapeutic region; and
    a second control region disposed at the second surface of the therapeutic region,
    wherein the therapeutic region includes the therapeutic agent, and the first and second control regions do not include the therapeutic agent.

* * * * *